US008921653B2

(12) United States Patent
Spangenberg et al.

(10) Patent No.: US 8,921,653 B2
(45) Date of Patent: Dec. 30, 2014

(54) MODIFICATION OF LIGNIN BIOSYNTHESIS

(75) Inventors: German Spangenberg, Bundoora (AU); Angela Jane Lidgett, Richmond (AU); Robyn Louise Heath, Clifton Hill (AU); Russell Leigh McInnes, Bundoora (AU); Damian Paul Lynch, Northcote (AU); Ulrik John, Northcote (AU); Aidyn Mouradov, Mill Park (AU)

(73) Assignees: Agriculture Victoria Services Pty Ltd, Attwood, Victoria (AU); Dairy Australia Limited, Southbank, Victoria (AU)

( * ) Notice: Subject to any disclaimer, the term of this patent is extended or adjusted under 35 U.S.C. 154(b) by 1043 days.

(21) Appl. No.: 12/119,294

(22) Filed: May 12, 2008

(65) Prior Publication Data
US 2008/0313774 A1 Dec. 18, 2008

Related U.S. Application Data

(63) Continuation-in-part of application No. 10/311,459, filed as application No. PCT/AU01/00699 on Jun. 14, 2001, now Pat. No. 7,429,649.

(51) Int. Cl.
C12N 15/05 (2006.01)
C12N 15/82 (2006.01)
A01H 5/10 (2006.01)
C12N 15/00 (2006.01)
C12N 9/00 (2006.01)
C12N 9/04 (2006.01)
C12N 9/10 (2006.01)
C12N 9/02 (2006.01)

(52) U.S. Cl.
CPC .......... *C12N 9/0006* (2013.01); *C12N 15/8216* (2013.01); *C12N 9/93* (2013.01); *C12N 15/8223* (2013.01); *C12N 9/1007* (2013.01); *C12N 15/8255* (2013.01); *C12N 9/0008* (2013.01)
USPC ......... 800/284; 800/286; 800/295; 435/320.1

(58) Field of Classification Search
None
See application file for complete search history.

(56) References Cited

U.S. PATENT DOCUMENTS

| 5,952,486 | A | 9/1999 | Bloksberg et al. |
| 6,015,943 | A | 1/2000 | Boudet et al. |
| 2005/0069884 | A1 | 3/2005 | Spangenberg et al. |
| 2005/0091707 | A1 | 4/2005 | Spangenberg et al. |
| 2005/0150008 | A1 | 7/2005 | Demmer et al. |
| 2008/0034453 | A1* | 2/2008 | Cheikh et al. ................. 800/294 |

FOREIGN PATENT DOCUMENTS

| WO | 9305159 | 3/1993 | |
| WO | 9324638 | 12/1993 | |
| WO | 9712982 | 4/1997 | |
| WO | 9839454 | 9/1998 | |
| WO | WO 98/39454 | * 9/1998 | ............ C12N 15/53 |
| WO | 9910498 | 3/1999 | |
| WO | 9931243 | 6/1999 | |
| WO | 00/22099 A1 | 4/2000 | |
| WO | 0173090 A2 | 10/2001 | |
| WO | 01/95702 A1 | 12/2001 | |
| WO | 0226994 A1 | 4/2002 | |
| WO | 03040306 A2 | 5/2003 | |
| WO | 03105723 A2 | 12/2003 | |
| WO | 2006104891 A2 | 10/2006 | |
| WO | 2007/066214 A2 | 6/2007 | |
| WO | 2008049848 A1 | 5/2008 | |
| WO | 2008064289 A2 | 5/2008 | |

OTHER PUBLICATIONS

Piquemal et al 1998 The Plant Journal 13:71-83, provided in U.S. Appl. No. 10/311,459.*
GenBank Accession AP278698 2000 Larsen, Cinnamoyl CoA Reductase from *Lolium perenne*, provided in U.S. Appl. No. 10/311,459.*
Civardi et al., "Molecular Cloning and Characterization of Two cDNAs Encoding Enzymes Required for Secondary Cell Wall Biosynthesis in Maize.," NATO Asi Series, 1998, pp. 135-146, H 104.
GenBank accession AF052223, Heath, et al., "*Lolium perenne* 4-coumarate—CoA ligase 4CL3 mRNA, complete cds," Mar. 7, 2000.
GenPept accession AAF37734, Heath, et al., "4-coumarate—CoA ligase 4CL3 [*Lolium perenne*]," Mar. 7, 2000.
GenBank accession AF052222, Heath, et al., "*Lolium perenne* 4-ccoumarate—CoA ligase 4CL2 mRNA, complete cds", Mar. 7, 2000.
GenPept accession AAF37733, Heath, et al., "4-coumarate—CoA ligase 4CL2 [*Lolium perenne*]," Mar. 7, 2000.
GenBank accession AF052221, Heath, et al., "*Lolium perenne* 4-coumarate—CoA ligase 4CL1 mRNA, complete cds," Mar. 7, 2000.
GenPept accession AAF37732, Heath, et al., "4-coumarate—CoA ligase 4CL1 [*Lolium perenne*," Mar. 7, 2000.
Pichon et al., "Cloning and characterization of two maise cDNAs encoding Cinnamoyl-CoA Reductase (CCR) and differential expression of the corresponding genes," Plant Molecular Biology, 1998, pp. 671-676, vol. 38.
GenBank accession AJ231134, Selman-Housein et al., "*Saccharum officinarum* mRNA for cinnamoyl-CoA reductase," Jan. 25, 2000.
Baucher, et al., "Down-regulation of cinnamyl alcohol dehydrogenase in transgenic alfalfa (*Medicago sativa* L.) and the effect on lignin composition and digestibility," Plant Molecular Biology, 1999, pp. 437-447, vol. 39.
GenBank accession AF010290, McAlister, et al., "*Lolium perenne* cinnamyl alcohol dehydrogenase mRNA, complete cds," Sep. 23, 1997.
GenPept accession AAB70908, Heath, et al., "Cinnamyl alcohol dehydrogenase (*Lolium perenne*)," Sep. 22, 1997.

(Continued)

*Primary Examiner* — Brent T Page
*Assistant Examiner* — Jeffrey Bolland
(74) *Attorney, Agent, or Firm* — Larson & Anderson, LLC

(57) ABSTRACT

The present invention relates to the modification of lignin biosynthesis in plants and, more particularly, to enzymes involved in the lignin biosynthetic pathway and nucleic acids encoding such enzymes.

31 Claims, 93 Drawing Sheets

(56) References Cited

OTHER PUBLICATIONS

Heath et al., "cDNA Cloning and Differential Expression of Three Caffeic Acid O-Methyltransferase Homologues from Perennial Ryegrass (*Lolium perenne*)," Journal of Plant Physiology, 1998, pp. 649-657, vol. 153.
GenBank accession AF033540, Heath et al., "*Lolium perenne* caffeic acid O-methyltransferase (OMT3) mRNA, complete cds", Jan. 29, 1999.
GenBank accession AF033539, Heath et al., "*Lolium perenne* caffeic acid O-methyltransferase (OMT2) mRNA, complete cds", Jan. 29, 1999.
GenBank accession AF033538, Heath et al., "*Lolium perenne* caffeic acid O-methyltransferase (OMT1) mRNA, complete cds", Jan. 29, 1999.
GenBank accession AF010291, Heath, et al., "*Lolium perenne* bispecific caffeic acid/5-hydroxyferulic acid O-methyltransferase mRNA, complete cds," Jun. 3, 1998.
Capellades, et al., "The maize caffeic acid O-methyltransferase gene promoter is active in transgenic tobacco and maize plant tissues," Plant Molecular Biology, 1996, pp. 307-322, vol. 31.
Larsen, et al., "*Lolium perenne* cinnamoyl CoA reductase (CCR) mRNA, complete cds", EMBL, XP-002166672, Sep. 5, 2000, pp. 1-2.
Larsen, K., "Cloning and characterization of a ryegrass (*Lolium perenne*) gene encoding cinnamoyl-CoA reductase (CCR)", Plant Science, Mar. 2004, pp. 569-581, vol. 166, No. 3.
Larsen, K., "Cloning and characterization of a ryegrass (*Lolium perenne*) gene encoding cinnamoyl-CoA reductase (CCR)", Database ID Q9FUW8, XP-002298872, Mar. 1, 2001.
McInnes, et al., "Isolation and characterization of a cinnamoly-CoA reductase gene from perennial ryegrass (*Lolium perenne*)", Journal of Plant Physiology, Apr. 2002, pp. 415-422, vol. 159, No. 4.
LaCombe et al., "Cinnamoyl CoA reductase, the first committed enzyme of the lignin branch biosynthetic pathway: closing, expression and phylogenetic relationships", The Plant Journal, Mar. 1997, pp. 429-441, vol. 11, No. 3.
Piquemal, et al, "Down-regulation of Cinnamoyl-CoA Reductase induces significant changes of lignin profiles in transgenic tobacco plants", The Plant Journal, 1998, pp. 71-83, vol. 13, No. 1.
Database UniProt, Cinnamyl alcohol dehydrogenase-like protein, subunit a (Cinnamyl alcohol dehydrogenase-like like protein, LCADa) (Putative alcohol dehydrogenase) (EC 1.1.1.195), XP-002310805, Aug. 1, 1998.
Tavares, et al., "Organization and structural evolution of four multigene families in *Arabidopsis thaliana*: AtLCAD, AtLGT, AtMYST and AtHD-GL2", Plant Molecular Biology, Mar. 2000, pp. 703-707, vol. 42, No. 5.
Halpin, et al., "Manipulation of lignin quality by downregulation of cinnamyl alcohol dehydrogenase", The Plant Journal, 1994, pp. 339-350, vol. 6, No. 3.
Baucher, et al., "Higher extractability of lignin in poplar (*Populus tremula* x *P. alba*) by reducing cinnamyl alcohol dehydrogenase activity", Somatic Cell Genetics and Molecular Genetics of Trees, 1996, pp. 153-158.
Chen, et al., "Lignin deposition and associated changes in anatomy, enzyme activity, gene expression, and ruminal degradability in stems of tall fescue at different developmental stages", Journal of Agricultural and Food Chemistry, Sep. 25, 2002, pp. 5558-5565, vol. 50, No. 20.
Auh, et al., "Structure and Expression of Caffeic Acid O-Methyltransferase cDNAs from Tall Fescue (*Festuca arundinacea*)." Forge Biotechnology Group. May 25, 1999. <http://www.ncbi.nlm.nih.gov/entrez/viewer.fcgi?db=nucleotide &val=14578616>.
Auh, et al., "Structure and Expression of Caffeic Acid O-Methyltransferase cDNAs from Tall Fescue (*Festuca arundinacea*)." Forge Biotechnology Group. May 25, 1999. <http://www.ncbi.nlm.nih.gov/entrez/viewer.fcgi?db=nucleotide &val=14578610>.
Auh, et al., "Structure and Expression of Caffeic Acid O-Methyltransferase cDNAs from Tall Fescue (*Festuca arundinacea*)." Forge Biotechnology Group. May 25, 1999. <http://www.ncbi.nlm.nih.gov/entrez/viewer.fcgi?db=nucleotide &val=14578614>.
Auh, et al., "Structure and Expression of Caffeic Acid O-Methyltransferase cDNAs from Tall Fescue (*Festuca arundinacea*)." Forge Biotechnology Group. May 25, 1999. <http://www.ncbi.nlm.nih.gov/entrez/viewer.fcgi?db=nucleotide &val=14578612>.
Darbyshire, S.J., "*Lolium arundinaceum*", <http://www.itis.gov/servlet/SingleRpt/SingleRpt?search_topic=TSN&search_value=507979>.
Heath, et al., "cDNA Cloning and Differential Expression of Three Caffeic Acid O-Methyltransferase Homologues from *Lolium perenne*." Plant Sciences & Biotechnology. Nov. 10, 1997. <http://www.ncbi.nlm.nih.gov/entrez/viewer.fcgi?db=nucleotide &val=4104219>.
McAlister, et al., "Sequence and Expression of a Stem-Abundant Caffeic Acid O-Methyltransferase cDNA from Perennial Ryegrass (*Lolium perenne*)." CSIRO Plant Industry. Jun. 16, 1997. <http://www.ncbi.nlm.nih.gov/entrez/viewer.fcgi?db=nucleotide &val=2388663>.
Wikipedia. "Regulatory sequence." <http://www.en.wikipedia.org/wiki/Regulatory_sequence>.
Selman-Housein, Guillermo et al. "Molecular Cloning of cDNA's coding for three sugarcane enzymes involved in lignification" 1999, pp. 163-171, vol. 143.
Fukushima, R. et al. "Extraction and Isolation of lignin for utilization as a standard to determine lignin concentration using the acetyl bromide spectrophotometric method" Journal of Agricultural and Food Chemistry, Jul. 2001, pp. 3133-3139, vol. 49, No. 7.
GenBank Accession No. AY061888, McInnes, R. et al. Isolation and characterization of a cinnamoyl-CoA reductase gene from perennial ryegrass (*Lolium perenne* L.), Dec. 26, 2001.
Goderis, I et al. "A set of modular plant transformation vectors allowing flexible insertion of up to six expression units" Plant Molecular Biology, pp. 17-27, vol. 50.
Lichtenstein, C. et al. "Genetic Engineering of Plants" In DNA Cloning vol. III, 1985, pp. 67-119.
Liyama, K. et al. "Determination of lignin in herbaceous plants by an improved acetyl bromide procedure" Journal of Science Food and Agriculture, 1990, pp. 145-161, vol. 51.
McAlister, F. et al. "Sequence and expression of a stem-abudant caffeic acid O-methyltransferase cDNA from perennial ryegrass (*Lolium perenne*)" Australian Journal of Plant Physiology, 1998, pp. 225-235, vol. 25.
Moore, K.J. et al. "Describing and Quantifying growth stages of perennial forage grasses" Agronomy Journal, 1991, pp. 1073-1077, vol. 83.
Rolando, C. et al. "Thioacidolysis" Methods in Lignin Chemistry, 1992, pp. 334-349.
Somssich, I. et al. "*Arabidopsis thaliana* defense-related protein ELI3 is an aromatic alcohol:NADP+ oxidoreductase" PNAS, Nov. 1996, pp. 14199-14203, vol. 93.
Spangenberg, G. et al. "Transgenic Tall Fescue (*Festuca arundinacea*) and Red Fescue (*F. rubra*) Plants from Microprojectile Bombardment of Embryogenic Suspension Cells" Journal of Plant Physiology, 1995, pp. 693-701, vol. 145.
Sundaresan, V. et al. "Patterns of gene action in plant development revealed by enhancer trap and gene trap transposable elements" Genes and Development, 1995, pp. 1797-1810, vol. 9.
Van Der Rest, B. et al. "Down-regulation of cinnamoyl-CoA reductase in tomato (*Solanum lycopersicum* L.) induces dramatic changes in soluble phenolic pools" Journal of Experimental Botany, 2006, pp. 1399-1411, vol. 57 No. 6.

(56) References Cited

OTHER PUBLICATIONS

Zubieta, C. et al. "Structural Basis for the Modulation of Lignin Monomer Methylation by Caffeic Acid/5-Hydroxyferulic Acid 3/5-o-Methyltransferase" The Plant Cell, Jun. 2002, pp. 1265-1277, vol. 14.

Jorgensen, R. A. et al., A Paragenetic Perspective on Integration of RNA Silencing into the Epigenome and Its Role in the Biology of Higher Plants, Cold Spring Harbor Symposia on Quantitative Biology, 2006, pp. 481-485, vol. 71, No. 0.

Brodersen P et al, The diversity of RNA silencing pathways in plants, Trends in Genetics, 2006, pp. 268-280, vol. 22, No. 5, Elsevier Science Publishers B.V., Amsterdam, NL.

Auh, et al, GENBANK Accession No. AF153824, Structure and expression of caffeic acid O-methyltransferase cDNAs from Tall fescue (*Festuca arundinacea*) Jul. 1, 2001.

Auh et al., GENBANK Accession No. AF153823, Structure and expression of caffeic acid O-methyltransferase cDNAs from tall fescue (*Festuca arundinacea*), Jul. 1, 2001.

Que et al., The Frequency and Degree of Cosuppression by Sense Chalcone Synthase Transgenes Are Dependent on Transgene Promoter Strength and Are Reduced by Premature Nonsense Codons in the Transgene Coding Sequence, The Plant Cell, 1997, pp. 1357-1368, vol. 9.

\* cited by examiner

```
       CGGCACGAGTGGACTTTCCGACGCCGGAGTCGCCGATGATGACCGCCTTGAGGAGGTAGT
  1    ---------+---------+---------+---------+---------+---------+    60

CGTAGTCGTCCTCCGCCCTGTACGCGCCGCTGCCCGCCATTTCCTTCCTCGCCTCGCGGG
  61   ---------+---------+---------+---------+---------+---------+    120

TCCTCCTCCCCGACCTGCGCTAGGCTCTGGATCTCGCGGGGTTTGGGCGCGGCGTCCTCG
  121  ---------+---------+---------+---------+---------+---------+    180

CTGTGAGCTCGTGCCGAATTCGGCACGAGCCACCTTCGAGGCGTGCACTGGTACGAGCTC
  181  ---------+---------+---------+---------+---------+---------+    240

GCGAGCCATTGTCAGTGCAGTGTAGGCTCTGCTACTCGTTGGCCATTCCAAGAAGCTCTC
  241  ---------+---------+---------+---------+---------+---------+    300

TGCTCCCTGAAACCAGAGGATCATGATCACGGTGGCGGCGCCCGAGGTGCAGCAGCCGCA
  301  ---------+---------+---------+---------+---------+---------+    360
                             M  I  T  V  A  A  P  E  V  Q  Q  P  Q

GATCGCGGCGGCTGCTGCGGCCGTGGAGGCGGCGGCACCGGAGGCGACGACGATCTTCCG
  361  ---------+---------+---------+---------+---------+---------+    420
        I  A  A  A  A  A  V  E  A  A  A  P  E  A  T  T  I  F  R

GTCCAGGCTCCCGGACATCGACATCCCGACCCACATGCCCCTGCACGACTATTGCTTCGC
  421  ---------+---------+---------+---------+---------+---------+    480
        S  R  L  P  D  I  D  I  P  T  H  M  P  L  H  D  Y  C  F  A

GACGGCAGCCTCGGCCCCGGACGCGCCGTGCCTCATCACCGCGGCCACGGGGAAGACCTA
  481  ---------+---------+---------+---------+---------+---------+    540
        T  A  A  S  A  P  D  A  P  C  L  I  T  A  A  T  G  K  T  Y

CACGTTCGCCGAGACGCACCTGCTGTGCCGCAAGGCCGCGGCGGCGCTGCACGGGCTCGG
  541  ---------+---------+---------+---------+---------+---------+    600
        T  F  A  E  T  H  L  L  C  R  K  A  A  A  A  L  H  G  L  G

CGTGCGCCACGGGGACCGGATCATGCTGCTGCTCCAGAACTCCGTGGAGTTCGCGCTCGC
  601  ---------+---------+---------+---------+---------+---------+    660
        V  R  H  G  D  R  I  M  L  L  L  Q  N  S  V  E  F  A  L  A

CTTCTTCGGCGCGTCCATGCTCGGCGCCGTCAGCACGGCGGCGAACCCGTTCTGCACGCC
  661  ---------+---------+---------+---------+---------+---------+    720
        F  F  G  A  S  M  L  G  A  V  S  T  A  A  N  P  F  C  T  P

GCAGGAGATCCACAAGCAGCTCGTGGCCTCCGGCGCGAAGCTGGTCGTCACGCAGTCCGC
  721  ---------+---------+---------+---------+---------+---------+    780
        Q  E  I  H  K  Q  L  V  A  S  G  A  K  L  V  V  T  Q  S  A
```

FIGURE 2

```
         CTACGTCGACAAGCTCCGGCACGAGGCCTTCCCCCGAATCGGCGAGGCCCTCACCGTGAT
781      ---------+---------+---------+---------+---------+---------+   840
          Y  V  D  K  L  R  H  E  A  F  P  R  I  G  E  A  L  T  V  I

CACCATCGACGAGGACGACGGCACCCCGGACGGCTGCCAGCCGTTCTGGGCCCTCGTGTC
841      ---------+---------+---------+---------+---------+---------+   900
          T  I  D  E  D  D  G  T  P  D  G  C  Q  P  F  W  A  L  V  S

AGCCGCCGACGAGAACAGCGTCCCGGAGTCTCCCATCTCGCCGGACGACGCGGTGGCGCT
901      ---------+---------+---------+---------+---------+---------+   960
          A  A  D  E  N  S  V  P  E  S  P  I  S  P  D  D  A  V  A  L

GCCCTACTCGTCGGGCACGACGGGGCTGCCCAAGGGCGTGGTGCTGACGCACGGGGGGCT
961      ---------+---------+---------+---------+---------+---------+   1020
          P  Y  S  S  G  T  T  G  L  P  K  G  V  V  L  T  H  G  G  L

GGTGTCGAGCGTGGCGCAGCAGGTGGACGGCGAGAACCCGAACCTGCACATGCGGGCGGG
1021     ---------+---------+---------+---------+---------+---------+   1080
          V  S  S  V  A  Q  Q  V  D  G  E  N  P  N  L  H  M  R  A  G

GGAGGACGTGGTGCTCTGCGTGCTGCCGCTCTTCCACATCTTCTCGCTCAACTCGGTGCT
1081     ---------+---------+---------+---------+---------+---------+   1140
          E  D  V  V  L  C  V  L  P  L  F  H  I  F  S  L  N  S  V  L

GCTGTGCGCGCTGCGGGCGGGCGCCGCCGTGATGCTGATGCCTAGGTTCGAGATGGGGGC
1141     ---------+---------+---------+---------+---------+---------+   1200
          L  C  A  L  R  A  G  A  A  V  M  L  M  P  R  F  E  M  G  A

CATGCTGGAGGGCATCGAGCGGTGGCGCGTCACGGTGGCGGCCGTGGTGCCGCCGCTGGT
1201     ---------+---------+---------+---------+---------+---------+   1260
          M  L  E  G  I  E  R  W  R  V  T  V  A  A  V  V  P  P  L  V

GCTCGCGCTCGCCAAGAACCCCGGGGTGGAGAAGCACGACCTCAGCTCCATTCGGATCGT
1261     ---------+---------+---------+---------+---------+---------+   1320
          L  A  L  A  K  N  P  G  V  E  K  H  D  L  S  S  I  R  I  V

GCTCTCCGGCGCCGCGCCGCTCGGCAAGGAGCTCGAGGACGCGCTACGTGGCCGCCTGCC
1321     ---------+---------+---------+---------+---------+---------+   1380
          L  S  G  A  A  P  L  G  K  E  L  E  D  A  L  R  G  R  L  P

GCAGGCCATCTTCGGACAGGGCTACGGGATGACGGAGGCCGGGCCGGTGCTGTCCATGTG
1381     ---------+---------+---------+---------+---------+---------+   1440
          Q  A  I  F  G  Q  G  Y  G  M  T  E  A  G  P  V  L  S  M  C

CCCGGCGTTCGCGCGGGAGCCGACGCCGGCCAAGTCCGGCTCGTGCGGCACCGTGGTGCG
1441     ---------+---------+---------+---------+---------+---------+   1500
          P  A  F  A  R  E  P  T  P  A  K  S  G  S  C  G  T  V  V  R
```

FIGURE 2 CONTINUED

```
      CAACGCCCAGCTCAAGGTGGTCGACCCCGACACCGGCGTCTCCCTCGGCCGCAACCTCCC
1501  ---------+---------+---------+---------+---------+---------+  1560
       N  A  Q  L  K  V  V  D  P  D  T  G  V  S  L  G  R  N  L  P

CGGCGAGATCTGCATCCGCGGCCCGCAGATCATGAAAGGATACTTGAATGATCCCGTGGC
1561  ---------+---------+---------+---------+---------+---------+  1620
       G  E  I  C  I  R  G  P  Q  I  M  K  G  Y  L  N  D  P  V  A

CACGGCCGCGACCATCGACGTCGAGGGGTGGCTCCACACCGGCGACATCGGCTACGTCGA
1621  ---------+---------+---------+---------+---------+---------+  1680
       T  A  A  T  I  D  V  E  G  W  L  H  T  G  D  I  G  Y  V  D

CGACGACGACGAGGTCTTCATCGTCGACCGCGTCAAGGAGCTCATCAAGTTCAAGGGCTT
1681  ---------+---------+---------+---------+---------+---------+  1740
       D  D  D  E  V  F  I  V  D  R  V  K  E  L  I  K  F  K  G  F

CCAGGTACCGCCGGCCGAGCTCGAGGCTCTGCTCATCGCGCATCCGTCCATCGCCGACGC
1741  ---------+---------+---------+---------+---------+---------+  1800
       Q  V  P  P  A  E  L  E  A  L  L  I  A  H  P  S  I  A  D  A

GGCCGTCGTCCCGCAAAAGGATGATGCCGCCGGCGAGGTCCCGGTTGCCTTCGTGGTCCG
1801  ---------+---------+---------+---------+---------+---------+  1860
       A  V  V  P  Q  K  D  D  A  A  G  E  V  P  V  A  F  V  V  R

CGCCGCCGACTCCGACATCGCCGAGGAGGCCATCAAGGAGTTCGTATCCAAGCAGGTGGT
1861  ---------+---------+---------+---------+---------+---------+  1920
       A  A  D  S  D  I  A  E  E  A  I  K  E  F  V  S  K  Q  V  V

GTTCTACAAGAGGCTGCACAAGGTCTACTTCACCCACGCGATACCCAAGTCGGCGTCGGG
1921  ---------+---------+---------+---------+---------+---------+  1980
       F  Y  K  R  L  H  K  V  Y  F  T  H  A  I  P  K  S  A  S  G

GAAGATACTCAGGAAAGAACTCAGAGCTAAACTCGCCGCCCCGGCCACTGCCTGAAGAGT
1981  ---------+---------+---------+---------+---------+---------+  2040
       K  I  L  R  K  E  L  R  A  K  L  A  A  P  A  T  A  *  R  V

GGTTCATGGCTTCATGCTAATCATTTCGATCAGAAAGGCACTTCTAGCATATATGTTCCA
2041  ---------+---------+---------+---------+---------+---------+  2100
       V  H  G  F  M  L  I  I  S  I  R  K  A  L  L  A  Y  M  F  H

CCTTTTGTTTCATTTGGAAGATTGTATTCCAGCTAGTGGCCAGTGACTGAGTAAGGGATG
2101  ---------+---------+---------+---------+---------+---------+  2160
       L  L  F  H  L  E  D  C  I  P  A  S  G  Q  *

GGGATAAAAGTTTTGTCTACGTTTTCTTTTACGCTACTCTCTCCATTGGGGAGTACAATG
2161  ---------+---------+---------+---------+---------+---------+  2220

TATCAGGGGATTCGTGATTGAAGTTAATCAAGATTGGTTCAATTATAAAAAAAAAAAAAA
2221  ---------+---------+---------+---------+---------+---------+  2280

AAAA
2281  ----  2284
```

FIGURE 2 CONTINUED

```
    CGGCACGAGCGCCATTCCTCCACCTTCAGCTCCGGCCAAAGATTTCCATCCGGCGAGATC
1   ---------+---------+---------+---------+---------+---------+  60

CATGGGCTCCATCGCGGCGGACGCGCCTCCCGCGGAGCTGGTGTTCCGGTCCAAGCTCCC
61  ---------+---------+---------+---------+---------+---------+  120
     M  G  S  I  A  A  D  A  P  P  A  E  L  V  F  R  S  K  L  P

GGACATCGAGATCCCGACCCACCTGACGCTGCAGGACTACTGCTTCCAGCGCCTGCCGGA
121 ---------+---------+---------+---------+---------+---------+  180
     D  I  E  I  P  T  H  L  T  L  Q  D  Y  C  F  Q  R  L  P  E

GCTCTCCGCGCGCGCCTGCCTCATCGACGGCGCCACGGGCGCCGCGCTCACCTACGGCGA
181 ---------+---------+---------+---------+---------+---------+  240
     L  S  A  R  A  C  L  I  D  G  A  T  G  A  A  L  T  Y  G  E

GGTGGACGCCCTGTCCCGCCGCTGCGCCGCGGGGCTGCGCCGCCTCGGCGTCGGCAAGGG
241 ---------+---------+---------+---------+---------+---------+  300
     V  D  A  L  S  R  R  C  A  A  G  L  R  R  L  G  V  G  K  G

CGACGTCGTCATGGCGCTCCTCCGCAACTGCCCCGAGTTCGCCTTCGTGTTCCTCGGCGC
301 ---------+---------+---------+---------+---------+---------+  360
     D  V  V  M  A  L  L  R  N  C  P  E  F  A  F  V  F  L  G  A

GGCCCGGCTCGGCGCCGCCACCACCACCGCCAACCCGTTCTACACGCCCCACGAGATCCA
361 ---------+---------+---------+---------+---------+---------+  420
     A  R  L  G  A  A  T  T  T  A  N  P  F  Y  T  P  H  E  I  H

CCGCCAGGCCACCGCCGCCGGGGCCAGGGTCATCGTCACCGAGGCCTGCGCCGTCGAGAA
421 ---------+---------+---------+---------+---------+---------+  480
     R  Q  A  T  A  A  G  A  R  V  I  V  T  E  A  C  A  V  E  K

GGTGCGCGCCTTCGCCGCCGAGAGAGGGATTCCCGTCGTCTCCGTCGACGAGGGCGTCGA
481 ---------+---------+---------+---------+---------+---------+  540
     V  R  A  F  A  A  E  R  G  I  P  V  V  S  V  D  E  G  V  D

CGGCGGCTGCCTCCCGTTCGCCGAGACTCTGCTCGGGGAAGAAAGCGGGGAGCGGTTCGT
541 ---------+---------+---------+---------+---------+---------+  600
     G  G  C  L  P  F  A  E  T  L  L  G  E  E  S  G  E  R  F  V

CGACGAGGCGGTCGACCCCGACGACGTGGTGGCGCTGCCGTACTCGTCCGGCACCACCGG
601 ---------+---------+---------+---------+---------+---------+  660
     D  E  A  V  D  P  D  D  V  V  A  L  P  Y  S  S  G  T  T  G

CCTGCCCAAGGGCGTCATGCTCACCCACCGCAGCCTCGTCACCAGCGTCGCCCAGCAGGT
661 ---------+---------+---------+---------+---------+---------+  720
     L  P  K  G  V  M  L  T  H  R  S  L  V  T  S  V  A  Q  Q  V

GGACGGTGAGAACCCGAACCTGCACTTCAGCTCGTCGGACGTGCTGCTGTGCGTGCTGCC
721 ---------+---------+---------+---------+---------+---------+  780
     D  G  E  N  P  N  L  H  F  S  S  S  D  V  L  L  C  V  L  P
```

FIGURE 3

```
         GCTGTTCCACATCTACTCGCTCAACTCGGTGCTGCTCGCCGGTCTCCGCGCCGGGTGCGC
 781     ---------+---------+---------+---------+---------+---------+     840
          L  F  H  I  Y  S  L  N  S  V  L  L  A  G  L  R  A  G  C  A

GATCGTGATCATGCGCAAGTTCGACCACGGCGCGCTGGTGGACCTGGTGCGCACGCACGG
 841     ---------+---------+---------+---------+---------+---------+     900
          I  V  I  M  R  K  F  D  H  G  A  L  V  D  L  V  R  T  H  G

CGTCACCGTGGCGCCATTCGTGCCGCCCATCGTGGTGGAGATCGCCAAGAGCGCGCGGGT
 901     ---------+---------+---------+---------+---------+---------+     960
          V  T  V  A  P  F  V  P  P  I  V  V  E  I  A  K  S  A  R  V

GACCGCCGCGGACCTGGCGTCCATCCGGCTGGTCATGTCGGGGGCGGCGCCCATGGGCAA
 961     ---------+---------+---------+---------+---------+---------+    1020
          T  A  A  D  L  A  S  I  R  L  V  M  S  G  A  A  P  M  G  K

GGAGCTGCAGGACGCGTTCATGGCCAAGATCCCCAACGCCGTGCTCGGCCAGGGATATGG
1021     ---------+---------+---------+---------+---------+---------+    1080
          E  L  Q  D  A  F  M  A  K  I  P  N  A  V  L  G  Q  G  Y  G

GATGACCGAGGCCGGCCCTGTGCTGGCGATGTGCCTGGCCTTCGCCAAGGAGCCGTTCGC
1081     ---------+---------+---------+---------+---------+---------+    1140
          M  T  E  A  G  P  V  L  A  M  C  L  A  F  A  K  E  P  F  A

GGTCAAGTCCGGTTCCTGCGGCACCGTCGTCAGGAACGCCGAGCTCAAGATCGTCGACCC
1141     ---------+---------+---------+---------+---------+---------+    1200
          V  K  S  G  S  C  G  T  V  V  R  N  A  E  L  K  I  V  D  P

CGACACCGGCGCCTCCCTCGGCCGCAACCTGCCGGGGGAGATCTGCATCCGCGGCAAGCA
1201     ---------+---------+---------+---------+---------+---------+    1260
          D  T  G  A  S  L  G  R  N  L  P  G  E  I  C  I  R  G  K  Q

GATCATGAAAGGTTACCTAAATGATCCGGTGGCCACAAAGAACACCATTGACAAGGACGG
1261     ---------+---------+---------+---------+---------+---------+    1320
          I  M  K  G  Y  L  N  D  P  V  A  T  K  N  T  I  D  K  D  G

TTGGCTGCATACTGGTGACATTGGTTATGTCGATGATGACGACGAGATCTTTATTGTCGA
1321     ---------+---------+---------+---------+---------+---------+    1380
          W  L  H  T  G  D  I  G  Y  V  D  D  D  D  E  I  F  I  V  D

CAGACTGAAGGAGATAATTAAATATAAGGGATTCCAAGTACCTCCGGCGGAACTTGAAGC
1381     ---------+---------+---------+---------+---------+---------+    1440
          R  L  K  E  I  I  K  Y  K  G  F  Q  V  P  P  A  E  L  E  A

CCTTCTCATTACACACCCTGAAATCAAGGATGCTGCTGTCGTATCGATGCAAGACGAACT
1441     ---------+---------+---------+---------+---------+---------+    1500
          L  L  I  T  H  P  E  I  K  D  A  A  V  V  S  M  Q  D  E  L

TGCTGGTGAAGTTCCGGTTGCGTTTGTTGTGCGGACTGAGGGTTCAGAGATCAGCGAAAA
1501     ---------+---------+---------+---------+---------+---------+    1560
          A  G  E  V  P  V  A  F  V  V  R  T  E  G  S  E  I  S  E  N
```

FIGURE 3 CONTINUED

```
              CGAGATCAAGCAGTTCGTTGCAAAAGAGGTTGTTTTCTACAAGAGGATCTGCAAAGTGTT
     1561     ---------+---------+---------+---------+---------+---------+     1620
               E  I  K  Q  F  V  A  K  E  V  V  F  Y  K  R  I  C  K  V  F

CTTCGCGGATTCCATTCCAAAGAGTCCATCTGGCAAGATCCTCAGGAAGGACCTGAGAGC
     1621     ---------+---------+---------+---------+---------+---------+     1680
               F  A  D  S  I  P  K  S  P  S  G  K  I  L  R  K  D  L  R  A

AAAGCTCGCCGCAGGCATTCCCAGCAGTAATACCACACAGTCCAAAAGCTAAGTCAGATA
     1681     ---------+---------+---------+---------+---------+---------+     1740
               K  L  A  A  G  I  P  S  S  N  T  T  Q  S  K  S  *

TATTGTTTCCCAACCTTACACACCTCTGTCCAACACCATGTAATGTTCTTAATATAAACG
     1741     ---------+---------+---------+---------+---------+---------+     1800

GAAATTATTACATATAGAAGGGCTGATTCTTTTTACTAGATGTGTCCAACATATGATATG
     1801     ---------+---------+---------+---------+---------+---------+     1860

CTTGTTAGGCCGATGATGTGTAACCTGTCATGTATAGATACCGCCTTTTTTTGACAAGAA
     1861     ---------+---------+---------+---------+---------+---------+     1920

AGGCTGATTATAATGTATACCGTGAACTGAATATTTGTTCAGGGAGATCAAAAAAAAAAA
     1921     ---------+---------+---------+---------+---------+---------+     1980

AAAAAAAAAAAA
     1981     ---------+---   1992
```

FIGURE 3 CONTINUED

```
       CGGCACGAGATCTCCCACGACTAATTTAGAAGAAGATTTACTTAGTCTCTGCTTCTCGCT
  1    ---------+---------+---------+---------+---------+---------+   60

CGATCGCCGGCCGGTGAGGTAGCTAGCTAGCTACTCGTACTAGACCATTACCATGGGTTC
 61    ---------+---------+---------+---------+---------+---------+  120
                                                            M  G  S

CGTGCCGGAGGAGTCAGTGGTGGCGGTGGCACCGGCGGAGACGGTGTTCCGGTCGAAGCT
121    ---------+---------+---------+---------+---------+---------+  180
       V  P  E  E  S  V  V  A  V  A  P  A  E  T  V  F  R  S  K  L

CCCCGACATCGAGATCAACAACGAGCAGACGCTGCAGAGCTACTGCTTCGAGAAGATGGC
181    ---------+---------+---------+---------+---------+---------+  240
       P  D  I  E  I  N  N  E  Q  T  L  Q  S  Y  C  F  E  K  M  A

CGAGGTCGCGTCCCGCCCCTGCATCATCGACGGCCAGACGGGCGCCTCCTACACCTACAC
241    ---------+---------+---------+---------+---------+---------+  300
       E  V  A  S  R  P  C  I  I  D  G  Q  T  G  A  S  Y  T  Y  T

GGAGGTCGACTCCCTGACCCGTCGCGCCGCGGCGGGGCTGCGCCGCATGGGCGTGGGGAA
301    ---------+---------+---------+---------+---------+---------+  360
       E  V  D  S  L  T  R  R  A  A  A  G  L  R  R  M  G  V  G  K

GGGCGACGTGGTGATGAACCTGCTGCGCAACTGCCCGGAGTTCGCCTTCTCCTTCCTGGG
361    ---------+---------+---------+---------+---------+---------+  420
       G  D  V  V  M  N  L  L  R  N  C  P  E  F  A  F  S  F  L  G

CGCGGCGCGGCTGGGCGCCGCCACCACCACCGCCAACCCGTTCTACACCCCGCACGAGAT
421    ---------+---------+---------+---------+---------+---------+  480
       A  A  R  L  G  A  A  T  T  T  A  N  P  F  Y  T  P  H  E  I

CCACCGCCAGGCGGAGGCGGCGGGCGCCAAGCTGATCGTGACCGAGGCCTGCGCCGTGGA
481    ---------+---------+---------+---------+---------+---------+  540
       H  R  Q  A  E  A  A  G  A  K  L  I  V  T  E  A  C  A  V  E

GAAGGTGCTGGAGTTCGCGGCGGGGCGGGGCGTGCCCGTGGTCACCGTCGACGGGAGGCG
541    ---------+---------+---------+---------+---------+---------+  600
       K  V  L  E  F  A  A  G  R  G  V  P  V  V  T  V  D  G  R  R

CGACGGGTGCGTGGACTTCGCGGAGCTGATCGCCGGCGAGGAGCTGCCCGAGGCGGACGA
601    ---------+---------+---------+---------+---------+---------+  660
       D  G  C  V  D  F  A  E  L  I  A  G  E  E  L  P  E  A  D  E

GGCCGGGGTCCTCCCCGACGACGTCGTCGCCCTGCCCTACTCCTCCGGCACCACCGGGCT
661    ---------+---------+---------+---------+---------+---------+  720
       A  G  V  L  P  D  D  V  V  A  L  P  Y  S  S  G  T  T  G  L

CCCCAAGGGCGTCATGCTCACCCACCGCAGCCTCGTCACCAGCGTCGCCCAGCTGGTCGA
721    ---------+---------+---------+---------+---------+---------+  780
       P  K  G  V  M  L  T  H  R  S  L  V  T  S  V  A  Q  L  V  D
```

FIGURE 4

```
       CGGGTCGAACCCTAACGTGTGCTTCAACAAGGACGACGCGCTGCTGTGCCTGCTGCCGCT
781    ---------+---------+---------+---------+---------+---------+    840
        G  S  N  P  N  V  C  F  N  K  D  D  A  L  L  C  L  L  P  L

CTTCCACATCTACTCGCTGCACACGGTGCTGCTGGCGGGGCTCCGCGTCGGCGCCGCCAT
841    ---------+---------+---------+---------+---------+---------+    900
        F  H  I  Y  S  L  H  T  V  L  L  A  G  L  R  V  G  A  A  I

CGTCATCATGCGCAAGTTCGACGTCGGCGCGCTGGTGGACCTCGTCCGCGCGCACCGCAT
901    ---------+---------+---------+---------+---------+---------+    960
        V  I  M  R  K  F  D  V  G  A  L  V  D  L  V  R  A  H  R  I

CACCATCGCGCCATTCGTGCCGCCCATCGTCGTGGAGATCGCCAAGAGCGACCGCGTCGG
961    ---------+---------+---------+---------+---------+---------+   1020
        T  I  A  P  F  V  P  P  I  V  V  E  I  A  K  S  D  R  V  G

CGCCGACGACCTCGCATCCATCCGCATGGTGCTCTCCGGCGCCGCGCCCATGGGCAAGGA
1021   ---------+---------+---------+---------+---------+---------+   1080
        A  D  D  L  A  S  I  R  M  V  L  S  G  A  A  P  M  G  K  D

CCTCCAGGACGCCTTCATGGCCAAGATCCCCAACGCCGTGCTCGGACAGGGGTACGGGAT
1081   ---------+---------+---------+---------+---------+---------+   1140
        L  Q  D  A  F  M  A  K  I  P  N  A  V  L  G  Q  G  Y  G  M

GACCGAGGCTGGGCCGGTGCTGGCCATGTGCCTGGCGTTCGCCAAGGAGCCGTTCAAGGT
1141   ---------+---------+---------+---------+---------+---------+   1200
        T  E  A  G  P  V  L  A  M  C  L  A  F  A  K  E  P  F  K  V

CAAGTCCGGGTCGTGCGGAACCGTGGTGCGCAACGCCGAGCTCAAGGTCGTCGACCCCGA
1201   ---------+---------+---------+---------+---------+---------+   1260
        K  S  G  S  C  G  T  V  V  R  N  A  E  L  K  V  V  D  P  D

CACCGGCGCATCCCTCGGCCGGAACCAGCCTGGCGAGATTTGCGTCCGGGGGAAGCAGAT
1261   ---------+---------+---------+---------+---------+---------+   1320
        T  G  A  S  L  G  R  N  Q  P  G  E  I  C  V  R  G  K  Q  I

CATGATAGGTTACCTGAACGACCCAGAGTCGACCAAGAACACCATCGACAAGGACGGCTG
1321   ---------+---------+---------+---------+---------+---------+   1380
        M  I  G  Y  L  N  D  P  E  S  T  K  N  T  I  D  K  D  G  W

GCTGCACACCGGAGACATCGGCTTGGTGGATGACGACGACGAGATCTTCATCGTCGACAG
1381   ---------+---------+---------+---------+---------+---------+   1440
        L  H  T  G  D  I  G  L  V  D  D  D  D  E  I  F  I  V  D  R

GCTCAAGGAGATCATCAAGTACAAGGGCTTCCAAGTGGCGCCGGCGGAGCTCGAGGCCCT
1441   ---------+---------+---------+---------+---------+---------+   1500
        L  K  E  I  I  K  Y  K  G  F  Q  V  A  P  A  E  L  E  A  L

CCTCCTCACGAACCCGGAGGTCAAGGACGCCGCCGTCGTAGGGGTGAAGGATGATCTCTG
1501   ---------+---------+---------+---------+---------+---------+   1560
        L  L  T  N  P  E  V  K  D  A  A  V  V  G  V  K  D  D  L  C
```

FIGURE 4 CONTINUED

```
            CGGCGAAGTCCCGGTCGCCTTCATTAAGAGGATCGAAGGATCTGAGATCAACGAGAACGA
1561        ---------+---------+---------+---------+---------+---------+    1620
             G   E   V   P   V   A   F   I   K   R   I   E   G   S   E   I   N   E   N   E

GATCAAGCAATTCGTCTCAAAGGAGGTTGTTTTCTACAAGAGGATCAACAAGGTCTACTT
1621        ---------+---------+---------+---------+---------+---------+    1680
             I   K   Q   F   V   S   K   E   V   V   F   Y   K   R   I   N   K   V   Y   F

CACCGACTCCATTCCCAAGAACCCTTCCGGCAAGATCCTAAGGAAGGACTTGAGAGCCAG
1681        ---------+---------+---------+---------+---------+---------+    1740
             T   D   S   I   P   K   N   P   S   G   K   I   L   R   K   D   L   R   A   R

GCTCGCCGCTGGCATCCCCACCGAAGTTGCCGCGCCGAGAAGCTAAGGGCCGCTTCTCAG
1741        ---------+---------+---------+---------+---------+---------+    1800
             L   A   A   G   I   P   T   E   V   A   A   P   R   S   *

GAACGCAGTCACCCATGGTGCTGTTTAGGTGCTGTTATAGACCACACCAAATGGGGAAAG
1801        ---------+---------+---------+---------+---------+---------+    1860

AAACTACGGGAGGGGATCATATTATTGTTGCAGGAGATATCAGTTTGTTGATTCGCCCTG
1861        ---------+---------+---------+---------+---------+---------+    1920

CTTGTGTAATGTTGATAAAATGAAATGATATAATAGATGTGTTGTTTTATTTTTTGACCA
1921        ---------+---------+---------+---------+---------+---------+    1980

TGTAAGAACAAGGCTGTTTTATACACTACTTATTTTTTGAAAAAAAAAAAAAAAAAAAAA
1981        ---------+---------+---------+---------+---------+--------      2038
```

FIGURE 4 CONTINUED

```
           10         20         30         40         50         60
Lp4CL1  MITVAAPEVQQPQIAAAAAAVEAAAPEATTIFRSRLPDIDIPTHMPLHDYCFATAASAPD
Lp4CL2         MGSIAADAPPAEL..VFRSKLPDIEIPTHLTLQDYCFQRLPELSA
Lp4CL3         MGSVPEESVVAVAPAETVFRSKLPDIEINNEQTLQSYCFEKMAEVAS 70         80         90        100        110        120
Lp4CL1  APCLITAATGKTYTFAETHLLCRKAAAALHGLGVRHGDRIMLLLQNSVEFALAFFGASML
Lp4CL2  RACLIDGATGAALTYGEVDALSRRCAAGLRRLGVGKGDVVMALLRNCPEFAFVFLGAARL
Lp4CL3  RPCIIDGQTGASYTYTEVDSLTRRAAAGLRRMGVGKGDVVMNLLRNCPEFAFSFLGAARL 130        140        150        160        170        180
Lp4CL1  GAVSTAANPFCTPQEIHKQLVASGAKLVVTQSAYVDKLRHEAFPRIGEALTVITIDEDDG
Lp4CL2  GAATTTANPFYTPHEIHRQATAAGARVIVTEACAVEKVRAFAAERGIPVVSV......DE
Lp4CL3  GAATTTANPFYTPHEIHRQAEAAGAKLIVTEACAVEKVLEFAAGRGVPVVTV......DG 190        200        210        220        230        240
Lp4CL1  TPDGCQPFWALVSAADENSVPESPIS..PDDAVALPYSSGTTGLPKGVVLTHGGLVSSVA
Lp4CL2  GVDGCLPFAETLLGEESGERFVDEAVDPDDVVALPYSSGTTGLPKGVMLTHRSLVTSVA
Lp4CL3  RRDGCVDF.AELIAGEELPEADEAGVL.PDDVVALPYSSGTTGLPKGVMLTHRSLVTSVA 250        260        270        280        290        300
Lp4CL1  QQVDGENPNLHMRAGEDVVLCVLPLFHIFSLNSVLLCALRAGAAVMLMPRFEMGAMLEGI
Lp4CL2  QQVDGENPNLHFSS.SDVLLCVLPLFHIYSLNSVLLAGLRAGCAIVIMRKFDHGALVDLV
Lp4CL3  QLVDGSNPNVCFNK.DDALLCLLPLFHIYSLHTVLLAGLRVGAAIVIMRKFDVGALVDLV 310        320        330        340        350        360
Lp4CL1  ERWRVTVAAVVPPLVLALAKNPGVEKHDLSSIRIVLSGAAPLGKELEDALRGRLPQAIFG
Lp4CL2  RTHGVTVAPFVPPIVVEIAKSARVTAADLASIRIVMSGAAPMGKELQDAFMAKIPNAVLG
Lp4CL3  RAHRITIAPFVPPIVVEIAKSDRVGADDLASIRMVLSGAAPMGKDLQDAFMAKIPNAVLG 370        380        390        400        410        420
Lp4CL1  QGYGMTEAGPVLSMCPAFAREPTPAKSGSCGTVVRNAQLKVVDPDTGVSLGRNLPGEICI
Lp4CL2  QGYGMTEAGPVLAMCLAFAKEPFAVKSGSCGTVVRNAELKIVDPDTGASLGRNLPGEICI
Lp4CL3  QGYGMTEAGPVLAMCLAFAKEPFKVKSGSCGTVVRNAELKVVDPDTGASLGRNQPGEICV 430        440        450        460        470        480
Lp4CL1  RGPQIMKGYLNDPVATAATIDVEGWLHTGDIGYVDDDDEVFIVDRVKELIKFKGFQVPPA
Lp4CL2  RGKQIMKGYLNDPVATKNTIDKDGWLHTGDIGYVDDDDEIFIVDRLKEIIKYKGFQVPPA
Lp4CL3  RGKQIMIGYLNDPESTKNTIDKDGWLHTGDIGLVDDDDEIFIVDRLKEIIKYKGFQVAPA 490        500        510        520        530        540
Lp4CL1  ELEALLIAHPSIADAAVVPQKDDAAGEVPVAFVVRAADSDTAEEAIKEFVSKQVVFYKRL
Lp4CL2  ELEALLITHPEIKDAAVVSMQDELAGEVPVAFVVRTEGSEISENEIKQFVAKEVVFYKRI
Lp4CL3  ELEALLLTNPEVKDAAVVGVKDDLCGEVPVAFIKRIEGSEINENEIKQFVSKEVVFYKRI 550        560        570
Lp4CL1  HKVYFTHAIPKSASGKILRKELRAKLAAPATA
Lp4CL2  CKVFFADSIPKSPSGKILRKDLRAKLAAGIPSSNTTQSKS
Lp4CL3  NKVYFTDSIPKNPSGKILRKDLRARLAAGIPTEVAAPRS
```

FIGURE 5

```
     GGCACGAGGAATCCTACCAAACCGAGCTACCAGATCCTTCTCTACTAATCGAGCTCCCTA
  1  ---------+---------+---------+---------+---------+---------+   60

CGCTGCTCCGCCTGTCTTCGTTTCCGCCTCACCGCCGGCCGGTTCTCCGCTCCAAGCTAC
 61  ---------+---------+---------+---------+---------+---------+  120

GTCCGTCCGTCCACATATATAGCATCGACATGACCATCGCCGAGGTCGTGGCTGCCGGAG
121  ---------+---------+---------+---------+---------+---------+  180
                                    M   T   I   A   E   V   V   A   A   G   D

ACACCGCCGCCGCGGTGGTGCAGCCCGCCGGGAACGGGCAGACCGTGTGCGTGACCGGCG
181  ---------+---------+---------+---------+---------+---------+  240
      T   A   A   A   V   V   Q   P   A   G   N   G   Q   T   V   C   V   T   G   A

CCGCCGGGTACATCGCGTCGTGGCTCGTCAAGCTGCTGCTGGAGAAGGGGTACACCGTCA
241  ---------+---------+---------+---------+---------+---------+  300
      A   G   Y   I   A   S   W   L   V   K   L   L   L   E   K   G   Y   T   V   K

AGGGCACCGTCAGGAACCCAGACGACCCGAAGAACGCGCACCTGAGGGCGCTCGACGGCG
301  ---------+---------+---------+---------+---------+---------+  360
      G   T   V   R   N   P   D   D   P   K   N   A   H   L   R   A   L   D   G   A

CCGCCGACCGGCTGGTCCTCTGCAAGGCCGACCTCCTCGACTACGACGCCATCCGCCGCG
361  ---------+---------+---------+---------+---------+---------+  420
      A   D   R   L   V   L   C   K   A   D   L   L   D   Y   D   A   I   R   R   A

CCATCGACGGCTGCCACGGCGTCTTCCACACCGCGTCCCCCGTCACCGACGACCCCGAGC
421  ---------+---------+---------+---------+---------+---------+  480
        I   D   G   C   H   G   V   F   H   T   A   S   P   V   T   D   D   P   E   Q

AAATGGTGGAGCCGGCGGTGAGGGGCACGCAGTACGTCATAGACGCGGCGGCGGAGGCCG
481  ---------+---------+---------+---------+---------+---------+  540
        M   V   E   P   A   V   R   G   T   Q   Y   V   I   D   A   A   A   E   A   G

GCACGGTGCGGCGGATGGTGCTCACCTCCTCCATCGGCGCCGTCACCATGGACCCCAACC
541  ---------+---------+---------+---------+---------+---------+  600
        T   V   R   R   M   V   L   T   S   S   I   G   A   V   T   M   D   P   N   R

GCGGGCCGGACGTGGTCGTCGACGAGTCGTGCTGGAGCGACCTCGACTTCTGCAAGAAAA
601  ---------+---------+---------+---------+---------+---------+  660
        G   P   D   V   V   V   D   E   S   C   W   S   D   L   D   F   C   K   K   T

CCAGGAACTGGTACTGCTACGGGAAGGCGGTTGCGGAGCAGGCGGCATCGGAGTTGGCGC
661  ---------+---------+---------+---------+---------+---------+  720
        R   N   W   Y   C   Y   G   K   A   V   A   E   Q   A   A   S   E   L   A   R

GGCAGCGCGGCGTGGACCTTGTGGTGGTGAACCCGGTGCTGGTGATCGGCCCCCTGCTGC
721  ---------+---------+---------+---------+---------+---------+  780
        Q   R   G   V   D   L   V   V   V   N   P   V   L   V   I   G   P   L   L   Q
```

FIGURE 10

```
             AGCCGACGGTGAACGCCAGCATCGGCCACATCCTCAAGTACCTGGACGGGTCGGCCAGCA
   781       ---------+---------+---------+---------+---------+---------+   840
               P  T  V  N  A  S  I  G  H  I  L  K  Y  L  D  G  S  A  S  K

AGTTCGCCAACGCCGTGCAGGCGTACGTGGACGTCCGCGACGTGGCCGACGCCCACCTCC
   841       ---------+---------+---------+---------+---------+---------+   900
               F  A  N  A  V  Q  A  Y  V  D  V  R  D  V  A  D  A  H  L  R

GCGTCTTCGAGTGCGCCGCCGCGTCCGGCCGCCACCTCTGCGCCGAGCGCGTCCTCCACC
   901       ---------+---------+---------+---------+---------+---------+   960
               V  F  E  C  A  A  A  S  G  R  H  L  C  A  E  R  V  L  H  R

GCGAGGACGTCGTGCGCATCCTCGCCAAGCTCTTCCCCGAGTACCCCGTCCCCACCAGGT
   961       ---------+---------+---------+---------+---------+---------+  1020
               E  D  V  V  R  I  L  A  K  L  F  P  E  Y  P  V  P  T  R  C

GCTCTGATGAGACGAACCCGAGGAAGCAGCCATACAAGATGTCGAACCAGAAGCTCCAGG
  1021       ---------+---------+---------+---------+---------+---------+  1080
               S  D  E  T  N  P  R  K  Q  P  Y  K  M  S  N  Q  K  L  Q  D

ACCTCGGACTCGAGTTCAGGCCGGTGAGCCAGTCCCTGTACGAGACGGTGAAGAGCCTCC
  1081       ---------+---------+---------+---------+---------+---------+  1140
               L  G  L  E  F  R  P  V  S  Q  S  L  Y  E  T  V  K  S  L  Q

AGGAGAAGGGCCACCTTCCGGTGCTCAGCGAGCAGGCAGAGGCGGACAAGGAAACCCTAG
  1141       ---------+---------+---------+---------+---------+---------+  1200
               E  K  G  H  L  P  V  L  S  E  Q  A  E  A  D  K  E  T  L  A

CTGCCGAGCTGCAGGCAGGGGTTACCATCCGAGCATGAGGAACAAGAAATCAACCATGTC
  1201       ---------+---------+---------+---------+---------+---------+  1260
               A  E  L  Q  A  G  V  T  I  R  A  *

CATACTGCTACTGTCATGTAAACCAGCTGTTGAATGCCTAAAATCTAAGTTCTTGTAATA
  1261       ---------+---------+---------+---------+---------+---------+  1320

CTGTGTTGTTTCATGTGGACTAGATTGATCGAATAAACATCTCTACACAAGGTTGCTAAA
  1321       ---------+---------+---------+---------+---------+---------+  1380

AAAAAAAAAAAAAAA
  1381       ---------+-----  1395
```

FIGURE 10 CONTINUED

```
     GGCACGAGCAACAAGTCATCAATGGCGGAAGGCTTGCCGGCGCTCGGTTGGGCTGCGAGG
  1  ---------+---------+---------+---------+---------+---------+  60
                              M  A  E  G  L  P  A  L  G  W  A  A  R

GACGCCTCCGGTCACCTCTCCCCTTACAGCTTCTCGAGAAGCGTTCCGAAGGACGACgAT
 61  ---------+---------+---------+---------+---------+---------+  120
     D  A  S  G  H  L  S  P  Y  S  F  S  R  S  V  P  K  D  D  D

GTGACGATCAAGGTGCTCTTCTGCGGGATCTGCCACACTGACCTCCACATCATCAAGAAC
121  ---------+---------+---------+---------+---------+---------+  180
     V  T  I  K  V  L  F  C  G  I  C  H  T  D  L  H  I  I  K  N

GACTGGGGCAACGCCCTCTACCCCATCGTCCCAGGGCATGAGATCGTGGGCGTCGTCGCC
181  ---------+---------+---------+---------+---------+---------+  240
     D  W  G  N  A  L  Y  P  I  V  P  G  H  E  I  V  G  V  V  A

AGCGTCGGCAGCGGCGTCAGCAGCTTCAAGGCCGGCgACACGGTGGGCGTGGGCTACTTC
241  ---------+---------+---------+---------+---------+---------+  300
     S  V  G  S  G  V  S  S  F  K  A  G  D  T  V  G  V  G  Y  F

CTCGACTCCTGCCGCACCTGCTACAGCTGCAGCAAGGGGTACGAGAACTTCTGCCCCACC
301  ---------+---------+---------+---------+---------+---------+  360
     L  D  S  C  R  T  C  Y  S  C  S  K  G  Y  E  N  F  C  P  T

CTGACGCTCACCTCCAACGGCGTCGACGGCGGCGGCGCCACCACCCAGGGCGGCTTCTCC
361  ---------+---------+---------+---------+---------+---------+  420
     L  T  L  T  S  N  G  V  D  G  G  G  A  T  T  Q  G  G  F  S

GACGTCCTCGTCGTCAACAAGGACTACGTCATCCGCGTCCCGGACAACCTGCCCCTGGCC
421  ---------+---------+---------+---------+---------+---------+  480
     D  V  L  V  V  N  K  D  Y  V  I  R  V  P  D  N  L  P  L  A

GGCGCGGCACCTCTCCTCTGCGCCGGCGTCACAGTCTACAGCCCTATGGTGGAGTACGGC
481  ---------+---------+---------+---------+---------+---------+  540
     G  A  A  P  L  L  C  A  G  V  T  V  Y  S  P  M  V  E  Y  G

CTCAACGCCCCcgGGAAGCACyTCGGcGTCGTCGGCCTGGGCGGGCTCGGCCACGTCGcC
541  ---------+---------+---------+---------+---------+---------+  600
     L  N  A  P  G  K  H  X  G  V  V  G  L  G  G  L  G  H  V  A

GTCAAGTTCGGCAAGGCCTTCGGGATGACCGTCACCGTCATCAGCTCCTCGGACAGGAAG
601  ---------+---------+---------+---------+---------+---------+  660
     V  K  F  G  K  A  F  G  M  T  V  T  V  I  S  S  S  D  R  K

CGCGACGAGGCGCTCGGCCGCCTCGGCGCCGACGCcTTCCTCGTCAGCAGCGACCCCGAG
661  ---------+---------+---------+---------+---------+---------+  720
     R  D  E  A  L  G  R  L  G  A  D  A  F  L  V  S  S  D  P  E
```

FIGURE 13

```
            CAGATGAAGGCGGCGGCGGGCACCATGGACGGCATCATCGACACGGTGTCCGCGGGCCAC
721         ---------+---------+---------+---------+---------+---------+    780
            Q  M  K  A  A  A  G  T  M  D  G  I  I  D  T  V  S  A  G  H

CCGATCGTGCCGCTGCTCGACCTGCTCAAGCCCATGGGGCAGATGGTCGTGGTGGGCGCG
781         ---------+---------+---------+---------+---------+---------+    840
            P  I  V  P  L  L  D  L  L  K  P  M  G  Q  M  V  V  V  G  A

CCCAGCAAGCCGCTCGAGCTCCCGGCCTTCGCCATCATCGGCGGCGGCAAGCGCCTCGCC
841         ---------+---------+---------+---------+---------+---------+    900
            P  S  K  P  L  E  L  P  A  F  A  I  I  G  G  G  K  R  L  A

GGGAGCGGCACCGGCAGCGTCGCACACTGCCagGCCATGCTCGACTTCGCGGGCAAGCAC
901         ---------+---------+---------+---------+---------+---------+    960
            G  S  G  T  G  S  V  A  H  C  Q  A  M  L  D  F  A  G  K  H

GGCATCACCGCCGACGTCGAGGTCGTCAAGATGGACTACgGTCAACACCGCCATCGAGCG
961         ---------+---------+---------+---------+---------+---------+    1020
            G  I  T  A  D  V  E  V  V  K  M  D  Y  G  Q  H  R  H  R  A

GCTAGAGAAGAACGACGTCAGGTACCGCTTCGTCATCGACGTCGCCGGCAGCCACCTGCA
1021        ---------+---------+---------+---------+---------+---------+    1080
            A  R  E  E  R  R  Q  V  P  L  R  H  R  R  R  Q  P  P  A

GGGCACCGCCGCTTAACTTGTGCTACACAATGTGGACGCGCGCTCGTTTGGTCCAGAAAA
1081        ---------+---------+---------+---------+---------+---------+    1140
            G  H  R  R  L  T  C  A  T  Q  C  G  R  A  L  V  W  S  R  K

AGGTTCGCCGGCTCACAGCCACATGAACAAGTCAATGAGTCGTTGGTGTGTTGTTTATCT
1141        ---------+---------+---------+---------+---------+---------+    1200
            R  F  A  G  S  Q  P  H  E  Q  V  N  E  S  L  V  C  C  L  S

TCATTCCACATATGGGACGCAGTTCCAGATTTTCATGTCAAATAATTGCGTCGTGTGCGG
1201        ---------+---------+---------+---------+---------+---------+    1260
            S  F  H  I  W  D  A  V  P  D  F  H  V  K

TTGTCAAGACTCAAATAGGAGAAAAAAAGACTCGTGATTTCGTTTTGCAAAAAAAAAAAA
1261        ---------+---------+---------+---------+---------+---------+    1320

AAAAA
1321        -----   1325
```

FIGURE 13 CONTINUED

```
     GGCACGAGTCGCCTCCAACGTCTTCCCTTAACCGGCCGTCCCTACGCtTGCACCACCACC
  1  ---------+---------+---------+---------+---------+---------+  60

ACGCACAGACAGAGCAGTTTCCCAGCCCCCGCCGGAACCGGATGGCACCCACGGCGGCGG
 61  ---------+---------+---------+---------+---------+---------+  120
                                               M  A  P  T  A  A  E

AGCAGACGGAGCACCACCAGCACACCAGGAAGGCGGTGGGGCTGGCGGCGCGCGACGACG
121  ---------+---------+---------+---------+---------+---------+  180
      Q  T  E  H  H  Q  H  T  R  K  A  V  G  L  A  A  R  D  D  A

CCGGCCACCTCTCCCCGCTCGCCATCACACGGAGGAGCACAGGAGACGACGATGTGGTGA
181  ---------+---------+---------+---------+---------+---------+  240
      G  H  L  S  P  L  A  I  T  R  R  S  T  G  D  D  D  V  V  I

TAAAGATTTTGTACTGCGGAATCTGCCACTCTGACCTGCACGCCCTGAAGAACGACTGGA
241  ---------+---------+---------+---------+---------+---------+  300
        K  I  L  Y  C  G  I  C  H  S  D  L  H  A  L  K  N  D  W

AGAACTCAAGGTACCCGATGATCCCCGGGCACGAGATCGCCGGCGAGGTCACGGAGGTGG
301  ---------+---------+---------+---------+---------+---------+  360
      K  N  S  R  Y  P  M  I  P  G  H  E  I  A  G  E  V  T  E  V  G

GCAAGAACGTGAGCAAGTTCAAGGCCGGCGACCGCGTGGGCGTCGGGTGCATGGTGAACT
361  ---------+---------+---------+---------+---------+---------+  420
        K  N  V  S  K  F  K  A  G  D  R  V  G  V  G  C  M  V  N  S

CGTGCCGGTCGTGCGAGAGCTGCGACAAGGGCTTCGAGAACCACTGCCCGGGCATGATCC
421  ---------+---------+---------+---------+---------+---------+  480
         C  R  S  C  E  S  C  D  K  G  F  E  N  H  C  P  G  M  I  L

TCACCTACAACTCGGTCGACGTCGACGGCACCGTCACCTACGGCGGCTACTCCAGCATGG
481  ---------+---------+---------+---------+---------+---------+  540
       T  Y  N  S  V  D  V  D  G  T  V  T  Y  G  G  Y  S  S  M  V

TGGTGGTGCACGAGCGGTTCGTGGTCCGGTTCCCCGACGCCATGCCGCTGGACAAGGGCG
541  ---------+---------+---------+---------+---------+---------+  600
       V  V  H  E  R  F  V  V  R  F  P  D  A  M  P  L  D  K  G  A

CGCCGCTGCTGTGCGCCGGCATCACCGTGTACAGCCCCATGAAGTACCACGGGCTCAACG
601  ---------+---------+---------+---------+---------+---------+  660
        P  L  L  C  A  G  I  T  V  Y  S  P  M  K  Y  H  G  L  N  V

TTCCCGGGCTGCACCTCGGCGTGCTGGGGCTGGGCGGGCTGGGCCACGTTGCGGTCAAGT
661  ---------+---------+---------+---------+---------+---------+  720
        P  G  L  H  L  G  V  L  G  L  G  G  L  G  H  V  A  V  K  F

TCGGCAAGGCCTTCGGAATGAAAGTGACGGTGATCAGCTCGTCGCCGGGGAAGAAGGAGG
721  ---------+---------+---------+---------+---------+---------+  780
         G  K  A  F  G  M  K  V  T  V  I  S  S  S  P  G  K  K  E  E
```

FIGURE 14

```
           AGGCCCTGGGGCGGCTGGGCGCCGACGCGTTCATCGTCAGCAAGGACGCCGACGAGATGA
781        ---------+---------+---------+---------+---------+---------+    840
             A  L  G  R  L  G  A  D  A  F  I  V  S  K  D  A  D  E  M  K

AGGCTGTGATAGCACCATGGATGGCATCANTAAACACGGTATCTGCAAACATCCCCCTGA
841        ---------+---------+---------+---------+---------+---------+    900
             A  V  I  A  P  W  M  A  S  X  N  T  V  S  A  N  I  P  L  T

CCCCTCTCTTCGGGCTGCTCAAGCCCAACGGCAAGATGATCATGGTCGGCCTCCCCGAGA
901        ---------+---------+---------+---------+---------+---------+    960
              P  L  F  G  L  L  K  P  N  G  K  M  I  M  V  G  L  P  E  K

AGCCCATCGAGATTCCTCCCTTCGCTCTAGTTGCCACGAATAAGACCCTGGCCGGGAGCA
961        ---------+---------+---------+---------+---------+---------+    1020
              P  I  E  I  P  P  F  A  L  V  A  T  N  K  T  L  A  G  S  I

TCATCGGCGGCATGAGCGACACGCAGGAGATGCTGGACCTCGCGGCGAAGCACGGCGTGA
1021       ---------+---------+---------+---------+---------+---------+    1080
              I  G  G  M  S  D  T  Q  E  M  L  D  L  A  A  K  H  G  V  T

CGGCCGACATCGAGGTGGTCGGCGCGGAGTATGTGAACACGGCCTTGGAGCGCCTTGCCA
1081       ---------+---------+---------+---------+---------+---------+    1140
              A  D  I  E  V  V  G  A  E  Y  V  N  T  A  L  E  R  L  A  K

AGAACGACGTCAGGTATCGCTTCGTCATCGACATCGGCAACACCCTCGACAATGTTGCGG
1141       ---------+---------+---------+---------+---------+---------+    1200
              N  D  V  R  Y  R  F  V  I  D  I  G  N  T  L  D  N  V  A  A

CCACCACCGAGTGAACGTACTCAGCACTGCTTACGATCTACGTTGTTCCACTGTTAGTGC
1201       ---------+---------+---------+---------+---------+---------+    1260
              T  T  E  *

TCCGTAGTAAACAATAAACGATCAAAACTCTTGTCATCTGGTGCATTGGTGTAGACATGG
1261       ---------+---------+---------+---------+---------+---------+    1320

TTGTTTGCGAGGAAACTGAGTTGAAGGATGGATGGATAAAAAAAAAAAAAAAAAAAAAA
1321       ---------+---------+---------+---------+---------+-------      1378
```

FIGURE 14 CONTINUED

```
                              pBluescript
                GCGGCCGCTCTAAAACTAGTGGATCCCCCGGGCTGCAGGAATTCGATATCAAGCTTATnG
                     SalI
                ATACCGTCGACAGCGGTTnCAAATCGCCGGTCCTGGGGTGGAAGTGnAGCAGTGGGAAGA
                +---------+---------+---------+---------+---------+---------  -4581

TGTGTGCGAGGGGTTGTGTTTTGGATGnAAGACAGGCGGGCCAGTGGAGAACAAGAGAGA
        -4580   +---------+---------+---------+---------+---------+---------  -4521

ACGCGAGAGGCCAAAGTATCCGCAGCCCCGCAAACAAGGCCTAGATTTGGGTTAAGTTTG
        -4520   +---------+---------+---------+---------+---------+---------  -4461

GGTCGTCTCAGACACCGCGGCCATCCTTTTAGGTGGTCCGCGCGCTGGACCGTATTTTTA
        -4460   +---------+---------+---------+---------+---------+---------  -4401

TCTGAGTTGACCCATTCAGACGCGCAGACACGAGATGGATGGTGCAGTwAgAGATGACCT
        -4400   +---------+---------+---------+---------+---------+---------  -4341

HindIII
                AAGTACAArAACCTCTCCCCGA.GCTGCCGCCATCcGTCACTTACCGAGCGAcAAAGcTT
        -4340   +---------+---------+---------+---------+---------+---------  -4281

CCCACTTCATCACACTCAGCCCAGCAAGCATACTGATGGTGAGCGCACTCGCGGCTGTGC
        -4280   +---------+---------+---------+---------+---------+---------  -4221

CCACCGACCCCACGCCATCCAAAACCAACTCTACTTTTCACCmCACCAACAAAAGACAAA
        -4220   +---------+---------+---------+---------+---------+---------  -4161

ATATGGTGGATTTTGTGATGAGATGGAAGCGGAGCTTGTCAGAATGGGAAACGCATAAAT
        -4160   +---------+---------+---------+---------+---------+---------  -4101

CGAGAACACGTATACAGTGCTGGAAATTGGATGACTAAGCCCCAAGGGTTAGAAAAAAAA
        -4100   +---------+---------+---------+---------+---------+---------  -4041

XbaI
                TnAGACCATGTCTAGATGGAATTAGACATTTTTTGATATAATAGAAGCGGGACTTGGCGC
        -4040   +---------+---------+---------+---------+---------+---------  -3981

GACAATTTCAAACTTCGTCCCTAACAGGTATCGAACtTTCGAtAGTTAGCGTGTGCTACT
        -3980   +---------+---------+---------+---------+---------+---------  -3921

GCggAcCCCCAACCACtTGTGTTAAGCCCACATCgGTTAAGGCCCAAGGGTTAGATGAAA
        -3920   +---------+---------+---------+---------+---------+---------  -3861

GTACCAATCTCACTCATTTGCGACTAGCTACAAAACTTGCTTTTCACATGTACGGTCATA
        -3860   +---------+---------+---------+---------+---------+---------  -3801

CTACAATTTTGACCTTGGTAACGTAAGTATGGACTGTATGGTGTGCTAAGGTGTGTTGGC
        -3800   +---------+---------+---------+---------+---------+---------  -3741

AGCTCAAATAAACCCAAAAATTTCAACACACGTCAACCATGAACTGAGATTCACACCAAC
        -3740   +---------+---------+---------+---------+---------+---------  -3681

GGCTGAGCCGTCTCCTTTAAAAGATAGAGGGAGAAAACCATAATCACCATTGGTGGTCAT
        -3680   +---------+---------+---------+---------+---------+---------  -3621

GTGTGAGTGTGCAAGCAAAAAAAAATGGAGAAGCCAAAACCCGTTGAGAGAGTGCGAGAG
        -3620   +---------+---------+---------+---------+---------+---------  -3561

CATACAAGAACACCACAACAAAGTGTGAAGGAGAAAAAGAATATGAGATAAGATTTCGGA
        -3560   +---------+---------+---------+---------+---------+---------  -3501
```

FIGURE 18

```
              AATACTTTTGCACACCCATGCATGGGTGTGGGTGTTTCCGTCACCGTCTATGTATTTCTC
       -3500  +---------+---------+---------+---------+---------+---------  -3441

GAAATTCATGCCCACCATGGTAGATAAAAATATTTTTTTCTCTCTCCTCTTTTTATTCAA
       -3440  +---------+---------+---------+---------+---------+---------  -3381

ATCTCAAAGCAtAAkrArTGGTGACAGAACGATAAGATTCCTACCTAGCTTTCTGAGATC
       -3380  +---------+---------+---------+---------+---------+---------  -3321

CCACTAGTTTATCTTCAAGCTGGTGATTGAAGGATTAACCATGCTTGAATTAGATTGGCT
       -3320  +---------+---------+---------+---------+---------+---------  -3261

TCAAACTTGGTAGTAGCTTGTTTCATACTTTGATTACTTTGGTATGGTTAGTTGGTTTGA
       -3260  +---------+---------+---------+---------+---------+---------  -3201

GATTTTGGTCAATGTAGAATCAGATTTGAGAGCGATTGTCAGCTTGAATTGCCGCAGTTT
       -3200  +---------+---------+---------+---------+---------+---------  -3141

TAGCACATACTAGTTTGGATAGATGAACAGTTTGGAGAGACAAATAATGTCTATACGAGC
       -3140  +---------+---------+---------+---------+---------+---------  -3081

TCATCGGATAATATTAGTCTATGGCTTTTGCTTCGGTGTCCCCTCTGCAAACTTTACCCC
       -3080  +---------+---------+---------+---------+---------+---------  -3021

TCTGTAGATGGTAGGATTTTCTGATATCCTTTCATGGTTTAAGGGTGTGCGTGTAAGGAA
       -3020  +---------+---------+---------+---------+---------+---------  -2961

CGGGAGATACCGGATCACACCTTTTCGTCTACACTTTACAAGCATGTAACACCTAAGATT
       -2960  +---------+---------+---------+---------+---------+---------  -2901

GATTGATATCTAGGCTTACACCCCAATGGAGGTAAACTAATATTATTGAAATGCGACTTT
       -2900  +---------+---------+---------+---------+---------+---------  -2841

TCAAAAGTCCCAATATAACCTTGACGATGATCTTACAACTACTCGCGCCAGTCTTGTATG
       -2840  +---------+---------+---------+---------+---------+---------  -2781

KpnI
              ATATCAGATTGGCCGAGGATCGTGGGTACCTTGTAGTGGACTATGATGCTCATGGAGGTT
       -2780  +---------+---------+---------+---------+---------+---------  -2721

GTATGGACATGTTGTAATGCTGGTTTTCTCTAGGTTTTTTCTAATCAACTTGGCATTCTT
       -2720  +---------+---------+---------+---------+---------+---------  -2661

CTCCTTAACACATAATAAGAGGGAATACCTCCATACATTATTCTGAAAAAGCATGGCCA
       -2660  +---------+---------+---------+---------+---------+---------  -2601

ACAATGAAACAGAAACAAGTACGACAGTCTATACCCGACCCAAACAATGGCTCAGGTCTT
       -2600  +---------+---------+---------+---------+---------+---------  -2541

TCACGATGCATAGTTTGTTAGCATGTATTTTATAGTAGGAACTAAAATTTAAAGACAACT
       -2540  +---------+---------+---------+---------+---------+---------  -2481

TGCnAAAACAATTTTGTCTCTTGAGTGTTTTTTAAGGATGCGGCATTTATCGATTATACA
       -2480  +---------+---------+---------+---------+---------+---------  -2421

TTACATATGTGATTGGATtAGCCAACTTTTTGTCTTCCgATGATCATATGAAAGGGTTGT
       -2420  +---------+---------+---------+---------+---------+---------  -2361

ATCTTAGGGCATCTCCAATGGGnAGACTCAAATGCAAAAAAAtnGTCCGTTTGGGTCTTC
       -2360  +---------+---------+---------+---------+---------+---------  -2301

CnGGACAAAACCTGCTCCCAACGGGGCAACCCAACTTAAAAACGGACAGGTGCAGCGTCC
       -2300  +---------+---------+---------+---------+---------+---------  -2241
```

FIGURE 18 CONTINUED

```
          GGCnTGACCCAAAACTGACGCAAATTTGGnAnATTTTTGGGGCnAGCCAGACGAACGCGG
-2240     +---------+---------+---------+---------+---------+---------     -2181

GCGTCCACTGTATCCGACTATGTCCGCATCCTGGCCCATCTGACAGTGACACAAAATACA
-2180     +---------+---------+---------+---------+---------+---------     -2121

ACCACATGCGCCCCCCACCCTTCTCTCTCCTCCGTTCGCCTTTTCCCATGGAAnCnGTCC
-2120     +---------+---------+---------+---------+---------+---------     -2061

TCGCTCCTCGCCGGAATTGATCTCGCCTAACCATGCTCCGCCGCCACCcTCGcCTkAAGG
-2060     +---------+---------+---------+---------+---------+---------     -2001

CCCCAgCCGCCGCTACcTCCTTTTTGTCAGCCCTATTgGAAGTCGCCGgAGTTGAAACGA
-2000     +---------+---------+---------+---------+---------+---------     -1941

GCGCCGCCAGCCTcGACACCGCCGAGCAAGACGAAGACTGGGCGGAGCTCGCCGAGACGG
-1940     +---------+---------+---------+---------+---------+---------     -1881

GACGGGGACGGAGCTCGCCATGCGTGCCTCGCAGGGGCGCGATGGGGGCGGAGCTCGCCG
-1880     +---------+---------+---------+---------+---------+---------     -1821

PstI
          TGGCTGGCTGCAGCACCTCGGGCCGCTGCTAGCCGTGCCACGACGCGAGCATGCGCCTCG
-1820     +---------+---------+---------+---------+---------+---------     -1761

ACGCCGCCCCGTGCTACCTCGTCGCGCGCCCAGGGCCGCCCCGCCCCTGCCGACCGgCGg
-1760     +---------+---------+---------+---------+---------+---------     -1701

CGgAgACGCGAcCTTCGCGgACGTGCCCGGCGGCAGAGACGCGTCCTTCGCGACAGCGCC
-1700     +---------+---------+---------+---------+---------+---------     -1641

CTCCTCGATCTCCGTCGAGCCGCATACGCgGcTAgGAgGGACGCGGGCGTCCCCGGTGTC
-1640     +---------+---------+---------+---------+---------+---------     -1581

GGCCTCCGTTGTGGCGCATCGCGGGCGCGGCCTCCGTCGAGGcGCATCGCGGGCGTGGCC
-1580     +---------+---------+---------+---------+---------+---------     -1521

TCGTGGCGCAGCCTGCCCTGATTCGGTCTGAGGCGCGGCGCGGAGCTTCCTCGCGGCGGC
-1520     +---------+---------+---------+---------+---------+---------     -1461

GCGGGCGGAGCCTCCTCGCTGCGGCGCGACCTGCTCTGCCGCGGTCCGAGACGCGGCGCG
-1460     +---------+---------+---------+---------+---------+---------     -1401

GGCAGAGCTTCCTCGCGGCGGCTCGGGCGCGGCTTCCTCGCGGCGATGGCGCTTCCAGGC
-1400     +---------+---------+---------+---------+---------+---------     -1341

TCGCACGCGGCCTCCGGCGTGGCGCAGCGAGAGCGCAGCCTCCGGTGAGTTAGGCACAGG
-1340     +---------+---------+---------+---------+---------+---------     -1281

CGCGACACGACATCCCCGGCCTCGGCCTCCGGCGTGGCGCAGCGCGAGCGCGACGTAGCC
-1280     +---------+---------+---------+---------+---------+---------     -1221

TAGGTTGGCAACTAGTaCTACGAGGAAGAAAGAGGAGAAACAATTATTTGGGTCACAGCG
-1220     +---------+---------+---------+---------+---------+---------     -1161

TTGGGCGTACTGTGCGATCCAAACGGACACCCgGACGCGAaACGATGTCAGCGTGTCCGC
-1160     +---------+---------+---------+---------+---------+---------     -1101

GTGGcGACCCAAACGACCCGAAACGGACGTCcGTTTGGGTCGGTGCGTTGGAGATGCCCT
-1100     +---------+---------+---------+---------+---------+---------     -1041
```

FIGURE 18 CONTINUED

```
        TACTCCCCATCCTCAAATGAGTCTAATTATATATCTTGTTGTAAGTTTTAAAAAAGTTAA
-1040   +---------+---------+---------+---------+---------+---------  -981

ACTTTGATCAACATTAGTAATGATAGTAGCAACGAATACAAAATTAAATTGTAAAAATAT
 -980   +---------+---------+---------+---------+---------+---------  -921

ATTATGAAACTTTATTTTAAGATGGATCTAGTTATACTAATTTTCTGCGGATGGAGGAAG
 -920   +---------+---------+---------+---------+---------+---------  -861

TAGCTAAATATTGTTAATTTCTAAATAAAAAATTAAAACTTTAACTTAAAACAAAAGTTA
 -860   +---------+---------+---------+---------+---------+---------  -801

Putative Myb Binding domains
        CAAGCATAATTATCTGtGGATGGAGGAAGtAGCTAAGATACACCAATCCTCTCTCTACAT
 -800   +---------+---------+---------+---------+---------+---------  -741

TACCTAGCATGCCACATCAGGAAACTATTTAGGATAAGCTCCAAGGAACCACCCAGAACA
 -740   +---------+---------+---------+---------+---------+---------  -681

ACAATTTACATGGCCTGGCTAACCTAATGACAATTTCCGAGCAACTGGTGGTGGTGGTAC
 -680   +---------+---------+---------+---------+---------+---------  -621

GCGTTCCTTGTTCAATTGTCTCTATTACAAGAGTGGCCCTGTATAGGTAAAAAAAAATAA
 -620   +---------+---------+---------+---------+---------+---------  -561

HindIII                      PstI
        CAAGCTTCCAAGGACGGCCATGTTCCTTGTTCCTGCAGGCTGCACGTACTCACGACGAAG
 -560   +---------+---------+---------+---------+---------+---------  -501

TGTATCTCGTGTTCTGGACATTTGTCTCGCGCATTTTGTAACCATGAAATTAAAAATGTG
 -500   +---------+---------+---------+---------+---------+---------  -441

GTGGCCTGCTATATCTGTATGGGGGTATCATGCACTCCTTCGCAGAGGAATCCAGACGAC
 -440   +---------+---------+---------+---------+---------+---------  -381

GATTTACACGTGTTTCCACCTTAGCTTTTTTTAAGTGTGTGTGTAAGGAACGATCATATA
 -380   +---------+---------+---------+---------+---------+---------  -321

XhoI
        ACTGCCCCTGAATGCTGCATATATATAAACCGACTCCATCATGTACTCGAGACAAGGTCG
 -320   +---------+---------+---------+---------+---------+---------  -261

TCAAGAAAAACAAACTATGCCTATCTCACTAGCAATGATTTGAGAGTACAGCTTTTCCGG
 -260   +---------+---------+---------+---------+---------+---------  -201

TGCCATATTTTTTCCTATATATCTTTTTCTGAAGAACAAGAAAAAAAAAACAGTTGGTGT
 -200   +---------+---------+---------+---------+---------+---------  -141

GGTGGTTGGTGAAGCGAGAAAGCCCCATATAAGCCCTGCTCACCCTCCCCGCAAAGCACA
 -140   +---------+---------+---------+---------+---------+---------   -81

PvuI
        ACTCATAGCTCGGGTCTCTCGCTCACACCAAAATCGCCCACCAGCACCAGCATCTCTCGA
  -80   +---------+---------+---------+---------+---------+---------   -21

TCGGCAGACGCATAGATCGATGGGCTCCACCGCCGCCGACATGGCCGCGTCCGCGGACGA
  -20   +---------+---------+---------+---------+---------+---------    39
                                        M  G  S  T  A  A  D  M  A  A  S  A  D  E

GGACGCGTGCATGTTCGCCCTCCAGCTCGCTTCCTCGTCGGTCCTCCCGATGACGCTGAA
   40   +---------+---------+---------+---------+---------+---------    99
         D  A  C  M  F  A  L  Q  L  A  S  S  V  L  P  M  T  L  K
```

FIGURE 18 CONTINUED

```
      GAACGCCATCGAGCTTGGCCTCCTGGAGATCCTGGTGGCCGCCGGCGGCAAGTCGCTGAC
100   +---------+---------+---------+---------+---------+---------    159
         N  A  I  E  L  G  L  L  E  I  L  V  A  A  G  G  K  S  L  T

CCCGACCGAGGTGGCCGCCAAGCTCCCGTCCGCGGCGAACCCGGAAGCGCCGGACATGGT
160   +---------+---------+---------+---------+---------+---------    219
            P  T  E  V  A  A  K  L  P  S  A  A  N  P  E  A  P  D  M  V

GGACCGCATACTCCGGCTGCTCGCGTCGTACAACGTCGTGACGTGCCTGGTGGAGGAGGG
220   +---------+---------+---------+---------+---------+---------    279
         D  R  I  L  R  L  L  A  S  Y  N  V  V  T  C  L  V  E  E  G

CAAGGACGGCCGCCTCTCCCGGAGCTACGGCGCCGCGCCCGTGTGCAAGTTCCTCACCCC
280   +---------+---------+---------+---------+---------+---------    339
         K  D  G  R  L  S  R  S  Y  G  A  A  P  V  C  K  F  L  T  P

CAACGAGGACGGCGTCTCCATGGCGGCGCTCGCGCTCATGAACCAGGACAAGGTCCTCAT
340   +---------+---------+---------+---------+---------+---------    399
         N  E  D  G  V  S  M  A  A  L  A  L  M  N  Q  D  K  V  L  M

Intron/exon boundary
      GGAGAGCTG↓GTGAGTCTCTCAGTGGAGCTAGTTACTGTAGATCCGAATTCGTTCCCTTTA
400   +---------+---------+---------+---------+---------+---------    459
         E  S
                                 SalI        pBluescript
      GTGAGGGTTAATTCCGCGGCCGCGTCGACCTCGAGGGGGGGCCCGGTACCCAATTCGCCC
460   +---------+---------+---------+

TATAGTGAGTCGTATTACGCGCGCTCACTGGCCGTCGTTTTACAACGTCGTGACTGGGAA
      AACCCTGGCGTTACCCAACTTAATCGCCTTGCAGCACATCCCCCTTTCGCCAGCTGGCGT
      AATAGCGAAGAGGCCCGCACCGATCGCCCTTCCCAACAGTTGCGCAGCCTGAATGGCGAA
      TGGGACGCGCCCTGTAGCGGCGCATTAAGCGCGGCGGGTGTTGTG    744
```

FIGURE 18 CONTINUED pLpOMTGUS

A
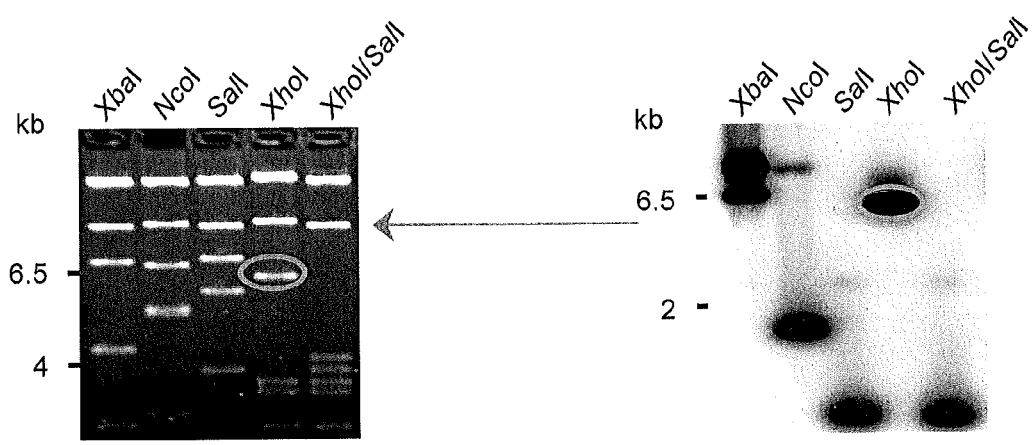
B
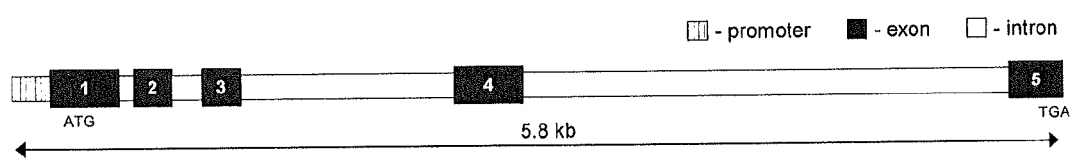
C
| Exon | Lp CCR1 | Eg CCR1 | Es CCR1 | Pb CCR1 |
|---|---|---|---|---|
| 1 | 173 bp | 133 bp | 133 bp | 139 bp |
| 2 | 155 bp | 155 bp | 155 bp | 155 bp |
| 3 | 189 bp | 186 bp | 186 bp | 186 bp |
| 4 | 353 bp | 353 bp | 353 bp | 353 bp |
| 5 | 220 bp | 218 bp | 184 bp | 184 bp |
FIGURE 21

A
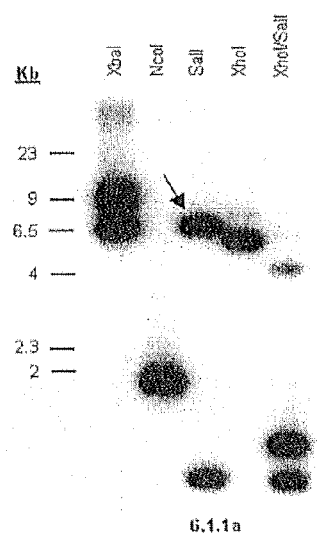
B
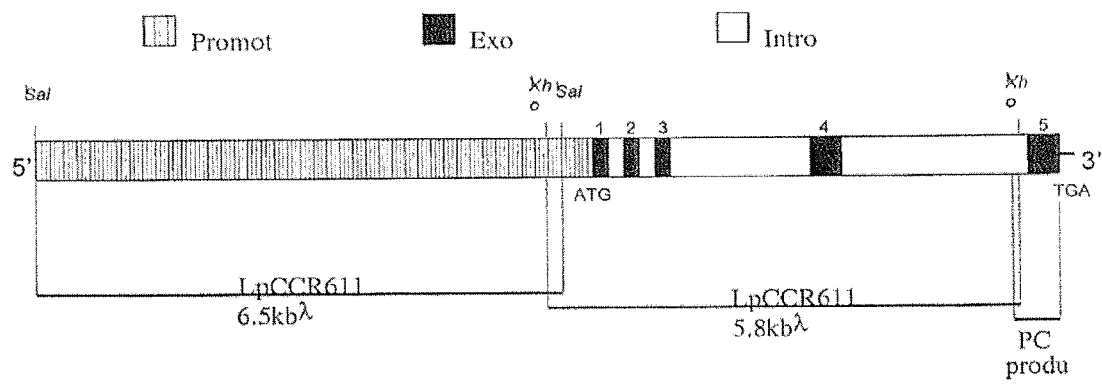
FIGURE 22

```
     TCCCGTATCTTCAACGTGACACCCCTACACTTCCTGCTTGTCTTGGAGATTTACACACAC
  1  ------+---------+---------+---------+---------+---------+   60

ACGGCAATTACCAGGAGTATCTTCCTAGATTATTTTTTCGATAAGGATCTTCCAGATAT
 61  ------+---------+---------+---------+---------+---------+   120

AGCATGTGAATCTCTGTACTACTACTGTTTGTCAAGCAAAATTAACATTGACATCAGTGT
121  ------+---------+---------+---------+---------+---------+   180

TTTTGTTGGGGGCAGCGGAATCTTTGACGCCTCTTCTTGCCTCTCAAGACATGTCACCCT
181  ------+---------+---------+---------+---------+---------+   240

CACTAGTTAGTGTGCCAGCTGGTAGTACTACGTACGATGCTCCCTCCCTCCGTAATTATT
241  ------+---------+---------+---------+---------+---------+   300

CAACCTTTTTGCTCTCTCTTTTTATAAAGTCAAACCTTTTAAATCTGACCAGATATCTGC
301  ------+---------+---------+---------+---------+---------+   360

TAAAAAATTAGCAGACATGCATACATCAAAGCAGTAGTCCTCCCTCCGTTTAAAATTACC
361  ------+---------+---------+---------+---------+---------+   420

TGGGTTTATTCAAATAAAGTCAAACTCTGTAAAATTCAATTAAATATTTAGAAAAATCTA
421  ------+---------+---------+---------+---------+---------+   480

ACAGCACCTGTAGTATAAAAGTATGCTCCCTCTGTTTGTAAAAAAGCTAAGCAACTTTTT
481  ------+---------+---------+---------+---------+---------+   540

TGAGATACGGATAAATCTTTAGCTAAAACATGTCTATATACCTTTGTATCTAGATAAAGT
541  ------+---------+---------+---------+---------+---------+   600

TGGAAAGCTTTTTTAGAAACAGACAAAGTATGTGTTTGACATTATGAATGTTGAGTATTT
601  ------+---------+---------+---------+---------+---------+   660

TTCCTCTAATCTTGATCAAATTTTACAAATTTTGGCTTGAATAGAGGGACCATTATTAGT
661  ------+---------+---------+---------+---------+---------+   720

ATGAAACTACATAAATTTGTAAAACACTCAACATAATTTACGATGGGTCAGTGATAGCAC
721  ------+---------+---------+---------+---------+---------+   780

TAACTTAGCTTTTCATAAATGCCACTGCTTTTCAATAGAGCATGAAGCAGGACAAATTTA
781  ------+---------+---------+---------+---------+---------+   840

TTCGTGTGACTTGAATAGAGGGAGCCTGTTCTGGTTCAACTCACCCTGCATGTGTGTCTT
841  ------+---------+---------+---------+---------+---------+   900

CATCCCTTTTGCTCTTCCTATCTGTGGTGTCAATTGAGTGTCCCACGTGCATGTGGGCGA
901  ------+---------+---------+---------+---------+---------+   960
```

FIGURE 26

961  AACTTGAACCTAGAAATTGACATGCTCCCACTGCCCGGAGCGGAGTATCTTTGTGCTTTG  1020

1021 TTACCCTTATTGTTGCTACGTACTACAGTGTTTAGATTGGAACTTCATAATCAAAAGAAC  1080

1081 TTAGTTTCCTACAATTTTTTGCTAAGCAATATAATGAGCAATCAAACTTCTATATCTGTG  1140

1141 GCAAATAACTAATCCATTATAGTTACAGTTTAGATGCAGACGCCAGTGTTTCTTCCCCTT  1200

1201 TTCGGAAAAAAGCTATTCCATAATAAGTGTTGGAAATTTAATAAATGGGTACTACGAATT  1260

1261 TGAAAAAAAAGTGTCAAAAATTCACTAAGAAAGTACGTAGTACAAATTTAAACTAAGAT  1320

1321 TCCGACACTTATTAGGATCGGAGAGAGTAAGTAGCAAACTACTACTCCATCCACCTAAAA  1380

1381 CACGTGATTTAACTTTGTCTAGATACGGATAGAAAGTTGGGATACATCCGTATCTTAAAA  1440

1441 AAAAACGCACTTATTTTAGACGAAGGAGGGAGTATTTCAACCTTGATTTTAAACGGAATC  1500

1501 TACAAAGGGAATACATGGATTGTACAAGTGGGCTGACCGTATCCATTATGTACTCGTACT  1560

1561 TTGCAGTTTGAAAGCAAAGGCTAGTGTAATTTGTAGGTGGTTCTAGGCGTCTAGCTGTTT  1620

1621 CATGGCGTTATCACAGCCGTGCCAGTGTGCTCAGGGCCGTACATAAGTTGCTTGGTGTAT  1680

1681 GTGTCGATCTAGGATTTGCCGTCTTACAATTTTGCTTTCCAACTTATTTTCTGTAAAGAG  1740

1741 ATCGATGTGAACTTCTCTGTCGAGTAAACTGAAATTGTCTGAATAAATATAACTCGGCAG  1800

1801 ATTATGTTTTATCGTTTGCATGCGTAACAGGCTACACAAATTGCTCGAGTCAGCAGCGAG  1860

1861 TTGAGCTCACAACGAATCCATCAGCAAAATACTATACTATAGTAGCACATCGTTTCTTT  1920

FIGURE 26 CONTINUED

```
       TTTCATGACGTTTCTGTTTCTTCCTAACTTTCCAGGAGCACCGGAGACGACGATGTGGTG
1921   ---------+---------+---------+---------+---------+---------+   1980
                                          R  S  T  G  D  D  D  V  V

ATAAAGATTTTGTACTGCGGAATCTGCCACTCTGACCTGCACGCCCTGAAGAACGACTGG
1981   ---------+---------+---------+---------+---------+---------+   2040
       I  K  I  L  Y  C  G  I  C  H  S  D  L  H  A  L  K  N  D  W

AAGAACTCAAGGTACCCGATGATCCCCGGGCACGAGATCGCCGGCGAGGTCACGGAGGTG
2041   ---------+---------+---------+---------+---------+---------+   2100
       K  N  S  R  Y  P  M  I  P  G  H  E  I  A  G  E  V  T  E  V

GGCAAGAACGTGAGCAAGTTCAAGGCCGGCGACCGCGTGGGCGTCGGGTGCATGGTGAAC
2101   ---------+---------+---------+---------+---------+---------+   2160
       G  K  N  V  S  K  F  K  A  G  D  R  V  G  V  G  C  M  V  N

TCGTGCCGGTCGTGCGAGAGCTGCGACAAGGGCTTCGAGAACCACTGCCCGGGCATGATC
2161   ---------+---------+---------+---------+---------+---------+   2220
       S  C  R  S  C  E  S  C  D  K  G  F  E  N  H  C  P  G  M  I

CTCACCTACAACTCGGTCGACGTCGACGGCACCGTCACCTACGGCGGCTACTCCAGCATG
2221   ---------+---------+---------+---------+---------+---------+   2280
       L  T  Y  N  S  V  D  V  D  G  T  V  T  Y  G  G  Y  S  S  M

GTGGTGGTGCACGAGCGGTTCGTGGTCCGGTTCCCCGACGCCATGCCGCTGGACAAGGGC
2281   ---------+---------+---------+---------+---------+---------+   2340
       V  V  V  H  E  R  F  V  V  R  F  P  D  A  M  P  L  D  K  G

GCGCCGCTGCTGTGCGCCGGCATCACCGTGTACAGCCCCATGAAGTACCACGGGCTCAAC
2341   ---------+---------+---------+---------+---------+---------+   2400
       A  P  L  L  C  A  G  I  T  V  Y  S  P  M  K  Y  H  G  L  N

GTTCCCGGGCTGCACCTCGGCGTGCTGGGGCTGGGCGGGCTGGGCCACGTTGCGGTCAAG
2401   ---------+---------+---------+---------+---------+---------+   2460
       V  P  G  L  H  L  G  V  L  G  L  G  G  L  G  H  V  A  V  K

TTCGGCAAGGCCTTCGGAATGAAAGTGACGGTGATCAGCTCGTCGCCGGGGAAGAAGGAG
2461   ---------+---------+---------+---------+---------+---------+   2520
       F  G  K  A  F  G  M  K  V  T  V  I  S  S  S  P  G  K  K  E

GAGGCCCTGGGGCGGCTGGGCGCCGACGCGTTCATCGTCAGCAAGGACGCCGACGAGATG
2521   ---------+---------+---------+---------+---------+---------+   2580
       E  A  L  G  R  L  G  A  D  A  F  I  V  S  K  D  A  D  E  M

AAGGTAGGCGGACCCGCTGGTTCAGGTTACTTCCCCTGTCCGGTGCAGAAGAAAGAGGAA
2581   ---------+---------+---------+---------+---------+---------+   2640
       K
```

FIGURE 26 CONTINUED

G at 851 bp (coding sequence) missing from cDNA in cv Ellett
▼

```
        CTTGAGGGTTCATGTTTGTTTTGCGTTGGTGATGTCTTTGCAGGCTGTGATGAGCACCAT
2641    ---------+---------+---------+---------+---------+---------+   2700
                                                        A  V  M  S  T  M

GGATGGCATCATAAACACGGTATCTGCAAACATCCCCCTGACCCCTCTCTTCGGGCTGCT
2701    ---------+---------+---------+---------+---------+---------+   2760
         D  G  I  I  N  T  V  S  A  N  I  P  L  T  P  L  F  G  L  L

CAAGCCCAACGGCAAGATGATCATGGTCGGCCTCCCCGAGAAGCCCATCGAGATTCCTCC
2761    ---------+---------+---------+---------+---------+---------+   2820
         K  P  N  G  K  M  I  M  V  G  L  P  E  K  P  I  E  I  P  P

CTTCGCTCTAGTTGCCAGTAAGTCTTAGGATCTCTTGCAATAAGGAGAAATCATGCACTG
2821    ---------+---------+---------+---------+---------+---------+   2880
         F  A  L  V  A

ATCGATCAGAGAAATGAGATAGCATCCTGATGAACATTGTACGTGTGTGCAGCGAATAAG
2881    ---------+---------+---------+---------+---------+---------+   2940
                                                                  N  K

ACCCTGGCCGGGAGCATCATCGGCGGCATGAGCGACACGCAGGAGATGCTGGACCTCGCG
2941    ---------+---------+---------+---------+---------+---------+   3000
         T  L  A  G  S  I  I  G  G  M  S  D  T  Q  E  M  L  D  L  A

GCGAAGCACGGCGTGACGGCCGACATCGAGGTGGTCGGCGCGGAGTATGTGAACACGGCC
3001    ---------+---------+---------+---------+---------+---------+   3060
         A  K  H  G  V  T  A  D  I  E  V  V  G  A  E  Y  V  N  T  A

TTGGAGCGCCTTGCCAAGAACGACGTCAGGTATCGCTTCGTCATCGACATCGGCAACACC
3061    ---------+---------+---------+---------+---------+---------+   3120
         L  E  R  L  A  K  N  D  V  R  Y  R  F  V  I  D  I  G  N  T

CTCGACAAGGTTGCGGCCACCACCGAGTGAACGTACTCAGCACTGCTTACGATCTACGTT
3121    ---------+---------+---------+---------+---------+---------+   3180
         L  D  K  V  A  A  T  T  E  *

GTTCCACTGTTAGTGCTCCGTAGTAAACAATAAACGATCAAAACTCTTGTCATCTGGTGC
3181    ---------+---------+---------+---------+---------+---------+   3240

ATTGGTGTAGACATGGTTGTTTGCGAGGAAACTGAGTTGAAGGATGGATGGATAAGTTTG
3241    ---------+---------+---------+---------+---------+---------+   3300

CTTCTTGCCGTGTTAATGGATTACCTACTTAGCTTCACTGCAATTAACAAATTAAGAAAC
3301    ---------+---------+---------+---------+---------+---------+   3360

GACACACCCAAAAGACTTTCGTCAGTTTTCTTGGATTATACAAGTCGTTATGGTTGGGTG
3361    ---------+---------+---------+---------+---------+---------+   3420
```

FIGURE 26 CONTINUED

```
       TCAGTGTGTCACAGATAATCATACTATGGTATTTAACCTGGAAGATCGTTTTTTTGGCGG
3421   ---------+---------+---------+---------+---------+---------+   3480

CAACTCAGTGGGTTTTCCCACTATGTATATTTATAAATATTCAACAAGTCATGAGGTACA
3481   ---------+---------+---------+---------+---------+---------+   3540

AAGGGTTGTTGCTAGAGGATAGCAACAAGAAGCTAGCCAAAAGATCATAGGCTTAAAAAA
3541   ---------+---------+---------+---------+---------+---------+   3600

GAGAGAAAAGAAAACAAAACTGCTATAGTTATCGAAATCTCTCAGCTCAAATTTTAAAAC
3601   ---------+---------+---------+---------+---------+---------+   3660

CAGCATAAGACTTTCTAGAAGCCTTATGAACAAGAAGAGCTAGCTCATCTTTAAACCTTT
3661   ---------+---------+---------+---------+---------+---------+   3720

TCCTGCATCTGTAAAGATTGAGGGTGCAACCCTTGAATATAAAATCATTCCTGTCATCCA
3721   ---------+---------+---------+---------+---------+---------+   3780

GATAGACTATGTAGTCAAAATAGTCATTTCCATGAAGAAGGGCACTTTTAATACATTTTT
3781   ---------+---------+---------+---------+---------+---------+   3840

GAGACTTGGTATGATACTCTGAATGTCAACACCCTGGAAGATCTTTTCACTCCTATGGAA
3841   ---------+---------+---------+---------+---------+---------+   3900

GGACAAGAAAGCATTTCAACTCCTTTTACTAAGGAAGAGATTGACAAGGTGATTCAGAGA
3901   ---------+---------+---------+---------+---------+---------+   3960

ATTCCTTTAGACACTATAGAAAGTCACAAGGTGCCAACGGCGCAATCCTGTGCCGACGGC
3961   ---------+---------+---------+---------+---------+---------+   4020

TTTTTATCGGGGAAGCCAGCATCGGTACCGAGACCGGCAGCCCACCAACTAGGCCGTCGG
4021   ---------+---------+---------+---------+---------+---------+   4080

CACACATCCTCCAGTGTCGGCGGCCAACATCGGCATAAGTTGGCCCGTTGGGCATCAACT
4081   ---------+---------+---------+---------+---------+---------+   4140

CCCCCGTCGGAACAGGTCTAGCGCATGGACCGTCGTGATGGCGGCGGCAACGACGTCATC
4141   ---------+---------+---------+---------+---------+---------+   4200

CTATGCCGACGGCCTAGCCGTCGGCCTAGCTTGCCAGCGCTATGCCGACGTCACATTGCC
4201   ---------+---------+---------+---------+---------+---------+   4260

ATCGGCACATGCTAGTTTTTTTTTCTTTTTTCTACATGCCAAATTGTATATGTATATATA
4261   ---------+---------+---------+---------+---------+---------+   4320

CTCATTTACTTATTACTTCCAATTATTTTAATGTGTATATATTTTGCTCACCAATTGTAC
4321   ---------+---------+---------+---------+---------+---------+   4380
```

FIGURE 26 CONTINUED

```
         GAATTTGTACCCTCCGAGAAATTGCTAAAATGATGGAGTGACCTACAACGAGCCTTGGAT
  4381   ---------+---------+---------+---------+---------+---------+  4440

ATGTGAGTTCTTCTTGCCCCATTGCACAAAAATTGTAAATATTAGGGTTTACTGGATCCA
  4441   ---------+---------+---------+---------+---------+---------+  4500

CTAGTTCTAGAGCGGCCGCCACCGCGGGGAGCTCCAGCTTTTGTTCCCTTTAGTA
  A)     ---------+---------+---------+---------+---------+-----  4555
```

FIGURE 26 CONTINUED

```
     GGCACGAGTCGCCTCCAACGTCTTCCCTTAACCGGCCGTCCCTACGCtTGCACCACCACC
  1  ---------+---------+---------+---------+---------+---------+  60

ACGCACAGACAGAGCAGTTTCCCAGCCCCCGCCGGAACCGGATGGCACCCACGGCGGCGG
 61  ---------+---------+---------+---------+---------+---------+ 120
                                             M  A  P  T  A  A  E

AGCAGACGGAGCACCACCAGCACACCAGGAAGGCGGTGGGGCTGGCGGCGCGCGACGACG
121  ---------+---------+---------+---------+---------+---------+ 180
       Q  T  E  H  H  Q  H  T  R  K  A  V  G  L  A  A  R  D  D  A

CCGGCCACCTCTCCCCGCTCGCCATCACACGGAGGAGCACAGGAGACGACGATGTGGTGA
181  ---------+---------+---------+---------+---------+---------+ 240
       G  H  L  S  P  L  A  I  T  R  R  S  T  G  D  D  D  V  V  I

TAAAGATTTTGTACTGCGGAATCTGCCACTCTGACCTGCACGCCCTGAAGAACGACTGGA
241  ---------+---------+---------+---------+---------+---------+ 300
       K  I  L  Y  C  G  I  C  H  S  D  L  H  A  L  K  N  D  W  K

AGAACTCAAGGTACCCGATGATCCCCGGGCACGAGATCGCCGGCGAGGTCACGGAGGTGG
301  ---------+---------+---------+---------+---------+---------+ 360
       N  S  R  Y  P  M  I  P  G  H  E  I  A  G  E  V  T  E  V  G

GCAAGAACGTGAGCAAGTTCAAGGCCGGCGACCGCGTGGGCGTCGGGTGCATGGTGAACT
361  ---------+---------+---------+---------+---------+---------+ 420
       K  N  V  S  K  F  K  A  G  D  R  V  G  V  G  C  M  V  N  S

CGTGCCGGTCGTGCGAGAGCTGCGACAAGGGCTTCGAGAACCACTGCCCGGGCATGATCC
421  ---------+---------+---------+---------+---------+---------+ 480
       C  R  S  C  E  S  C  D  K  G  F  E  N  H  C  P  G  M  I  L

TCACCTACAACTCGGTCGACGTCGACGGCACCGTCACCTACGGCGGCTACTCCAGCATGG
481  ---------+---------+---------+---------+---------+---------+ 540
       T  Y  N  S  V  D  V  D  G  T  V  T  Y  G  G  Y  S  S  M  V

TGGTGGTGCACGAGCGGTTCGTGGTCCGGTTCCCCGACGCCATGCCGCTGGACAAGGGCG
541  ---------+---------+---------+---------+---------+---------+ 600
       V  V  H  E  R  F  V  V  R  F  P  D  A  M  P  L  D  K  G  A

CGCCGCTGCTGTGCGCCGGCATCACCGTGTACAGCCCCATGAAGTACCACGGGCTCAACG
601  ---------+---------+---------+---------+---------+---------+ 660
       P  L  L  C  A  G  I  T  V  Y  S  P  M  K  Y  H  G  L  N  V

TTCCCGGGCTGCACCTCGGCGTGCTGGGGCTGGGCGGGCTGGGCCACGTTGCGGTCAAGT
661  ---------+---------+---------+---------+---------+---------+ 720
       P  G  L  H  L  G  V  L  G  L  G  G  L  G  H  V  A  V  K  F

TCGGCAAGGCCTTCGGAATGAAAGTGACGGTGATCAGCTCGTCGCCGGGGAAGAAGGAGG
721  ---------+---------+---------+---------+---------+---------+ 780
       G  K  A  F  G  M  K  V  T  V  I  S  S  S  P  G  K  K  E  E
```

FIGURE 27

```
                AGGCCCTGGGGCGGCTGGGCGCCGACGCGTTCATCGTCAGCAAGGACGCCGACGAGATGA
         781    ---------+---------+---------+---------+---------+---------+    840
                  A  L  G  R  L  G  A  D  A  F  I  V  S  K  D  A  D  E  M  K

G at 851 bp (coding sequence) missing from cDNA in cv Ellett
                                          ▼
                AGGCTGTGATGAGCACCATGGATGGCATCATAAACACGGTATCTGCAAACATCCCCCTGA
         841    ---------+---------+---------+---------+---------+---------+    900
                   A  V  M  S  T  M  D  G  I  I  N  T  V  S  A  N  I  P  L  T CCCCTCTCTTCGGGCTGCTCAAGCCCAACGGCAAGATGATCATGGTCGGCCTCCCCGAGA
         901    ---------+---------+---------+---------+---------+---------+    960
                    P  L  F  G  L  L  K  P  N  G  K  M  I  M  V  G  L  P  E  K AGCCCATCGAGATTCCTCCCTTCGCTCTAGTTGCCACGAATAAGACCCTGGCCGGGAGCA
         961    ---------+---------+---------+---------+---------+---------+    1020
                     P  I  E  I  P  P  F  A  L  V  A  T  N  K  T  L  A  G  S  I TCATCGGCGGCATGAGCGACACGCAGGAGATGCTGGACCTCGCGGCGAAGCACGGCGTGA
        1021    ---------+---------+---------+---------+---------+---------+    1080
                    I  G  G  M  S  D  T  Q  E  M  L  D  L  A  A  K  H  G  V  T CGGCCGACATCGAGGTGGTCGGCGCGGAGTATGTGAACACGGCCTTGGAGCGCCTTGCCA
        1081    ---------+---------+---------+---------+---------+---------+    1140
                   A  D  I  E  V  V  G  A  E  Y  V  N  T  A  L  E  R  L  A  K AGAACGACGTCAGGTATCGCTTCGTCATCGACATCGGCAACACCCTCGACAATGTTGCGG
        1141    ---------+---------+---------+---------+---------+---------+    1200
                    N  D  V  R  Y  R  F  V  I  D  I  G  N  T  L  D  N  V  A  A CCACCACCGAGTGAACGTACTCAGCACTGCTTACGATCTACGTTGTTCCACTGTTAGTGC
        1201    ---------+---------+---------+---------+---------+---------+    1260
                  T  T  E  *

TCCGTAGTAAACAATAAACGATCAAAACTCTTGTCATCTGGTGCATTGGTGTAGACATGG
        1261    ---------+---------+---------+---------+---------+---------+    1320

TTGTTTGCGAGGAAACTGAGTTGAAGGATGGATGGATAAAAAAAAAAAAAAAAAAAAAAA
    A)          ---------+---------+---------+---------+---------+---------    1378

GGCACGAGTCGCCTCCAACGTCTTCCCTTAACCGGCCGTCCCTACGCtTGCACCACCACC
           1    ---------+---------+---------+---------+---------+---------+    60

ACGCACAGACAGAGCAGTTTCCCAGCCCCCGCCGGAACCGGATGGCACCCACGGCGGCGG
          61    ---------+---------+---------+---------+---------+---------+    120
                                                           M  A  P  T  A  A  E

AGCAGACGGAGCACCACCAGCACACCAGGAAGGCGGTGGGGCTGGCGGCGCGCGACGACG
         121    ---------+---------+---------+---------+---------+---------+    180
                   Q  T  E  H  H  Q  H  T  R  K  A  V  G  L  A  A  R  D  D  A
```

FIGURE 27 CONTINUED

```
      CCGGCCACCTCTCCCCGCTCGCCATCACACGGAGGAGCACAGGAGACGACGATGTGGTGA
181   ---------+---------+---------+---------+---------+---------+   240
       G  H  L  S  P  L  A  I  T  R  R  S  T  G  D  D  D  V  V  I

TAAAGATTTTGTACTGCGGAATCTGCCACTCTGACCTGCACGCCCTGAAGAACGACTGGA
241   ---------+---------+---------+---------+---------+---------+   300
       K  I  L  Y  C  G  I  C  H  S  D  L  H  A  L  K  N  D  W  K

AGAACTCAAGGTACCCGATGATCCCCGGGCACGAGATCGCCGGCGAGGTCACGGAGGTGG
301   ---------+---------+---------+---------+---------+---------+   360
       N  S  R  Y  P  M  I  P  G  H  E  I  A  G  E  V  T  E  V  G

GCAAGAACGTGAGCAAGTTCAAGGCCGGCGACCGCGTGGGCGTCGGGTGCATGGTGAACT
361   ---------+---------+---------+---------+---------+---------+   420
       K  N  V  S  K  F  K  A  G  D  R  V  G  V  G  C  M  V  N  S

CGTGCCGGTCGTGCGAGAGCTGCGACAAGGGCTTCGAGAACCACTGCCCGGGCATGATCC
421   ---------+---------+---------+---------+---------+---------+   480
       C  R  S  C  E  S  C  D  K  G  F  E  N  H  C  P  G  M  I  L

TCACCTACAACTCGGTCGACGTCGACGGCACCGTCACCTACGGCGGCTACTCCAGCATGG
481   ---------+---------+---------+---------+---------+---------+   540
       T  Y  N  S  V  D  V  D  G  T  V  T  Y  G  G  Y  S  S  M  V

TGGTGGTGCACGAGCGGTTCGTGGTCCGGTTCCCCGACGCCATGCCGCTGGACAAGGGCG
541   ---------+---------+---------+---------+---------+---------+   600
       V  V  H  E  R  F  V  V  R  F  P  D  A  M  P  L  D  K  G  A

CGCCGCTGCTGTGCGCCGGCATCACCGTGTACAGCCCCATGAAGTACCACGGGCTCAACG
601   ---------+---------+---------+---------+---------+---------+   660
       P  L  L  C  A  G  I  T  V  Y  S  P  M  K  Y  H  G  L  N  V

TTCCCGGGCTGCACCTCGGCGTGCTGGGGCTGGGCGGGCTGGGCCACGTTGCGGTCAAGT
661   ---------+---------+---------+---------+---------+---------+   720
       P  G  L  H  L  G  V  L  G  L  G  G  L  G  H  V  A  V  K  F

TCGGCAAGGCCTTCGGAATGAAAGTGACGGTGATCAGCTCGTCGCCGGGGAAGAAGGAGG
721   ---------+---------+---------+---------+---------+---------+   780
       G  K  A  F  G  M  K  V  T  V  I  S  S  S  P  G  K  K  E  E

AGGCCCTGGGGCGGCTGGGCGCCGACGCGTTCATCGTCAGCAAGGACGCCGACGAGATGA
781   ---------+---------+---------+---------+---------+---------+   840
       A  L  G  R  L  G  A  D  A  F  I  V  S  K  D  A  D  E  M  K

G missing at 851 bp in the cDNA isolated from cv Ellett
         resulted in a premature stop codon (truncated CAD2)
                                    ▼
      AGGCTGTGATAGCACCATGGATGGCATCATAAACACGGTATCTGCAAACATCCCCCTGAC
841   ---------+---------+---------+---------+---------+---------+   900
       A  V  I  A  P  W  M  A  S  *
```

FIGURE 27 CONTINUED

```
       CCCTCTCTTCGGGCTGCTCAAGCCCAACGGCAAGATGATCATGGTCGGCCTCCCCGAGAA
  901  --------+---------+---------+---------+---------+---------+   960

GCCCATCGAGATTCCTCCCTTCGCTCTAGTTGCCACGAATAAGACCCTGGCCGGGAGCAT
  961  --------+---------+---------+---------+---------+---------+  1020

CATCGGCGGCATGAGCGACACGCAGGAGATGCTGGACCTCGCGGCGAAGCACGGCGTGAC
 1021  --------+---------+---------+---------+---------+---------+  1080

GGCCGACATCGAGGTGGTCGGCGCGGAGTATGTGAACACGGCCTTGGAGCGCCTTGCCAA
 1081  --------+---------+---------+---------+---------+---------+  1140

GAACGACGTCAGGTATCGCTTCGTCATCGACATCGGCAACACCCTCGACAATGTTGCGGC
 1141  --------+---------+---------+---------+---------+---------+  1200

CACCACCGAGTGAACGTACTCAGCACTGCTTACGATCTACGTTGTTCCACTGTTAGTGCT
 1201  --------+---------+---------+---------+---------+---------+  1260

CCGTAGTAAACAATAAACGATCAAAACTCTTGTCATCTGGTGCATTGGTGTAGACATGGT
 1261  --------+---------+---------+---------+---------+---------+  1320

TGTTTGCGAGGAAACTGAGTTGAAGGATGGATGGATAAAAAAAAAAAAAAAAAAAAA
   A)  --------+---------+---------+---------+---------+-------  1377
```

FIGURE 27 CONTINUED

A
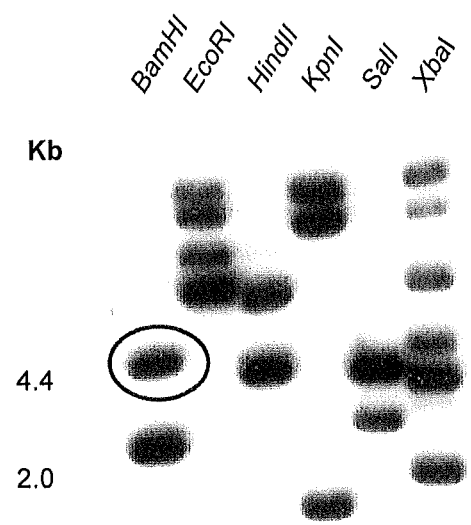
B
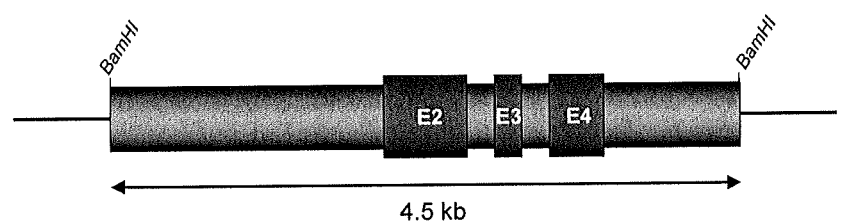
FIGURE 28

FIGURE 29A
A)
p35S4cl1
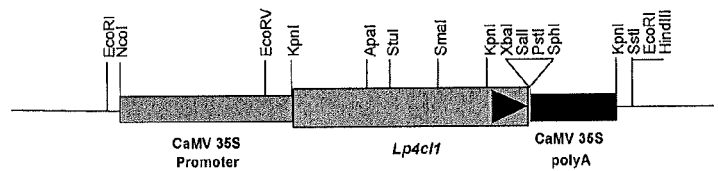
p35Slc41
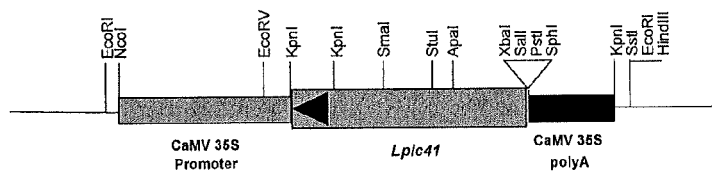
p35S4cl2
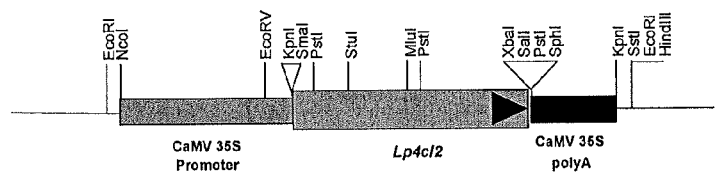
p35Slc43
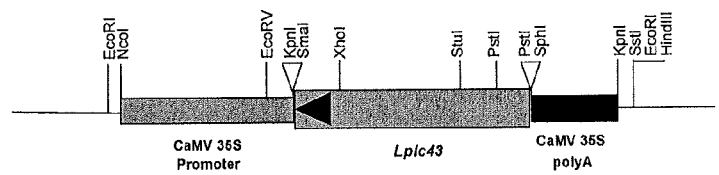
p35Slc42
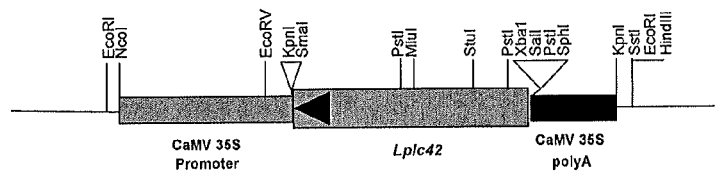
p35S4cl3
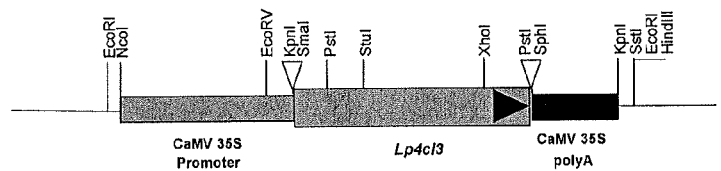

FIGURE 29B
B)
pUbi4cl1
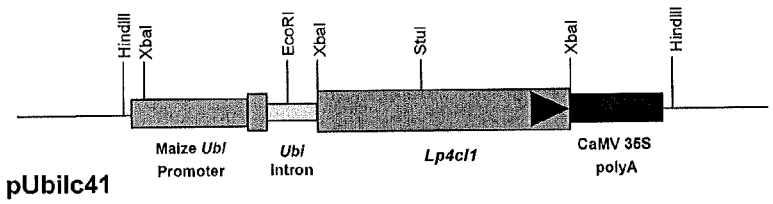
pUbilc41
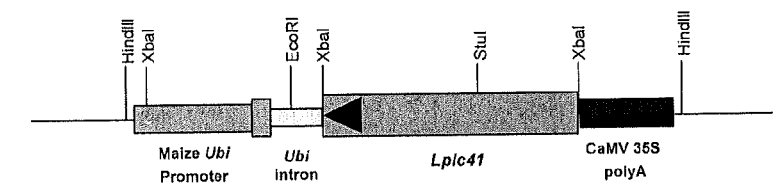
pUbi4cl2
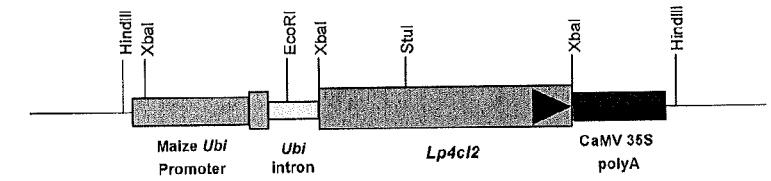
pUbilc42
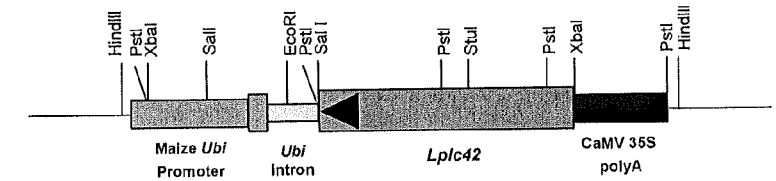
pUbi4cl3
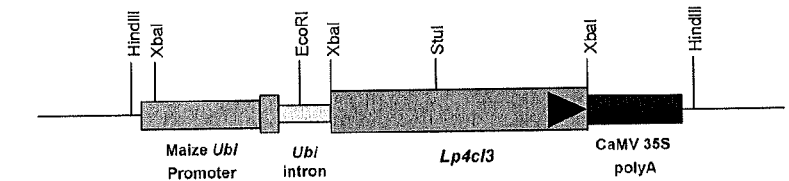
pUbilc43
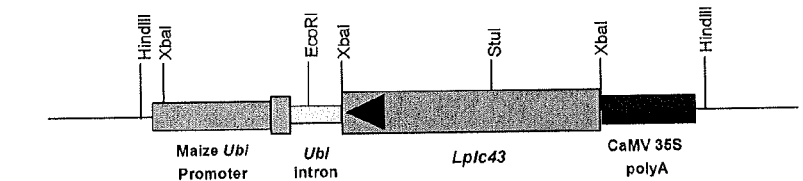

A)
p35SCCR1
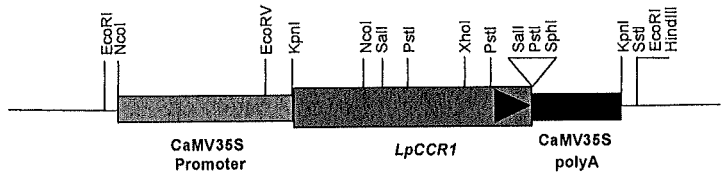
p35SRCC1
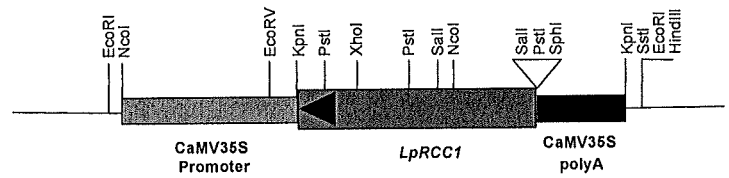
B)
pUbiCCR1
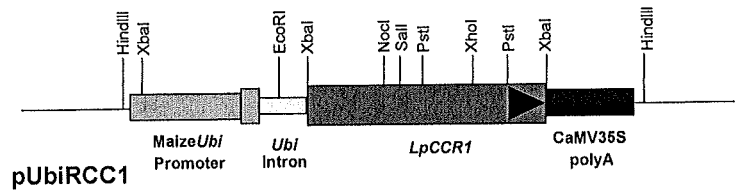
pUbiRCC1
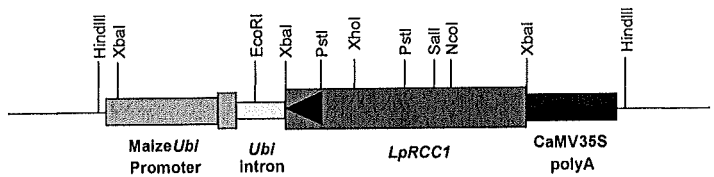
FIGURE 30

A)
p35SCAD1
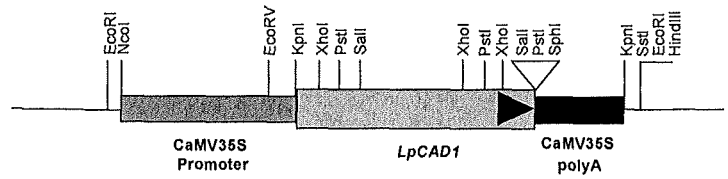
p35SDAC1
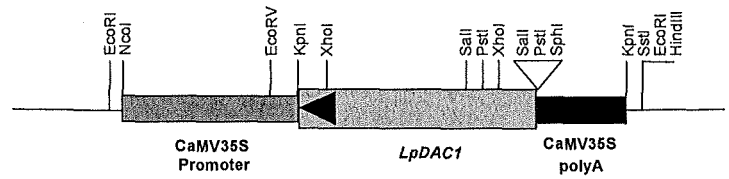
B)
pUbiCAD1
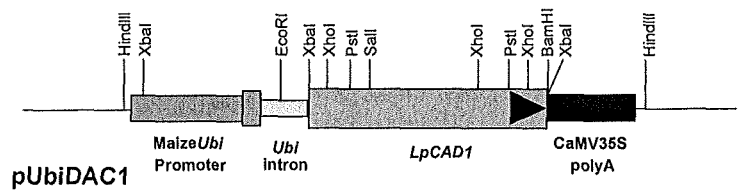
pUbiDAC1
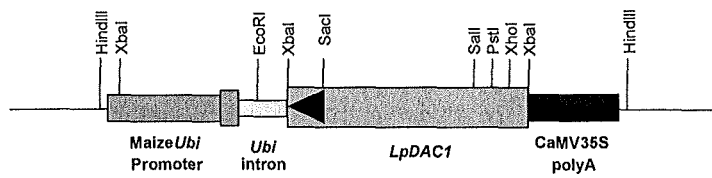
FIGURE 31

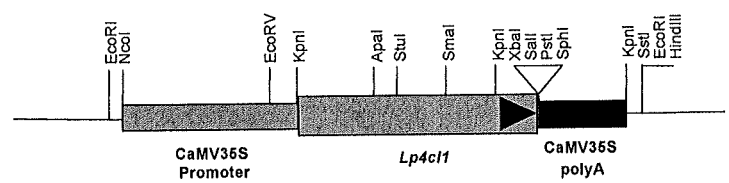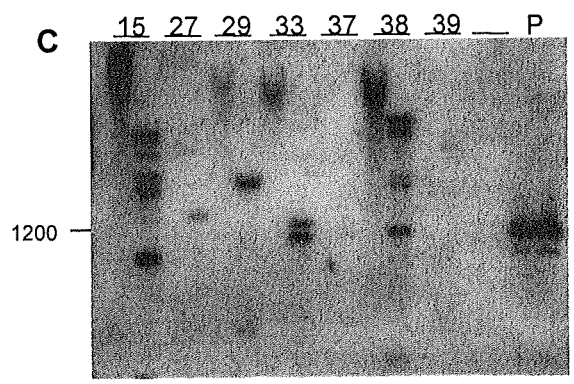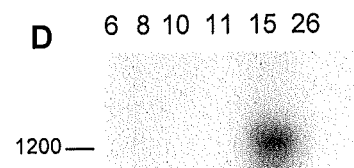
FIGURE 32

A
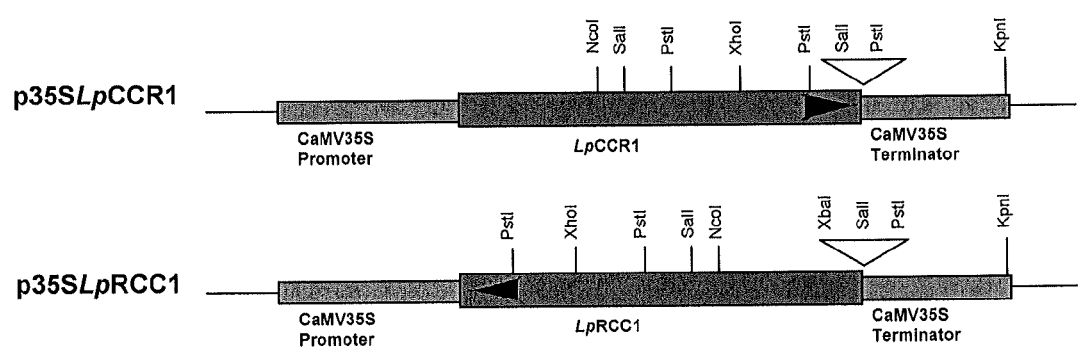
B
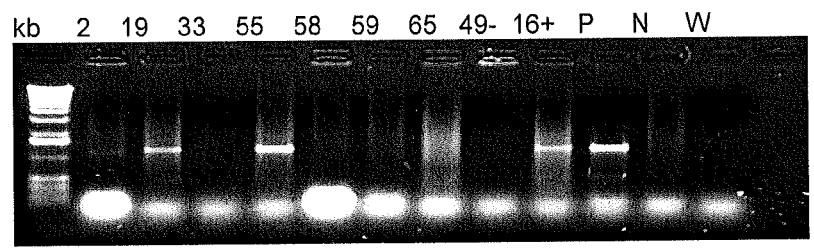
FIGURE 33

A
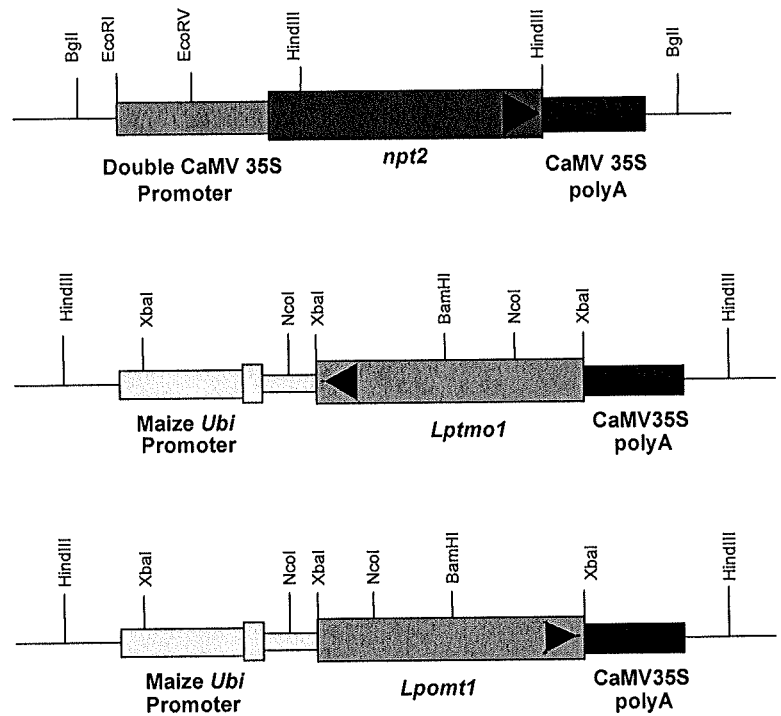
B
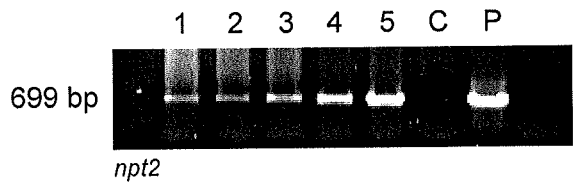
FIGURE 35

FIGURE 35 CONTINUED
C
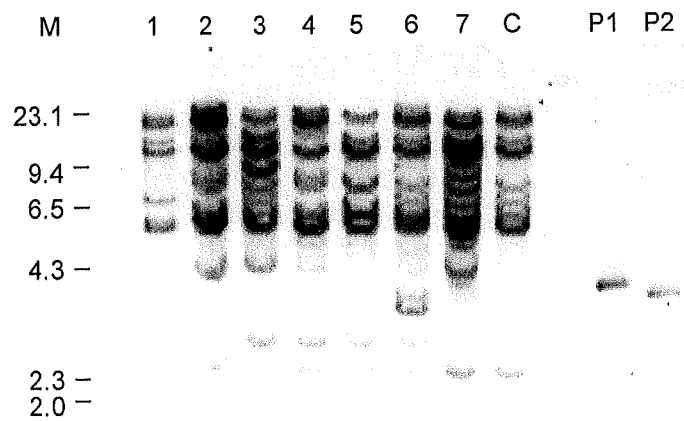
D
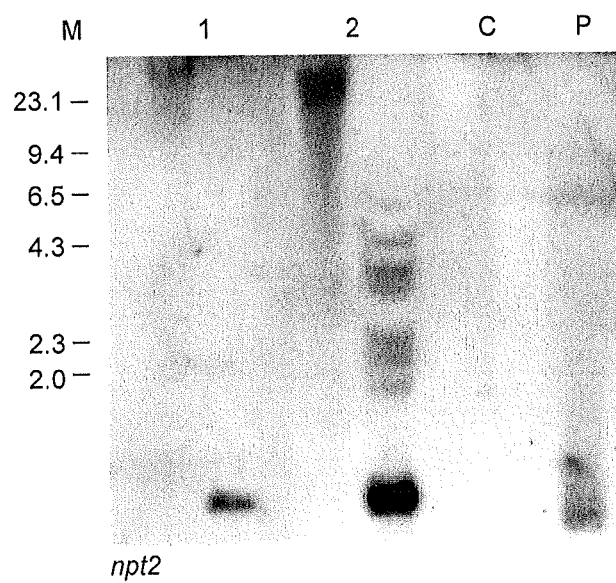
E
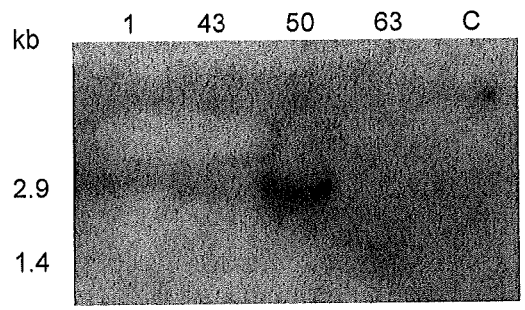

```
-2206  CGGGATCAACTTGGATGTCCTTTGCGGGCACGGTTTCAGGAACAACGACACATGCAGCAG
       ------+---------+---------+---------+---------+---------+---  -2147

-2146  GGATCTCCTCCAAAGACTCACACAAAGGTGACATGAGCGCCCGCTTTTTTGAAGCCAAGT
       ------+---------+---------+---------+---------+---------+---  -2087

-2086  TGGCTAAGAAATCGCAAAGCTTGGTGGAGTCGGCCACCTCAGGATCTGCAACAAAAGGCA
       ------+---------+---------+---------+---------+---------+---  -2027

-2026  CCAAGGGAGCTGCCAACACATCAACCACAACATCATGTTCAAACGCAGTCTCCTCAAGCC
       ------+---------+---------+---------+---------+---------+---  -1967

-1966  TCGAATGCTCAACCGAAAGAGAGGCAGAAGCTTCAACAAAAAACTCAGCCAACCCAAAGC
       ------+---------+---------+---------+---------+---------+---  -1907

-1906  CCTCGACGTCATCAGAGATTAGGCTCTGAGGACCCGCAGGGAAGCAACCTTGTCAACAAC
       ------+---------+---------+---------+---------+---------+---  -1847

-1846  CGCATCCGGCAGAAAAGGAGCAAGACCGGAGCAACCCTCAAGAGGCACACGAAAGACGTC
       ------+---------+---------+---------+---------+---------+---  -1787

-1786  GAAGCCAAGAGGAGACGAGTCGCAGGGACGGCGGACAGGCGAGAAGGGGCCGTAGAACTC
       ------+---------+---------+---------+---------+---------+---  -1727

-1726  CAAGAGCTCGGCGTCCCTCGACCTAGCATCCGAAGCACTGACCGGGGCACTCAATGCATA
       ------+---------+---------+---------+---------+---------+---  -1667

-1666  ACTTTATCTTGATGGCATATGTACTCAAACCCATACAATGTTCACCATGCATTATCTATG
       ------+---------+---------+---------+---------+---------+---  -1607

-1606  GAACATTCCTTCATATACAACTtCTGAGTGGTCAGTGCATAGGAATTTTCATTAACAACC
       ------+---------+---------+---------+---------+---------+---  -1547

-1546  AAAAACATACTTGGGGCCTACACACACTTTCACAGCATGGAAAACTTGTTAGCTTTTTAA
       ------+---------+---------+---------+---------+---------+---  -1487

-1486  AGAGTTGCAAAATCTGTCAAGCGAATGTTCTTGTGATAATTGGAACGAAGCATGTTTCCC
       ------+---------+---------+---------+---------+---------+---  -1427

-1426  CATTTTCAATGTGTGTCTCTTACCCTAACTAGCACCCGACCAACAAAATCTGACCATCCT
       ------+---------+---------+---------+---------+---------+---  -1367
```

FIGURE 38

```
              AGTTATATCATCATAGAGACCCACATGTAGGTTGACCCCCATAACACTTGTGTGGATATC
    -1366     ------+---------+---------+---------+---------+---------+---    -1307

ATGGAAAATGGCCTTGATCAACACTTTCTTTCCTACTTGGTACAAATGGTTATGGACTTA
    -1306     ------+---------+---------+---------+---------+---------+---    -1247

CTCAATTAGTGCTTTAGAGAGCTTTGGCTGCAGACTTTGTAGCTTCCCAATATTCATAGG
    -1246     ------+---------+---------+---------+---------+---------+---    -1187

TCCCTCCGGAGTGGGCAGCCCCATCTACATAGGCTCAAAACCAGATTTTTGTAACATGTT
    -1186     ------+---------+---------+---------+---------+---------+---    -1127

AGACACTTTCAACTTCATCATAGACCATCAAGGAGCTGGCATGTGACAGTGATATATGTA
    -1126     ------+---------+---------+---------+---------+---------+---    -1067

TCAATTACCCATTCAACACGAATAGCTTGCTCATGCATGGTTAGTCTTGCGGCGGCGGGG
    -1066     ------+---------+---------+---------+---------+---------+---    -1007

CGGGACCATCGAACACACCGCCGGGCGGTCAGTAGGCTAGGGTTAGATAAAATCTAGCCG
    -1006     ------+---------+---------+---------+---------+---------+---     -947

TTTTCATTCAAACTTGTGATATATAATCAAATTTAAATAAAAACCTTTATTTTCGTGCAT
     -946     ------+---------+---------+---------+---------+---------+---     -887

TTTTATTTATTTGAGGGCGTGTTTGGGGGACACGGCTGGAAAGTGACATCCCCAAACACT
     -886     ------+---------+---------+---------+---------+---------+---     -827

GCACGAAGAAAACGCGTCGCCAAAAAATTCGATCCGGCGTCAGTCCTTTGGGAGACGATT
     -826     ------+---------+---------+---------+---------+---------+---     -767

TGGATGACGCGGCTAGAGATGCTCTAAGTTCTCCACGCCATGTTTCTTTCTATATATACA
     -766     ------+---------+---------+---------+---------+---------+---     -707

CACAGCCCAAGGTCCATGAAAAGTAAAACGGCACGACGACACGCACCGGCGACAACTTCA
     -706     ------+---------+---------+---------+---------+---------+---     -647

CATTACGGCACATCGCTATTACGGACCACATACAACTCCACCGCTATTCTCAGCCAAGTC
     -646     ------+---------+---------+---------+---------+---------+---     -587

ATACATGACATGATCCAATGGACGACTTTGTGAGCGAAACTAGAACCTTGCGGGGTTTAG
     -586     ------+---------+---------+---------+---------+---------+---     -527

ATTTTCCAATGTGGATAAGTTGTACGCGCCGACTAGCTTTACACTTGGTTGAAAAAAGCT
     -526     ------+---------+---------+---------+---------+---------+---     -467
```

FIGURE 38 CONTINUED

```
        TATTGTAGCACGACTTCTCACTGACATAGGAATGTAAACAGTCTCTCCACGCCATGTTTC
-466    ------+---------+---------+---------+---------+---------+---    -407

TTTCTAGTAGTAGCATACTAGTAGTAACTTCTCTTTGTCCTACACACACCCAGGGTCCAA
-406    ------+---------+---------+---------+---------+---------+---    -347

GAAAGGAAAACGGCACGACGGCACCCACCGACGACGACGACTCCACATCACGGTTCGGTA
-346    ------+---------+---------+---------+---------+---------+---    -287

AAAAAAGTCAAAACTCGCTGACGTGGCACCACCGGTCGCAGTCAACTGACGCGCTCCTCT
-286    ------+---------+---------+---------+---------+---------+---    -227

GCGCAGGTyTCACTtCAAGTTTCACCTACCACTGTGGGCCCACCGCCAaTGTGGGCCCCG
-226    ------+---------+---------+---------+---------+---------+---    -167

CGAGCTtCTtACTCACTGACCTGTCTCCCACCAGCCTCCTCGCCGGTATATTACCCCGGC
-166    ------+---------+---------+---------+---------+---------+---    -107

CCCCAATTTCCTCTGCCTTCCCACGAGCAGCAGCCGGAGCACGGAATCCCGGCCGCCATT
-106    ------+---------+---------+---------+---------+---------+---     -47

CCTCCACCTTCAGCTCCGCCCAAAGATTTCCATCCGGCGAGATCCATGGGCTCCATCGCG
 -46    ------+---------+---------+---------+---------+---------+---      13
                                                      M   G   S   I   A

GCGGACGCGCCTCCCGCGGAGCTGGTGTTCCGGTCCAAGCTCCCGGACATCGAGATCCCG
  14    ------+---------+---------+---------+---------+---------+---      73
         A   D   A   P   P   A   E   L   V   F   R   S   K   L   P   D   I   E   I   P

ACCCACCTGACGCTGCAGGACTACTGCTTCCAGCGCCTGCCGGAGCTCTCCGCGCGCGCC
  74    ------+---------+---------+---------+---------+---------+---     133
         T   H   L   T   L   Q   D   Y   C   F   Q   R   L   P   E   L   S   A   R   A

TGCCTCATCGACGGCGCCACGGGCGCCGCGCTCACCTACGCCGACGTGGACGCCCTCACG
 134    ------+---------+---------+---------+---------+---------+---     193
         C   L   I   D   G   A   T   G   A   A   L   T   Y   A   D   V   D   A   L   T

CGCCGCTGCGCCGCGGGCCTCCGCCGCCTGGGGGTCCGCAAGGGCGACGTCGTCATGGCG
 194    ------+---------+---------+---------+---------+---------+---     253
         R   R   C   A   A   G   L   R   R   L   G   V   R   K   G   D   V   V   M   A

CTGCTCCGCAACTGCCCCGAGTTCGCCTTCGTGTTCCTCGGCGCCGCCCGGCTCGGCGCC
 254    ------+---------+---------+---------+---------+---------+---     313
         L   L   R   N   C   P   E   F   A   F   V   F   L   G   A   A   R   L   G   A
```

FIGURE 38 CONTINUED

```
     GCCACCACCACCGCCAACCCGTTCTACACGCCCCACGAGATCCACCGCCAGGCGACCGCC
314  ------+---------+---------+---------+---------+---------+---  373
     A  T  T  T  A  N  P  F  Y  T  P  H  E  I  H  R  Q  A  T  A

GCCGGGGCCAGGGTCATCGTCACCGAGGCCTGCGCCGTCGAGAAGGTGCGCGCCTTCGCC
374  ------+---------+---------+---------+---------+---------+---  433
     A  G  A  R  V  I  V  T  E  A  C  A  V  E  K  V  R  A  F  A

GCCGAGAGAG
434  ------+---  443
     A  E  R
```

FIGURE 38 CONTINUED

```
       TCGACGCGGCCGCGTAATACGACTCACTATAGGGCGAAGAATTCGGATCATATGGATTCG
-6735  -----+---------+---------+---------+---------+---------+----  -6676

ACACTGGAATTTACTCCCATCGGGAGCGTGCAAACAAAAAGGTGTTATAGCAAGAAGACA
-6675  -----+---------+---------+---------+---------+---------+----  -6616

CTGGCAACATTGCCAGCACAGAATTTGTTACAATCATAGAAAGTTTTATGACAGGACATT
-6615  -----+---------+---------+---------+---------+---------+----  -6556

GTTTCAACCGAAAGCAAGATTACAACAATATAATCAAGGGCTTGGGTCTGGTTGGACATG
-6555  -----+---------+---------+---------+---------+---------+----  -6496

CTCGGTCCAATGGACGATTTATTTGCCGAGACCAGCTCAAGGAGTTGACGAGCACACTTA
-6495  -----+---------+---------+---------+---------+---------+----  -6436

AGCGCCGAGATCTTAAAGGCACCCAAGTCAACAAGTCGCCCATCTTGCTCTTTTGGCAGC
-6435  -----+---------+---------+---------+---------+---------+----  -6376

TCCTTGGACATCTCTTCGATATTGGCTTTGAAGCCATGACCCATCATAAGCTGAAAGGCT
-6375  -----+---------+---------+---------+---------+---------+----  -6316

AGGAGGGCACCATAGGTACGCGAAGTACGTTTGAATACCTCGAGGACCTCCCTCGTGTTG
-6315  -----+---------+---------+---------+---------+---------+----  -6256

ATGGCGAAAGCATCGATCAGCTGCCCCAAGGTCTTGTTTTGATCGATCTTGGGGAAGATC
-6255  -----+---------+---------+---------+---------+---------+----  -6196

ATCGAGTGCATCCGCGTCATGGATCCTTTACCCTTCTGAAGGAGGTCCTGAAAAAGCTGG
-6195  -----+---------+---------+---------+---------+---------+----  -6136

TGAGACCCGAGGGTCATTGACAAAGCATTCGCCGGAGAATTATTCGGCAATTTATCTAGA
-6135  -----+---------+---------+---------+---------+---------+----  -6076

GCCTCAGCAGGGATGTAGGCAGCTTCTGGAGAAAGTGAAAGAGGAGGAGCTCACTAACCA
-6075  -----+---------+---------+---------+---------+---------+----  -6016

AAATCAAATCGATAAAGCAAAAATCGGAAAGGAGGCCAAAAGGGGATTACTGAGCAAGGC
-6015  -----+---------+---------+---------+---------+---------+----  -5956

CAAGGAAGATTGGCGAAGGAGCTCATCTTTTTCAATCGCCCGAGCTTCGGCAGCAAGCCT
-5955  -----+---------+---------+---------+---------+---------+----  -5896

GGATGCCTCTTCATCCTTCAGCCTCTTTCTTAGCCCCTCGAGCTCATCCTTAAAGGAATC
-5895  -----+---------+---------+---------+---------+---------+----  -5836

AACCTCCTGGCGGGCCTCGGCAGCTATCTTTATCGCACCCTCCAGCTTCGAGGAAGAAGA
-5835  -----+---------+---------+---------+---------+---------+----  -5776

CTCGACCTCCTTTTGCAGCCGAGTCTTGTCAACTTCCAGAGAAGTGTATTGGGAGGCGAA
-5775  -----+---------+---------+---------+---------+---------+----  -5716

GGCCTCCAGAGAAGAGATAACAGCTCACAAATCCTTAAGAGATAAGGAAAAATAATTAGA
-5715  -----+---------+---------+---------+---------+---------+----  -5656

CGAAGAACTGGTTGTCAACAAACTTATAATTTGATCAGGGAAATCGTCCCACATGGATAT
-5655  -----+---------+---------+---------+---------+---------+----  -5596

ATCGTTAAAACAGGAAAAGCTTACAGGTTTCCCTGGAGGAGAAGCTGTAACCACGGCAGT
-5595  -----+---------+---------+---------+---------+---------+----  -5536
```

FIGURE 39

```
        CAAAGAAATCTCCTTCCCTTTGGAAAGGGAAGAAGTTGTCGATATTTGAGCCATGGGGGC
-5535   -----+---------+---------+---------+---------+---------+----   -5476

TGCGGCAGGAGTCGAAGCCTCGGAAGCGGCTGGATTCGGCACGATGGCACCAGATTTGGC
-5475   -----+---------+---------+---------+---------+---------+----   -5416

CTTCTTGGCCGGAGGCTCGATGAAGCCATCTTCACTGCAAGAACAAAAAACTAGCGAAGT
-5415   -----+---------+---------+---------+---------+---------+----   -5356

CAGAATTCAATGCATATGGCGAAGTTAGAACACAATCCTGGAAAAGGAAGCAAGGACTTA
-5355   -----+---------+---------+---------+---------+---------+----   -5296

CAATTCATAGAGACCATCTTCATCGGCAAAGCCGCCGGATGATCTCTTTGGAGGTAGTGC
-5295   -----+---------+---------+---------+---------+---------+----   -5236

CTCGGCCTTTTCCGTAGCTGCATCAACAAAGGCAGCACGATCAGCATCGTCATCATGCAT
-5235   -----+---------+---------+---------+---------+---------+----   -5176

TGACCCCGCTGTATCGCTCATATCATCGGCAGAGAATCGAGGATTGATGGAAAAAGCCTC
-5175   -----+---------+---------+---------+---------+---------+----   -5116

AGGATTCATCGGATCATCATGTTGATCTATCGGGCTTGCATTCCCTAGAGTATGGGACCC
-5115   -----+---------+---------+---------+---------+---------+----   -5056

TACAAGGACTAAGGAATCCCTTTTCTTGGAAAAATTGTTCGACAGGTCTTGCAAACGTTC
-5055   -----+---------+---------+---------+---------+---------+----   -4996

AAGAGCCGTAAGGATCTGTCGTAGTTGACGAGTGAGAATAATGGCAGTTAAAATAATCAA
-4995   -----+---------+---------+---------+---------+---------+----   -4936

AGGAACATGACAATAAGAGCATAAAGGGGAAATTTACCTCGGTTGGCAGATGACCAGCGT
-4935   -----+---------+---------+---------+---------+---------+----   -4876

CAAATGGCGGTTGAGGAGATATCAGTGGAATTGAATCTTCCTGGCTAAAGAGGGTGAGAC
-4875   -----+---------+---------+---------+---------+---------+----   -4816

ACCGGACTTCGTCAAGCAGTTCTTTTTCGGATAATTCAGCAATATTTACTCTAGTCTCGT
-4815   -----+---------+---------+---------+---------+---------+----   -4756

CCCTGGGACCCGAATACAACCACATCGGATGGGTCCTAGACATGATCGGCTGAACTCGAT
-4755   -----+---------+---------+---------+---------+---------+----   -4696

GTTTTAAGAACACAGCGGCTACCTCAGTACCTATCATGGTTTGACCATCGGATTCTTTGA
-4695   -----+---------+---------+---------+---------+---------+----   -4636

TCCGAAGGAATCTATCAAATAACTTGTCTACTGTTGGTTTTTCATCGGGTGAGAGGATAT
-4635   -----+---------+---------+---------+---------+---------+----   -4576

TTTTCCAAGACTTCTTGGGCTTGCTTCTAGAACATCGGAGAATTGGGGGGGAGCTGGGAG
-4575   -----+---------+---------+---------+---------+---------+----   -4516

TCGGCTGCTGATGAGTCCTTAATATAAAACCACTTCAGCCTCCAGCCTTGCACGGATTCT
-4515   -----+---------+---------+---------+---------+---------+----   -4456

TTCATCGGGAAGTTGAAGTAGTTGACTTCCTTACGAGCAACAAAACCAACCCCACCAATG
-4455   -----+---------+---------+---------+---------+---------+----   -4396
```

FIGURE 39 CONTINUED

```
       ACGAAGGACCCACCACTGCTGTTATATCTTTTCACGAAGAAAATCTTCTTCCACAAACCA
-4395  -----+---------+---------+---------+---------+---------+----  -4336

AAGTGGGGCTCAATGCCCAAAAACGCTTCGCAGAGGGTGATAAAGATGGCAAGGTGAAGG
-4335  -----+---------+---------+---------+---------+---------+----  -4276

ATTGAGTTGGGGGTTAACTTCCATAATTGAATCTCATACACTCGAAGGAGGTGGTGAAGA
-4275  -----+---------+---------+---------+---------+---------+----  -4216

AATTTGTGAGCGGGAAGCGAAAGACCTCGGTACAAGAAGGATAAGAACATCACAGTAAAA
-4215  -----+---------+---------+---------+---------+---------+----  -4156

CCGGCAGGAGGATTGGGCCGTGAAATTGCACCTGGAAGAATAACATTCCCCTCGTCAGAA
-4155  -----+---------+---------+---------+---------+---------+----  -4096

GAAATTATTACGAGGCTCCGGGCCCTCTTTTCATCTCGCTTCGTGGTGGTAGAAGCTGGC
-4095  -----+---------+---------+---------+---------+---------+----  -4036

CAATCGCCAGGGATAGGCCCGGCCGTGGAGCTTGACGGCGCTGGCGGTGCCGGAGCTGAG
-4035  -----+---------+---------+---------+---------+---------+----  -3976

GGAGGAGCATCTGGCGCGCTTCTCCGCGGCGGATTCGAAGGAGCCCTGACGGTGGTGCCA
-3975  -----+---------+---------+---------+---------+---------+----  -3916

CTGCTCACGGCGCTGGTGGCGAGAGTGGGATTCTTCTTCTTCACCATTGTGAGATTTGAG
-3915  -----+---------+---------+---------+---------+---------+----  -3856

GGAGATCTGGGAGTTGCGACGGTGGCGTGGTAGTTGCAAACGAAAAGGATGAATGAGGAA
-3855  -----+---------+---------+---------+---------+---------+----  -3796

GAAGGGACGCAAGGATGAAGTGTGGAAAGGGGAGTTTACCCCAAGAGATTATAAAGTGAA
-3795  -----+---------+---------+---------+---------+---------+----  -3736

AGGAAAACCTGAGAATTGAGCGGGCACGTGTCGTTGCTCTCAATTTATTGAGGGGATTTT
-3735  -----+---------+---------+---------+---------+---------+----  -3676

TTCTCATCATAGATCGCGGAAATCGAGGAGTCACCTTGGTAACTGCACGCAAGTAGTGGT
-3675  -----+---------+---------+---------+---------+---------+----  -3616

CATTTCTTAAACAGAACCGCATAGAAGTAGGATGGGACCGTCAGGTCACGTCCTATCAGT
-3615  -----+---------+---------+---------+---------+---------+----  -3556

CAGATTTACAACAGTAATTACATCATCACTGACGTCAAAGTATGCTTGAAGTATCCGAAG
-3555  -----+---------+---------+---------+---------+---------+----  -3496

AAAAGTCGAAATTTGGGCTCGAAGACTTTCTTGCAGAGAAGCGCGTGAAAGGAATATCTA
-3495  -----+---------+---------+---------+---------+---------+----  -3436

AGGAAAGGGTCAAAACATTCGGCTCGAGTCTACGCACGGATTGCAAGCATCCGTACCTAG
-3435  -----+---------+---------+---------+---------+---------+----  -3376

ACTCGGGGGCTACTCCCATCGGGAGCGCTGGACGTGCACCCGATAAATTTAGACGAGGAT
-3375  -----+---------+---------+---------+---------+---------+----  -3316

GAAAACCGGAAACCCAAGTGCTACTCCCATCGGGAGCGCCGATTACGCACCCGACAAACT
-3315  -----+---------+---------+---------+---------+---------+----  -3256

TTTTTGCACTCCAGGATCATGCCCGGGGACTTAATTCTGTGTAGAGTAGCGTTGTTTTGT
-3255  -----+---------+---------+---------+---------+---------+----  -3196
```

FIGURE 39 CONTINUED

```
         CTTCGGCAGTTAACCAGCAAAGCTGGACACGTTACTCAATATCCTTTACGCATTAAACCC
-3195    -----+---------+---------+---------+---------+---------+----    -3136

TTACTTGAAGAATTGAAGCCCCGATGCAAATATATCGGATGACCTATGAAGGCCTGCGGA
-3135    -----+---------+---------+---------+---------+---------+----    -3076

AAGCTTCGGGAGAAGAAGACATTCGAGTGGCACAACTTGAGTCTACGAACGGATTGCAAG
-3075    -----+---------+---------+---------+---------+---------+----    -3016

CATCCGTACCTAGACTCGGGGGCTACTCCCATCGGGAGCGCTGGACTCGCACCCGATAGA
-3015    -----+---------+---------+---------+---------+---------+----    -2956

AGGAGATGATGATATTACAAGAAGGACAAGAAGTATCAAGGGAGAAGAACATTCGGTGGA
-2955    -----+---------+---------+---------+---------+---------+----    -2896

GGCATGCTTTAGTCTCTACCCGAAAAAACTTCGGCTAGACACTCGGGGGGCTACTGACGT
-2895    -----+---------+---------+---------+---------+---------+----    -2836

GGGCATTACCCTTCGGGTAACTGATATTGCCCTATCCTGTACGACCCAACTGGAGGCCCA
-2835    -----+---------+---------+---------+---------+---------+----    -2776

TGAAGACACTCGAAGGCAAGGTGGACCACTACGTCGGTGCCGAAGGGGGTTCCTTGAAGA
-2775    -----+---------+---------+---------+---------+---------+----    -2716

ACAAGACGAAGAAAAGAAGAATACAAGAAAAGTATAGAACTAGGATCTTTTGTAACCTGG
-2715    -----+---------+---------+---------+---------+---------+----    -2656

TCGTACCCGGACAGATCTCTCGAGACCTGGCCCCCTACATATGGGCTAGGAGAGGGGCTG
-2655    -----+---------+---------+---------+---------+---------+----    -2596

CCGAGAGGGACACACACAATCTTAGCAATTTTAGCCACCATAAGTCCAGAGCAAGGTCCC
-2595    -----+---------+---------+---------+---------+---------+----    -2536

CGTAGAACTTAGCCTCTCGACGAGATCACAGCCGAAACCTTCGGCACCCCATTGTAACCC
-2535    -----+---------+---------+---------+---------+---------+----    -2476

GATATTTTCATAGTCAAGATCAGACAGGTAGGACGTAAGGGTTTTACCTCATCGAGGGCC
-2475    -----+---------+---------+---------+---------+---------+----    -2416

CCGAACCTGGGTAAATCGCTCTCCCCGCTTGTTTGATAACCGATGGCTTGTGTCAGCTTA
-2415    -----+---------+---------+---------+---------+---------+----    -2356

CATGATTCCATCTACCCTAAACCTCAAACGGAGGGCATTGCCGAGGAGTACCCTCGACAT
-2355    -----+---------+---------+---------+---------+---------+----    -2296

TCCCCTCCACCAATGGTCTCACATAAATTCAACAAAGCAAACTCATAAAAAGTTTAATGA
-2295    -----+---------+---------+---------+---------+---------+----    -2236

GTTTCAGAAAGAAATAAAACTAGGCCCCTCCTTTGAGAATCTACGAATGATTCACCATAT
-2235    -----+---------+---------+---------+---------+---------+----    -2176

CATCTCGCAGTTAGTGATGAGTAACTAAGTCTCAAATTTCCCGACGCATGGCGAAAAAGG
-2175    -----+---------+---------+---------+---------+---------+----    -2116

TAGCGAACTTAAAATGTGAGGAATGAATGCCACATATGCATGGTGCATCGAGTATTCTCA
-2115    -----+---------+---------+---------+---------+---------+----    -2056

TTTTAGTCTTGGATTACTCCCTTTAGATGTTGACACCATCCCAAAAATACAACTTGGACA
-2055    -----+---------+---------+---------+---------+---------+----    -1996
```

FIGURE 39 CONTINUED

```
        AGTTGTTCATTTCACTAGTATGAATTTCAGTAAATCGGGCAATACTCCAACACTCATTCA
-1995   -----+---------+---------+---------+---------+---------+----   -1936

CCCCCTAGGCGAGGTTAGCTCAGATCAACGTCGGGTGTCTTCATCGAGTTAATGTCGTCA
-1935   -----+---------+---------+---------+---------+---------+----   -1876

CACGCACACACACGTACGCGCACACACACGTGCGCAAACAAAAAGAAAACTAGGAACCTT
-1875   -----+---------+---------+---------+---------+---------+----   -1816

CTCACGTAGCCTAGGTCTTGTCCTGTAAGAAAAAACCCAGGTCCACCCTAGTTTCGAACC
-1815   -----+---------+---------+---------+---------+---------+----   -1756

AAAATATTTTTGAAGATACATTAGTAAGATATTTTTGAAAATAAAACCGCAAAAAGGGAA
-1755   -----+---------+---------+---------+---------+---------+----   -1696

TTGAAAAATATGGACTGGCTGTTTTGTCCAAAACCACATCTTTCGGAGAACCACGAGGGT
-1695   -----+---------+---------+---------+---------+---------+----   -1636

ATCTATTGATGGGCTCATACTATACCTGGGCATGTGTTGGGCCAGGCCTCATGTCGGGCC
-1635   -----+---------+---------+---------+---------+---------+----   -1576

GAGGAAAGCCCGACGCTGAAAAATCAGGCCCAAGCTTAACCCGGCCCGACCAAATACCCA
-1575   -----+---------+---------+---------+---------+---------+----   -1516

CCAAACCCGTTGGGCCATCAGGTTGCGGGCCGGGCAGTAGTGTAAAACACCGATTTCGGG
-1515   -----+---------+---------+---------+---------+---------+----   -1456

CTACATAGGCCCGGCTCGTTTGTCGGGCAAACATTTCTAGACCTAAGCCCGAGTTTTTCG
-1455   -----+---------+---------+---------+---------+---------+----   -1396

GGCCGGGCTGCCCATGGCCAGGTATAGCTCATAACGACGTATGACATTTCGAGCAATTGA
-1395   -----+---------+---------+---------+---------+---------+----   -1336

TGCAAAGCACGTGTAGGGTTTTATCCCATCCGTGTGGCGTGTGTAGGGTGTAAATGAATA
-1335   -----+---------+---------+---------+---------+---------+----   -1276

GGATAATTTCCTCGCCGAAACTGGTCCCAAATTCGCTTTGAAGTGTCCATATATGATTTT
-1275   -----+---------+---------+---------+---------+---------+----   -1216

AAAGAATGTGACAAATAAAGATATCCAATTTCGAAATAGTGCTCCGGATACGGTATAGGA
-1215   -----+---------+---------+---------+---------+---------+----   -1156

TATGGTATAGCAAATAACATGCTGATATGGATTGTCCGATATTAAATTAAGATAATCCAA
-1155   -----+---------+---------+---------+---------+---------+----   -1096

ATGTTTTAAACCGCATAATTCGATTTTTGAGTCAAAAGCGAATGCCAATTCAGAAGGTTA
-1095   -----+---------+---------+---------+---------+---------+----   -1036

GCAGTTATTGAGTTTCAAAATTTATTTGGCGAGCATATCTAGTTCTAAATTCTATCACGT
-1035   -----+---------+---------+---------+---------+---------+----   -976

AAATTGTGTCTTTTTTTAATAACTACACAAGACTAAAAGTTTAAATCTCTCTCAAGATTT
-975    -----+---------+---------+---------+---------+---------+----   -916

GCGAAAACTATAGCTATCTACTGATATATATATCCGACTATATTTGTTTTCGGACCGCAT
-915    -----+---------+---------+---------+---------+---------+----   -856

GCGTCCTATTTCCGATTCGAATCTGCACTCCGATATATCCACATTGAATCTAAAACCGAT
-855    -----+---------+---------+---------+---------+---------+----   -796
```

FIGURE 39 CONTINUED

```
        CAATATTTGCTCCGATCTAAATCCGGAAAAATATGTGGTGAAGGATATGGTATAAGCAAA
-795    -----+---------+---------+---------+---------+---------+----    -736

ATCCGATTTGATCCATTTGTACCTCTAGGCGTGTGCAAGACCTGGAGGAAAGAATGGCGC
-735    -----+---------+---------+---------+---------+---------+----    -676

ATCTGTAGGGTGCAGTCCCACCGGTGGAAAATGTGAGCTCACCGTATTGTCCCCCGATGG
-675    -----+---------+---------+---------+---------+---------+----    -616

AGCATCGAAACGGAGTCGGAACACGATTTGCGCCACGTACAGAGCATGCATGATTTCCCT
-615    -----+---------+---------+---------+---------+---------+----    -556

TGTATGCGGTCCAGGATCTTAAACTGCCTTCCATTTCCAGGAACCTACCGATTGGCTGCA
-555    -----+---------+---------+---------+---------+---------+----    -496

AGCCGTAGCTAGCGGTTTGAAGTCACGGCATTGCCGCCCCGATTAACCCACCCGTCGCG
-495    -----+---------+---------+---------+---------+---------+----    -436

CGCGCGGTCGGTCGTTTCACCGTCCTGCCTAGGCTACGCACGCGCGCGCGCAGTTGGGCC
-435    -----+---------+---------+---------+---------+---------+----    -376

AGTTGTAGGTAAGCCGACTCGAGATCACACACCCGGCCTCACCTACTACCTCTCGCCGTC
-375    -----+---------+---------+---------+---------+---------+----    -316

GCGGTCACCGTGTCACACTCACGCCCAGGGGAGCCACCCGCCCACACGGCGCCTAGCTCA
-315    -----+---------+---------+---------+---------+---------+----    -256

TCCCCTCTCACTACTCTTCTTCTCCTCCCTCTCACCTCGCCGTCGACCCAGCTCCCGGCT
-255    -----+---------+---------+---------+---------+---------+----    -196

CTATAAATTCCGCACTACTCGAACCAACATCGCCCAGGCCTTTGCCTTTTACGACGAATC
-195    -----+---------+---------+---------+---------+---------+----    -136

CTACCAAACCGAGCTACCAGATCCTTCTCTACTAATCGAGCTCCCTACGCTGCTCCGCCT
-135    -----+---------+---------+---------+---------+---------+----    -76

GTCTTCGTTTCCGCCTCACCGCCGGCCGGTTCTCCGCTCCAAGCTACGTCCGTCCGTCCA
-75     -----+---------+---------+---------+---------+---------+----    -16

CATATATAGCATCGACATGACCATCGCCGAGGTCGTGGCTGCCGGAGACACCGCCGCCGC
-15     -----+---------+---------+---------+---------+---------+----     44
                        M  T  I  A  E  V  V  A  A  G  D  T  A  A  A

GGTGGTGCAGCCCGCCGGGAACGGGCAGACCGTGTGCGTGACCGGCGCCGCCGGGTACAT
45      -----+---------+---------+---------+---------+---------+----    104
         V  V  Q  P  A  G  N  G  Q  T  V  C  V  T  G  A  A  G  Y  I

CGCGTCGTGGCTCGTCAAGCTGCTGCTGGAGAAGGGGTACACCGTCAAGGGCACCGTCAG
105     -----+---------+---------+---------+---------+---------+----    164
         A  S  W  L  V  K  L  L  L  E  K  G  Y  T  V  K  G  T  V  R

GAACCCAGGCATGTCACCCATGCATTCATCATTTTCTTACTAGTCGTATGCGTTATGCGA
165     -----+---------+---------+---------+---------+---------+----    224
         N  P  G

CTTGTGTATTAACTATTGTGGACTGCATGCAGACGACCCGAAGAACGCGCACCTGAGGGC
225     -----+---------+---------+---------+---------+---------+----    284
                                              D  P  K  N  A  H  L  R  A
```

FIGURE 39 CONTINUED

```
           GCTCGACGGCGCCGCCGACCGGCTGGTCCTCTGCAAGGCCGACCTCCTCGACTACGACGC
  285      -----+---------+---------+---------+---------+---------+----    344
            L  D  G  A  A  D  R  L  V  L  C  K  A  D  L  L  D  Y  D  A

CATCCGCCGCGCCATCGACGGCTGCCACGGCGTCTTCCACACCGCGTCCCCCGTCACCGA
  345      -----+---------+---------+---------+---------+---------+----    404
            I  R  R  A  I  D  G  C  H  G  V  F  H  T  A  S  P  V  T  D

CGACCCCGTACGTACTCCATAGAACTCGGCACCCCTAGCTTCTCTCCGTTCTCTCTGTAT
  405      -----+---------+---------+---------+---------+---------+----    464
            D  P

GTCTGTCACCGTCGATCGCCATGGCAGCACGCATGCATGCGCGCGCAACGCTAGCTAGAC
  465      -----+---------+---------+---------+---------+---------+----    524

GCTGACCGACTCATTGTGCAGGAGCAAATGGTGGAGCCGGCGGTGAGGGGCACGCAGTAC
  525      -----+---------+---------+---------+---------+---------+----    584
                             E  Q  M  V  E  P  A  V  R  G  T  Q  Y

GTCATAGACGCGGCGGCGGAGGCCGGCACGGTGCGGCGGATGGTGCTCACCTCCTCCATC
  585      -----+---------+---------+---------+---------+---------+----    644
            V  I  D  A  A  A  E  A  G  T  V  R  R  M  V  L  T  S  S  I

GGCGCCGTCACCATGGACCCCAACCGCGGGCCGGACGTGGTCGTCGACGAGTCGTGCTGG
  645      -----+---------+---------+---------+---------+---------+----    704
            G  A  V  T  M  D  P  N  R  G  P  D  V  V  V  D  E  S  C  W

AGCGACCTCGACTTCTGCAAGAAAACCAGGGTGGGTGCTGCATGCTCAATTTTTATTATC
  705      -----+---------+---------+---------+---------+---------+----    764
            S  D  L  D  F  C  K  K  T  R

ATAGCTACCCTTTTTCTGCACCATGCTGCATTTCTTTTCCAAAAACAACTCTCAAAAGAT
  765      -----+---------+---------+---------+---------+---------+----    824

ATGCTACGTGGTGAGTTCCTATAGCTGAATTATTACAACTACCACCCTATCGATCACTAC
  825      -----+---------+---------+---------+---------+---------+----    884

CGCCCTAAAAGTGTTCAACTTTTGAAGGCAACCAAAACCAATACATGAACGACGATCGTG
  885      -----+---------+---------+---------+---------+---------+----    944

TGCGCTTGTCGTCGTTATCATTAGCCTCTGTAGCTCTAATTTTCACCTATGTACGCATGG
  945      -----+---------+---------+---------+---------+---------+----   1004

ATAGACGATTCGGAAATACAGTTCAGTTTACCTACCATATACTATGCCGAAATCGAACGC
 1005      -----+---------+---------+---------+---------+---------+----   1064

ACACAGGTGTGAGGCAGCAGCCGCTCACGAGTTATGCGCCGAAACCGACATCTCGGAATC
 1065      -----+---------+---------+---------+---------+---------+----   1124

TTCAGTCCACAATCAAAAAATAGACACCTGGTACCACTACAAAATTATACTCCTACTGTA
 1125      -----+---------+---------+---------+---------+---------+----   1184

TATTGGTAAAACAAAACATTTTCTTTTTTATTTGATAGGAGTGCTGCAAATTAAAGTTCT
 1185      -----+---------+---------+---------+---------+---------+----   1244

TTGTGTCATTTTTCAAAGGAAAAAAAAAACACCTTTACCACTCTTCTTCCTTGCCATCAT
 1245      -----+---------+---------+---------+---------+---------+----   1304
```

FIGURE 39 CONTINUED

```
     TTTTTTTTTTACCAAAGTTTGTTCTGTCAAATGAACATATATATAGTTCGGTGCTATGTCA
1305 -----+---------+---------+---------+---------+---------+----  1364

GTGCCATTTACCGGCCACTAGCTAGTAGGACTGCCATGTTCCAGCAAATTGTCTAGTGGA
1365 -----+---------+---------+---------+---------+---------+----  1424

CCGGAGTGGCCAAAAGGAGCCAATTATGTAGGGTTGCAAGCGGGATCACACAAAAGCCTC
1425 -----+---------+---------+---------+---------+---------+----  1484

GCCTCTAGTTCATTTTATCAATTAAGTGGTACTTTCTCAGGGACCCCCCTTGCAACTCTA
1485 -----+---------+---------+---------+---------+---------+----  1544

CCATTACATCCGTGCAAAATAAAAGCTAGCATCACGCACCAGATTTAGTACTCCCTCCGT
1545 -----+---------+---------+---------+---------+---------+----  1604

TTTTATTTAGTTCGCATTCTAGGTTCAGCCAAAGTCATACTTTGCAAAGTTTAACCAAAA
1605 -----+---------+---------+---------+---------+---------+----  1664

TTATAAGAAAAAAATATCAATAATCATCATACAAAATACATATAATATAAGAGTAAACCT
1665 -----+---------+---------+---------+---------+---------+----  1724

TATAACGATTCTACAATAGATTTTTTTATTGCATATGTCAATATTTTTTCATAAATATTT
1725 -----+---------+---------+---------+---------+---------+----  1784

ACTCAAAATTATAAGGTTTGACTTTGACTAAACCCAGAACCTTCTTAGAGAGGAAGAAAT
1785 -----+---------+---------+---------+---------+---------+----  1844

GCATGGGCAAAAGCAAATCATGCATATGGGCAGGAGTAACATTTTTTTGACTTTCATAGA
1845 -----+---------+---------+---------+---------+---------+----  1904

AAGTACTGTATGGCACTAAACGGTCTAAACCGGACACTGGAAGCAAATCGTGCACGTGGG
1905 -----+---------+---------+---------+---------+---------+----  1964

CAATATTATCTACCGTCGCGTCGCCAGTCTCCCCATGCCCATGACCATGCTTGGAATTTT
1965 -----+---------+---------+---------+---------+---------+----  2024

AGTCTCGCCGGAGCTGCCGAGTGCATGCATAGTGACGAGTTTCAATAGGCCACTATATAT
2025 -----+---------+---------+---------+---------+---------+----  2084

GTGATCATGGCTCTTGATTTGTCACTTTCTTTTTTTGCCGAAGGATATAGTAGTATTACT
2085 -----+---------+---------+---------+---------+---------+----  2144

TTCTCTGCTATCACAAAGAAAGAACTGATTGTGTCTAGTCTAGGTGGTCTCAGAATTCTG
2145 -----+---------+---------+---------+---------+---------+----  2204

CATGACTCCAGAGTATTCTTGATGCCACTTGTTTGTTATTGCAAGAAACTTAATTCGGAG
2205 -----+---------+---------+---------+---------+---------+----  2264

ACAACCAAAAGCTCATCCCATGTCTCTGGAACTAGTAGACATAAGAAAATCTCATGGTAT
2265 -----+---------+---------+---------+---------+---------+----  2324

CAGTTTGCTATTTATCTACAACTGAAACGGCATGTTTGGTTTTATTAAATTCAGAACTGG
2325 -----+---------+---------+---------+---------+---------+----  2384
                                                              N  W

TACTGCTACGGGAAGGCGGTTGCGGAGCAGGCGGCATCGGAGTTGGCGCGGCAGCGCGGC
2385 -----+---------+---------+---------+---------+---------+----  2444
      Y  C  Y  G  K  A  V  A  E  Q  A  A  S  E  L  A  R  Q  R  G
```

FIGURE 39 CONTINUED

```
       GTGGACCTTGTGGTGGTGAACCCGGTGCTGGTGATCGGCCCCCTGCTGCAGCCGACGGTG
2445   -----+---------+---------+---------+---------+---------+----   2504
        V  D  L  V  V  V  N  P  V  L  V  I  G  P  L  L  Q  P  T  V

AACGCCAGCATCGGCCACATCCTCAAGTACCTGGACGGGTCGGCCAGCAAGTTCGCCAAC
2505   -----+---------+---------+---------+---------+---------+----   2564
        N  A  S  I  G  H  I  L  K  Y  L  D  G  S  A  S  K  F  A  N

GCCGTGCAGGCGTACGTGGACGTCCGCGACGTGGCCGACGCCCACCTCCGCGTCTTCGAG
2565   -----+---------+---------+---------+---------+---------+----   2624
        A  V  Q  A  Y  V  D  V  R  D  V  A  D  A  H  L  R  V  F  E

TGCGCCGCCGCGTCCGGCCGCCACCTCTGCGCCGAGCGCGTCCTCCACCGCGAGGACGTC
2625   -----+---------+---------+---------+---------+---------+----   2684
        C  A  A  A  S  G  R  H  L  C  A  E  R  V  L  H  R  E  D  V

GTGCGCATCCTCGCCAAGCTCTTCCCCGAGTACCCCGTCCCCACCAGGTACGCGTACGAC
2685   -----+---------+---------+---------+---------+---------+----   2744
        V  R  I  L  A  K  L  F  P  E  Y  P  V  P  T  R

CTGCTTGCTAGCCGCTTCCGTTAATTCCATTGCCTTAATTGATTGCATGATGCCGCTCCT
2745   -----+---------+---------+---------+---------+---------+----   2804

AATTTACTCACTTGCGTAACTAATTGCATTCATATATGATCTACCAACCGTGGAGAAAAT
2805   -----+---------+---------+---------+---------+---------+----   2864

TAGCAAGAGTCTGTCGGGGCGTCCCGGTCCAGTGCAGTTAACCTGCATGTCGATGGTCTG
2865   -----+---------+---------+---------+---------+---------+----   2924

CAGGTTGCAGCTTACTTGTGGTTCTTTAGTTCAGAGACACAGAGCAATTGGGCACTAAGC
2925   -----+---------+---------+---------+---------+---------+----   2984

AAAACTGACATCACTGGTAATTAGGTAGCTCCCACACACTGAAGTGGGTGGATCCCATCG
2985   -----+---------+---------+---------+---------+---------+----   3044

GTAGTAGGTAAGGGTGGATAGTACTGGACGAGAGCTCGATCGTTGTTGTAAAAAAGCGAG
3045   -----+---------+---------+---------+---------+---------+----   3104

TGACCACCACTTCACCATCCACTGCAAGTAGCTGCTAGTGAACCATCCAACCAGCTCCCT
3105   -----+---------+---------+---------+---------+---------+----   3164

GGATCACTCTGCTCCGTCCGTACCTTCAGCTACCTACAGAAGCGACATGAACACACAGAC
3165   -----+---------+---------+---------+---------+---------+----   3224

ACACAAGGCCGGCTCACCATTCGCATAGGTCAAACCAAATGTTGGTGAACGGCAACATCG
3225   -----+---------+---------+---------+---------+---------+----   3284

CCACAAGTCGCGTGCTAGTTCGAGGTTGTGTCCGGTGTACCGAGGCCACACTATTCGTGC
3285   -----+---------+---------+---------+---------+---------+----   3344

TGCCCGTCGCTGATATTTGCACGCGTAGCTGTCGACGAAAGTAGGTGGACTGACAGATAC
3345   -----+---------+---------+---------+---------+---------+----   3404

ACATATCCTCATTGCCTTCTCTGCTCGGTTTCTGCTAGGATTGCCATCTTCAGGAGTGCC
3405   -----+---------+---------+---------+---------+---------+----   3464

TATCCGCACGGCAGAAACGCGTAGCATCAGGCCAGAAAGCAGCGTGCGTGATATCGTAAC
3465   -----+---------+---------+---------+---------+---------+----   3524
```

FIGURE 39 CONTINUED

```
       CCAGACGGTCTTCACCTGTCCATTCTGGGCTACCTGGCATACTACCTCGGTGCCGCTGTG
3525   -----+---------+---------+---------+---------+---------+----    3584

CCGCTGACCAATTCGTGCACGACCACTATAGCAAAACCCTATGCATGTAACTGCTTCAAG
3585   -----+---------+---------+---------+---------+---------+----    3644

ATCAGCAGTGACATGTGCAATATAAACCTCAAGTGTGCACTCTAGTGCGTACTGATAAAA
3645   -----+---------+---------+---------+---------+---------+----    3704

CCGTATAACTGGTGACCCAGTCATTCTTCTCTTTTTTATTTGTTTGGACCAAACGAACAC
3705   -----+---------+---------+---------+---------+---------+----    3764

AGCATGTTATCCATCACCAACAAGTGGCGCTGATTTTTCAAACTACACTGGGATCATACT
3765   -----+---------+---------+---------+---------+---------+----    3824

GGAAACCAAAGCAGGAGAACATCTTCGAACCAAGAGATGTTTACTAAATTTGAAAGAAAA
3825   -----+---------+---------+---------+---------+---------+----    3884

TGTACTGACAAGTAATCTGTCTGAAGCAAGACACATACTACCTCGGTTCGAACGTGGGAC
3885   -----+---------+---------+---------+---------+---------+----    3944

ACCATGCCCGTGCCATATTTGCTAGGCACCACTCTGCCGTCGATTGTATCCCAACGGAGG
3945   -----+---------+---------+---------+---------+---------+----    4004

GAGTATCGATTTGCGCAAAGTTCCTACATACATAGCCGCTCAAGATATAATCTTACGACC
4005   -----+---------+---------+---------+---------+---------+----    4064

TTCCGTCGAAATCGGTGATACGTCGCAACCTATAGCTAACTTGGCAGAGCATAAAATAAC
4065   -----+---------+---------+---------+---------+---------+----    4124

TATCTAAGGTTGGGGTCTCCCTCTTTTCAATCAACCTTTCATACCGAATGATGGGAGTGT
4125   -----+---------+---------+---------+---------+---------+----    4184

TTGTGAAAACATCTCTTGGTCGACTCAGCATTAGCGCCCTACCAATTTCTCTGTGGACAA
4185   -----+---------+---------+---------+---------+---------+----    4244

TGCCACCTTAAATCGTTTTTTAGTCTTCATGATTTACTCCCCCTTATATCTGGCCGTAGT
4245   -----+---------+---------+---------+---------+---------+----    4304

CCCTCTTTTCCATTTTTCTTGTCTGGTTTTAAGTCAAATTTAGACTACTAAAACAACAGC
4305   -----+---------+---------+---------+---------+---------+----    4364

AAGATTTTATGGAAGGGAGGTAGTGCAAAACAGAAAGTCCGATCGAAATGCGTGCCAATT
4365   -----+---------+---------+---------+---------+---------+----    4424

TGTCGTCGCGGCGGCCGGACTAAAATGGATCTGCATGTGCATACCGTTCGTCGGAGTATC
4425   -----+---------+---------+---------+---------+---------+----    4484

CTGCGAACGGTCGTGTGTTTAGTCAACATTAATGTGAGGTTCATGTGATACTCTTGCTTG
4485   -----+---------+---------+---------+---------+---------+----    4544

AAAGATACTACTACTGCTACCTCGTAGAACTGAATGAAAGTATGTGGGACTGTTCAGCTC
4545   -----+---------+---------+---------+---------+---------+----    4604

TCTGCACATGTCAAATGTCGTTACTCATACCTTTCGTCAGAGCATCCTGCGACGCGCGCC
4605   -----+---------+---------+---------+---------+---------+----    4664

GGTGCCGAAATTTCGCCGTGTGTTTAGTCAAGATCAACGTGAGGTTCATGCGGTACCCTA
4665   -----+---------+---------+---------+---------+---------+----    4724
```

FIGURE 39 CONTINUED

```
      TCTGGCTTCGAAGATACCAAGCAGACTGCGGCTAGATTGTCATTTTGATGTCGCAATCTT
4725  -----+---------+---------+---------+---------+---------+----  4784

CACCAAACCTGCCCTTCCGGACCACAGCAGCAGTACGTAACAATGGTGTCATCGCCATGC
4785  -----+---------+---------+---------+---------+---------+----  4844

GTTGCTCGTGTCCAAGGAAACGGAGGAATCTCGGCTTCCCACAAGTCACGCATCGATGTT
4845  -----+---------+---------+---------+---------+---------+----  4904

CACACCTGAATTGGTCGACGTTTCTTCTTCTAGACTAGAAAAAGATTACAGAACAACGCA
4905  -----+---------+---------+---------+---------+---------+----  4964

AGCTTCGTTCAAGTCCATACTTCTGTTCAGTATACTCCTGATGATTGCAGTTATATCAGC
4965  -----+---------+---------+---------+---------+---------+----  5024

ATGTCTATTCTGAATTTTTGCACTTCTATTCAAAGGATGGGCTGGAATTGCTACTGACTT
5025  -----+---------+---------+---------+---------+---------+----  5084

TGGTGTGATGTGTGTGGCACAGGTGCTCTGATGAGACGAACCCGAGGAAGCAGCCATACA
5085  -----+---------+---------+---------+---------+---------+----  5144
                                 C  S  D  E  T  N  P  R  K  Q  P  Y  K

AGATGTCGAACCAGAAGCTCCAGGACCTCGGACTCGAGTTCAGGCCGGTGAGCCAGTCCC
5145  -----+---------+---------+---------+---------+---------+----  5204
       M  S  N  Q  K  L  Q  D  L  G  L  E  F  R  P  V  S  Q  S  L

TGTACGAGACGGTGAAGAGCCTCCAGGAGAAGGGCCACCTTCCGGTGCTCAGCGAGCAGG
5205  -----+---------+---------+---------+---------+---------+----  5264
       Y  E  T  V  K  S  L  Q  E  K  G  H  L  P  V  L  S  E  Q  A

CAGAGGCGGACAAGGAAACCCTAGCTGCCGAGCTGCAGGCAGGGGTTACCATCCGAGCAT
5265  -----+---------+---------+---------+---------+---------+----  5324
       E  A  D  K  E  T  L  A  A  E  L  Q  A  G  V  T  I  R  A  *

GAGGAACAAGAAATCAACCATGTCCATACTGCTACTGTCATGTAAACCAGCTGTTGAATG
5325  -----+---------+---------+---------+---------+---------+----  5384

CCTAAAATCTAAGTTCTTGTAATACTGTGTTGTTTCATGTGGACTAGATTGATCG
5385  -----+---------+---------+---------+---------+---------   5439
```

FIGURE 39 CONTINUED

LpCCR1 cDNA sequence
Deleted base
ATGACCATCGCCGAG

Modified forward primer sequence
CAAGTTTGTACAAAAAAGCAGGCTATGACCATCGCGAG
*Att*B1 site                        Start site

FIGURE 47

SEQUENCE LISTING

```
<160> NUMBER OF SEQ ID NOS: 18

<210> SEQ ID NO 1
<211> LENGTH: 2284
<212> TYPE: DNA
<213> ORGANISM: Lolium perenne
```

```
<400> SEQUENCE: 1
cggcacgagt ggactttccg acgccggagt cgccgatgat gaccgccttg aggaggtagt      60
cgtagtcgtc ctccgccctg tacgcgccgc tgcccgccat ttccttcctc gcctcgcggg     120
tcctcctccc cgacctgcgc taggctctgg atctcgcggg gtttgggcgc ggcgtcctcg     180
ctgtgagctc gtgccgaatt cggcacgagc caccttcgag gcgtgcactg gtacgagctc     240
gcgagccatt gtcagtgcag tgtaggctct gctactcgtt ggccattcca agaagctctc     300
tgctccctga aaccagagga tcatgatcac ggtggcggcg cccgaggtgc agcagccgca     360
gatcgcggcg gctgctgcgg ccgtggaggc ggcggcaccg gaggcgacga cgatcttccg     420
gtccaggctc ccggacatcg acatcccgac ccacatgccc ctgcacgact attgcttcgc     480
gacggcagcc tcggcccggg acgcgccgtg cctcatcacc gcggccacgg ggaagaccta     540
cacgttcgcc gagacgcacc tgctgtgccg caaggccgcg gcggcgctgc acgggctcgg     600
cgtgcgccac ggggaccgga tcatgctgct gctccagaac tccgtggagt tcgcgctcgc     660
cttcttcggc gcgtccatgc tcggcgccgt cagcacggcg gcgaacccgt tctgcacgcc     720
gcaggagatc cacaagcagc tcgtggcctc cggcgcgaag ctggtcgtca cgcagtccgc     780
ctacgtcgac aagctccggc acgaggcctt ccccccgaatc ggcgaggccc tcaccgtgat     840
caccatcgac gaggacgacg caccccggga cggctgccag ccgttctggg ccctcgtgtc     900
agccgccgac gagaacagcg tcccggagtc tcccatctcg ccggacgacg cggtggcgct     960
gccctactcg tcgggcacga cggggctgcc caagggcgtg gtgctgacgc acgggggggct    1020
ggtgtcgagc gtggcgcagc aggtggacgg cgagaacccg aacctgcaca tgcgggcggg    1080
ggaggacgtg gtgctctgcg tgctgccgct cttccacatc ttctcgctca actcggtgct    1140
gctgtgcgcg ctgcgggcgg gcgccgccgt gatgctgatg cctaggttcg agatgggggc    1200
catgctggag ggcatcgagc ggtggcgcgt cacggtggcg gccgtggtgc cgccgctggt    1260
gctcgcgctc gccaagaacc ccggggtgga aagcacgac ctcagctcca ttcggatcgt    1320
gctctccggc gccgcgccgc tcggcaagga gctcgaggac gcgctacgtg gccgcctgcc    1380
gcaggccatc ttcggacagg gctacgggat gacggaggcc gggccggtgc tgtccatgtg    1440
cccggcgttc gcgcgggagc cgacgccggc caagtccggc tcgtgcggca ccgtggtgcg    1500
caacgcccag ctcaaggtgg tcgacccccga caccggcgtc tccctcggcc gcaacctccc    1560
cggcgagatc tgcatccgcg gcccgcagat catgaaagga tacttgaatg atcccgtggc    1620
cacggccgcg accatcgacg tcgaggggtg gctccacacc ggcgacatcg gctacgtcga    1680
cgacgacgac gaggtcttca tcgtcgaccg cgtcaaggag ctcatcaagt tcaagggctt    1740
ccaggtaccg ccggccgagc tcgaggctct gctcatcgcg catccgtcca tcgccgacgc    1800
ggccgtcgtc ccgcaaaagg atgatgccgc cggcgaggtc ccggttgcct tcgtggtccg    1860
cgccgccgac tccgacatcg ccgaggaggc catcaaggag ttcgtatcca agcaggtggt    1920
gttctacaag aggctgcaca aggtctactt cacccacgcg atacccaagt cggcgtcggg    1980
gaagatactc aggaaagaac tcagagctaa actcgccgcc ccggccactg cctgaagagt    2040
ggttcatggc ttcatgctaa tcatttcgat cagaaaggca cttctagcat atatgttcca    2100
ccttttgttt catttggaag attgtattcc agctagtggc cagtgactga gtaagggatg    2160
gggataaaag ttttgtctac gttttctttt acgctactct ctccattggg gagtacaatg    2220
tatcagggga ttcgtgattg aagttaatca agattggttc aattataaaa aaaaaaaaa     2280
aaaa                                                                 2284
```

<210> SEQ ID NO 2
<211> LENGTH: 606
<212> TYPE: PRT
<213> ORGANISM: Lolium perenne

<400> SEQUENCE: 2

```
Met Ile Thr Val Ala Ala Pro Glu Val Gln Pro Gln Ile Ala Ala
1               5                   10                  15

Ala Ala Ala Val Glu Ala Ala Pro Glu Ala Thr Thr Ile Phe
            20                  25                  30

Arg Ser Arg Leu Pro Asp Ile Asp Ile Pro Thr His Met Pro Leu His
        35                  40                  45

Asp Tyr Cys Phe Ala Thr Ala Ala Ser Ala Pro Asp Ala Pro Cys Leu
    50                  55                  60

Ile Thr Ala Ala Thr Gly Lys Thr Tyr Thr Phe Ala Glu Thr His Leu
65                  70                  75                  80

Leu Cys Arg Lys Ala Ala Ala Leu His Gly Leu Gly Val Arg His
                85                  90                  95

Gly Asp Arg Ile Met Leu Leu Gln Asn Ser Val Glu Phe Ala Leu
                100                 105                 110

Ala Phe Phe Gly Ala Ser Met Leu Gly Ala Val Ser Thr Ala Ala Asn
    115                 120                 125

Pro Phe Cys Thr Pro Gln Glu Ile His Lys Gln Leu Val Ala Ser Gly
    130                 135                 140

Ala Lys Leu Val Val Thr Gln Ser Ala Tyr Val Asp Lys Leu Arg His
145                 150                 155                 160

Glu Ala Phe Pro Arg Ile Gly Glu Ala Leu Thr Val Ile Thr Ile Asp
                165                 170                 175

Glu Asp Asp Gly Thr Pro Asp Gly Cys Gln Pro Phe Trp Ala Leu Val
                180                 185                 190

Ser Ala Ala Asp Glu Asn Ser Val Pro Glu Ser Pro Ile Ser Pro Asp
            195                 200                 205

Asp Ala Val Ala Leu Pro Tyr Ser Ser Gly Thr Thr Gly Leu Pro Lys
210                 215                 220

Gly Val Val Leu Thr His Gly Gly Leu Val Ser Ser Val Ala Gln Gln
225                 230                 235                 240

Val Asp Gly Glu Asn Pro Asn Leu His Met Arg Ala Gly Glu Asp Val
                245                 250                 255

Val Leu Cys Val Leu Pro Leu Phe His Ile Phe Ser Leu Asn Ser Val
            260                 265                 270

Leu Leu Cys Ala Leu Arg Ala Gly Ala Ala Val Met Leu Met Pro Arg
        275                 280                 285

Phe Glu Met Gly Ala Met Leu Glu Gly Ile Glu Arg Trp Arg Val Thr
    290                 295                 300

Val Ala Ala Val Val Pro Pro Leu Val Leu Ala Leu Ala Lys Asn Pro
305                 310                 315                 320

Gly Val Glu Lys His Asp Leu Ser Ser Ile Arg Ile Val Leu Ser Gly
                325                 330                 335

Ala Ala Pro Leu Gly Lys Glu Leu Glu Asp Ala Leu Arg Gly Arg Leu
            340                 345                 350

Pro Gln Ala Ile Phe Gly Gln Gly Tyr Gly Met Thr Glu Ala Gly Pro
        355                 360                 365

Val Leu Ser Met Cys Pro Ala Phe Ala Arg Glu Pro Thr Pro Ala Lys
```

```
                    370                 375                 380
Ser Gly Ser Cys Gly Thr Val Val Arg Asn Ala Gln Leu Lys Val Val
385                 390                 395                 400

Asp Pro Asp Thr Gly Val Ser Leu Gly Arg Asn Leu Pro Gly Glu Ile
                405                 410                 415

Cys Ile Arg Gly Pro Gln Ile Met Lys Gly Tyr Leu Asn Asp Pro Val
            420                 425                 430

Ala Thr Ala Ala Thr Ile Asp Val Glu Gly Trp Leu His Thr Gly Asp
            435                 440                 445

Ile Gly Tyr Val Asp Asp Asp Glu Val Phe Ile Val Asp Arg Val
        450                 455                 460

Lys Glu Leu Ile Lys Phe Lys Gly Phe Gln Val Pro Pro Ala Glu Leu
465                 470                 475                 480

Glu Ala Leu Leu Ile Ala His Pro Ser Ile Ala Asp Ala Ala Val Val
                485                 490                 495

Pro Gln Lys Asp Asp Ala Ala Gly Glu Val Pro Val Ala Phe Val Val
                500                 505                 510

Arg Ala Ala Asp Ser Asp Ile Ala Glu Glu Ala Ile Lys Glu Phe Val
                515                 520                 525

Ser Lys Gln Val Val Phe Tyr Lys Arg Leu His Lys Val Tyr Phe Thr
            530                 535                 540

His Ala Ile Pro Lys Ser Ala Ser Gly Lys Ile Leu Arg Lys Glu Leu
545                 550                 555                 560

Arg Ala Lys Leu Ala Ala Pro Ala Thr Ala Arg Val Val His Gly Phe
                565                 570                 575

Met Leu Ile Ile Ser Ile Arg Lys Ala Leu Leu Ala Tyr Met Phe His
                580                 585                 590

Leu Leu Phe His Leu Glu Asp Cys Ile Pro Ala Ser Gly Gln
            595                 600                 605

<210> SEQ ID NO 3
<211> LENGTH: 1992
<212> TYPE: DNA
<213> ORGANISM: Lolium perenne

<400> SEQUENCE: 3
cggcacgagc gccattcctc caccttcagc tccggccaaa gatttccatc cggcgagatc    60
catgggctcc atcgcggcgg acgcgcctcc cgcggagctg gtgttccggt ccaagctccc   120
ggacatcgag atcccgaccc acctgacgct gcaggactac tgcttccagc gcctgccgga   180
gctctccgcg cgcgcctgcc tcatcgacgg cgccacgggc gccgcgctca cctacggcga   240
ggtggacgcc ctgtcccgcc gctgcgccgc ggggctgcgc cgcctcggcg tcggcaaggg   300
cgacgtcgtc atggcgctcc tccgcaactg ccccgagttc gccttcgtgt tcctcggcgc   360 ggccccggctc ggcgccgcca ccaccaccgc caacccgttc tacacgcccc acgagatcca   420
ccgccaggcc accgccgccg gggccagggt catcgtcacc gaggcctgcg ccgtcgagaa   480
ggtgcgcgcc ttcgccgccg agagagggat cccgtcgtc tccgtcgacg agggcgtcga   540
cggcggctgc ctcccgttcg ccgagactct gctcggggaa gaaagcgggg agcggttcgt   600
cgacgaggcg gtcgaccccg acgacgtggt ggcgctgccg tactcgtccg gcaccaccgg   660
cctgcccaag gcgtcatgc tcacccaccg cagcctcgtc accagcgtcg cccagcaggt   720
ggacggtgag aacccgaacc tgcacttcag ctcgtcggac gtgctgctgt gcgtgctgcc   780
gctgttccac atctactcgc tcaactcggt gctgctcgcc ggtctccgcg ccgggtgcgc   840
```

-continued

```
gatcgtgatc atgcgcaagt tcgaccacgg cgcgctggtg gacctggtgc gcacgcacgg    900
cgtcaccgtg gcgccattcg tgccgcccat cgtggtggaa atcgccaaga gcgcgcgggt    960
gaccgccgcg gacctggcgt ccatccggct ggtcatgtcg ggggcggcgc ccatgggcaa   1020
ggagctgcag gacgcgttca tggccaagat ccccaacgcc gtgctcggcc agggatatgg   1080
gatgaccgag gccggccctg tgctggcgat gtgcctggcc ttcgccaagg agccgttcgc   1140
ggtcaagtcc ggttcctgcg caccgtcgt caggaacgcc gagctcaaga tcgtcgaccc   1200
cgacaccggc gcctccctcg gccgcaacct gccgggggag atctgcatcc gcggcaagca   1260
gatcatgaaa ggttacctaa atgatccggt ggccacaaag aacaccattg acaaggacgg   1320
ttggctgcat actggtgaca ttggttatgt cgatgatgac gacgagatct ttattgtcga   1380
cagactgaag gagataatta aatataaggg attccaagta cctccggcgg aacttgaagc   1440
ccttctcatt acacaccctg aaatcaagga tgctgctgtc gtatcgatgc aagacgaact   1500
tgctggtgaa gttccggttg cgtttgttgt gcggactgag ggttcagaga tcagcgaaaa   1560
cgagatcaag cagttcgttg caaaagaggt tgttttctac aagaggatct gcaaagtgtt   1620
cttcgcggat tccattccaa agagtccatc tggcaagatc ctcaggaagg acctgagagc   1680
aaagctcgcc gcaggcattc ccagcagtaa taccacacag tccaaaagct aagtcagata   1740
tattgttttcc aaccttaca cacctctgtc aacaccatg taatgttctt aatataaacg    1800
gaaattatta catatagaag ggctgattct ttttactaga tgtgtccaac atatgatatg   1860
cttgttaggc cgatgatgtg taacctgtca tgtatagata ccgccttttt ttgacaagaa   1920
aggctgatta taatgtatac cgtgaactga atatttgttc agggagatca aaaaaaaaaa   1980
aaaaaaaaaa aa                                                       1992
```

<210> SEQ ID NO 4
<211> LENGTH: 556
<212> TYPE: PRT
<213> ORGANISM: Lolium perenne

<400> SEQUENCE: 4

```
Met Gly Ser Ile Ala Ala Asp Ala Pro Pro Ala Glu Leu Val Phe Arg
1               5                   10                  15

Ser Lys Leu Pro Asp Ile Glu Ile Pro Thr His Leu Thr Leu Gln Asp
                20                  25                  30

Tyr Cys Phe Gln Arg Leu Pro Glu Leu Ser Ala Arg Ala Cys Leu Ile
            35                  40                  45

Asp Gly Ala Thr Gly Ala Ala Leu Thr Tyr Gly Glu Val Asp Ala Leu
        50                  55                  60

Ser Arg Arg Cys Ala Ala Gly Leu Arg Arg Leu Gly Val Gly Lys Gly
65                  70                  75                  80

Asp Val Val Met Ala Leu Leu Arg Asn Cys Pro Glu Phe Ala Phe Val
                85                  90                  95

Phe Leu Gly Ala Ala Arg Leu Gly Ala Ala Thr Thr Thr Ala Asn Pro
            100                 105                 110

Phe Tyr Thr Pro His Glu Ile His Arg Gln Ala Thr Ala Ala Gly Ala
            115                 120                 125

Arg Val Ile Val Thr Glu Ala Cys Ala Val Glu Lys Val Arg Ala Phe
        130                 135                 140

Ala Ala Glu Arg Gly Ile Pro Val Val Ser Val Asp Glu Gly Val Asp
145                 150                 155                 160
```

-continued

Gly Gly Cys Leu Pro Phe Ala Glu Thr Leu Leu Gly Glu Glu Ser Gly
                165                 170                 175

Glu Arg Phe Val Asp Glu Ala Val Asp Pro Asp Val Val Ala Leu
            180                 185                 190

Pro Tyr Ser Ser Gly Thr Thr Gly Leu Pro Lys Gly Val Met Leu Thr
            195                 200                 205

His Arg Ser Leu Val Thr Ser Val Ala Gln Gln Val Asp Gly Glu Asn
        210                 215                 220

Pro Asn Leu His Phe Ser Ser Asp Val Leu Cys Val Leu Pro
225                 230                 235                 240

Leu Phe His Ile Tyr Ser Leu Asn Ser Val Leu Leu Ala Gly Leu Arg
                245                 250                 255

Ala Gly Cys Ala Ile Val Ile Met Arg Lys Phe Asp His Gly Ala Leu
            260                 265                 270

Val Asp Leu Val Arg Thr His Gly Val Thr Val Ala Pro Phe Val Pro
        275                 280                 285

Pro Ile Val Val Glu Ile Ala Lys Ser Ala Arg Val Thr Ala Ala Asp
290                 295                 300

Leu Ala Ser Ile Arg Leu Val Met Ser Gly Ala Ala Pro Met Gly Lys
305                 310                 315                 320

Glu Leu Gln Asp Ala Phe Met Ala Lys Ile Pro Asn Ala Val Leu Gly
                325                 330                 335

Gln Gly Tyr Gly Met Thr Glu Ala Gly Pro Val Leu Ala Met Cys Leu
            340                 345                 350

Ala Phe Ala Lys Glu Pro Phe Ala Val Lys Ser Gly Ser Cys Gly Thr
            355                 360                 365

Val Val Arg Asn Ala Glu Leu Lys Ile Val Asp Pro Asp Thr Gly Ala
        370                 375                 380

Ser Leu Gly Arg Asn Leu Pro Gly Glu Ile Cys Ile Arg Gly Lys Gln
385                 390                 395                 400

Ile Met Lys Gly Tyr Leu Asn Asp Pro Val Ala Thr Lys Asn Thr Ile
                405                 410                 415

Asp Lys Asp Gly Trp Leu His Thr Gly Asp Ile Gly Tyr Val Asp Asp
            420                 425                 430

Asp Asp Glu Ile Phe Ile Val Asp Arg Leu Lys Glu Ile Ile Lys Tyr
        435                 440                 445

Lys Gly Phe Gln Val Pro Pro Ala Glu Leu Glu Ala Leu Leu Ile Thr
            450                 455                 460

His Pro Glu Ile Lys Asp Ala Val Val Ser Met Gln Asp Glu Leu
465                 470                 475                 480

Ala Gly Glu Val Pro Val Ala Phe Val Val Arg Thr Glu Gly Ser Glu
                485                 490                 495

Ile Ser Glu Asn Glu Ile Lys Gln Phe Val Ala Lys Glu Val Val Phe
            500                 505                 510

Tyr Lys Arg Ile Cys Lys Val Phe Phe Ala Asp Ser Ile Pro Lys Ser
        515                 520                 525

Pro Ser Gly Lys Ile Leu Arg Lys Asp Leu Arg Ala Lys Leu Ala Ala
530                 535                 540

Gly Ile Pro Ser Ser Asn Thr Thr Gln Ser Lys Ser
545                 550                 555

<210> SEQ ID NO 5
<211> LENGTH: 2038
<212> TYPE: DNA

<213> ORGANISM: Lolium perenne

<400> SEQUENCE: 5

```
cggcacgaga tctcccacga ctaatttaga agaagattta cttagtctct gcttctcgct      60
cgatcgccgg ccggtgaggt agctagctag ctactcgtac tagaccatta ccatgggttc     120
cgtgccggag gagtcagtgg tggcggtggc accggcggag acggtgttcc ggtcgaagct     180
ccccgacatc gagatcaaca acgagcagac gctgcagagc tactgcttcg agaagatggc     240
cgaggtcgcg tcccgcccct gcatcatcga cggccagacg ggcgcctcct acacctacac     300
ggaggtcgac tccctgaccc gtcgcgccgc ggcggggctg cgccgcatgg gcgtgtgggaa     360
gggcgacgtg gtgatgaacc tgctgcgcaa ctgcccggag ttcgccttct ccttcctggg     420
cgcggcgcgg ctgggcgccg ccaccaccac cgccaacccg ttctacaccc cgcacgagat     480
ccaccgccag gcggaggcgg cgggcgccaa gctgatcgtg accgaggcct cgccgtgga    540
gaaggtgctg gagttcgcgg cggggcgggg cgtgcccgtg gtcaccgtcg acggggaggcg     600
cgacgggtgc gtggacttcg cggagctgat cgccggcgag gagctgcccg aggcggacga     660
ggccggggtc ctccccgacg acgtcgtcgc cctgccctac tcctccggca ccacgggct     720
ccccaagggc gtcatgctca cccaccgcag cctcgtcacc agcgtcgccc agctggtcga    780
cgggtcgaac cctaacgtgt gcttcaacaa ggacgacgcg ctgctgtgcc tgctgccgct     840
cttccacatc tactcgctgc acacggtgct gctggcgggg ctccgcgtcg cgccgccat     900
cgtcatcatg cgcaagttcg acgtcggcgc gctggtggac ctcgtccgcg cgcaccgcat     960
caccatcgcg ccattcgtgc cgcccatcgt cgtggagatc gccaagagcg accgcgtcgg    1020
cgccgacgac ctcgcatcca tccgcatggt gctctccggc gccgcgccca tgggcaagga    1080
cctccaggac gccttcatgg ccaagatccc caacgccgtg ctcggacagg ggtacgggat    1140
gaccgaggct gggccggtgc tggccatgtg cctggcgttc gccaaggagc cgttcaaggt    1200
caagtccggg tcgtgcggaa ccgtggtgcg caacgccgag ctcaaggtcg tcgaccccga    1260
caccggcgca tccctcggcc ggaaccagcc tggcgagatt tgcgtccggg ggaagcagat    1320
catgataggt tacctgaacg acccagagtc gaccaagaac accatcgaca aggacggctg    1380
gctgcacacc ggagacatcg gcttggtgga tgacgacgac gagatcttca tcgtcgacag    1440
gctcaaggag atcatcaagt acaagggctt ccaagtggcg ccggcggagc tcgaggccct    1500
cctcctcacg aacccggagg tcaaggacgc cgccgtcgta ggggtgaagg atgatctctg    1560
cggcgaagtc ccggtcgcct tcattaagag gatcgaagga tctgagatca acgagaacga    1620
gatcaagcaa ttcgtctcaa aggaggttgt tttctacaag aggatcaaca aggtctactt    1680
caccgactcc attcccaaga acccttccgg caagatccta aggaaggact tgagagccag    1740
gctcgccgct ggcatcccca ccgaagttgc cgcgccgaga agctaagggc cgcttctcag    1800
gaacgcagtc acccatggtg ctgtttaggt gctgttatag accacaccaa atggggaaag    1860
aaactacggg aggggatcat attattgttg caggagatat cagtttgttg attcgccctg    1920
cttgtgtaat gttgataaaa tgaaatgata taatagatgt gttgttttat tttttgacca    1980
tgtaagaaca aggctgtttt atacactact tatttttgaa aaaaaaaaa aaaaaaa        2038
```

<210> SEQ ID NO 6
<211> LENGTH: 557
<212> TYPE: PRT
<213> ORGANISM: Lolium perenne

<400> SEQUENCE: 6

```
Met Gly Ser Val Pro Glu Ser Val Ala Val Ala Pro Ala Glu
1               5                   10                  15

Thr Val Phe Arg Ser Lys Leu Pro Asp Ile Glu Ile Asn Asn Glu Gln
            20                  25                  30

Thr Leu Gln Ser Tyr Cys Phe Glu Lys Met Ala Glu Val Ala Ser Arg
        35                  40                  45

Pro Cys Ile Ile Asp Gly Gln Thr Gly Ala Ser Tyr Thr Tyr Thr Glu
    50                  55                  60

Val Asp Ser Leu Thr Arg Arg Ala Ala Gly Leu Arg Arg Met Gly
65                  70                  75                  80

Val Gly Lys Gly Asp Val Val Met Asn Leu Leu Arg Asn Cys Pro Glu
                85                  90                  95

Phe Ala Phe Ser Phe Leu Gly Ala Ala Arg Leu Gly Ala Ala Thr Thr
                100                 105                 110

Thr Ala Asn Pro Phe Tyr Thr Pro His Glu Ile His Arg Gln Ala Glu
            115                 120                 125

Ala Ala Gly Ala Lys Leu Ile Val Thr Glu Ala Cys Ala Val Glu Lys
        130                 135                 140

Val Leu Glu Phe Ala Ala Gly Arg Gly Val Pro Val Val Thr Val Asp
145                 150                 155                 160

Gly Arg Arg Asp Gly Cys Val Asp Phe Ala Glu Leu Ile Ala Gly Glu
                165                 170                 175

Glu Leu Pro Glu Ala Asp Glu Ala Gly Val Leu Pro Asp Asp Val Val
            180                 185                 190

Ala Leu Pro Tyr Ser Ser Gly Thr Thr Gly Leu Pro Lys Gly Val Met
        195                 200                 205

Leu Thr His Arg Ser Leu Val Thr Ser Val Ala Gln Leu Val Asp Gly
210                 215                 220

Ser Asn Pro Asn Val Cys Phe Asn Lys Asp Asp Ala Leu Leu Cys Leu
225                 230                 235                 240

Leu Pro Leu Phe His Ile Tyr Ser Leu His Thr Val Leu Leu Ala Gly
                245                 250                 255

Leu Arg Val Gly Ala Ala Ile Val Ile Met Arg Lys Phe Asp Val Gly
            260                 265                 270

Ala Leu Val Asp Leu Val Arg Ala His Arg Ile Thr Ile Ala Pro Phe
        275                 280                 285

Val Pro Pro Ile Val Val Glu Ile Ala Lys Ser Asp Arg Val Gly Ala
    290                 295                 300

Asp Asp Leu Ala Ser Ile Arg Met Val Leu Ser Gly Ala Ala Pro Met
305                 310                 315                 320

Gly Lys Asp Leu Gln Asp Ala Phe Met Ala Lys Ile Pro Asn Ala Val
                325                 330                 335

Leu Gly Gln Gly Tyr Gly Met Thr Glu Ala Gly Pro Val Leu Ala Met
            340                 345                 350

Cys Leu Ala Phe Ala Lys Glu Pro Phe Lys Val Lys Ser Gly Ser Cys
        355                 360                 365

Gly Thr Val Val Arg Asn Ala Glu Leu Lys Val Val Asp Pro Asp Thr
    370                 375                 380

Gly Ala Ser Leu Gly Arg Asn Gln Pro Gly Glu Ile Cys Val Arg Gly
385                 390                 395                 400

Lys Gln Ile Met Ile Gly Tyr Leu Asn Asp Pro Glu Ser Thr Lys Asn
                405                 410                 415
```

```
Thr Ile Asp Lys Asp Gly Trp Leu His Thr Gly Asp Ile Gly Leu Val
            420                 425                 430
Asp Asp Asp Glu Ile Phe Ile Val Asp Arg Leu Lys Glu Ile Ile
        435                 440                 445
Lys Tyr Lys Gly Phe Gln Val Ala Pro Ala Glu Leu Glu Ala Leu Leu
    450                 455                 460
Leu Thr Asn Pro Glu Val Lys Asp Ala Ala Val Val Gly Val Lys Asp
465                 470                 475                 480
Asp Leu Cys Gly Glu Val Pro Val Ala Phe Ile Lys Arg Ile Glu Gly
                485                 490                 495
Ser Glu Ile Asn Glu Asn Glu Ile Lys Gln Phe Val Ser Lys Glu Val
            500                 505                 510
Val Phe Tyr Lys Arg Ile Asn Lys Val Tyr Phe Thr Asp Ser Ile Pro
        515                 520                 525
Lys Asn Pro Ser Gly Lys Ile Leu Arg Lys Asp Leu Arg Ala Arg Leu
    530                 535                 540
Ala Ala Gly Ile Pro Thr Glu Val Ala Ala Pro Arg Ser
545                 550                 555

<210> SEQ ID NO 7
<211> LENGTH: 1395
<212> TYPE: DNA
<213> ORGANISM: Lolium perenne

<400> SEQUENCE: 7
ggcacgagga atcctaccaa accgagctac cagatccttc tctactaatc gagctcccta        60
cgctgctccg cctgtcttcg tttccgcctc accgccggcc ggttctccgc tccaagctac       120
gtccgtccgt ccacatatat agcatcgaca tgaccatcgc cgaggtcgtg gctgccggag       180
acaccgccgc cgcggtggtg cagcccgccg ggaacgggca gaccgtgtgc gtgaccggcg       240
ccgccgggta catcgcgtcg tggctcgtca agctgctgct ggagaagggg tacaccgtca       300
agggcaccgt caggaaccca gacgacccga agaacgcgca cctgagggcg ctcgacggcg       360
ccgccgaccg gctggtcctc tgcaaggccg acctcctcga ctacgacgcc atcgccgcg       420 ccatcgacgg ctgccacggc gtcttccaca ccgcgtcccc cgtcaccgac gaccccgagc       480
aaatggtgga gccggcggtg aggggcacgc agtacgtcat agacgcggcg gcggaggccg       540
gcacggtgcg gcggatggtg ctcacctcct ccatcggcgc cgtcaccatg gaccccaacc       600
gcgggccgga cgtggtcgtc gacgagtcgt gctggagcga cctcgacttc tgcaagaaaa       660
ccaggaactg gtactgctac gggaaggcgg ttgcggagca ggcggcatcg gagttggcgc       720
ggcagcgcgg cgtggacctt gtggtggtga accggtgct ggtgatcggc cccctgctgc       780
agccgacggt gaacgccagc atcggccaca tcctcaagta cctggacggg tcggccagca       840
agttcgccaa cgccgtgcag gcgtacgtgg acgtccgcga cgtggccgac gcccacctcc       900
gcgtcttcga gtcgccgcc cgtccggcc gccacctctg cgccgagcgc gtcctccacc       960
gcgaggacgt cgtgcgcatc ctcgccaagc tcttccccga gtacccgtc cccaccaggt      1020 gctctgatga gacgaacccg aggaagcagc catacaagat gtcgaaccag aagtccagg       1080 acctcggact cgagttcagg ccggtgagcc agtccctgta cgagacggtg aagagcctcc      1140
aggagaaggg ccaccttccg gtgctcagcg agcaggcaga ggcggacaag gaaaccctag      1200
ctgccgagct gcaggcaggg gttaccatcc gagcatgagg aacaagaaat caaccatgtc      1260
catactgcta ctgtcatgta aaccagctgt tgaatgccta aaatctaagt tcttgtaata      1320
```
ctgtgttgtt tcatgtggac tagattgatc gaataaacat ctctacacaa ggttgctaaa    1380
aaaaaaaaaa aaaaa    1395

<210> SEQ ID NO 8
<211> LENGTH: 362
<212> TYPE: PRT
<213> ORGANISM: Lolium perenne

<400> SEQUENCE: 8

Met Thr Ile Ala Glu Val Val Ala Ala Gly Asp Thr Ala Ala Val
1               5                   10                  15

Val Gln Pro Ala Gly Asn Gly Gln Thr Val Cys Val Thr Gly Ala Ala
            20                  25                  30

Gly Tyr Ile Ala Ser Trp Leu Val Lys Leu Leu Glu Lys Gly Tyr
        35                  40                  45

Thr Val Lys Gly Thr Val Arg Asn Pro Asp Asp Pro Lys Asn Ala His
    50                  55                  60

Leu Arg Ala Leu Asp Gly Ala Ala Asp Arg Leu Val Leu Cys Lys Ala
65                  70                  75                  80

Asp Leu Leu Asp Tyr Asp Ala Ile Arg Arg Ala Ile Asp Gly Cys His
                85                  90                  95

Gly Val Phe His Thr Ala Ser Pro Val Thr Asp Asp Pro Glu Gln Met
            100                 105                 110

Val Glu Pro Ala Val Arg Gly Thr Gln Tyr Val Ile Asp Ala Ala Ala
        115                 120                 125

Glu Ala Gly Thr Val Arg Arg Met Val Leu Thr Ser Ser Ile Gly Ala
130                 135                 140

Val Thr Met Asp Pro Asn Arg Gly Pro Asp Val Val Asp Glu Ser
145                 150                 155                 160

Cys Trp Ser Asp Leu Asp Phe Cys Lys Lys Thr Arg Asn Trp Tyr Cys
                165                 170                 175

Tyr Gly Lys Ala Val Ala Glu Gln Ala Ala Ser Glu Leu Ala Arg Gln
            180                 185                 190

Arg Gly Val Asp Leu Val Val Val Asn Pro Val Leu Val Ile Gly Pro
        195                 200                 205

Leu Leu Gln Pro Thr Val Asn Ala Ser Ile Gly His Ile Leu Lys Tyr
    210                 215                 220

Leu Asp Gly Ser Ala Ser Lys Phe Ala Asn Ala Val Gln Ala Tyr Val
225                 230                 235                 240

Asp Val Arg Asp Val Ala Asp Ala His Leu Arg Val Phe Glu Cys Ala
                245                 250                 255

Ala Ala Ser Gly Arg His Leu Cys Ala Glu Arg Val Leu His Arg Glu
            260                 265                 270

Asp Val Val Arg Ile Leu Ala Lys Leu Phe Pro Glu Tyr Pro Val Pro
        275                 280                 285

Thr Arg Cys Ser Asp Glu Thr Asn Pro Arg Lys Gln Pro Tyr Lys Met
    290                 295                 300

Ser Asn Gln Lys Leu Gln Asp Leu Gly Leu Glu Phe Arg Pro Val Ser
305                 310                 315                 320

Gln Ser Leu Tyr Glu Thr Val Lys Ser Leu Gln Glu Lys Gly His Leu
                325                 330                 335

Pro Val Leu Ser Glu Gln Ala Glu Ala Asp Lys Glu Thr Leu Ala Ala
            340                 345                 350

Glu Leu Gln Ala Gly Val Thr Ile Arg Ala

<210> SEQ ID NO 9
<211> LENGTH: 1325
<212> TYPE: DNA
<213> ORGANISM: Lolium perenne

<400> SEQUENCE: 9

```
ggcacgagca acaagtcatc aatggcggaa ggcttgccgg cgctcggttg ggctgcgagg    60
gacgcctccg gtcacctctc cccttacagc ttctcgagaa gcgttccgaa ggacgacgat   120
gtgacgatca aggtgctctt ctgcgggatc tgccacactg acctccacat catcaagaac   180
gactggggca acgccctcta ccccatcgtc ccagggcatg agatcgtggg cgtcgtcgcc   240
agcgtcggca gcggcgtcag cagcttcaag gccggcgaca cggtgggcgt gggctacttc   300
ctcgactcct gccgcacctg ctacagctgc agcaaggggt acgagaactt ctgccccacc   360
ctgacgctca cctccaacgg cgtcgacggc ggcggcgcca ccacccaggg cggcttctcc   420
gacgtcctcg tcgtcaacaa ggactacgtc atccgcgtcc cggacaacct gcccctggcc   480
ggcgcggcac ctctcctctg cgccggcgtc acagtctaca gccctatggt ggagtacggc   540
ctcaacgccc ccgggaagca cytcggcgtc gtcggcctgg cgggctcgg ccacgtcgcc    600
gtcaagttcg gcaaggcctt cgggatgacc gtcaccgtca tcagctcctc ggacaggaag   660
cgcgacgagg cgctcggccg cctcggcgcc gacgccttcc tcgtcagcag cgaccccgag   720
cagatgaagg cggcggcggg caccatggac ggcatcatcg acacggtgtc cgcgggccac   780
ccgatcgtgc cgctgctcga cctgctcaag cccatggggc agatggtcgt ggtgggcgcg   840
cccagcaagc cgctcgagct cccggccttc gccatcatcg gcggcggcaa cgcctcgcc    900
gggagcggca ccggcagcgt cgcacactgc caggccatgc tcgacttcgc gggcaagcac   960
ggcatcaccg ccgacgtcga ggtcgtcaag atggactacg tcaacaccg ccatcgagcg   1020
gctagagaag aacgacgtca ggtaccgctt cgtcatcgac gtcgccggca gccacctgca  1080
gggcaccgcc gcttaacttg tgctacacaa tgtggacgcg cgctcgtttg gtccagaaaa  1140
aggttcgccg gctcacagcc acatgaacaa gtcaatgagt cgttggtgtg ttgtttatct  1200
tcattccaca tatgggacgc agttccagat tttcatgtca ataattgcg tcgtgtgcgg   1260
ttgtcaagac tcaaatagga gaaaaaaga ctcgtgattt cgttttgcaa aaaaaaaaa   1320
aaaaa                                                              1325
```

<210> SEQ ID NO 10
<211> LENGTH: 407
<212> TYPE: PRT
<213> ORGANISM: Lolium perenne
<220> FEATURE:
<221> NAME/KEY: MISC_FEATURE
<222> LOCATION: (181)..(181)
<223> OTHER INFORMATION: any amino acid

<400> SEQUENCE: 10

```
Met Ala Glu Gly Leu Pro Ala Leu Gly Trp Ala Ala Arg Asp Ala Ser
1               5                   10                  15

Gly His Leu Ser Pro Tyr Ser Phe Ser Arg Ser Val Pro Lys Asp Asp
            20                  25                  30

Asp Val Thr Ile Lys Val Leu Phe Cys Gly Ile Cys His Thr Asp Leu
        35                  40                  45

His Ile Ile Lys Asn Asp Trp Gly Asn Ala Leu Tyr Pro Ile Val Pro
    50                  55                  60
```

```
Gly His Glu Ile Val Gly Val Ala Ser Val Ser Gly Val Ser
 65                  70                  75                  80

Ser Phe Lys Ala Gly Asp Thr Val Gly Val Gly Tyr Phe Leu Asp Ser
                 85                  90                  95

Cys Arg Thr Cys Tyr Ser Cys Ser Lys Gly Tyr Glu Asn Phe Cys Pro
                100                 105                 110

Thr Leu Thr Leu Thr Ser Asn Gly Val Asp Gly Gly Ala Thr Thr
                115                 120                 125

Gln Gly Gly Phe Ser Asp Val Leu Val Asn Lys Asp Tyr Val Ile
130                 135                 140

Arg Val Pro Asp Asn Leu Pro Leu Ala Gly Ala Pro Leu Leu Cys
145                 150                 155                 160

Ala Gly Val Thr Val Tyr Ser Pro Met Val Glu Tyr Gly Leu Asn Ala
                165                 170                 175

Pro Gly Lys His Xaa Gly Val Val Gly Leu Gly Gly Leu Gly His Val
                180                 185                 190

Ala Val Lys Phe Gly Lys Ala Phe Gly Met Thr Val Thr Val Ile Ser
                195                 200                 205

Ser Ser Asp Arg Lys Arg Asp Glu Ala Leu Gly Arg Leu Gly Ala Asp
210                 215                 220

Ala Phe Leu Val Ser Ser Asp Pro Gln Met Lys Ala Ala Gly
225                 230                 235                 240

Thr Met Asp Gly Ile Ile Asp Thr Val Ser Ala Gly His Pro Ile Val
                245                 250                 255

Pro Leu Leu Asp Leu Leu Lys Pro Met Gly Gln Met Val Val Val Gly
                260                 265                 270

Ala Pro Ser Lys Pro Leu Glu Leu Pro Ala Phe Ala Ile Ile Gly Gly
                275                 280                 285

Gly Lys Arg Leu Ala Gly Ser Gly Thr Gly Ser Val Ala His Cys Gln
                290                 295                 300

Ala Met Leu Asp Phe Ala Gly Lys His Gly Ile Thr Ala Asp Val Glu
305                 310                 315                 320

Val Val Lys Met Asp Tyr Gly Gln His Arg His Arg Ala Ala Arg Glu
                325                 330                 335

Glu Arg Arg Gln Val Pro Leu Arg His Arg Arg Arg Gln Pro Pro
                340                 345                 350

Ala Gly His Arg Arg Leu Thr Cys Ala Thr Gln Cys Gly Arg Ala Leu
                355                 360                 365

Val Trp Ser Arg Lys Arg Phe Ala Gly Ser Gln Pro His Glu Gln Val
                370                 375                 380

Asn Glu Ser Leu Val Cys Cys Leu Ser Ser Phe His Ile Trp Asp Ala
385                 390                 395                 400

Val Pro Asp Phe His Val Lys
                405

<210> SEQ ID NO 11
<211> LENGTH: 1378
<212> TYPE: DNA
<213> ORGANISM: Lolium perenne
<220> FEATURE:
<221> NAME/KEY: misc_feature
<222> LOCATION: (870)..(870)
<223> OTHER INFORMATION: any nucleotide

<400> SEQUENCE: 11
```

```
ggcacgagtc gcctccaacg tcttcccta accggccgtc cctacgcttg caccaccacc        60
acgcacagac agagcagttt cccagccccc gccggaaccg gatggcaccc acggcggcgg       120
agcagacgga gcaccaccag cacaccagga aggcggtggg gctggcggcg cgcgacgacg       180
ccggccacct ctccccgctc gccatcacac ggaggagcac aggagacgac gatgtggtga       240
taaagatttt gtactgcgga atctgccact ctgacctgca cgccctgaag aacgactgga       300
agaactcaag gtaccgatg atccccgggc acgagatcgc cggcgaggtc acggaggtgg       360
gcaagaacgt gagcaagttc aaggccggcg accgcgtggg cgtcgggtgc atggtgaact       420
cgtgccggtc gtgcgagagc tgcgacaagg gcttcgagaa ccactgcccg ggcatgatcc       480
tcacctacaa ctcggtcgac gtcgacggca ccgtcaccta cggcggctac tccagcatgg       540
tggtggtgca cgagcggttc gtggtccggt tccccgacgc catgccgctg acaagggcg       600 cgccgctgct gtgcgccggc atcaccgtgt acagccccat gaagtaccac gggctcaacg       660
ttcccgggct gcacctcggc gtgctggggc tgggcgggct gggccacgtt gcggtcaagt       720
tcggcaaggc cttcggaatg aaagtgacgg tgatcagctc gtcgccgggg aagaaggagg       780
aggccctggg gcggctgggc gccgacgcgt tcatcgtcag caaggacgcc gacgagatga       840
aggctgtgat agcaccatgg atggcatcan taaacacggg atctgcaaac atcccctga       900 cccctctctt cgggctgctc aagcccaacg gcaagatgat catggtcggc ctccccgaga       960
agcccatcga gattcctccc ttcgctctag ttgccacgaa taagaccctg gccgggagca      1020
tcatcggcgg catgagcgac acgcaggaga tgctggacct cgcggcgaag cacggcgtga      1080
cggccgacat cgaggtggtc ggcgcggagt atgtgaacac ggccttggag cgccttgcca      1140
agaacgacgt caggtatcgc ttcgtcatcg acatcggcaa caccctcgac aatgttgcgg      1200
ccaccaccga gtgaacgtac tcagcactgc ttacgatcta cgttgttcca ctgttagtgc      1260
tccgtagtaa acaataaacg atcaaaactc ttgtcatctg gtgcattggt gtagacatgg      1320
ttgtttgcga ggaaactgag ttgaaggatg gatggataaa aaaaaaaaaa aaaaaaa       1378
```

<210> SEQ ID NO 12
<211> LENGTH: 370
<212> TYPE: PRT
<213> ORGANISM: Lolium perenne
<220> FEATURE:
<221> NAME/KEY: MISC_FEATURE
<222> LOCATION: (257)..(257)
<223> OTHER INFORMATION: any amino acid

<400> SEQUENCE: 12

```
Met Ala Pro Thr Ala Ala Glu Gln Thr Glu His His Gln His Thr Arg
1               5                   10                  15

Lys Ala Val Gly Leu Ala Ala Arg Asp Asp Ala Gly His Leu Ser Pro
            20                  25                  30

Leu Ala Ile Thr Arg Arg Ser Thr Gly Asp Asp Val Val Ile Lys
        35                  40                  45

Ile Leu Tyr Cys Gly Ile Cys His Ser Asp Leu His Ala Leu Lys Asn
    50                  55                  60

Asp Trp Lys Asn Ser Arg Tyr Pro Met Ile Pro Gly His Glu Ile Ala
65                  70                  75                  80

Gly Glu Val Thr Glu Val Gly Lys Asn Val Ser Lys Phe Lys Ala Gly
                85                  90                  95

Asp Arg Val Gly Val Gly Cys Met Val Asn Ser Cys Arg Ser Cys Glu
            100                 105                 110
```

```
Ser Cys Asp Lys Gly Phe Glu Asn His Cys Pro Gly Met Ile Leu Thr
        115                 120                 125
Tyr Asn Ser Val Asp Val Asp Gly Thr Val Thr Tyr Gly Gly Tyr Ser
    130                 135                 140
Ser Met Val Val Val His Glu Arg Phe Val Val Arg Phe Pro Asp Ala
145                 150                 155                 160
Met Pro Leu Asp Lys Gly Ala Pro Leu Leu Cys Ala Gly Ile Thr Val
                165                 170                 175
Tyr Ser Pro Met Lys Tyr His Gly Leu Asn Val Pro Gly Leu His Leu
            180                 185                 190
Gly Val Leu Gly Leu Gly Gly Leu Gly His Val Ala Val Lys Phe Gly
        195                 200                 205
Lys Ala Phe Gly Met Lys Val Thr Val Ile Ser Ser Ser Pro Gly Lys
    210                 215                 220
Lys Glu Glu Ala Leu Gly Arg Leu Gly Ala Asp Ala Phe Ile Val Ser
225                 230                 235                 240
Lys Asp Ala Asp Glu Met Lys Ala Val Ile Ala Pro Trp Met Ala Ser
                245                 250                 255
Xaa Asn Thr Val Ser Ala Asn Ile Pro Leu Thr Pro Leu Phe Gly Leu
            260                 265                 270
Leu Lys Pro Asn Gly Lys Met Ile Met Val Gly Leu Pro Glu Lys Pro
        275                 280                 285
Ile Glu Ile Pro Pro Phe Ala Leu Val Ala Thr Asn Lys Thr Leu Ala
    290                 295                 300
Gly Ser Ile Ile Gly Gly Met Ser Asp Thr Gln Glu Met Leu Asp Leu
305                 310                 315                 320
Ala Ala Lys His Gly Val Thr Ala Asp Ile Glu Val Val Gly Ala Glu
                325                 330                 335
Tyr Val Asn Thr Ala Leu Glu Arg Leu Ala Lys Asn Asp Val Arg Tyr
            340                 345                 350
Arg Phe Val Ile Asp Ile Gly Asn Thr Leu Asp Asn Val Ala Ala Thr
        355                 360                 365
Thr Glu
    370

<210> SEQ ID NO 13
<211> LENGTH: 5119
<212> TYPE: DNA
<213> ORGANISM: Lolium perenne
<220> FEATURE:
<221> NAME/KEY: misc_feature
<222> LOCATION: (10)..(10)
<223> OTHER INFORMATION: any nucleotide
<220> FEATURE:
<221> NAME/KEY: misc_feature
<222> LOCATION: (38)..(38)
<223> OTHER INFORMATION: any nucleotide
<220> FEATURE:
<221> NAME/KEY: misc_feature
<222> LOCATION: (79)..(79)
<223> OTHER INFORMATION: any nucleotide
<220> FEATURE:
<221> NAME/KEY: misc_feature
<222> LOCATION: (592)..(592)
<223> OTHER INFORMATION: any nucleotide
<220> FEATURE:
<221> NAME/KEY: misc_feature
<222> LOCATION: (2154)..(2154)
<223> OTHER INFORMATION: any nucleotide
<220> FEATURE:
<221> NAME/KEY: misc_feature
<222> LOCATION: (2293)..(2293)
```

```
<223> OTHER INFORMATION: any nucleotide
<220> FEATURE:
<221> NAME/KEY: misc_feature
<222> LOCATION: (2314)..(2314)
<223> OTHER INFORMATION: any nucleotide
<220> FEATURE:
<221> NAME/KEY: misc_feature
<222> LOCATION: (2332)..(2332)
<223> OTHER INFORMATION: any nucleotide
<220> FEATURE:
<221> NAME/KEY: misc_feature
<222> LOCATION: (2394)..(2394)
<223> OTHER INFORMATION: any nucleotide
<220> FEATURE:
<221> NAME/KEY: misc_feature
<222> LOCATION: (2420)..(2420)
<223> OTHER INFORMATION: any nucleotide
<220> FEATURE:
<221> NAME/KEY: misc_feature
<222> LOCATION: (2422)..(2422)
<223> OTHER INFORMATION: any nucleotide
<220> FEATURE:
<221> NAME/KEY: misc_feature
<222> LOCATION: (2434)..(2434)
<223> OTHER INFORMATION: any nucleotide
<220> FEATURE:
<221> NAME/KEY: misc_feature
<222> LOCATION: (2564)..(2564)
<223> OTHER INFORMATION: any nucleotide
<220> FEATURE:
<221> NAME/KEY: misc_feature
<222> LOCATION: (2566)..(2566)
<223> OTHER INFORMATION: any nucleotide

<400> SEQUENCE: 13
gcagcggttn caaatcgccg gtcctggggt ggaagtgnag cagtgggaag atgtgtgcga      60
ggggttgtgt tttggatgna agacaggcgg gccagtggag aacaagagag aacgcgagag     120
gccaaagtat ccgcagcccc gcaaacaagg cctagatttg ggttaagttt gggtcgtctc     180
agacaccgcg gccatccttt taggtggtcc gcgcgctgga ccgtatttt atctgagttg      240
acccattcag acgcgcagac acgagatgga tggtgcagtw agagatgacc taagtacaar     300
aacctctccc cgagctgccg ccatccgtca cttaccgagc gacaaagctt cccacttcat     360
cacactcagc ccagcaagca tactgatggt gagcgcactc gcggctgtgc ccaccgaccc     420
cacgccatcc aaaaccaact ctactttca ccmcaccaac aaaagacaaa atatggtgga      480
ttttgtgatg agatggaagc ggagcttgtc agaatgggaa acgcataaat cgagaacacg     540
tatacagtgc tggaaattgg atgactaagc cccaagggtt agaaaaaaaa tnagaccatg     600
tctagatgga attagacatt ttttgatata ataggaagcgg gacttggcgc gacaatttca    660
aacttcgtcc ctaacaggta tcgaactttc gatagttagc gtgtgctact gcggaccccc     720
aaccacttgt gttaagccca catcggttaa ggcccaaggg ttagatgaaa gtaccaatct     780
cactcatttg cgactagcta caaaacttgc ttttcacatg tacggtcata ctacaatttt     840
gaccttggta acgtaagtat ggactgtatg gtgtgctaag gtgtgttggc agctcaaata    900
aacccaaaaa tttcaacaca cgtcaaccat gaactgagat tcacaccaac ggctgagccg    960
tctcctttaa aagatagagg gagaaaacca taatcaccat tggtggtcat gtgtgagtgt   1020
gcaagcaaaa aaaatggag aagccaaaac ccgttgagag agtgcgagag catacaagaa    1080
caccacaaca aagtgtgaag gagaaaaaga atatgagata agatttcgga aatacttttg   1140
cacacccatg catgggtgtg ggtgtttccg tcaccgtcta tgtatttctc gaaattcatg   1200
cccaccatgg tagataaaaa tattttttc tctctcctct ttttattcaa atctcaaagc    1260
ataakrartg gtgacagaac gataagattc ctacctagct ttctgagatc ccactagttt   1320
```

```
atcttcaagc tggtgattga aggattaacc atgcttgaat tagattggct tcaaacttgg    1380
tagtagcttg tttcatactt tgattacttt ggtatggtta gttggtttga gattttggtc    1440
aatgtagaat cagatttgag agcgattgtc agcttgaatt gccgcagttt tagcacatac    1500
tagtttggat agatgaacag tttggagaga caaataatgt ctatacgagc tcatcggata    1560
atattagtct atggcttttg cttcggtgtc ccctctgcaa actttacccc tctgtagatg    1620
gtaggatttt ctgatatcct ttcatggttt aagggtgtgc gtgtaaggaa cgggagatac    1680
cggatcacac cttttcgtct acactttaca agcatgtaac acctaagatt gattgatatc    1740
taggcttaca ccccaatgga ggtaaactaa tattattgaa atgcgacttt tcaaaagtcc    1800
caatataacc ttgacgatga tcttacaact actcgcgcca gtcttgtatg atatcagatt    1860
ggccgaggat cgtgggtacc ttgtagtgga ctatgatgct catggaggtt gtatggacat    1920
gttgtaatgc tggttttctc taggtttttt ctaatcaact tggcattctt ctccttaaca    1980
cataataaga gggaatacct ccatacatta ttctgaaaaa agcatggcca acaatgaaac    2040
agaaacaagt acgacagtct atcccgaccc aaacaatgg ctcaggtctt tcacgatgca    2100
tagtttgtta gcatgtattt tatagtagga actaaaattt aaagacaact tgcnaaaaca    2160
attttgtctc ttgagtgttt tttaaggatg cggcatttat cgattataca ttacatatgt    2220
gattggatta gccaactttt tgtcttccga tgatcatatg aaagggttgt atcttagggc    2280
atctccaatg ggnagactca aatgcaaaaa aatngtccgt ttgggtcttc cnggacaaaa    2340
cctgctccca acggggcaac ccaacttaaa aacggacagg tgcagcgtcc ggcntgaccc    2400
aaaactgacg caaatttggn anattttggg ggcnagccag acgaacgcgg cgtccactg    2460
tatccgacta tgtccgcatc ctggcccatc tgacagtgac acaaaataca accacatgcg    2520
cccccacc ttctctctcc tccgttcgcc ttttcccatg gaancngtcc tcgctcctcg    2580
ccggaattga tctcgcctaa ccatgctccg ccgccaccct cgcctkaagg ccccagccgc    2640
cgctacctcc ttttttgtcag ccctattgga agtcgccgga gttgaaacga cgccgccag    2700
cctcgacacc gccgagcaag acgaagactg ggcggagctc gccgagacgg gacggggacg    2760
gagctcgcca tgcgtgcctc gcaggggcgc gatggggggcg gagctcgccg tggctggctg    2820
cagcacctcg ggccgctgct agccgtgcca cgacgcgagc atgcgcctcg acgccgcccc    2880
gtgctacctc gtcgcgcgcc cagggccgcc ccgcccctgc cgaccggcgg cggagacgcg    2940
accttcgcgg acgtgcccgg cggcagagac gcgtccttcg cgacagcgcc ctcctcgatc    3000
tccgtcgagc cgcatacgcg gctaggaggg acgcgggcgt ccccggtgtc ggcctccgtt    3060
gtggcgcatc gcgggcgcgg cctccgtcga ggcgcatcgc gggcgtggcc tcgtggcgca    3120
gcctgccctg attcggtctg aggcgcgcg cggagcttcc tcgcggcggc gcgggcgag    3180
cctcctcgct gcggcgcgac ctgctctgcc gcggtccgag acgcggcgcg ggcagagctt    3240
cctcgcggcg gctcgggcgc ggcttcctcg cggcgatggc gcttccaggc tcgcacgcgg    3300
cctccggcgt ggcgcagcga gagcgcagcc tccggtgagt taggcacagg cgcgacacga    3360
catcccggc ctcggcctcc ggcgtggcgc agcgcgagcg cgacgtagcc taggttggca    3420
actagtacta cgaggaagaa agaggagaaa caattatttg ggtcacagcg ttgggcgtac    3480
tgtgcgatcc aaacggacac ccggacgcga acgatgtca gcgtgtccgc gtggcgaccc    3540
aaacgacccg aaacggacgt ccgtttgggt cggtgcgttg gagatgccct tactccccat    3600
cctcaaatga gtctaattat atatcttgtt gtaagtttta aaaagttaa actttgatca    3660
```

| | |
|---|---:|
| acattagtaa tgatagtagc aacgaataca aaattaaatt gtaaaaatat attatgaaac | 3720 |
| tttattttaa gatggatcta gttatactaa tttctgcgg atggaggaag tagctaaata | 3780 |
| ttgttaattt ctaaataaaa aattaaaact ttaacttaaa acaaaagtta caagcataat | 3840 |
| tatctgtgga tggaggaagt agctaagata caccaatcct ctctctacat tacctagcat | 3900 |
| gccacatcag gaaactattt aggataagct ccaaggaacc acccagaaca acaatttaca | 3960 |
| tggcctggct aacctaatga caatttccga gcaactggtg gtggtggtac gcgttccttg | 4020 |
| ttcaattgtc tctattacaa gagtggccct gtataggtaa aaaaaaataa caagcttcca | 4080 |
| aggacggcca tgttccttgt tcctgcaggc tgcacgtact cacgacgaag tgtatctcgt | 4140 |
| gttctggaca tttgtctcgc gcattttgta accatgaaat taaaaatgtg gtggcctgct | 4200 |
| atatctgtat gggggtatca tgcactcctt cgcagaggaa tccagacgac gatttacacg | 4260 |
| tgtttccacc ttagcttttt ttaagtgtgt gtgtaaggaa cgatcatata actgcccctg | 4320 |
| aatgctgcat atatataaac cgactccatc atgtactcga gacaaggtcg tcaagaaaaa | 4380 |
| caaactatgc ctatctcact agcaatgatt tgagagtaca gcttttccgg tgccatattt | 4440 |
| tttcctatat atcttttct gaagaacaag aaaaaaaaaa cagttggtgt ggtggttggt | 4500 |
| gaagcgagaa agccccatat aagccctgct caccctcccc gcaaagcaca actcatagct | 4560 |
| cgggtctctc gctcacacca aaatcgccca ccagcaccag catctctcga tcggcagacg | 4620 |
| catagatcga tgggctccac cgccgccgac atggccgcgt ccgcggacga ggacgcgtgc | 4680 |
| atgttcgccc tccagctcgc ttcctcgtcg gtcctcccga tgacgctgaa gaacgccatc | 4740 |
| gagcttggcc tcctggagat cctggtggcc gccggcggca agtcgctgac cccgaccgag | 4800 |
| gtggccgcca agctcccgtc cgcggcgaac ccggaagcgc cggacatggt ggaccgcata | 4860 |
| ctccggctgc tcgcgtcgta caacgtcgtg acgtgcctgg tggaggaggg caaggacggc | 4920 |
| cgcctctccc ggagctacgg cgccgcgccc gtgtgcaagt tcctcacccc caacgaggac | 4980 |
| ggcgtctcca tggcggcgct cgcgctcatg aaccaggaca aggtcctcat ggagagctgg | 5040 |
| tgagtctctc agtggagcta gttactgtag atccgaattc gttcccttta gtgagggtta | 5100 |
| attccgcggc cgcgtcgac | 5119 |

<210> SEQ ID NO 14
<211> LENGTH: 4555
<212> TYPE: DNA
<213> ORGANISM: Lolium perenne

<400> SEQUENCE: 14

| | |
|---|---:|
| tcccgtatct tcaacgtgac acccctacac ttcctgcttg tcttggagat ttacacacac | 60 |
| acggcaatta ccaggagtat cttcctagat tattttttc gataaggatc ttccagatat | 120 |
| agcatgtgaa tctctgtact actactgttt gtcaagcaaa attaacattg acatcagtgt | 180 |
| ttttgttggg ggcagcggaa tctttgacgc ctcttcttgc ctctcaagac atgtcaccct | 240 |
| cactagttag tgtgccagct ggtagtacta cgtacgatgc tccctccctc cgtaattatt | 300 |
| caaccttttt gctctctctt tttataaagt caaaccttt aaatctgacc agatatctgc | 360 |
| taaaaaatta gcagacatgc atacatcaaa gcagtagtcc tccctccgtt taaaattacc | 420 |
| tgggtttatt caaataaagt caaactctgt aaaattcaat taaatattta gaaaaatcta | 480 |
| acagcacctg tagtataaaa gtatgctccc tctgtttgta aaaaagctaa gcaacttttt | 540 |
| tgagatacgg ataaatcttt agctaaaaca tgtctatata cctttgtatc tagataaagt | 600 |
| tggaaagctt ttttagaaac agacaaagta tgtgtttgac attatgaatg ttgagtattt | 660 |

```
ttcctctaat cttgatcaaa ttttacaaat tttggcttga atagaggac cattattagt      720 atgaaactac ataaatttgt aaaacactca acataattta cgatgggtca gtgatagcac      780
taacttagct tttcataaat gccactgctt tcaatagag catgaagcag acaaattta       840 ttcgtgtgac ttgaatagag ggagcctgtt ctggttcaac tcaccctgca tgtgtgtctt      900
catccctttt gctcttccta tctgtggtgt caattgagtg tcccacgtgc atgtgggcga      960
aacttgaacc tagaaattga catgctccca ctgcccggag cggagtatct ttgtgctttg     1020 ttaccctttat tgttgctacg tactacagtg tttagattgg aacttcataa tcaaaagaac    1080
ttagtttcct acaattttt gctaagcaat ataatgagca atcaaacttc tatatctgtg     1140
gcaaataact aatccattat agttacagtt tagatgcaga cgccagtgtt tcttccccctt    1200 ttcggaaaaa agctattcca taataagtgt tggaaattta ataatgggt actacgaatt     1260 tgaaaaaaaa agtgtcaaaa attcactaag aaagtacgta gtacaaattt aaactaagat    1320
tccgacactt attaggatcg gagagagtaa gtagcaaact actactccat ccacctaaaa   1380
cacgtgattt aactttgtct agatacggat agaaagttgg gatacatccg tatcttaaaa    1440
aaaaacgcac ttatttaga cgaaggaggg agtatttcaa ccttgatttt aaacggaatc    1500
tacaaaggga atacatggat tgtacaagtg ggctgaccgt atccattatg tactcgtact    1560
ttgcagtttg aaagcaaagg ctagtgtaat ttgtaggtgg ttctaggcgt ctagctgttt   1620
catggcgtta tcacagccgt gccagtgtgc tcagggccgt acataagttg cttggtgtat    1680
gtgtcgatct aggatttgcc gtcttacaat tttgctttcc aacttatttt ctgtaaagag    1740
atcgatgtga acttctctgt cgagtaaact gaaattgtct gaataaatat aactcggcag    1800
attatgtttt atcgttttgca tgcgtaacag gctacacaaa ttgctcgagt cagcagcgag   1860
ttgagctcac aacgaatcca tcagcaaaaa tactatacta tagtagcaca tcgtttcttt   1920
tttcatgacg tttctgtttc ttcctaactt tccaggagca ccggagacga cgatgtggtg    1980
ataaagattt tgtactgcgg aatctgccac tctgacctgc acgccctgaa gaacgactgg    2040
aagaactcaa ggtacccgat gatccccggg cacgagatcg ccggcgaggt cacggaggtg    2100
ggcaagaacg tgagcaagtt caaggccggc gaccgcgtgg gcgtcgggtg catggtgaac    2160
tcgtgccggt cgtgcgagag ctgcgacaag ggcttcgaga accactgccc gggcatgatc    2220
ctcacctaca actcggtcga cgtcgacggc accgtcacct acgcggcta ctccagcatg     2280 gtggtggtgc acgagcggtt cgtggtccgg ttccccgacg ccatgccgct ggacaagggc    2340
gcgccgctgc tgtgcgccgg catcaccgtg tacagcccca tgaagtacca cgggctcaac    2400
gttcccgggc tgcacctcgg cgtgctgggg ctgggcgggc tgggccacgt tgcggtcaag    2460
ttcggcaagg ccttcggaat gaaagtgacg gtgatcagct cgtcgccggg gaagaaggag    2520
gaggccctgg ggcggctggg cgccgacgcg ttcatcgtca gcaaggacgc cgacgagatg    2580
aaggtaggcg gacccgctgg ttcaggttac ttccccctgtc cggtgcagaa gaagaggaa    2640 cttgagggtt catgtttgtt ttgcgttggt gatgtctttg caggctgtga tgagcaccat    2700
ggatggcatc ataaacacgg tatctgcaaa catccccctg accctctct tcgggctgct    2760 caagcccaac ggcaagatga tcatggtcgg cctccccgag aagcccatcg agattcctcc    2820
cttcgctcta gttgccagta agtcttagga tctcttgcaa taaggagaaa tcatgcactg   2880
atcgatcaga gaaatgagat agcatcctga tgaacattgt acgtgtgtgc agcgaataag    2940
accctggccg ggagcatcat cggcggcatg agcgacacgc aggagatgct ggacctcgcg    3000
```

```
gcgaagcacg gcgtgacggc cgacatcgag gtggtcggcg cggagtatgt gaacacggcc      3060
ttggagcgcc ttgccaagaa cgacgtcagg tatcgcttcg tcatcgacat cggcaacacc      3120
ctcgacaagg ttgcggccac caccgagtga acgtactcag cactgcttac gatctacgtt      3180
gttccactgt tagtgctccg tagtaaacaa taaacgatca aaactcttgt catctggtgc      3240
attggtgtag acatggttgt ttgcgaggaa actgagttga aggatggatg gataagtttg      3300
cttcttgccg tgttaatgga ttacctactt agcttcactg caattaacaa attaagaaac      3360
gacacaccca aaagactttc gtcagttttc ttggattata caagtcgtta tggttgggtg      3420
tcagtgtgtc acagataatc atactatggt atttaacctg gaagatcgtt tttttggcgg      3480
caactcagtg ggttttccca ctatgtatat ttataaatat tcaacaagtc atgaggtaca      3540
aagggttgtt gctagaggat agcaacaaga agctagccaa agatcatag gcttaaaaaa      3600 gagagaaaag aaaacaaaac tgctatagtt atcgaaatct ctcagctcaa attttaaaac      3660
cagcataaga ctttctagaa gccttatgaa caagaagagc tagctcatct ttaaaccttt      3720
tcctgcatct gtaaagattg agggtgcaac ccttgaatat aaaatcattc ctgtcatcca      3780
gatagactat gtagtcaaaa tagtcatttc catgaagaag ggcactttta atacattttt      3840
gagacttggt atgatactct gaatgtcaac accctggaag atcttttcac tcctatggaa      3900
ggacaagaaa gcatttcaac tccttttact aaggaagaga ttgacaaggt gattcagaga      3960
attcctttag acactataga aagtcacaag gtgccaacgg cgcaatcctg tgccgacggc      4020
tttttatcgg ggaagccagc atcggtaccg agaccggcag cccaccaact aggccgtcgg      4080
cacacatcct ccagtgtcgg cggccaacat cggcataagt tggcccgttg ggcatcaact      4140
cccccgtcgg aacaggtcta gcgcatggac cgtcgtgatg gcggcggcaa cgacgtcatc      4200
ctatgccgac ggcctagccg tcggcctagc ttgccagcgc tatgccgacg tcacattgcc      4260
atcggcacat gctagttttt ttttctttt tctacatgcc aaattgtata tgtatatata      4320
ctcatttact tattacttcc aattatttta atgtgtatat attttgctca ccaattgtac      4380
gaatttgtac cctccgagaa attgctaaaa tgatggagtg acctacaacg agccttggat      4440
atgtgagttc ttcttgcccc attgcacaaa aattgtaaat attagggttt actggatcca      4500
ctagttctag agcggccgcc accgcgggga gctccagctt tgttcccctt tagta          4555
```

<210> SEQ ID NO 15
<211> LENGTH: 312
<212> TYPE: PRT
<213> ORGANISM: Lolium perenne

<400> SEQUENCE: 15

```
Arg Ser Thr Gly Asp Asp Val Val Ile Lys Ile Leu Tyr Cys Gly
1               5                   10                  15

Ile Cys His Ser Asp Leu His Ala Leu Lys Asn Asp Trp Lys Asn Ser
            20                  25                  30

Arg Tyr Pro Met Ile Pro Gly His Glu Ile Ala Gly Glu Val Thr Glu
        35                  40                  45

Val Gly Lys Asn Val Ser Lys Phe Lys Ala Gly Asp Arg Val Gly Val
    50                  55                  60

Gly Cys Met Val Asn Ser Cys Arg Ser Cys Glu Ser Cys Asp Lys Gly
65                  70                  75                  80

Phe Glu Asn His Cys Pro Gly Met Ile Leu Thr Tyr Asn Ser Val Asp
                85                  90                  95

Val Asp Gly Thr Val Thr Tyr Gly Gly Tyr Ser Ser Met Val Val Val
```

```
                100                 105                 110
His Glu Arg Phe Val Arg Phe Pro Asp Ala Met Pro Leu Asp Lys
            115                 120                 125
Gly Ala Pro Leu Leu Cys Ala Gly Ile Thr Val Tyr Ser Pro Met Lys
130                 135                 140
Tyr His Gly Leu Asn Val Pro Gly Leu His Leu Gly Val Leu Gly Leu
145                 150                 155                 160
Gly Gly Leu Gly His Val Ala Val Lys Phe Gly Lys Ala Phe Gly Met
                165                 170                 175
Lys Val Thr Val Ile Ser Ser Ser Pro Gly Lys Lys Glu Lys Ala Val
            180                 185                 190
Met Ser Thr Met Asp Gly Ile Ile Asn Thr Val Ser Ala Asn Ile Pro
        195                 200                 205
Leu Thr Pro Leu Phe Gly Leu Leu Lys Pro Asn Gly Lys Met Ile Met
    210                 215                 220
Val Gly Leu Pro Glu Lys Pro Ile Glu Ile Pro Pro Phe Ala Leu Val
225                 230                 235                 240
Ala Asn Lys Thr Leu Ala Gly Ser Ile Ile Gly Gly Met Ser Asp Thr
                245                 250                 255
Gln Glu Met Leu Asp Leu Ala Ala Lys His Gly Val Thr Ala Asp Ile
            260                 265                 270
Glu Val Val Gly Ala Glu Tyr Val Asn Thr Ala Leu Glu Arg Leu Ala
        275                 280                 285
Lys Asn Asp Val Arg Tyr Arg Phe Val Ile Asp Ile Gly Asn Thr Leu
    290                 295                 300
Asp Lys Val Ala Ala Thr Thr Glu
305                 310

<210> SEQ ID NO 16
<211> LENGTH: 1378
<212> TYPE: DNA
<213> ORGANISM: Lolium perenne

<400> SEQUENCE: 16
ggcacgagtc gcctccaacg tcttcccctta accggccgtc cctacgcttg caccaccacc      60
acgcacagac agagcagttt cccagccccc gccggaaccg gatggcaccc acggcggcgg     120
agcagacgga gcaccaccag cacaccagga aggcggtggg gctggcggcg cgcgacgacg     180
ccggccacct ctccccgctc gccatcacac ggaggagcac aggagacgac gatgtggtga     240
taaagatttt gtactgcgga atctgccact ctgacctgca cgccctgaag aacgactgga     300
agaactcaag gtacccgatg atccccgggc acgagatcgc cggcgaggtc acggaggtgg     360
gcaagaacgt gagcaagttc aaggccggcg accgcgtggg cgtcgggtgc atggtgaact     420
cgtgccggtc gtgcgagagc tgcgacaagg gcttcgagaa ccactgcccg ggcatgatcc     480
tcacctacaa ctcggtcgac gtcgacggca ccgtcaccta cggcggctac tccagcatgg     540
tggtggtgca cgagcggttc gtggtccggt tccccgacgc catgccgctg acaagggcg     600
cgccgctgct gtgcgccggc atcaccgtgt acagccccat gaagtaccac gggctcaacg     660
ttcccgggct gcacctcggc gtgctggggc tgggcgggct gggccacgtt gcggtcaagt     720
tcggcaaggc cttcggaatg aaagtgacgg tgatcagctc gtcgccgggg aagaaggagg     780
aggccctggg cgcggctgggc gccgacgcgt tcatcgtcag caaggacgcc gacgagatga     840
aggctgtgat gagcaccatg gatggcatca taaacacggt atctgcaaac atccccctga     900
```

| cccctctctt cgggctgctc aagcccaacg gcaagatgat catggtcggc ctccccgaga | 960 |
| agcccatcga gattcctccc ttcgctctag ttgccacgaa taagaccctg gccgggagca | 1020 |
| tcatcggcgg catgagcgac acgcaggaga tgctggacct cgcggcgaag cacggcgtga | 1080 |
| cggccgacat cgaggtggtc ggcgcggagt atgtgaacac ggccttggag cgccttgcca | 1140 |
| agaacgacgt caggtatcgc ttcgtcatcg acatcggcaa caccctcgac aatgttgcgg | 1200 |
| ccaccaccga gtgaacgtac tcagcactgc ttacgatcta cgttgttcca ctgttagtgc | 1260 |
| tccgtagtaa acaataaacg atcaaaactc ttgtcatctg gtgcattggt gtagacatgg | 1320 |
| ttgtttgcga ggaaactgag ttgaaggatg gatggataaa aaaaaaaaaa aaaaaaa | 1378 |

<210> SEQ ID NO 17
<211> LENGTH: 2650
<212> TYPE: DNA
<213> ORGANISM: Lolium perenne

<400> SEQUENCE: 17

| cgggatcaac ttggatgtcc tttgcgggca cggtttcagg aacaacgaca catgcagcag | 60 |
| ggatctcctc caaagactca cacaaaggtg acatgagcgc ccgcttttt gaagccaagt | 120 |
| tggctaagaa atcgcaaagc ttggtggagt cggccacctc aggatctgca acaaaaggca | 180 |
| ccaagggagc tgccaacaca tcaaccacaa catcatgttc aaacgcagtc tcctcaagcc | 240 |
| tcgaatgctc aaccgaaaga gaggcagaag cttcaacaaa aaactcagcc aacccaaagc | 300 |
| cctcgacgtc atcagagatt aggctctgag gacccgcagg gaagcaacct tgtcaacaac | 360 |
| cgcatccggc agaaaaggag caagaccgga gcaaccctca gaggcacac gaaagacgtc | 420 |
| gaagccaaga ggagacgagt cgcagggacg gcggacaggc gagaaggggc cgtagaactc | 480 |
| caagagctcg gcgtccctcg acctagcatc cgaagcactg accggggcac tcaatgcata | 540 |
| actttatctt gatggcatat gtactcaaac ccatacaatg ttcaccatgc attatctatg | 600 |
| gaacattcct tcatatacaa cttctgagtg gtcagtgcat aggaattttc attaacaacc | 660 |
| aaaaacatac ttggggccta cacacacttt cacagcatgg aaaacttgtt agctttttaa | 720 |
| agagttgcaa aatctgtcaa gcgaatgttc ttgtgataat tggaacgaag catgtttccc | 780 |
| cattttcaat gtgtgtctct taccctaact agcacccgac caacaaaatc tgaccatcct | 840 |
| agttatatca tcatagagac ccacatgtag gttgaccccc ataacacttg tgtggatatc | 900 |
| atggaaaatg gccttgatca acactttctt tcctacttgg tacaaatggt tatggactta | 960 |
| ctcaattagt gctttagaga gctttggctg cagactttgt agcttcccaa tattcatagg | 1020 |
| tccctccgga gtgggcagcc ccatctacat aggctcaaaa ccagattttt gtaacatgtt | 1080 |
| agacactttc aacttcatca tagaccatca aggagctggc atgtgacagt gatatatgta | 1140 |
| tcaattaccc attcaacacg aatagcttgc tcatgcatgg ttagtcttgc ggcggcgggg | 1200 |
| cgggaccatc gaacacaccg ccgggcggtc agtaggctag ggttagataa atctagccg | 1260 |
| ttttcattca aacttgtgat atataatcaa atttaaataa aaacctttat tttcgtgcat | 1320 |
| ttttatttat ttgagggcgt gtttggggga cacggctgga aagtgacatc cccaaacact | 1380 |
| gcacgaagaa aacgcgtcgc caaaaaattc gatccgcgt cagtcctttg ggagacgatt | 1440 |
| tggatgacgc ggctagagat gctctaagtt ctccacgcca tgtttctttc tatatataca | 1500 |
| cacagcccaa ggtccatgaa agtaaaacg gcacgacgac acgcaccggc gacaacttca | 1560 |
| cattacggca catcgctatt acggaccaca tacaactcca ccgctattct cagccaagtc | 1620 |
| atacatgaca tgatccaatg gacgactttg tgagcgaaac tagaaccttg cggggtttag | 1680 |

-continued

```
attttccaat gtggataagt tgtacgcgcc gactagcttt acacttggtt gaaaaaagct    1740
tattgtagca cgacttctca ctgacatagg aatgtaaaca gtctctccac gccatgtttc    1800
tttctagtag tagcatacta gtagtaactt ctctttgtcc tacacacacc cagggtccaa    1860
gaaaggaaaa cggcacgacg gcacccaccg acgacgacga ctccacatca cggttcggta    1920
aaaaaagtca aaactcgctg acgtggcacc accggtcgca gtcaactgac gcgctcctct    1980
gcgcaggtyt cacttcaagt ttcacctacc actgtgggcc caccgccaat gtgggccccg    2040
cgagcttctt actcactgac ctgtctccca ccagcctcct cgccggtata ttaccccggc    2100
ccccaatttc ctctgccttc ccacgagcag cagccggagc acggaatccc ggccgccatt    2160
cctccacctt cagctccgcc caaagatttc catccggcga gatccatggg ctccatcgcg    2220
gcggacgcgc ctcccgcgga gctggtgttc cggtccaagc tcccggacat cgagatcccg    2280
acccacctga cgctgcagga ctactgcttc cagcgcctgc cggagctctc cgcgcgcgcc    2340
tgcctcatcg acggcgccac gggcgccgcg ctcacctacg ccgacgtgga cgccctcacg    2400
cgccgctgcg ccgcgggcct ccgccgcctg ggggtccgca agggcgacgt cgtcatggcg    2460
ctgctccgca actgccccga gttcgccttc gtgttcctcg gcgccgcccg gctcggcgcc    2520
gccaccacca ccgccaaccc gttctacacg ccccacgaga tccaccgcca ggcgaccgcc    2580
gccggggcca gggtcatcgt caccgaggcc tgcgccgtcg agaaggtgcg cgccttcgcc    2640
gccgagagag                                                          2650
```

<210> SEQ ID NO 18
<211> LENGTH: 12175
<212> TYPE: DNA
<213> ORGANISM: Lolium perenne

<400> SEQUENCE: 18

```
tcgacgcggc cgcgtaatac gactcactat agggcgaaga attcggatca tatggattcg      60
acactggaat ttactcccat cgggagcgtg caaacaaaaa ggtgttatag caagaagaca     120
ctggcaacat tgccagcaca gaatttgtta caatcataga aagttttatg acaggacatt     180
gtttcaaccg aaagcaagat tacaacaata taatcaaggg cttgggtctg gttggacatg     240
ctcggtccaa tggacgattt atttgccgag accagctcaa ggagttgacg agcacactta     300
agcgccgaga tcttaaaggc acccaagtca acaagtcgcc catcttgctc ttttggcagc     360
tccttggaca tctcttcgat attggctttg aagccatgac ccatcataag ctgaaaggct     420
aggagggcac ataggtacg cgaagtacgt ttgaatacct cgaggacctc cctcgtgttg     480
atggcgaaag catcgatcag ctgccccaag gtcttgtttt gatcgatctt ggggaagatc     540
atcgagtgca tccgcgtcat ggatccttta cccttctgaa ggaggtcctg aaaaagctgg     600
tgagacccga gggtcattga caaagcattc gccggagaat tattcggcaa tttatctaga     660
gcctcagcag ggatgtaggc agcttctgga gaaagtgaaa gaggaggagc tcactaacca     720
aaatcaaatc gataaagcaa aaatcggaaa ggaggccaaa aggggattac tgagcaaggc     780
caaggaagat tggcgaagga gctcatcttt ttcaatcgcc cgagcttcgg cagcaagcct     840
ggatgcctct tcatccttca gcctctttct tagcccctcg agctcatcct taaaggaatc     900
aacctcctgg cgggcctcgg cagctatctt tatcgcaccc tccagcttcg aggaagaaga     960
ctcgacctcc ttttgcagcc gagtcttgtc aacttccaga gaagtgtatt gggaggcgaa    1020
ggcctccaga gaagagataa cagctcacaa atccttaaga gataaggaaa ataattaga    1080
```

```
cgaagaactg gttgtcaaca aacttataat ttgatcaggg aaatcgtccc acatggatat   1140
atcgttaaaa caggaaaagc ttacaggttt ccctggagga gaagctgtaa ccacggcagt   1200
caaagaaatc tccttcccct tggaaaggga agaagttgtc gatatttgag ccatgggggc   1260
tgcggcagga gtcgaagcct cggaagcggc tggattcggc acgatggcac cagatttggc   1320
cttcttggcc ggaggctcga tgaagccatc ttcactgcaa gaacaaaaaa ctagcgaagt   1380
cagaattcaa tgcatatggc gaagttagaa cacaatcctg gaaaggaag caaggactta    1440 caattcatag agaccatctt catcggcaaa gccgccggat gatctctttg gaggtagtgc   1500
ctcggccttt tccgtagctg catcaacaaa ggcagcacga tcagcatcgt catcatgcat   1560 tgacccgct gtatcgctca tatcatcggc agagaatcga ggattgatgg aaaaagcctc    1620
aggattcatc ggatcatcat gttgatctat cgggcttgca ttccctagag tatgggaccc   1680
tacaaggact aaggaatccc ttttcttgga aaaattgttc gacaggtctt gcaaacgttc   1740
aagagccgta aggatctgtc gtagttgacg agtgagaata atggcagtta aataatcaa    1800 aggaacatga caataagagc ataaagggga aatttacctc ggttggcaga tgaccagcgt   1860
caaatggcgg ttgaggagat atcagtgaaa ttgaatcttc ctggctaaag agggtgagac   1920
accggacttc gtcaagcagt tctttttcgg ataattcagc aatatttact ctagtctcgt   1980
ccctgggacc cgaatacaac cacatcggat gggtcctaga catgatcggc tgaactcgat   2040
gttttaagaa cacagcggct acctcagtac ctatcatggt ttgaccatcg gattctttga   2100
tccgaaggaa tctatcaaat aacttgtcta ctgttggttt ttcatcgggt gagaggatat   2160
ttttccaaga cttcttgggc ttgcttctag aacatcggag aattgggggg gagctgggag   2220
tcggctgctg atgagtcctt aatataaaac cacttcagcc tccagccttg cacggattct   2280
ttcatcggga agttgaagta gttgacttcc ttacgagcaa caaaaccaac cccaccaatg   2340
acgaaggacc caccactgct gttatatctt ttcacgaaga aaatcttctt ccacaaacca   2400
aagtggggct caatgcccaa aaacgcttcg cagagggtga taaagatggc aaggtgaagg   2460
attgagttgg gggttaactt ccataattga atctcataca ctcgaaggag gtggtgaaga   2520
aatttgtgag cgggaagcga aagacctcgg tacaagaagg ataagaacat cacagtaaaa   2580
ccggcaggag gattgggccg tgaaattgca cctggaagaa taacattccc ctcgtcagaa   2640
gaaattatta cgaggctccg ggccctcttt tcatctcgct tcgtggtggt agaagctggc   2700
caatcgccag ggataggccc ggccgtggag cttgacggcg ctggcggtgc cggagctgag   2760
ggaggagcat ctggcgcgct ctccgcggc ggattcgaag gagccctgac ggtggtgcca    2820
ctgctcacgg cgctggtggc gagagtggga ttcttcttct tcaccattgt gagatttgag   2880
ggagatctgg gagttgcgac ggtggcgtgg tagttgcaaa cgaaaaggat gaatgaggaa   2940
gaagggacgc aaggatgaag tgtggaaagg ggagtttacc ccaagagatt ataaagtgaa   3000
aggaaaacct gagaattgag cgggcacgtg tcgttgctct caatttattg agggggatttt   3060 ttctcatcat agatcgcgga aatcgaggag tcaccttggt aactgcacgc aagtagtggt   3120
catttcttaa acagaaccgc atagaagtag gatgggaccg tcaggtcacg tcctatcagt   3180
cagatttaca acagtaatta catcatcact gacgtcaaag tatgcttgaa gtatccgaag   3240
aaaagtcgaa atttgggctc gaagactttc ttgcagagaa gcgcgtgaaa ggaatatcta   3300
aggaaagggt caaacattc ggctcgagtc tacgcacgga ttgcaagcat ccgtacctag    3360 actcggggc tactcccatc gggagcgctg gacgtgcacc cgataaattt agacgaggat    3420
gaaaaccgga aacccaagtg ctactcccat cgggagcgcc gattacgcac ccgacaaact   3480
```

```
tttttgcact ccaggatcat gcccggggac ttaattctgt gtagagtagc gttgttttgt    3540
cttcggcagt taaccagcaa agctggacac gttactcaat atcctttacg cattaaaccc    3600
ttacttgaag aattgaagcc ccgatgcaaa tatatcggat gacctatgaa ggcctgcgga    3660
aagcttcggg agaagaagac attcgagtgg cacaacttga gtctacgaac ggattgcaag    3720
catccgtacc tagactcggg ggctactccc atcgggagcg ctggactcgc acccgataga    3780
aggagatgat gatattacaa gaaggacaag aagtatcaag ggagaagaac attcggtgga    3840
ggcatgcttt agtctctacc cgaaaaaact tcggctagac actcgggggg ctactgacgt    3900
gggcattacc cttcgggtaa ctgatattgc cctatcctgt acgacccaac tggaggccca    3960
tgaagacact cgaaggcaag gtggaccact acgtcggtgc cgaaggggt tccttgaaga    4020 acaagacgaa gaaagaagaa atacaagaaa agtatagaac taggatcttt tgtaacctgg    4080
tcgtacccgg acagatctct cgagacctgg cccctacat atgggctagg agagggctg    4140 ccgagaggga cacacacaat cttagcaatt ttagccacca taagtccaga gcaaggtccc    4200
cgtagaactt agcctctcga cgagatcaca gccgaaacct tcggcacccc attgtaaccc    4260
gatattttca tagtcaagat cagacaggta ggacgtaagg gttttacctc atcgagggcc    4320
ccgaacctgg gtaaatcgct ctccccgctt gtttgataac cgatggcttg tgtcagctta    4380
catgattcca tctaccctaa acctcaaacg gagggcattg ccgaggagta ccctcgacat    4440 tccccctccac caatggtctc acataaattc aacaaagcaa actcataaaa agtttaatga    4500
gtttcagaaa gaaataaaac taggcccctc ctttgagaat ctacgaatga ttcaccatat    4560
catctcgcag ttagtgatga gtaactaagt ctcaaatttc ccgacgcatg gcgaaaaagg    4620
tagcgaactt aaaatgtgag gaatgaatgc cacatatgca tggtgcatcg agtattctca    4680
ttttagtctt ggattactcc ctttagatgt tgacaccatc ccaaaaatac aacttggaca    4740
agttgttcat ttcactagta tgaatttcag taaatcgggc aatactccaa cactcattca    4800
ccccctaggc gaggttagct cagatcaacg tcgggtgtct tcatcgagtt aatgtcgtca    4860
cacgcacaca cacgtacgcg cacacacacg tgcgcaaaca aaagaaaac taggaacctt    4920 ctcacgtagc ctaggtcttg tcctgtaaga aaaacccag gtccacccta gtttcgaacc    4980
aaaatatttt tgaagataca ttagtaagat attttttgaaa ataaaaccgc aaaaagggaa    5040
ttgaaaaata tggactggct gttttgtcca aaaccacatc tttcggagaa ccacgagggt    5100
atctattgat gggctcatac tatacctggg catgtgttgg gccaggcctc atgtcgggcc    5160
gaggaaagcc cgacgctgaa aaatcaggcc caagcttaac ccggcccgac caaataccca    5220
ccaaacccgt tgggccatca ggttgcgggc cgggcagtag tgtaaaacac cgatttcggg    5280
ctacataggc ccggctcgtt tgtcgggcaa acatttctag acctaagccc gagttttttcg    5340 ggccgggctg cccatggcca ggtatagctc ataacgacgt atgacatttc gagcaattga    5400
tgcaaagcac gtgtagggtt ttatcccatc cgtgtggcgt gtgtagggtg taaatgaata    5460
ggataatttc ctcgccgaaa ctggtcccaa attcgctttg aagtgtccat atatgatttt    5520
aaagaatgtg acaaataaag atatccaatt tcgaaatagt gctccggata cggtatagga    5580
tatggtatag caaataacat gctgatatgg attgtccgat attaaattaa gataatccaa    5640
atgttttaaa ccgcataatt cgattttttga gtcaaaagcg aatgccaatt cagaaggtta    5700
gcagttattg agtttcaaaa tttatttggc gagcatatct agttctaaat tctatcacgt    5760
aaattgtgtc ttttttttaat aactacacaa gactaaaagt ttaaatctct ctcaagattt    5820
```

-continued

```
gcgaaaacta tagctatcta ctgatatata tatccgacta tatttgtttt cggaccgcat    5880
gcgtcctatt tccgattcga atctgcactc cgatatatcc acattgaatc taaaaccgat    5940
caatatttgc tccgatctaa atccggaaaa atatgtggtg aaggatatgg tataagcaaa    6000
atccgatttg atccatttgt acctctaggc gtgtgcaaga cctggaggaa agaatggcgc    6060
atctgtaggg tgcagtccca ccggtggaaa atgtgagctc accgtattgt cccccgatgg    6120
agcatcgaaa cggagtcgga acacgatttg cgccacgtac agagcatgca tgatttccct    6180
tgtatgcggt ccaggatctt aaactgcctt ccatttccag gaacctaccg attggctgca    6240
agccgtagct agcggtttga agtcacggca ttgccgcccc cgattaaccc acccgtcgcg    6300
cgcgcggtcg gtcgtttcac cgtcctgcct aggctacgca cgcgcgcgcg cagttgggcc    6360
agttgtaggt aagccgactc gagatcacac acccggcctc acctactacc tctcgccgtc    6420
gcggtcaccg tgtcacactc acgcccaggg gagccacccg cccacacggc gcctagctca    6480
tcccctctca ctactcttct tctcctccct ctcacctcgc cgtcgaccca gctcccggct    6540
ctataaattc cgcactactc gaaccaacat cgcccaggcc tttgccttt acgacgaatc    6600
ctaccaaacc gagctaccag atccttctct actaatcgag ctccctacgc tgctccgcct    6660
gtcttcgttt ccgcctcacc gccggccggt tctccgctcc aagctacgtc cgtccgtcca    6720
catatatagc atcgacatga ccatcgccga ggtcgtggct gccggagaca ccgccgccgc    6780
ggtggtgcag cccgccggga acgggcagac cgtgtgcgtg accggcgccg ccgggtacat    6840
cgcgtcgtgg ctcgtcaagc tgctgctgga agggggtac accgtcaagg gcaccgtcag    6900
gaacccaggc atgtcaccca tgcattcatc attttcttac tagtcgtatg cgttatcgaa    6960
cttgtgtatt aactattgtg gactgcatgc agacgacccg aagaacgcgc acctgagggc    7020
gctcgacggc gccgccgacc ggctggtcct ctgcaaggcc gacctcctcg actacgacgc    7080
catccgccgc gccatcgacg gctgccacgg cgtcttccac accgcgtccc ccgtcaccga    7140
cgaccccgta cgtactccat agaactcggc acccctagct tctctccgtt ctctctgtat    7200
gtctgtcacc gtcgatcgcc atggcagcac gcatgcatgc gcgcgcaacg ctagctagac    7260
gctgaccgac tcattgtgca ggagcaaatg gtggagccgg cggtgagggg cacgcagtac    7320
gtcatagacg cggcggcgga ggccggcacg gtgcggcgga tggtgctcac ctcctccatc    7380
ggcgccgtca ccatggaccc caaccgcggg ccggacgtgg tcgtcgacga gtcgtgctgg    7440
agcgacctcg acttctgcaa gaaaaccagg gtgggtgctg catgctcaat ttttattatc    7500
atagctaccc ttttttctgca ccatgctgca tttcttttcc aaaaacaact ctcaaaagat    7560
atgctacgtg gtgagttcct atagctgaat tattacaact accaccctat cgatcactac    7620
cgccctaaaa gtgttcaact tttgaaggca accaaaacca atacatgaac gacgatcgtg    7680
tgcgcttgtc gtcgttatca ttagcctctg tagctctaat tttcacctat gtacgcatgg    7740
atagacgatt cggaaataca gttcagttta cctaccatat actatgccga atcgaacgc    7800
acacaggtgt gaggcagcag ccgctcacga gttatgcgcc gaaaccgaca tctcggaatc    7860
ttcagtccac aatcaaaaaa tagacacctg gtaccactac aaaattatac tcctactgta    7920
tattggtaaa acaaaacatt ttcttttta tttgatagga gtgctgcaaa ttaaagttct    7980
ttgtgtcatt tttcaaagga aaaaaaaac acctttacca ctcttcttcc ttgccatcat    8040
tttttttta ccaaagtttg ttctgtcaaa tgaacatata tatagttcgg tgctatgtca    8100
gtgccattta ccggccacta gctagtagga ctgccatgtt ccagcaaatt gtctagtgga    8160
ccggagtggc caaaggagc caattatgta gggttgcaag cgggatcaca caaaagcctc    8220
```

```
gcctctagtt cattttatca attaagtggt actttctcag ggaccccct tgcaactcta    8280
ccattacatc cgtgcaaaat aaaagctagc atcacgcacc agatttagta ctccctccgt    8340
ttttatttag ttcgcattct aggttcagcc aaagtcatac tttgcaaagt ttaaccaaaa    8400
ttataagaaa aaaatatcaa taatcatcat acaaaataca tataatataa gagtaaacct    8460
tataacgatt ctacaataga ttttttttatt gcatatgtca atattttttc ataaatattt    8520
actcaaaatt ataaggtttg actttgacta aacccagaac cttcttagag aggaagaaat    8580
gcatgggcaa aagcaaatca tgcatatggg caggagtaac atttttttga ctttcataga    8640
aagtactgta tggcactaaa cggtctaaac cggacactgg aagcaaatcg tgcacgtggg    8700
caatattatc taccgtcgcg tcgccagtct ccccatgccc atgaccatgc ttggaatttt    8760
agtctcgccg gagctgccga gtgcatgcat agtgacgagt ttcaataggc cactatatat    8820
gtgatcatgg ctcttgattt gtcactttct ttttttgccg aaggatatag tagtattact    8880
ttctctgcta tcacaaagaa agaactgatt gtgtctagtc taggtggtct cagaattctg    8940
catgactcca gagtattctt gatgccactt gtttgttatt gcaagaaact taattcggag    9000
acaaccaaaa gctcatccca tgtctctgga actagtagac ataagaaaat ctcatggtat    9060
cagtttgcta tttatctaca actgaaacgg catgtttggt tttattaaat tcagaactgg    9120
tactgctacg ggaaggcggt tgcggagcag gcggcatcgg agttggcgcg gcagcgcggc    9180
gtggaccttg tggtggtgaa cccggtgctg gtgatcggcc ccctgctgca gccgacggtg    9240
aacgccagca tcggccacat cctcaagtac ctggacgggt cggccagcaa gttcgccaac    9300
gccgtgcagg cgtacgtgga cgtccgcgac gtggccgacg cccacctccg cgtcttcgag    9360
tgcgccgccg cgtccggccg ccacctctgc gccgagcgcg tcctccaccg cgaggacgtc    9420
gtgcgcatcc tcgccaagct cttccccgag taccccgtcc ccaccaggta cgcgtacgac    9480
ctgcttgcta gccgcttccg ttaattccat tgccttaatt gattgcatga tgccgctcct    9540
aatttactca cttgcgtaac taattgcatt catatatgat ctaccaaccg tggagaaaat    9600
tagcaagagt ctgtcgggc gtcccggtcc agtgcagtta acctgcatgt cgatggtctg    9660
caggttgcag cttacttgtg gttctttagt tcagagacac agagcaattg ggcactaagc    9720
aaaactgaca tcactggtaa ttaggtagct cccacacact gaagtgggtg gatcccatcg    9780
gtagtaggta agggtggata gtactggacg agagctcgat cgttgttgta aaaaagcgag    9840
tgaccaccac ttcaccatcc actgcaagta gctgctagtg aaccatccaa ccagctccct    9900
ggatcactct gctccgtccg taccttcagc tacctacaga agcgacatga acacacagac    9960
acacaaggcc ggctcaccat tcgcataggt caaaccaaat gttggtgaac ggcaacatcg   10020
ccacaagtcg cgtgctagtt cgaggttgtg tccggtgtac cgaggccaca ctattcgtgc   10080
tgcccgtcgc tgatatttgc acgcgtagct gtcgacgaaa gtaggtggac tgacagatac   10140
acatatcctc attgccttct ctgctcggtt tctgctagga ttgccatctt caggagtgcc   10200
tatccgcacg gcagaaacgc gtagcatcag gccagaaagc agcgtgcgtg atatcgtaac   10260
ccagacggtc ttcacctgtc cattctgggc tacctggcat actacctcgg tgccgctgtg   10320
ccgctgacca attcgtgcac gaccactata gcaaaaccct atgcatgtaa ctgcttcaag   10380
atcagcagtg acatgtgcaa tataaacctc aagtgtgcac tctagtgcgt actgataaaa   10440
ccgtataact ggtgacccag tcattcttct ctttttttatt tgtttggacc aaacgaacac   10500
agcatgttat ccatcaccaa caagtggcgc tgattttttca aactacactg ggatcatact   10560
```

```
ggaaaccaaa gcaggagaac atcttcgaac caagagatgt ttactaaatt tgaaagaaaa    10620
tgtactgaca agtaatctgt ctgaagcaag acacatacta cctcggttcg aacgtgggac    10680
accatgcccg tgccatattt gctaggcacc actctgccgt cgattgtatc ccaacggagg    10740
gagtatcgat ttgcgcaaag ttcctacata catagccgct caagatataa tcttacgacc    10800
ttccgtcgaa atcggtgata cgtcgcaacc tatagctaac ttggcagagc ataaaataac    10860
tatctaaggt tggggtctcc ctcttttcaa tcaacctttc ataccgaatg atgggagtgt    10920
ttgtgaaaac atctcttggt cgactcagca ttagcgccct accaatttct ctgtggacaa    10980
tgccaccta aatcgttttt tagtcttcat gatttactcc cccttatatc tggccgtagt     11040
ccctctttc cattttcctt gtctggtttt aagtcaaatt tagactacta aaacaacagc     11100
aagattttat ggaagggagg tagtgcaaaa cagaaagtcc gatcgaaatg cgtgccaatt    11160
tgtcgtcgcg gcggccggac taaaatggat ctgcatgtgc ataccgttcg tcggagtatc    11220
ctgcgaacgg tcgtgtgttt agtcaacatt aatgtgaggt tcatgtgata ctcttgcttg    11280
aaagatacta ctactgctac ctcgtagaac tgaatgaaag tatgtgggac tgttcagctc    11340
tctgcacatg tcaaatgtcg ttactcatac ctttcgtcag agcatcctgc gacgcgcgcc    11400
ggtgccgaaa tttcgccgtg tgtttagtca agatcaacgt gaggttcatg cggtaccta     11460
tctggcttcg aagataccaa gcagactgcg gctagattgt cattttgatg tcgcaatctt    11520
caccaaacct gccttccgg accacagcag cagtacgtaa caatggtgtc atcgccatgc     11580
gttgctcgtg tccaaggaaa cggaggaatc tcggcttccc acaagtcacg catcgatgtt    11640
cacacctgaa ttggtcgacg tttcttcttc tagactagaa aaagattaca gaacaacgca    11700
agcttcgttc aagtccatac ttctgttcag tatactcctg atgattgcag ttatatcagc    11760
atgtctattc tgaatttttg cacttctatt caaaggatgg gctggaattg ctactgactt    11820
tggtgtgatg tgtgtggcac aggtgctctg atgagacgaa cccgaggaag cagccataca    11880
agatgtcgaa ccagaagctc caggacctcg gactcgagtt caggccggtg agccagtccc    11940
tgtacgagac ggtgaagagc ctccaggaga agggccacct tccggtgctc agcgagcagg    12000
cagaggcgga caaggaaacc ctagctgccg agctgcaggc aggggttacc atccgagcat    12060
gaggaacaag aaatcaacca tgtccatact gctactgtca tgtaaaccag ctgttgaatg    12120
cctaaaatct aagttcttgt aatactgtgt tgtttcatgt ggactagatt gatcg         12175
```

MODIFICATION OF LIGNIN BIOSYNTHESIS

This application is a continuation-in-part of U.S. patent application Ser. No. 10/311,459, the entire disclosure of which is incorporated herein by reference.

The present invention relates to the modification of lignin biosynthesis in plants and, more particularly, to enzymes involved in the lignin biosynthetic pathway and nucleic acids encoding such enzymes.

The present invention also relates to a regulatory element and, more particularly, to a promoter capable of causing expression of an exogenous gene in plant cells, such as a gene encoding an enzyme involved in the lignin biosynthetic pathway in plants.

The invention also relates to vectors including the nucleic acids and regulatory elements of the invention, plant cells, plants, seeds and other plant parts transformed with the regulatory elements, nucleic acids and vectors, and methods of using the nucleic acids, regulatory elements and vectors.

Lignins are complex phenolic polymers that strengthen plant cell walls against mechanical and chemical degradation. The process of lignification typically occurs during secondary thickening of the walls of cells with structural, conductive or defensive roles. Three monolignol precursors, sinapyl, coniferyl and p-coumaryl alcohol combine by dehydrogenative polymerisation to produce respectively the syringyl(S), guaiacyl(G) and hydroxyl(H) subunits of the lignin polymer, which can also become linked to cell-wall polysaccharides through the action of peroxidases and other oxidative isozymes. In grasses, biosynthesis of the monolignol precursors is a multistep process beginning with the aromatic amino-acids phenylalanine and tyrosine. It is the final two reduction/dehydrogenation steps of the pathway, catalysed by Cinnamoyl CoA Reductase (CCR) and Cinnamyl Alcohol Dehydrogenase (CAD) that are considered to be specific to lignin biosynthesis. The proportions of monolignols incorporated into the lignin polymer vary depending on plant species, tissue, developmental stage and sub-cellular location.

Caffeic acid O-methyl transferase (OMT), 4 coumarate CoA-ligase (4CL), cinnamoyl-CoA reductase (CCR) and cinnamyl alcohol dehydrogenase (CAD) are key enzymes involved in lignin biosynthesis.

Worldwide permanent pasture is estimated to cover 70% of agriculturally cultivated area. Ryegrasses (*Lolium* spp.) together with the closely related fescues (*Festuca* spp.) are of significant value in temperate grasslands. The commercially most important ryegrasses are Italian or annual ryegrass (*L. multiflorum* Lam.) and perennial ryegrass (*L. perenne* L.). They are the key forage species in countries where livestock production is an intensive enterprise, such as the Netherlands, United Kingdom and New Zealand. The commercially most important fescues are tall fescue (*F. anundinacea* Schreb.), meadow fescue (*F. pratensis*) and red fescue (*F. rubra*).

Perennial ryegrass (*Lolium perenne* L.) is the major grass species sown in temperate dairy pastures in Australia, and the key pasture grass in temperate climates throughout the world. A marked decline of the feeding value of grasses is observed in temperate pastures of Australia during late spring and early summer, where the nutritive value of perennial ryegrass based pasture is often insufficient to meet the metabolic demands of lactating dairy cattle. Perennial ryegrass is also an important turf grass.

Grass and legume in vitro dry matter digestibility has been negatively correlated with lignin content. In addition, natural mutants of lignin biosynthetic enzymes in maize, sorghum and pearl millet that have higher rumen digestibility have been characterised as having lower lignin content and altered S/G subunit ratio. Thus, lignification of plant cell walls is the major factor identified as responsible for lowering digestibility of forage tissues as they mature.

It would be desirable to have methods of altering lignin biosynthesis in plants, including grass species such as ryegrasses and fescues, by reducing the activity of key biosynthetic enzymes in order to reduce lignin content and/or alter lignin composition for enhancing dry matter digestibility and improving herbage quality. However, for some applications it may be desirable to enhance lignin biosynthesis to increase lignin content and/or alter lignin composition, for example to increase mechanical strength of wood, to increase mechanical strength of turf grasses, to reduce plant height and reduce lodging or improve disease resistance.

While nucleic acid sequences encoding some of the enzymes involved in the lignin biosynthetic pathway have been isolated for certain species of plants, there remains a need for materials useful in the modification of lignin biosynthesis in plants, particularly grass species such as ryegrasses and fescues.

Other phenotypic traits which may be improved by transgenic manipulation of plants include disease resistance, mineral content, nutrient quality and drought tolerance.

However, transgenic manipulation of phenotypic traits in plants requires the availability of regulatory elements capable of causing the expression of exogenous genes in plant cells.

It is an object of the present invention to overcome, or at least alleviate, one or more of the difficulties or deficiencies associated with the prior art.

In one aspect, the present invention provides substantially purified or isolated nucleic acids or nucleic acid fragments encoding the following enzymes from a ryegrass (*Lolium*) or fescue (*Festuca*) species: 4 coumarate CoA-ligase (4CL), cinnamoyl-CoA reductase (CCR) and cinnamyl alcohol dehydrogenase (CAD).

The ryegrass (*Lolium*) or fescue (*Festuca*) species may be of any suitable type, including Italian or annual ryegrass, perennial ryegrass, tall fescue, meadow fescue and red fescue. Preferably the ryegrass or fescue species is a ryegrass, more preferably perennial ryegrass (*Lolium perenne*).

The nucleic acid or nucleic acid fragment may be of any suitable type and includes DNA (such as cDNA or genomic DNA) and RNA (such as mRNA) that is single- or double-stranded, optionally containing synthetic, non-natural or altered nucleotide bases, and combinations thereof.

The term "isolated" means that the material is removed from its original environment (e.g. the natural environment if it is naturally occurring). For example, a naturally occurring nucleic acid present in a living plant is not isolated, but the same nucleic acid separated from some or all of the coexisting materials in the natural system, is isolated. Such nucleic acids could be part of a vector and/or such nucleic acids could be part of a composition, and still be isolated in that such a vector or composition is not part of its natural environment.

In a preferred embodiment of this aspect of the invention, the substantially purified or isolated nucleic acid or nucleic acid fragment encoding 4CL includes a nucleotide sequence selected from the group consisting of (a) sequences shown in FIGS. 2, 3 and 4 hereto (Sequence ID Nos: 1, 3 and 5; respectively) (b) complements of the sequences shown in FIGS. 2, 3 and 4 hereto (Sequence ID Nos: 1, 3 and 5, respectively); (c) sequences antisense to the sequences recited in (a) and (b); and (d) functionally active fragments and variants of the sequences recited in (a), (b) and (c).

In a further preferred embodiment of this aspect of the invention, the substantially purified or isolated nucleic acid or nucleic acid fragment encoding CCR includes a nucleotide sequence selected from the group consisting of (a) the sequence shown in FIG. 10 hereto (Sequence ID No: 7); (b) the complement of the sequence shown in FIG. 10 hereto (Sequence ID No: 7); (c) sequences antisense to the sequences recited in (a) and (b); and (d) functionally active fragments and variants of the sequences recited in (a), (b) and (c).

In a still further preferred embodiment of this aspect of the invention, the substantially purified or isolated nucleic acid or nucleic acid fragment encoding CAD includes a nucleotide sequence selected from the group consisting of (a) the sequences shown in FIGS. 13, 14, 26 and 27 hereto (Sequence ID Nos: 9, 11, 14 and 16, respectively); (c) sequences antisense to the sequences recited in (a) and (b); and (d) functionally active fragments and variants of the sequences recited in (a), (b) and (c).

By "functionally active" is meant that the fragment or variant (such as an analogue, derivative or mutant) is capable of modifying lignin biosynthesis in a plant. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence, more preferably at least approximately 90% identity, most preferably at least approximately 95% identity. Such functionally active variants and fragments include, for example, those having nucleic acid changes which result in conservative amino acid substitutions of one or more residues in the corresponding amino acid sequence. Preferably the fragment has a size of at least 10 nucleotides, more preferably at least 15 nucleotides, more preferably at least 20 nucleotides, more preferably at least 50 nucleotides, more preferably at least 100 nucleotides.

In a still further preferred embodiment of this aspect of the invention the functionally active fragment or variant may be capable of modifying lignin biosynthesis in a plant via sense suppression.

By "sense suppression" is meant that when the functionally active fragment or variant is introduced into the plant in sense orientation, it causes an identifiable decrease in expression of the corresponding gene.

Fragments and variants for sense suppression include those with additions, deletions, substitutions or derivatizations of one or more nucleotides in the nucleic acid or nucleic acid fragment according to the present invention.

Fragments and variants for sense suppression include those with short deletions of, for example 1 to approximately 500, 1 to approximately 300 or 1 to approximately 100 nucleotides, preferably consecutive nucleotides. In a preferred embodiment, the short deletion may be located at or near, for example within 100, 50 or 20 bases of, the 3' or 5' end of the nucleic acid.

In a preferred embodiment of this aspect of the invention, the functionally active fragment or variant capable of modifying lignin biosynthesis via sense suppression may be a functionally active fragment or variant of a nucleic acid or nucleic acid fragment encoding 4CL, CCR or CAD as herein before described.

Preferably the functionally active fragment or variant encodes a 4CL, CCR or CAD polypeptide without enzymatic activity or with substantially reduced enzymatic activity.

By "substantially reduced enzymatic activity" is meant enzymatic activity which is significantly lower, for example at least approximately 25%, 50% or 75% lower, than the enzymatic activity in a wild type plant.

Preferably the functionally active fragment or variant includes a frame-shift mutation relative to the corresponding nucleic acid or nucleic acid fragment of the present invention. This may result in a loss of or substantial reduction in enzymatic activity in the encoded polypeptide.

By a frame-shift mutation is meant a mutation that inserts or deletes a number of nucleotides that is not evenly divisible by three from a nucleic acid sequence. Due to the triplet nature of gene expression by codons, the insertion or deletion may disrupt the reading frame, or the grouping of the codons, resulting in a different translation from the original. The earlier in the sequence the deletion or insertion occurs, the more altered is the protein produced.

A frame-shift mutation may cause the reading of codons to be different, so most codons after the mutation (with a few exceptions due to redundancy) will code for different amino acids. Furthermore, the stop codon "UAA, UGA, or UAG" may not be read, or a stop codon may be created at an earlier site. The protein being created may be abnormally short, abnormally long, and/or contain the wrong amino acids. It is unlikely to be functional.

Deletions or additions occurring at or near the 5' end may preferably be within a short distance, for example within 20, 50 or 100 bases of the ATG start codon, preferably within a short distance downstream of the ATG start codon, for example within 20, 50 or 100 bases downstream of the ATG start codon.

Preferably, such deletions or additions occurring at or near the 5' end may result in a frame-shift mutation, so that the resulting polypeptide has little or no 4CL, CCR or CAD activity, respectively.

In a particularly preferred embodiment, the deletion or addition at or near the 5' end may be a deletion or addition of one, two, four, five, seven or eight bases, preferably consecutive bases, within a short distance downstream of the ATG start codon, so as to result in a frame-shift mutation, and a resulting polypeptide with little or no 4CL, CCR, or CAD activity, respectively. More preferably the frame-shift mutation is a deletion of one base.

Deletions occurring at or near the 3' end may preferably start at the 3' end or within a short distance, for example 20, 50 or 100 bases, of the 3' end, and extend in a 5' direction. Preferably, such deletions have a size of between approximately 50 to 500 nucleotides, more preferably approximately 100 to 300 nucleotides.

In a particularly preferred embodiment of this aspect of the invention, the functionally active fragment or variant capable of modifying lignin biosynthesis via sense suppression may be a functionally active fragment or variant of a nucleic acid or nucleic acid fragment encoding CCR, 4CL or CAD, more preferably CCR.

Accordingly, in a preferred embodiment the present invention provides a fragment or variant of the nucleic acid with the sequence shown in FIG. 10 hereto (Sequence ID No: 7), wherein said fragment or variant is capable of modifying lignin biosynthesis in a plant via sense suppression of a gene encoding CCR in said plant.

Preferably, the fragment or variant includes a short deletion at or near the 3' or 5' end of Sequence ID No. 7

Preferably the fragment or variant includes a frame-shift mutation relative to Sequence ID No. 7.

In a further preferred embodiment the present invention provides a fragment or variant of a nucleic acid selected from the group consisting of the nucleic acids with sequences shown in FIGS. 13, 14, 26 and 27 hereto (Sequence ID Nos:

9, 11, 14 and 16, respectively), wherein said fragment or variant is capable of modifying lignin biosynthesis in a plant via sense suppression of a gene encoding CAD in said plant.

Preferably, the fragment or variant includes a short deletion at or near the 3' or 5' end of a sequence selected from the group consisting of Sequence ID Nos. 9, 11, 14 and 16.

Preferably, the fragment or variant includes including a frame-shift mutation relative to Sequence ID No. 9, 11, 14 or 16, respectively.

In a further preferred embodiment, the present invention provides a fragment or variant of a nucleic acid selected from the group consisting of the nucleic acids with sequences shown in FIGS. 2, 3 and 4 hereto (Sequence ID Nos: 1, 3 and 5, respectively) wherein said fragment or variant is capable of modifying lignin biosynthesis in a plant via sense suppression of a gene encoding 4CL in said plant.

Preferably, the fragment or variant includes a short deletion at or near the 3' or 5' end of a sequence selected from the group consisting of Sequence ID Nos: 1, 3 and 5.

Preferably, the fragment or variant includes a frame-shift mutation relative to Sequence ID No: 1, 3 or 5, respectively.

In a second aspect of the present invention there is provided a vector including a nucleic acid or nucleic acid fragment according to the present invention.

In a preferred embodiment of this aspect of the invention, the vector may include a regulatory element such as a promoter, a nucleic acid or nucleic acid fragment according to the present invention and a terminator; said regulatory element, nucleic acid or nucleic acid fragment and terminator being operatively linked.

By "operatively linked" is meant that said regulatory element is capable of causing expression of said nucleic acid or nucleic acid fragment in a plant cell and said terminator is capable of terminating expression of said nucleic acid or nucleic acid fragment in a plant cell. Preferably, said regulatory element is upstream of said nucleic acid or nucleic acid fragment and said terminator is downstream of said nucleic acid or nucleic acid fragment.

The vector may be of any suitable type and may be viral or non-viral. The vector may be an expression vector. Such vectors include chromosomal, non-chromosomal and synthetic nucleic acid sequences, e.g. derivatives of plant viruses; bacterial plasmids; derivatives of the Ti plasmid from *Agrobacterium tumefaciens*; derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable or integrative or viable in the plant cell.

The regulatory element and terminator may be of any suitable type and may be endogenous to the target plant cell or may be exogenous, provided that they are functional in the target plant cell.

Preferably the regulatory element is a promoter. A variety of promoters which may be employed in the vectors of the present invention are well known to those skilled in the art. Factors influencing the choice of promoter include the desired tissue specificity of the vector, and whether constitutive or inducible expression is desired and the nature of the plant cell to be transformed (e.g. monocotyledon or dicotyledon). Particularly suitable promoters include the Cauliflower Mosaic Virus 35S (CaMV 35S) promoter, the maize Ubiquitin promoter, the rice Actin promoter, and ryegrass endogenous OMT, 4CL, CCR or CAD promoters.

A variety of terminators which may be employed in the vectors of the present invention are also well known to those skilled in the art. The terminator may be from the same gene as the promoter sequence or a different gene. Particularly suitable terminators are polyadenylation signals, such as the CaMV 35S polyA and other terminators from the nopaline synthase (nos) and the octopine synthase (ocs) genes.

The vector, in addition to the regulatory element, the nucleic acid or nucleic acid fragment of the present invention and the terminator, may include further elements necessary for expression of the nucleic acid or nucleic acid fragment, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (npt2) gene, the hygromycin phosphotransferase (hph) gene, the phosphinothricin acetyltransferase (bar or pat) gene], and reporter genes (such as beta-glucuronidase (GUS) gene (gusA)]. The vector may also contain a ribosome binding site for translation initiation. The vector may also include appropriate sequences for amplifying expression.

As an alternative to use of a selectable marker gene to provide a phenotypic trait for selection of transformed host cells, the presence of the vector in transformed cells may be determined by other techniques well known in the art, such as PCR (polymerase chain reaction), Southern blot hybridisation analysis, histochemical GUS assays, northern and Western blot hybridisation analyses.

Those skilled in the art will appreciate that the various components of the vector are operatively linked, so as to result in expression of said nucleic acid or nucleic acid fragment. Techniques for operatively linking the components of the vector of the present invention are well known to those skilled in the art. Such techniques include the use of linkers, such as synthetic linkers, for example including one or more restriction enzyme sites.

The vectors of the present invention may be incorporated into a variety of plants, including monocotyledons (such as grasses from the genera *Lolium, Festuca, Paspalum, Pennisetum, Panicum* and other forage and turf grasses, corn, oat, sugarcane, wheat and barley), dicotyledons (such as arabidopsis, tobacco, legumes, alfalfa, oak, eucalyptus, maple, canola, soybean and chickpea) and gymnosperms. In a preferred embodiment, the vectors are used to transform monocotyledons, preferably grass species such as ryegrasses (*Lolium* species) and fescues (*Festuca* species), more preferably perennial ryegrass (*Lolium perenne*) including forage and turf type cultivars.

Techniques for incorporating the vectors of the present invention into plant cells (for example by transduction, transfection or transformation) are well known to those skilled in the art. Such techniques include *Agrobacterium* mediated introduction, electroporation to tissues, cells and protoplasts, protoplast fusion, injection into reproductive organs, injection into immature embryos and high velocity projectile introduction to cells, tissues, calli, immature and mature embryos. The choice of technique will depend largely on the type of plant to be transformed.

Cells incorporating the vector of the present invention may be selected, as described above, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

In a further aspect of the present invention there is provided a plant cell, plant, plant seed or other plant part, including, e.g. transformed with, a vector of the present invention.

The plant cell, plant, plant seed or other plant part may be from any suitable species, including monocotyledons, dicotyledons and gymnosperms. In a preferred embodiment the plant cell, plant, plant seed or other plant part may be from a monocotyledon, preferably a grass species, more preferably a ryegrass (Lolium species) or fescue (Festuca species), even more preferably a ryegrass, most preferably perennial ryegrass, including forage- and turf-type cultivars.

The present invention also provides a plant, plant seed or other plant part derived from a plant cell of the present invention.

The present invention also provides a plant, plant seed or other plant part derived from a plant of the present invention.

In a further aspect of the present invention there is provided a method of modifying lignin biosynthesis in a plant, said method including introducing into said plant an effective amount of a nucleic acid or nucleic acid fragment and/or a vector according to the present invention.

By "an effective amount" is meant an amount sufficient to result in an identifiable phenotypic trait in said plant, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

Using the methods and materials of the present invention, plant lignin biosynthesis may be increased, decreased or otherwise modified relative to an untransformed control plant. It may be increased or otherwise modified, for example, by incorporating additional copies of a sense nucleic acid or nucleic acid fragment of the present invention. It may be decreased, for example, by incorporating an antisense nucleic acid or nucleic acid fragment of the present invention or by incorporating a functionally active fragment or variant which is capable of modifying lignin biosynthesis in a plant via sense suppression. In addition, the number of copies of genes encoding for different enzymes in the lignin biosynthetic pathway may be manipulated to modify the relative amount of each monolignol synthesized, thereby leading to the formation of lignin having altered composition.

Accordingly, in a preferred embodiment of this aspect of the invention there is provided a method of modifying lignin biosynthesis in a plant, said method including introducing into said plant in sense orientation an effective amount of a functionally active fragment or variant of a nucleic acid or nucleic acid fragment according to the present invention.

Preferably the functionally active fragment or variant is capable of modifying lignin biosynthesis in the plant via sense suppression.

Preferred functionally active fragments and variants for sense suppression include those hereinbefore described.

In a still further aspect of the present invention there is provided use of a nucleic acid or nucleic acid fragment according to the present invention, and/or nucleotide sequence information thereof, and/or single nucleotide polymorphisms thereof, as a molecular genetic marker.

More particularly, nucleic acids or nucleic acid fragments according to the present invention, and/or nucleotide sequence information thereof, and/or single nucleotide polymorphisms thereof, may be used as a molecular genetic marker for qualitative trait loci (QTL) tagging, mapping, DNA fingerprinting and in marker assisted selection, and may be used as candidate genes or perfect markers, particularly in ryegrasses and fescues. Even more particularly, nucleic acids or nucleic acid fragments according to the present invention, and/or nucleotide sequence information thereof, may be used as molecular genetic markers in forage and turf grass improvement, e.g. tagging QTLs for dry matter digestibility, herbage quality, mechanical stress tolerance, disease resistance, insect pest resistance, plant stature and leaf and stem colour.

In a still further aspect of the present invention there is provided a substantially purified or isolated polypeptide from a ryegrass (*Lolium*) or fescue (*Fustuca*) species, selected from the group consisting of the enzymes 4CL, CCR and CAD.

The ryegrass (*Lolium*) or fescue (*Festuca*) species may be of any suitable type, including Italian or annual ryegrass, perennial ryegrass, tall fescue, meadow fescue and red fescue. Preferably the species is a ryegrass, more preferably perennial ryegrass *L. perenne*).

In a preferred embodiment of this aspect of the invention, the substantially purified or isolated enzyme 4CL includes an amino acid sequence selected from the group consisting of sequences shown in FIGS. 2, 3 and 4 hereto (Sequence ID Nos: 2, 4 and 6, respectively); and functionally active fragments and variants thereof.

In a further preferred embodiment of this aspect of the invention, the substantially purified or isolated enzyme CCR includes an amino acid sequence selected from the group consisting of the sequence shown in FIG. 10 hereto (Sequence ID No: 8); and functionally active fragments and variants thereof.

In a still further preferred embodiment of this aspect of the invention, the substantially purified or isolated enzyme CAD includes an amino acid sequence selected from the group consisting of the sequence shown in FIGS. 13, 14, 26 and 27 hereto (Sequence ID Nos: 10, 12, 15 and 17, respectively); and functionally active fragments and variants thereof.

By "functionally active" in this context is meant that the fragment or variant has one or more of the biological properties of the enzymes 4CL, CCR and CAD, respectively. Additions, deletions, substitutions and derivatizations of one or more of the amino acids are contemplated so long as the modifications do not result in loss of functional activity of the fragment or variant. Preferably the fragment or variant has at least approximately 60% identity to the relevant part of the above mentioned sequence, more preferably at least approximately 80% identity, most preferably at least approximately 90% identity. Such functionally active variants and fragments include, for example, those having conservative amino acid substitutions of one or more residues in the corresponding amino acid sequence. Preferably the fragment has a size of at least 10 amino acids, more preferably at least 15 amino acids, most preferably at least 20 amino acids.

In a further embodiment of this aspect of the invention, there is provided a polypeptide recombinantly produced from a nucleic acid or nucleic acid fragment according to the present invention. Techniques for recombinantly producing polypeptides are well known to those skilled in the art.

In a still further aspect of the present invention there is provided a lignin or modified lignin substantially or partially purified or isolated from a plant, plant seed or other plant part of the present invention.

Such lignins may be modified from naturally occurring lignins in terms of the length, the degree of polymerisation (number of units), degree of branching and/or nature of linkages between units.

In a still further aspect, the present invention provides an isolated regulatory element capable of causing expression of an exogenous gene in plant cells. Preferably the regulatory element is isolated from a nucleic acid or nucleic acid fragment encoding OMT, 4CL, CCR or CAD.

The regulatory element may be a nucleic acid molecule, including DNA (such as cDNA or genomic DNA) and RNA (such as mRNA) that is single- or double-stranded, optionally containing synthetic, non-natural or altered nucleotide bases, and combinations thereof.

Preferably the regulatory element includes a promoter, more preferably an O-methyltransferase promoter, even more preferably an O-methyltransferase promoter from a ryegrass (*Lolium*) or fescue (*Festuca*) species, more preferably a ryegrass, most preferably perennial ryegrass (*Lolium perenne*).

In a particularly preferred embodiment of this aspect of the invention, the regulatory element includes a promoter from the caffeic acid O-methyltransferase gene corresponding to the cDNA homologue LpOMT1 from perennial ryegrass.

Preferably the regulatory element includes a nucleotide sequence including the first approximately 4630 nucleotides of the sequence shown in FIG. 18 hereto (Sequence ID No: 13); or a functionally active fragment or variant thereof.

By "functionally active" in this context is meant that the fragment or variant (such as an analogue, derivative or mutant) is capable of causing expression of a transgene in plant cells. Such variants include naturally occurring allelic variants and non-naturally occurring variants. Additions, deletions, substitutions and derivatizations of one or more of the nucleotides are contemplated so long as the modifications do not result in loss of functional activity of the regulatory element. Preferably the functionally active fragment or variant has at least approximately 80% identity to the relevant part of the above sequence, more preferably at least approximately 90% identity, most preferably at least approximately 95% identity. Preferably the fragment has a size of at least 100 nucleotides, more preferably at least 150 nucleotides, most preferably at least 200 nucleotides.

In a particularly preferred embodiment of this aspect of the invention, the regulatory element includes a nucleotide sequence selected from the group consisting of:
Nucleotides—4581 to −1
Nucleotides—4285 to −1
Nucleotides—4020 to −1
Nucleotides—2754 to −1
Nucleotides—1810 to −1
Nucleotides—831 to −1
Nucleotides—560 to −1
Nucleotides—525 to −1
Nucleotides—274 to −1
Nucleotides—21 to −1
of FIG. 18 hereto (Sequence ID No: 13);
or a functionally active fragment or variant thereof.

In another preferred embodiment the regulatory element includes a 4 coumarate-CoA ligase promoter, even more preferably a 4 coumarate-CoA ligase promoter from a ryegrass (*Lolium*) or fescue (*Festuca*) species, more preferably a ryegrass, most preferably perennial ryegrass (*Lolium perenne*).

In a particularly preferred embodiment of this aspect of the invention, the regulatory element includes a promoter from the 4 coumarate-CoA ligase gene corresponding to the cDNA homologue Lp4CL2 from perennial ryegrass.

Preferably the regulatory element includes a nucleotide sequence including the first approximately 2206 nucleotides of the sequence shown in FIG. 38 hereto (Sequence ID No: 17); or a functionally active fragment or variant thereof.

By "functionally active" in this context is meant that the fragment or variant (such as an analogue, derivative or mutant) is capable of causing expression of a transgene in plant cells. Such variants include naturally occurring allelic variants and non-naturally occurring variants. Additions, deletions, substitutions and derivatizations of one or more of the nucleotides are contemplated so long as the modifications do not result in loss of functional activity of the regulatory element. Preferably the functionally active fragment or variant has at least approximately 80% identity to the relevant part of the above sequence, more preferably at least approximately 90% identity, most preferably at least approximately 95% identity. Preferably the fragment has a size of at least 100 nucleotides, more preferably at least 150 nucleotides, most preferably at least 200 nucleotides.

In a particularly preferred embodiment of this aspect of the invention, the regulatory element includes a nucleotide sequence selected from the group consisting of:
Nucleotides—2206 to −1
Nucleotides—1546 to −1
Nucleotides—1186 to −1
Nucleotides—406 to −1
Nucleotides—166 to −1
of FIG. 38 hereto (Sequence ID No: 17);
or a functionally active fragment or variant thereof.

In another preferred embodiment the regulatory element includes a cinnamoyl-CoA reductase promoter, even more preferably a cinnamoyl-CoA reductase promoter from a ryegrass (*Lolium*) or fescue (*Festuca*) species, more preferably a ryegrass, most preferably perennial ryegrass (*Lolium perenne*).

In a particularly preferred embodiment of this aspect of the invention, the regulatory element includes a promoter from the cinnamoyl-CoA reductase gene corresponding to the LpCCR1 cDNA from perennial ryegrass.

Preferably the regulatory element includes a nucleotide sequence including the first approximately 6735 nucleotides of the sequence shown in FIG. 39 hereto (Sequence ID No: 18); or a functionally active fragment or variant thereof.

By "functionally active" in this context is meant that the fragment or variant (such as an analogue, derivative or mutant) is capable of causing expression of a transgene in plant cells. Such variants include naturally occurring allelic variants and non-naturally occurring variants. Additions, deletions, substitutions and derivatizations of one or more of the nucleotides are contemplated so long as the modifications do not result in loss of functional activity of the regulatory element. Preferably the functionally active fragment or variant has at least approximately 80% identity to the relevant part of the above sequence, more preferably at least approximately 90% identity, most preferably at least approximately 95% identity. Preferably the fragment has a size of at least 100 nucleotides, more preferably at least 150 nucleotides, most preferably at least 200 nucleotides.

In a particularly preferred embodiment of this aspect of the invention, the regulatory element includes a nucleotide sequence selected from the group consisting of:
Nucleotides—6735 to −1
Nucleotides—5955 to −1
Nucleotides—5415 to −1
Nucleotides—4455 to −1

Nucleotides—4035 to −1
Nucleotides—3195 to −1
Nucleotides—2595 to −1
Nucleotides—1755 to −1
Nucleotides—1275 to −1
Nucleotides—495 to −1
Nucleotides—255 to −1
Nucleotides—75 to −1
of FIG. 39 hereto (Sequence ID No: 18);
or a functionally active fragment or variant thereof.

By an "exogenous gene" is meant a gene not natively linked to said regulatory element. In certain embodiments of the present invention the exogenous gene is also not natively found in the relevant plant or plant cell.

The exogenous gene may be of any suitable type. The exogenous gene may be a nucleic acid such as DNA (e.g. cDNA or genomic DNA) or RNA (e.g. mRNA), and combinations thereof. The exogenous gene may correspond to a target gene, for example a gene capable of influencing disease resistance, herbage digestibility, nutrient quality, mineral content or drought tolerance or be a fragment or variant (such as an analogue, derivative or mutant) thereof which is capable of modifying expression of said target gene. Such variants include nucleic acid sequences which are antisense to said target gene or an analogue, derivative, mutant or fragment thereof. The transgene may code for a protein or RNA sequence depending the target condition and whether down or up-regulation of gene expression is required. Preferably, the target gene is selected from exogenous coding sequences coding for mRNA for a protein, this protein may be of bacterial origin (such as enzymes involved in cell wall modification and cell wall metabolism, cytokinin biosynthesis), or eukaryotic origin (such as pharmaceutically active polypeptides) or of plant origin (such as enzymes involved in the synthesis of phenolic compounds, cell wall metabolism, sugar metabolism, lignin biosynthesis). Preferably, the target gene is selected from the group comprising O-methyltransferase, 4 coumarate CoA-ligase, cinnamoyl CoA reductase, cinnamyl alcohol dehydrogenase, cinnamate 4 hydroxylase, phenolase, laccase, peroxidase, coniferol glucosyl transferase, coniferin beta-glucosidase, phenylalanine ammonia lyase, ferulate 5-hydroxylase, chitinase, glucanase, isopentenyltransferase, xylanase.

The plant cells, in which the regulatory element of the present invention is capable of causing expression of an exogenous gene, may be of any suitable type. The plant cells may be from monocotyledons (such as grasses from the genera *Lolium, Festuca, Paspalum, Pennisetum, Panicum* and other forage and turf grasses, corn, grains, oat, sugarcane, wheat and barley), dicotyledons (such as arabidopsis, tobacco, legumes, alfalfa, oak, eucalyptus and maple) and gymnosperms. Preferably the plant cells are from a monocotyledon, more preferably a grass species such as a ryegrass (*Lolium*) or fescue (*Festuca*) species, even more preferably a ryegrass, most preferably perennial ryegrass (*Lolium perenne*).

The regulatory element according to the present invention may be used to express exogenous genes to which it is operatively linked in the production of transgenic plants.

Accordingly, in a further aspect of the present invention there is provided a vector including a regulatory element according to the present invention.

In a preferred embodiment of this aspect of the invention, the vector may include a regulatory element according to the present invention, an exogenous gene as hereinbefore described, and a terminator; said regulatory element, exogenous gene and terminator being operatively linked, such that said regulatory element is capable of causing expression of said exogenous gene in plant cells. Preferably, said regulatory element is upstream of said exogenous gene and said terminator is downstream of said exogenous gene.

The vector may be of any suitable type and may be viral or non-viral. The vector may be an expression vector. Such vectors include chromosomal, non-chromosomal and synthetic nucleic acid sequences, e.g. derivatives of plant viruses; bacterial plasmids; derivatives of the Ti plasmid from *Agrobacterium tumefaciens*; derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable on integrative or viable in the plant cell.

The terminator may be of any suitable type and includes for example polyadenylation signals, such as the Cauliflower Mosaic Virus 35S polyA (CaMV 35S polyA) and other terminators from the nopaline synthase (nos) and the octopine synthase (ocs) genes.

The vector, in addition to the regulatory element, the exogenous nucleic acid and the terminator, may include further elements necessary for expression of the nucleic acid, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (npt2) gene, the hygromycin phosphotransferase (hph) gene, the phosphinothricin acetyltransferase (bar or pat) gene], and reporter genes (such as beta-glucuronidase (GUS) gene (gusA)]. The vector may also contain a ribosome binding site for translation initiation. The vector may also include appropriate sequences for amplifying expression.

The regulatory element of the present invention may also be used with other full promoters or partial promoter elements.

As an alternative to use of a selectable marker gene to provide a phenotypic trait for selection of transformed host cells, the presence of the vector in transformed cells may be determined by other techniques well known in the art, such as PCR (polymerase chain reaction), Southern blot hybridisation analysis, histochemical GUS assays, northern and Western blot hybridisation analyses.

Those skilled in the art will appreciate that the various components of the vector are operatively linked, so as to result in expression of said transgene. Techniques for operatively linking the components of the vector of the present invention are well known to those skilled in the art. Such techniques include the use of linkers, such as synthetic linkers, for example including one or more restriction sites.

The vectors of the present invention may be incorporated into a variety of plants, including monocotyledons, dicotyledons and gymnosperms. In a preferred embodiment the vectors are used to transform monocotyledons, preferably grass species such as ryegrasses (*Lolium* species) and fescues (*Festuca* species), more preferably perennial ryegrass (*Lolium perenne*) including forage- and turf-type cultivars.

Techniques for incorporating the vectors of the present invention into plant cells (for example by transduction, transfection or transformation) are well known to those skilled in the art. Such techniques include *Agrobacterium* mediated introduction, electroporation to tissues, cells and protoplasts, protoplast fusion, injection into reproductive organs, injection into immature embryos and high velocity projectile introduction to cells, tissues, calli, immature and mature embryos. The choice of technique will depend largely on the type of plant to be transformed.

Cells incorporating the vector of the present invention may be selected, as described above, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

In a further aspect of the present invention there is provided a plant cell, plant, plant seed or other plant part, including, e.g. transformed with, a vector of the present invention.

The plant cell, plant, plant seed or other plant part may be from any suitable species, including monocotyledons, dicotyledons and gymnosperms. In a preferred embodiment the plant cell, plant, plant seed or other plant part is from a monocotyledon, preferably a grass species, more preferably a ryegrass (*Lolium* species) or fescue (*Festuca* species), even more preferably perennial ryegrass (*Lolium* perenne), including forage- and turf-type cultivars.

The present invention also provides a plant, plant seed, or other plant part derived from a plant cell of the present invention.

The present invention also provides a plant, plant seed or other plant part derived from a plant of the present invention.

In a still further aspect of the present invention there is provided a recombinant plant genome including a regulatory element according to the present invention.

In a preferred embodiment of this aspect of the invention the recombinant plant genome further includes an exogenous gene operatively linked to said regulatory element.

In a further aspect of the present invention there is provided a method for expressing an exogenous gene in plant cells, said method including introducing into said plant cells an effective amount of a regulatory element and/or a vector according to the present invention.

By "an effective amount" is meant an amount sufficient to result in an identifiable phenotypic change in said plant cells or a plant, plant seed or other plant part derived therefrom. Such amounts can be readily determined by an appropriately skilled person, taking into account the type of plant cell, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

The present invention will now be more fully described with reference to the accompanying Examples and drawings. It should be understood, however, that the description following is illustrative only and should not be taken in any way as a restriction on the generality of the invention described above.

IN THE FIGURES

FIG. 2 shows the nucleotide (Sequence ID No: 1) and amino acid (Sequence ID No: 2) sequences of Lp4CL1.

FIG. 3 shows the nucleotide (Sequence ID No: 3) and amino acid (Sequence ID No: 4) sequences of Lp4CL2.

FIG. 4 shows the nucleotide (Sequence ID No: 5) and amino acid (Sequence ID No: 6) sequences of Lp4CL3.

FIG. 5 shows amino acid sequence alignment of deduced proteins encoded by Lp4CL1 (Sequence ID No: 2), Lp4CL2 (Sequence ID No: 4) and Lp4CL3 (Sequence ID No: 6).

Figure 6:
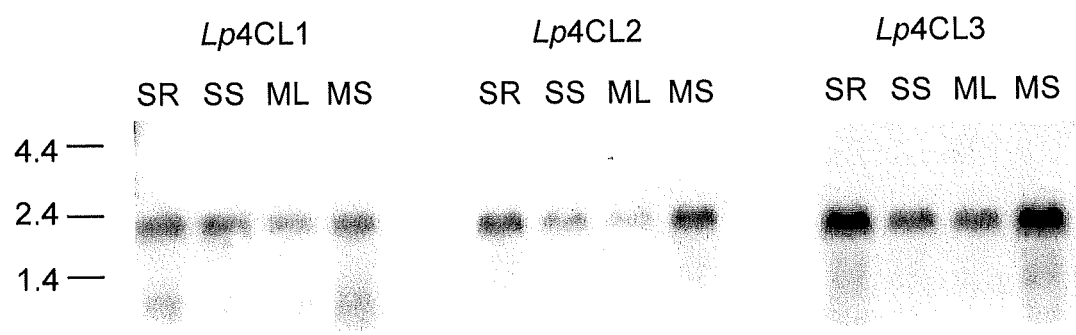

FIG. 6 shows northern hybridisation analysis of developing perennial ryegrass using Lp4CL1, Lp4CL2 and Lp4CL3 as hybridisation probes. SR: roots from seedlings (3-5 d post-germination), SS: shoots from seedlings (3-5 d post-germination), ML: leaves from 12-week-old plants, MS: stems from 12-week-old plants. Blots were washed in 0.2×SSPE, 0.1% SDS at 65° C. Lp4CL1, Lp4CL2 and Lp4CL3 do not cross hybridise at this stringency. Sizes are given in kb.

Figure 7:
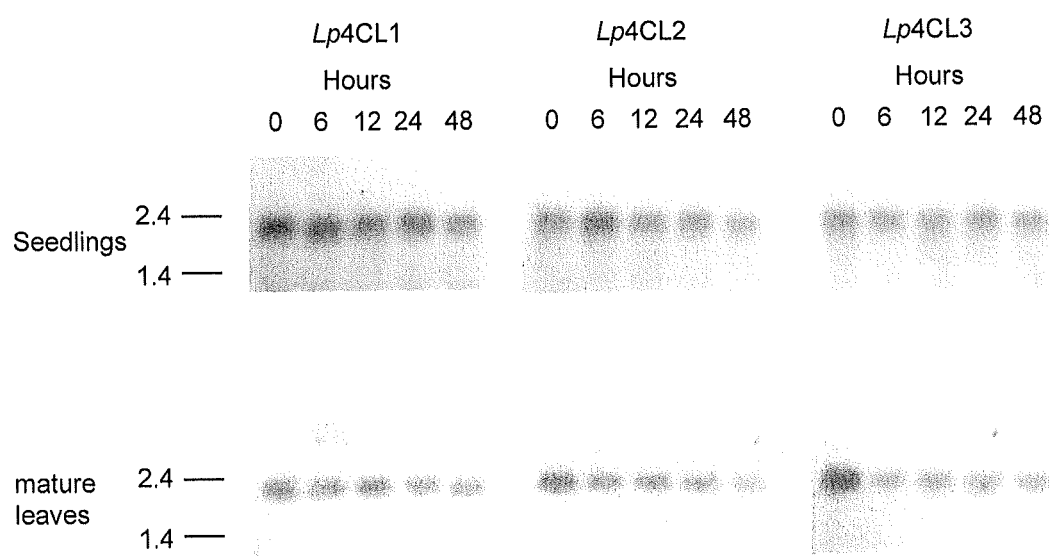

FIG. 7 shows northern hybridisation analysis showing the time course of expression of 4CL mRNA in wounded perennial ryegrass leaves. Sizes are given in kb.

Figure 8:
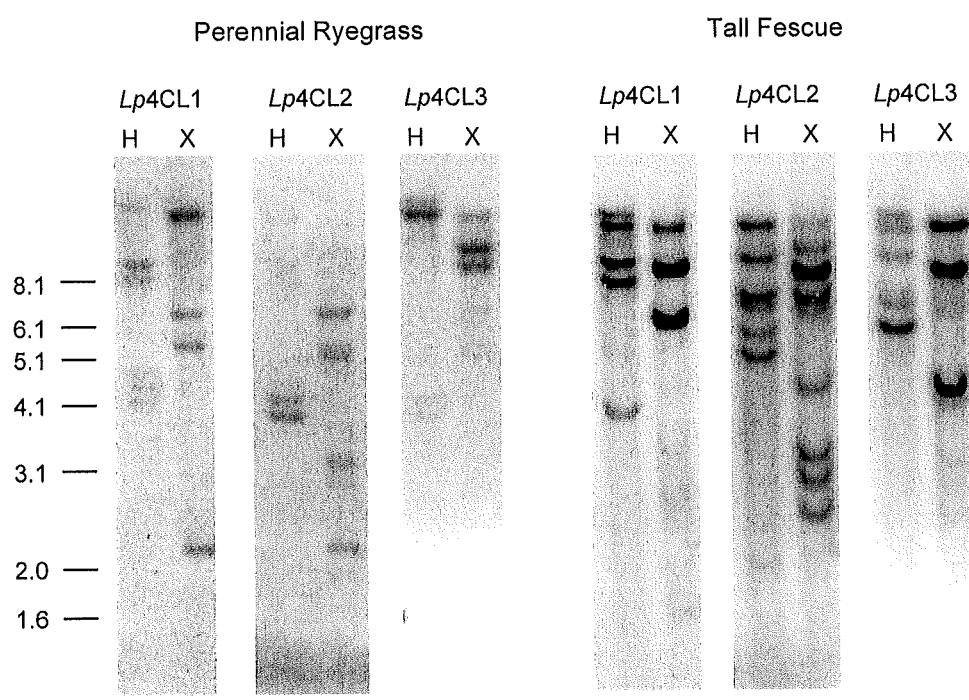

FIG. 8 shows genomic Southern hybridisation analysis using Lp4CL1, Lp4CL2 and Lp4CL3 as hybridisation probes. 10 μg of digested perennial ryegrass genomic DNA or 20 μg of digested tall fescue genomic DNA were separated on a 1.0% agarose gel, transferred to Hybond N+ membranes and then hybridised with $^{32}$P labelled Lp4CL1, Lp4CL2 or Lp4CL3 probes. The ryegrass Lp4CL1, Lp4CL2 and Lp4CL3 genes reveal homologous sequences in tall fescue and indicate that the ryegrass 4CL genes can be used to isolate and to manipulate the expression of the tall fescue (*Festuca arundinacea*) 4CL genes.

Figure 9:
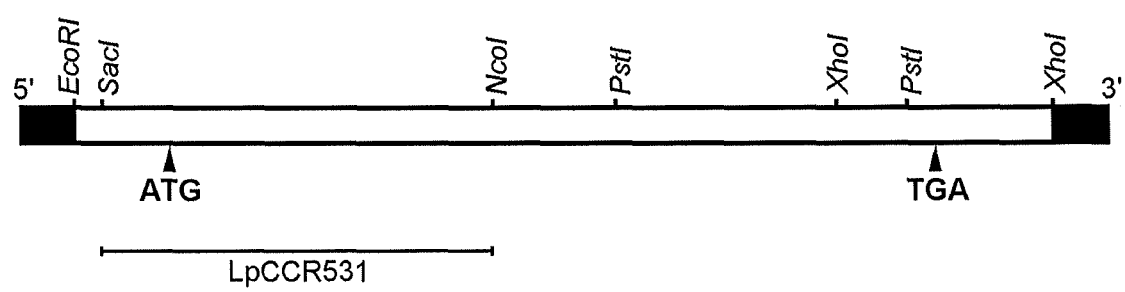

FIG. 9 shows restriction map of LpCCR1. An *L. perenne* seedling cDNA library constructed in Uni-ZAP™ (Stratagene) was screened in a solution containing 10×PIPES, 50% deionised formamide and 10% SDS at 42° C. Filters were washed at room temperature, three times in 0.1% SDS, 2×SSPE and then twice in 0.1% SDS, 0.2×SSPE. The location of the probe used for northern and Southern hybridisation analyses is indicated by the black line labelled LpCCR531.

FIG. 10 shows the nucleotide (Sequence ID No: 7) and amino acid (Sequence ID No: 8) sequences of LpCCR1.

Figure 11:
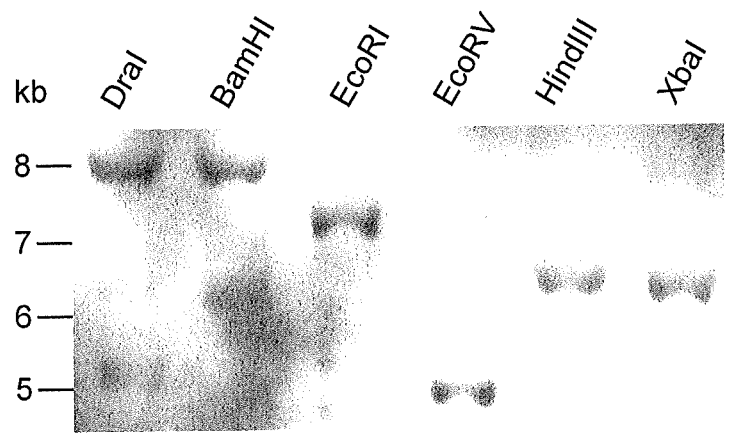

FIG. 11 shows Southern hybridisation analysis of DNA from double haploid (DH) perennial ryegrass using LpCCR1 as hybridisation probe. 10 μg of DH genomic DNA was digested with DraI, BamHI, EcoRI, EcoRV, HindIII or XbaI, separated on a 1% agarose gel and then capillary blotted onto nylon membrane (Amersham Hybond-N). The membrane was probed with the digoxigenin (DIG) labelled LpCCR531 fragment at 25 ng/ml in the hybridisation solution. Hybridisation was in 4×SSC, 50% formamide, 0.1% N-Lauroyl-sarcosine, 0.02% SDS, 2% Blocking solution at 42° C. The membrane was washed twice for five minutes in 2×SSC, 0.1% SDS at room temperature, then twice for fifteen minutes in 0.5×SSC, 0.1% SDS at 68° C. Molecular weight was determined by comparison to a DIG-labelled marker (Roche Molecular Biochemicals).

Figure 12:
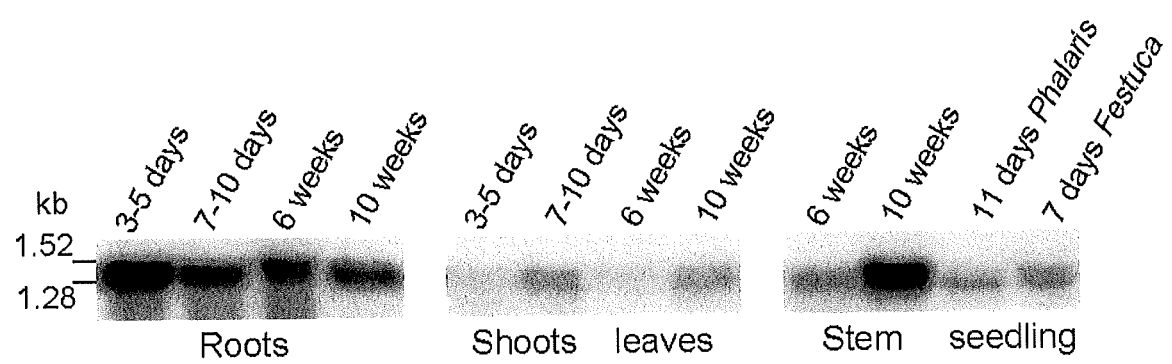

FIG. 12 shows northern hybridisation analysis of RNA samples from different organs and developmental stages of perennial ryegrass using LpCCR1 probe. Roots from seedlings (3-5 d post-germination), shoots from seedlings (3-5 d post-germination), roots from seedlings (7-10 d post-germination), leaves from seedlings (7-10 d post-germination), roots from 6 and 10 week old plants, leaves from 6 and 10 week old plants, stems from 6 and 10 week old plants, whole seedling from 11 day old Phalaris and 7 day old Festuca.

Total RNA was isolated using Trizol (GibcoBRL) and 15 μg was separated on a 1.2% Agarose gel containing 6% formamide and then capillary blotted onto nylon membrane (Amersham Hybond-N). The membrane was stained with 0.2% methylene blue/0.3M sodium acetate to visualise the marker and ensure that RNA was evenly loaded. 50 ng LpCCR531 was random-labelled with $^{32}$P-dCTP (Amersham Megaprime) and hybridisation conditions were 4×SSC, 50% formamide, 0.5% SDS, 5×denhardt solution, 5% dextrane sulphate, 0.1% Herring sperm DNA at 42° C. over-night. The ryegrass LpCCR1 gene reveal homologous transcripts in tall fescue and Phalaris, thus indicating that the ryegrass CCR gene can be used to manipulate the expression of the tall fescue (*Festuca arundinacea*) and Phalaris CCR endogenous genes.

FIG. 13 shows the nucleotide (Sequence ID No: 9) and amino acid (Sequence ID No: 10) sequences of LpCAD1.

FIG. 14 shows the nucleotide (Sequence ID No: 11) and amino acid (Sequence ID No: 12) sequences of LpCAD2.

Figure 15:
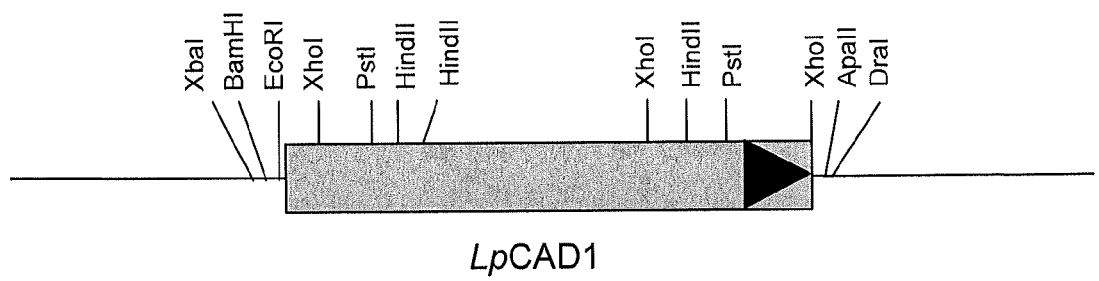

FIG. 15 shows a plasmid map of a cDNA clone encoding perennial ryegrass CAD homologue LpCAD1.

Figure 16:
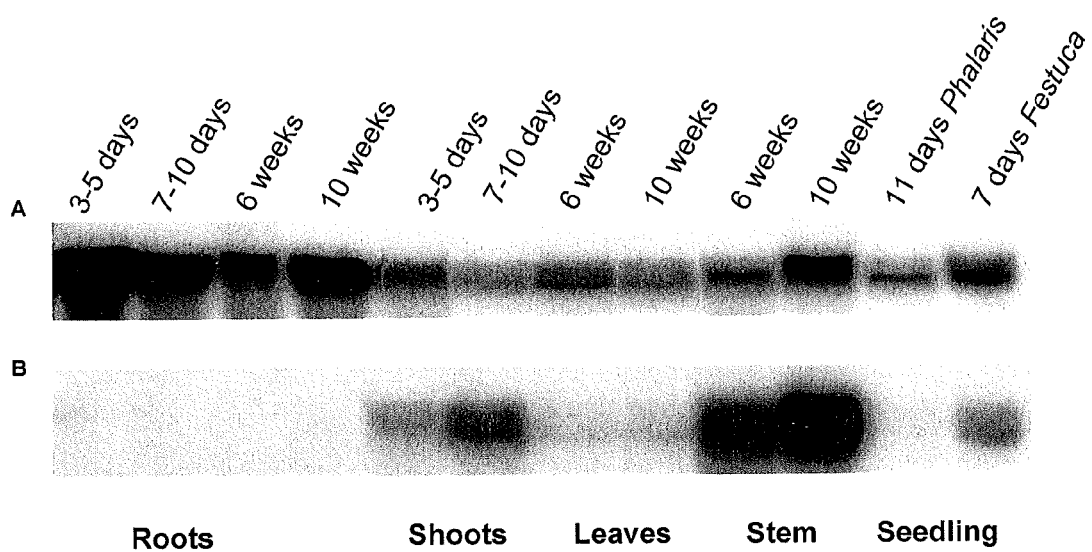

FIG. 16 shows northern hybridisation analysis of RNA samples from different organs and developmental stages of perennial ryegrass using A) LpCAD1 and B) LpCAD2 as hybridisation probes. Roots from seedlings 3-5 d post-germination, 7-10 d post-germination, 6 weeks and 10 weeks, Shoots from seedlings 3-5 d post-germination and 7-10 d post-germination, Leaves from 6 week old and 10 week old plants, stem tissue from 6 and 10 week old plants. RNA isolated from *Phalaris* and *Festuca* 11 and 7 day old seedlings. The ryegrass CAD genes reveal homologous transcripts in tall fescue and Phalaris, thus indicating that the ryegrass CAD gene can be used to manipulate the expression of the tall fescue and Phalaris CAD endogenous genes.

Figure 17:
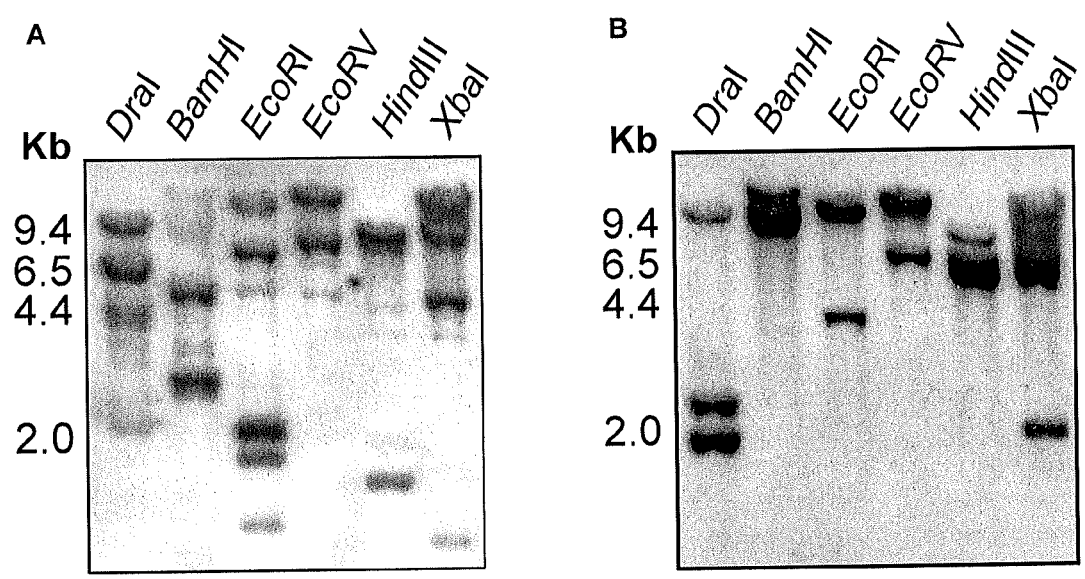

FIG. 17 shows genomic Southern hybridisation analysis. 10 μg of perennial ryegrass genomic DNA digested with a range of restriction enzymes was separated on a 0.8% agarose gel, transferred to Hybond N and then hybridised with a DIG labelled A) LpCAD1, and B) LpCAD2 hybridisation probe.

FIG. 18 shows the nucleotide sequence of the LpOmt1 promoter (Sequence ID No: 13).

Figure 19:
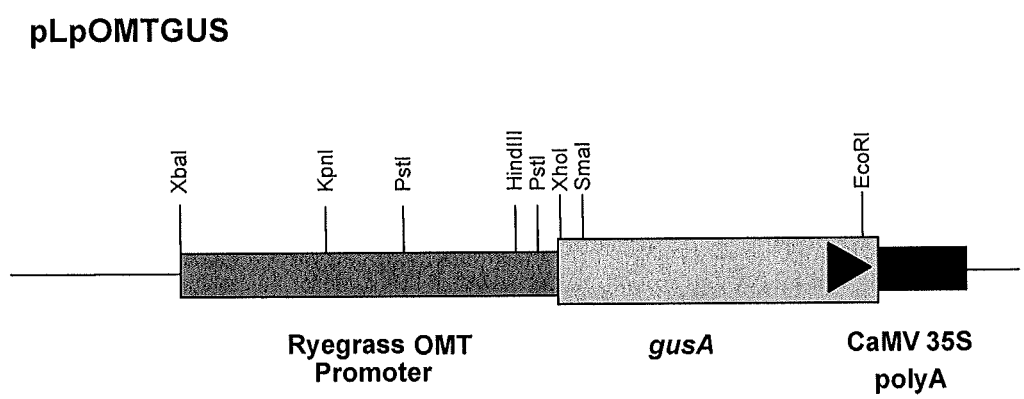

FIG. 19 shows a plasmid map of plant transformation vector carrying the reporter β-glucuronidase (GUS) gene (gusA) under control of the perennial ryegrass LpOmt1 promoter.

Figure 20:
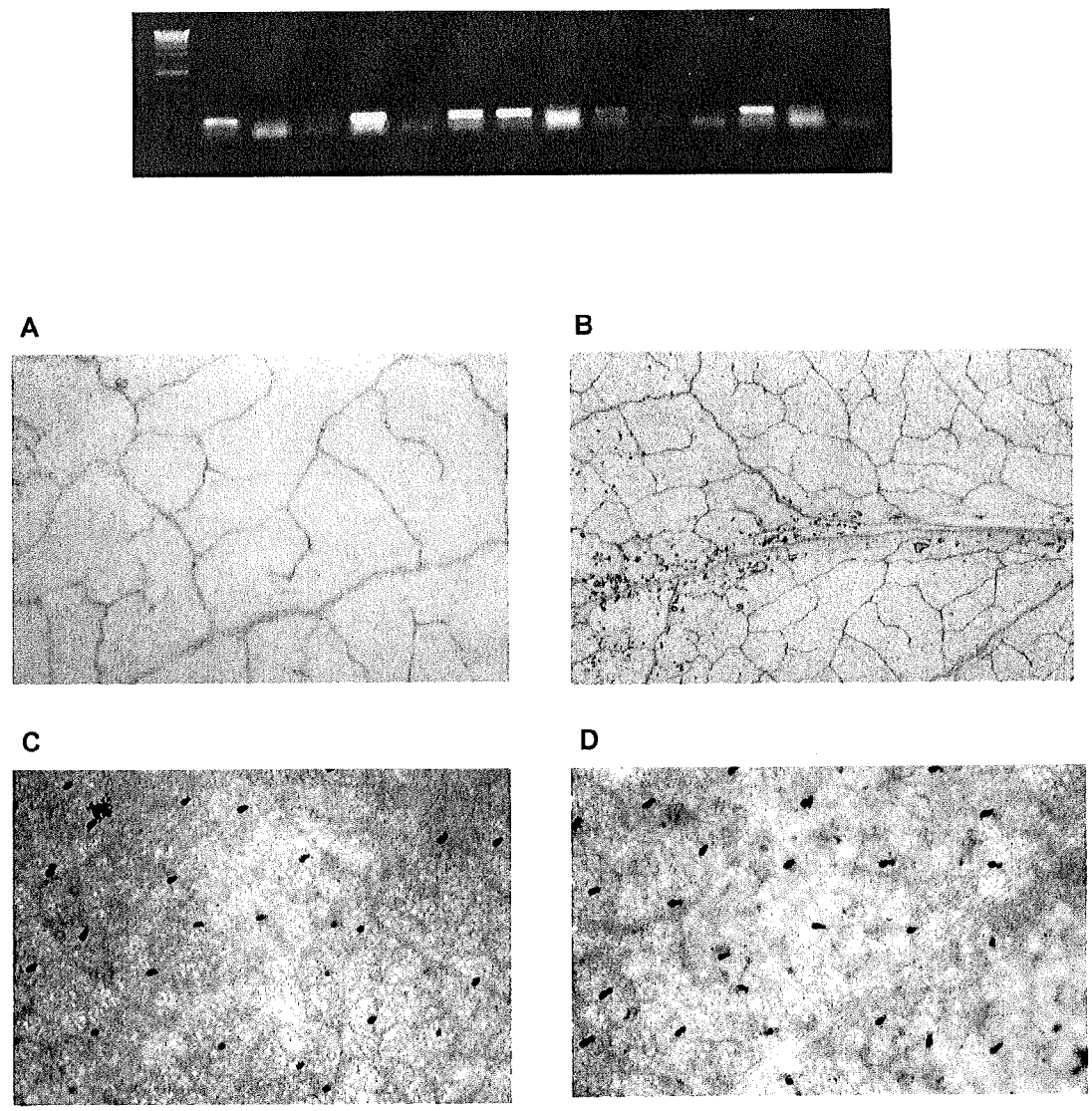

FIG. 20 (upper image) shows PCR analysis of transgenic tobacco plants containing the gusA gene under the control of the perennial ryegrass LpOMT1 promoter (upper figure). PCR reactions using gusA-specific primers were performed. FIG. 20 (lower images) show histochemical GUS assays, demonstrating xylem-specific gusA expression (A and B) and gusA expression in glandular leaf trichomes (C and D) in transgenic tobacco plants containing the gusA gene under the control of the perennial ryegrass LpOMT1 promoter.

FIG. 21 shows the isolation of the LpCCR1 genomic clone 1. A) Southern hybridization analysis of CCR genomic clone λLp6.1.1a digested with XbaI, NcoI, SalI, XhoI, XhoI/SalI DNA was separated on a 0.8% agarose gel, transferred to Hybond N and hybridized with a DIG labelled CCR1 probe. B) Map showing the genomic gene organisation of LpCCR1 clone 1 based on sequence results. C) Comparison of plant CCR exon size and number in different plant species (*Lolium perenne*, Lp., *Eucalyptus gunni*, Eg., *Eucalyptus saligna*, Es., *Populus balsamifera*, Pb.)

FIG. 22 shows the isolation of the LpCCR1 genomic clone 2. A) Southern hybridization analysis of CCR genomic clone λLp6.1.1a digested with XbaI, NcoI, SalI, XhoI, XhoI/SalI DNA was separated on a 0.8% agarose gel, transferred to Hybond N and hybridized with 200 bp of the CCR1 promoter (FIG. 21B). B) Map showing the promoter region of LpCCR1 clone 2 based on sequence results.

Figure 23:
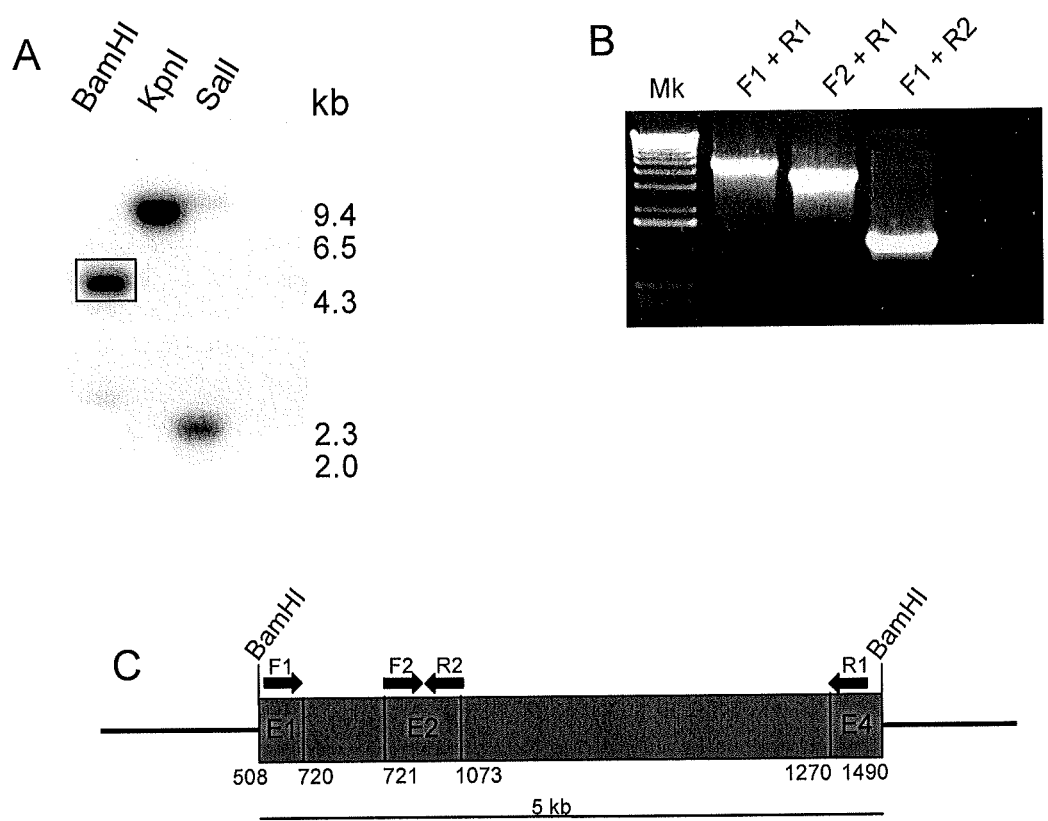

FIG. 23 shows the isolation of an Lp4CL genomic clone. A) Southern hybridisation analysis of 4CL genomic clone λLp4CL2 digested with BamHI, KpnIs or SalI. DNA was separated on a 0.8% agarose gel, transferred to Hybond N and hybridized with a DIG labelled 4CL1 hybridisation probe. B) 10 μl of a standard PCR reaction using forward and reverse oligonucleotides designed to positions outlined on C). The PCR products were separated on a 0.8% agarose gel and stained with ethidium bromide. C) Map showing the genomic gene organisation of λLp4CL2 based on sequence and PCR results.

Figure 24:
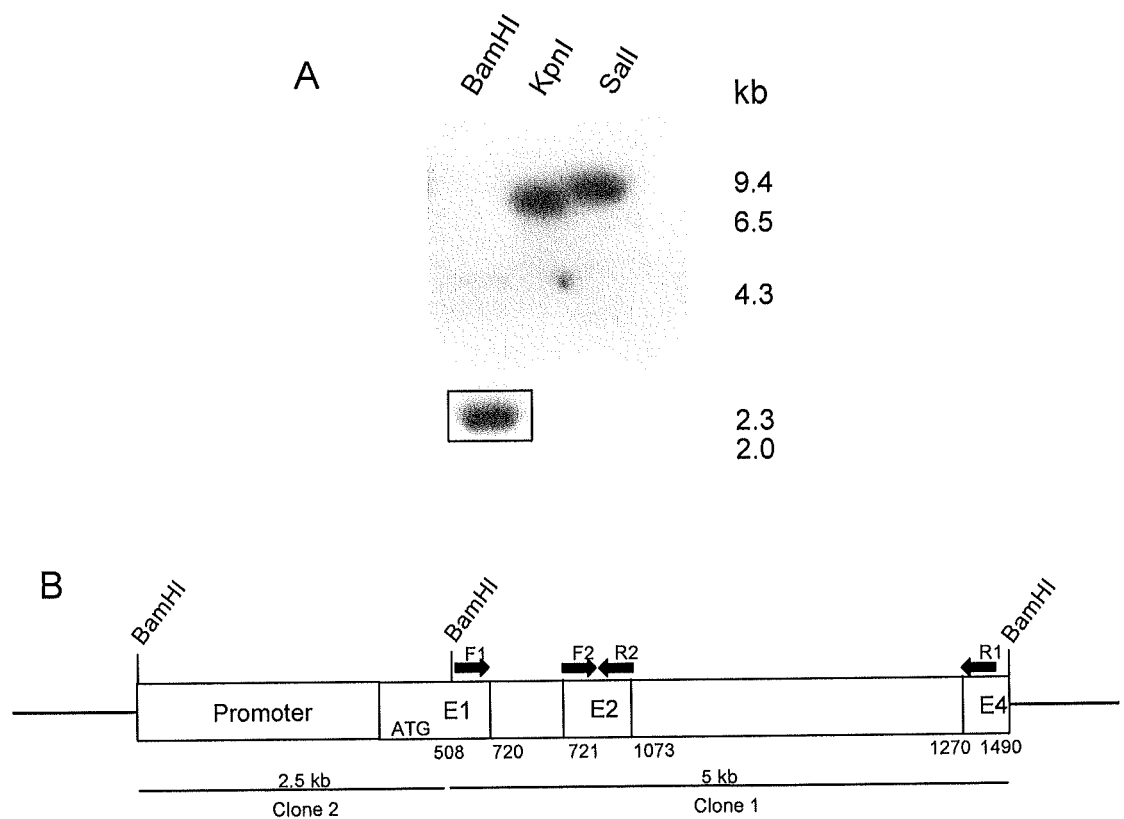

FIG. 24 shows the isolation of an Lp4CL genomic clone. A) Southern hybridisation analysis of 4CL genomic clone λLp4CL2 digested with BamHI, KpnI, SalI. DNA was separated on a 0.8% agarose gel, transferred to Hybond N and hybridized with a DIG labelled 4CL1 probe. B) Map showing the genomic gene organisation of Lp4CL2 clone 1 and the promoter region of clone 2.

Figure 25:
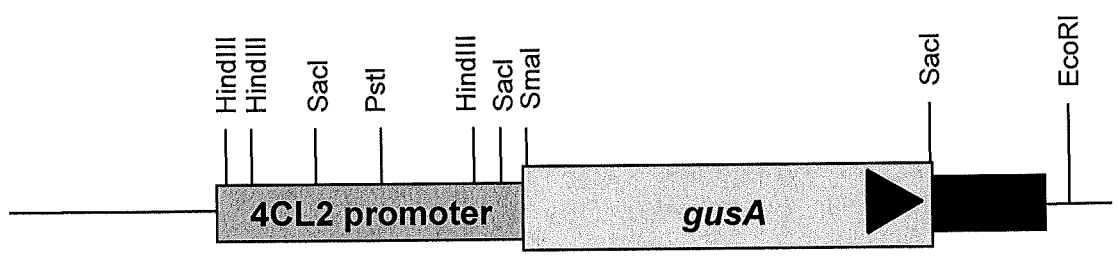

FIG. 25 shows plasmid map of plant transformation vector carrying the gusA gene under control of the perennial ryegrass Lp4CL2 promoter (Lp4CL2::gusA).

FIG. 26 shows nucleotide (Sequence ID No: 14) and amino acid (Sequence ID No:15) sequences of genomic clone CAD2 cv Barlano (Intron 1 and first 111 bp of the coding region are missing).

FIG. 27 shows nucleotide (Sequence ID No: 16) and amino acid (Sequence ID No:15) sequences of coding sequence deduced from genomic clone CAD2 cv Barlano (region in bold is missing from the genomic clone).

FIG. 28 shows the isolation of LpCAD2 genomic clone. A) Southern hybridization analysis of CAD genomic clone λLpCAD2 digested with BamHI, EcoRI, KpnI, SalI or XbaI. DNA was separated on a 0.8% agarose gel, transferred to Hybond N and hybridized with a DIG labelled CAD2 hybridisation probe. B) Map showing the genomic gene organisation of λLpCAD2 based on sequence results.

FIG. 29 shows A) Sense and antisense Lp4CL1, Lp4CL2 and Lp4CL3 transformation vectors under control of the CaMV 35S promoter; B) Sense and antisense Lp4CL1, Lp4CL2 and Lp4CL3 transformation vectors under control of the maize ubiquitin promoter.

FIG. 30 shows A) Sense and antisense LpCCR1 transformation vectors under control of the CaMV 35S promoter; B) Sense and antisense LpCCR1 transformation vectors under control of the maize ubiquitin promoter.

FIG. 31 shows A) Sense and antisense LpCAD1 transformation vectors under control of the CaMV 35S promoter; B) Sense and antisense LpCAD1 transformation vectors under control of the maize ubiquitin promoter.

FIG. 32 shows molecular analysis of Lp4CL1-transgenic tobacco. A) Plasmid map of transformation vector carrying a chimeric sense Lp4CL1 gene. B) PCR analysis of independent transgenic tobacco clones using Lp4CL1 specific primers. C) Southern hybridization analysis of independent transgenic tobacco plants using an Lp4CL1 specific probe. D) Northern hybridization analysis of independent transgenic tobacco plants using an Lp4CL1 specific probe.

FIG. 33 shows molecular analysis of LpCCR1-transgenic tobacco. A) Plasmid map of transformation vectors carrying a chimeric sense and antisense LpCCR1 gene. B) PCR analysis of independent sense transgenic tobacco clones using LpCCR1 specific primers.

Figure 34:
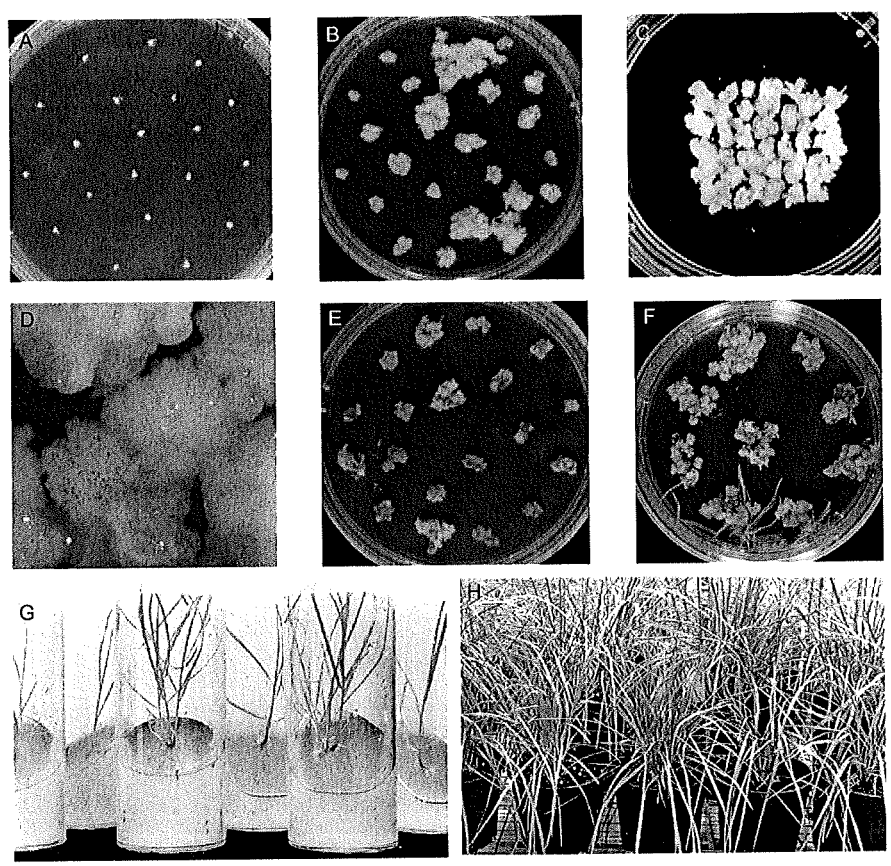

FIG. 34 shows protocol for suspension culture-independent production of transgenic perennial ryegrass plants. A) Isolated zygotic embryos, plated on MSM5 medium, day 0; B) Embryogenic callus formation and proliferation, 6-8 weeks after embryo isolation; C) Embryogenic calli arranged on high osmotic MSM3Plus medium prior to biolistic transformation; D) Histochemical GUS assay showing GUS expressing foci 3-4 days post-bombardment of chimeric gusA gene; E) Selection of embryogenic calli on MSM3 medium containing 100 mg/l paromomycin (Pm), 2 weeks after microprojectile bombardment; F) Regeneration of Pm resistant shoots on MSK medium containing 100 mg/l Pm, 4 weeks after microprojectile bombardment; G) In vitro plant regeneration from PM resistant embryogenic calli, 6 weeks after microprojectile bombardment; H) Transgenic perennial ryegrass plants 28 weeks after embryo isolation.

FIG. 35 shows molecular analysis of transgenic perennial ryegrass plants carrying sense and antisense LpOmt1 transgenes. Plasmid maps of vectors used for the co-transformation of perennial ryegrass embryogenic calli; pHP23 carrying a chimeric neomycin phosphotransferase (npt2) selectable marker gene; pUbiomt1 carrying a maize ubiquitin promoter driven sense LpOmt1 gene; pUbitmo1 carrying a maize ubiquitin promoter driven antisense LpOmt1 gene (top). PCR analysis using npt2-specific primers of 5 independent transgenic perennial ryegrass plants from biolistic transformation with sense and antisense LpOmt1 vectors (upper centre). Southern hybridization analysis with an omt1 hybridization probe of 7 independent perennial ryegrass plants co-transformed with sense (lanes 1-3) and antisense (lanes 4-7) LpOmt1 vectors (lower centre left). Southern hybridisation analysis with an npt2 hybridisation probe of independent perennial ryegrass plants (lower centre right). Northern hybridisation analysis of perennial ryegrass plants co-transformed with antisense LpOmt1 vector (bottom). C=negative control untransformed perennial ryegrass; P=positive plasmid control.

Figure 36:
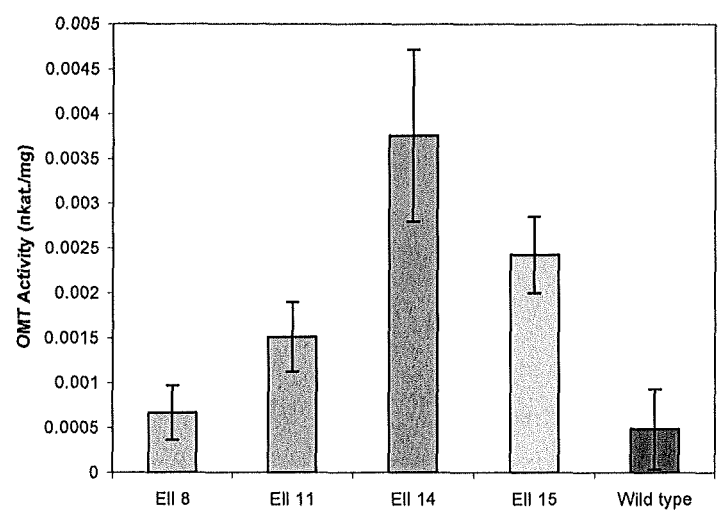

FIG. 36 shows biochemical analysis of LpOmt1-transgenic perennial ryegrass. OMT activity of leaf samples from selected independent LpOmt1-transgenic perennial ryegrass plants (EII8, EII11, EII14 and EII15) was determined and compared to untransformed perennial ryegrass negative control plant *L. perenne* cv. Ellett (wild type). Mean values and standard deviations of replicate assays are shown.

Figure 37:
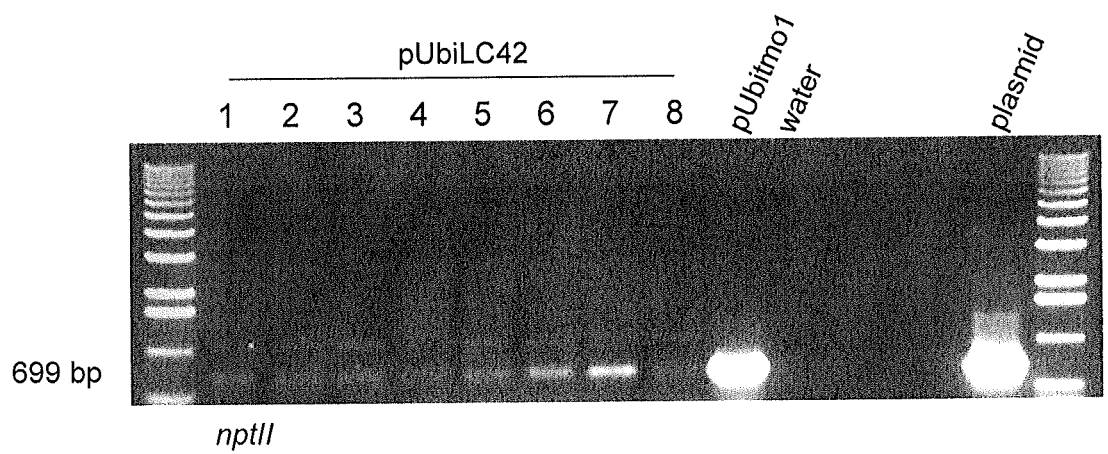

FIG. 37 shows PCR screening of transgenic ryegrass plants. PCR analysis using npt2-specific primers of 8 independent transgenic perennial ryegrass plants from biolistic transformation with antisense LpUbi4CL2 vector.

FIG. 38 shows the nucleotide sequence of genomic clone 4CL2 from perennial ryegrass (Sequence ID No: 17).

FIG. 39 shows the nucleotide sequence of genomic clone CCR1 from perennial ryegrass (Sequence ID No: 18).

Figure 40:
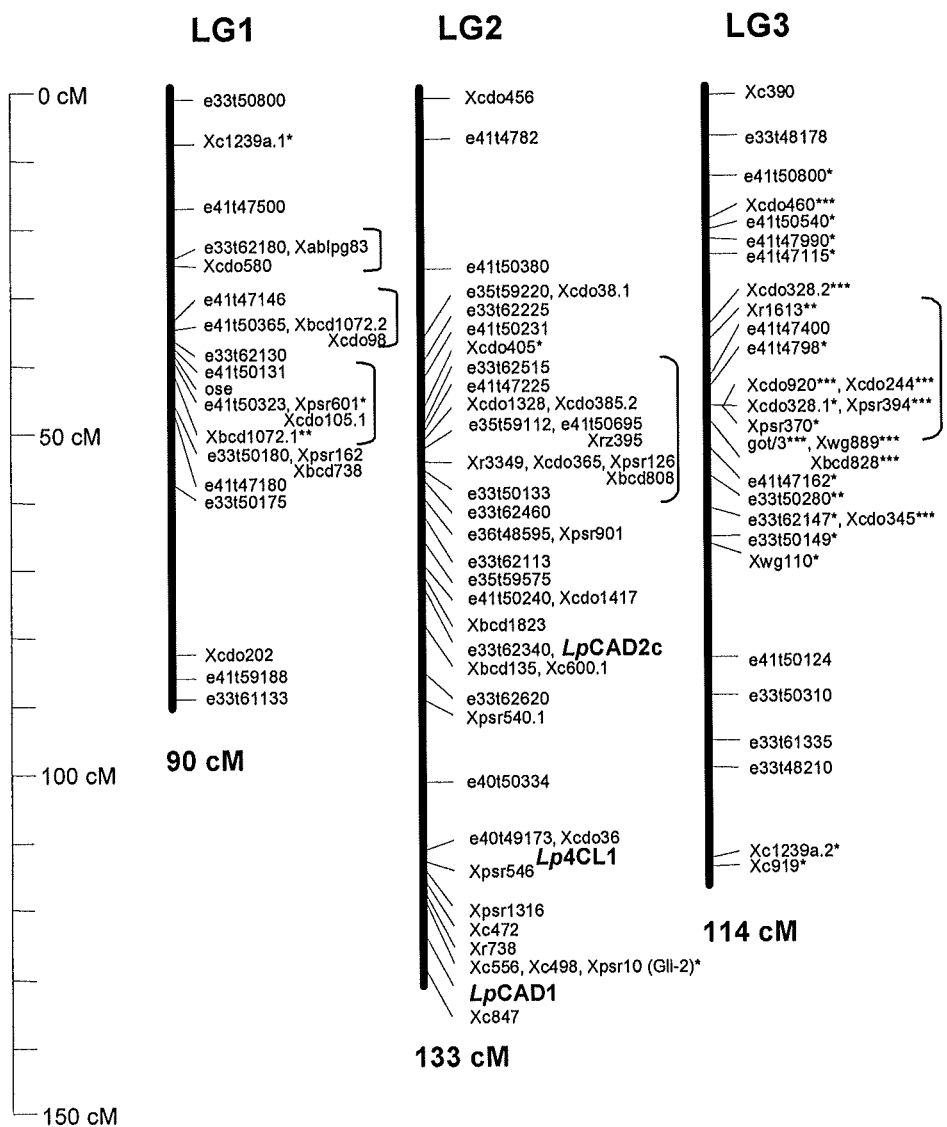
Figure 40:
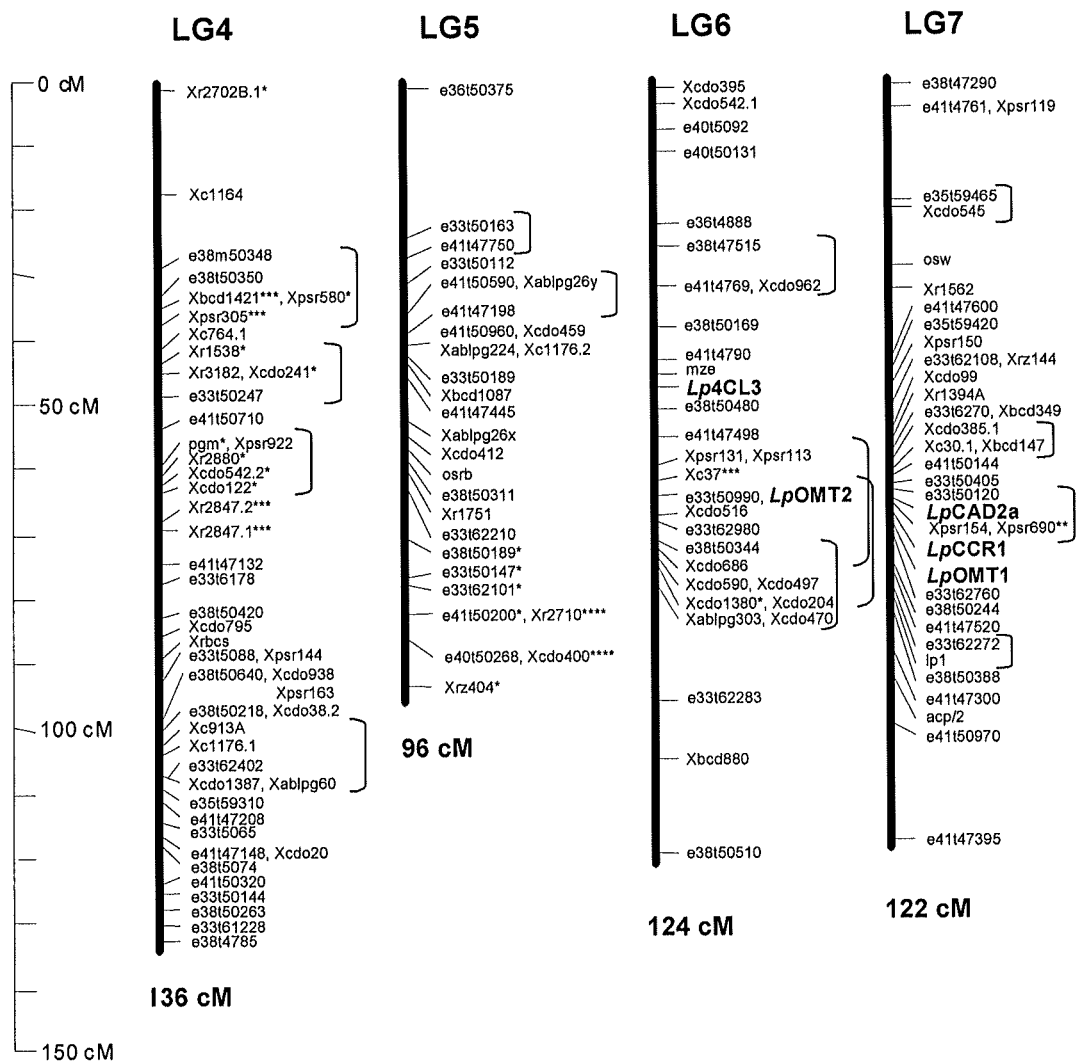

FIG. 40 shows the map location of Lp4CL1, Lp4CL3, LpCAD1, LpCAD2, LpCCR1, LpOMT1 and LpOMT2 (in bold) within the genetic linkage map of perennial ryegrass.

Figure 41:
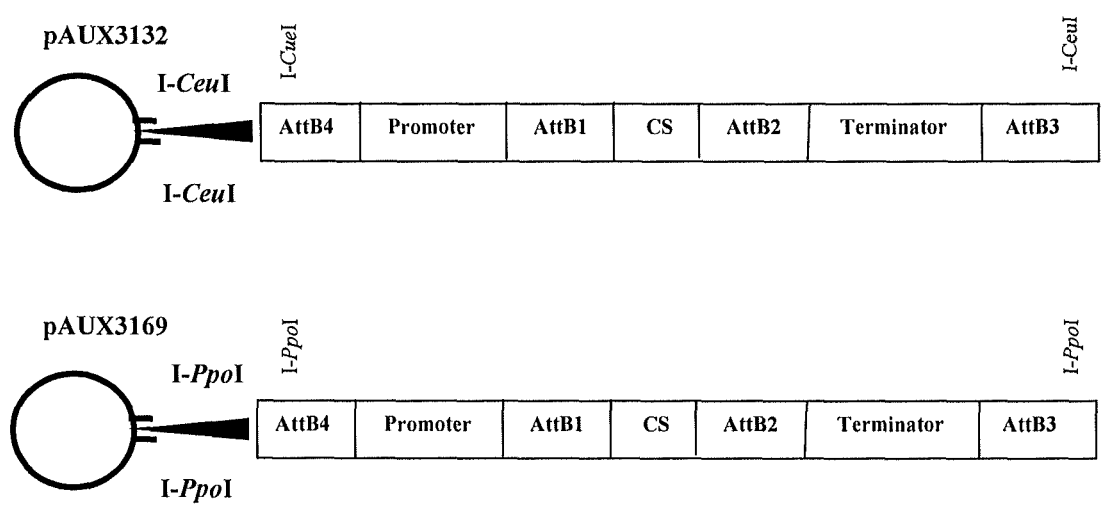

FIG. 41. Illustration of the Gateway-derived expression vectors used for generating the constructs for expressing perennial ryegrass lignin biosynthetic genes.

Figure 42:
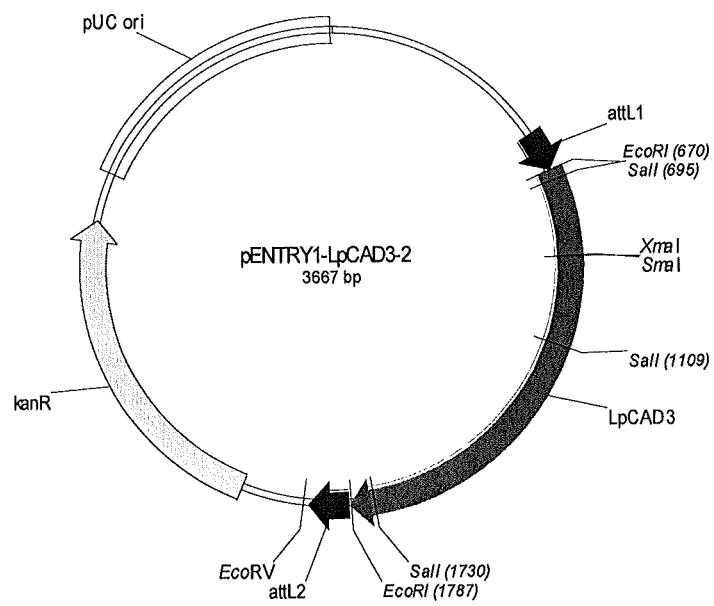

FIG. 42. Vector details of Gateway™ Entry clone for the LpCAD3 cDNA.

Figure 43:
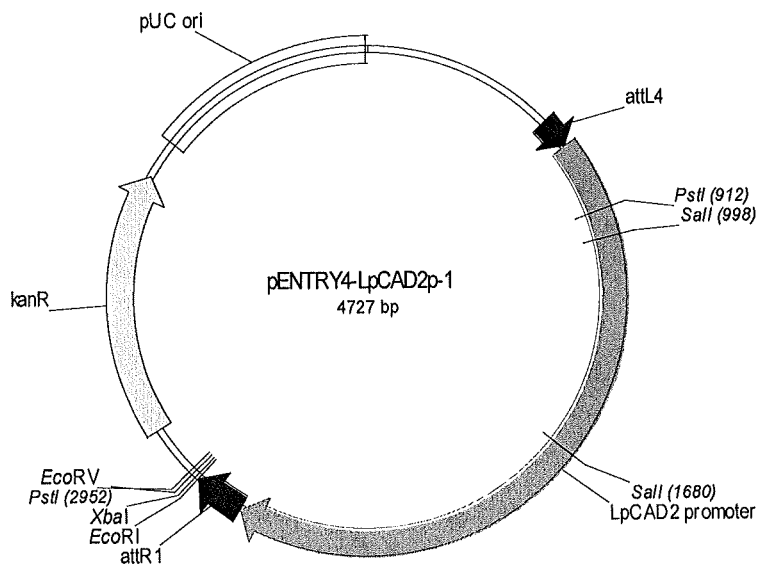

FIG. 43. Vector details of Gateway™ Entry clone for the promoter LpCAD2.

Figure 44:
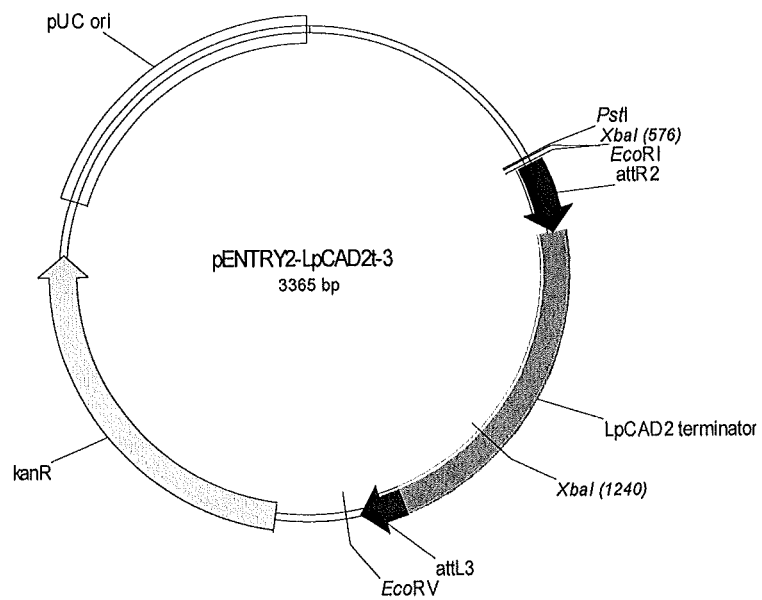

FIG. 44. Vector details of Gateway™ Entry clone for the terminator LpCAD2.

Figure 45:
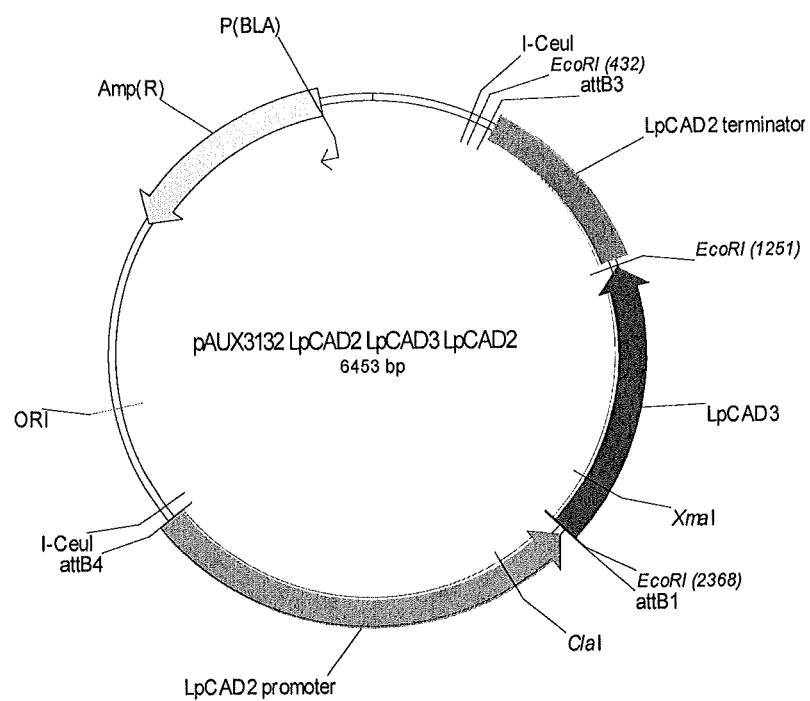

FIG. 45. Plasmid map of Construct 1, LpCAD2p::LpCAD3::LpCAD2t in vector pAUX3132.

Figure 46:
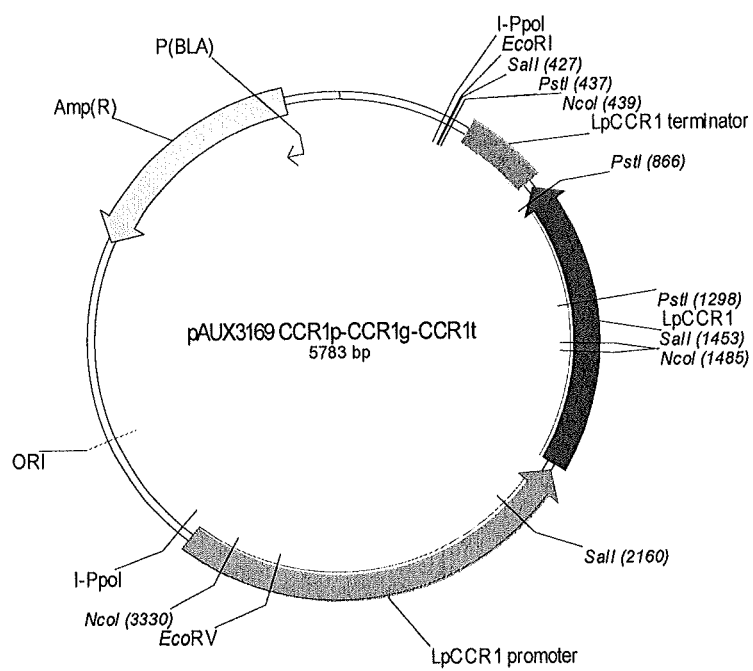

FIG. 46. Plasmid map of Construct 2, LpCCR1::LpCCR1::LpCCR1 in vector pAUX3169.

FIG. 47. Sequence of LpCCR1 gene and modified forward primer designed to introduce a single base deletion in the LpCCR1 gene.

Figure 48:
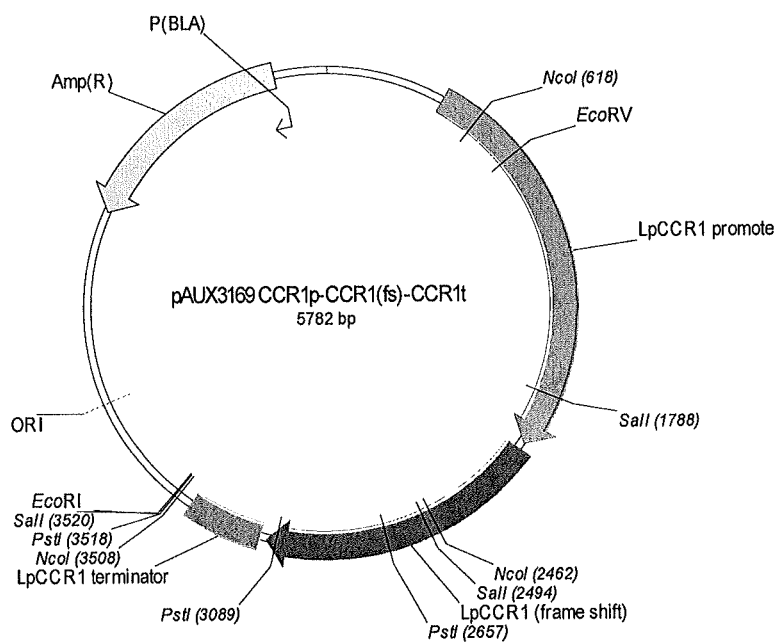

FIG. 48. Plasmid map of Construct 3, LpCCR1::LpCCR1 (fs)::LpCCR1 in vector pAUX3169.

Figure 49:
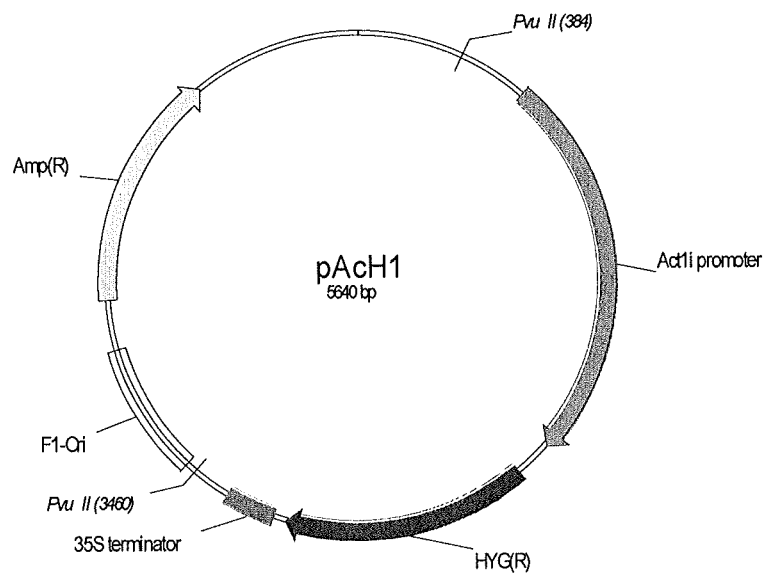

FIG. 49. Vector details for pAcH1 construct that was used as the plant selectable marker containing the expression construct Act1D::hph::35S.

Figure 50:
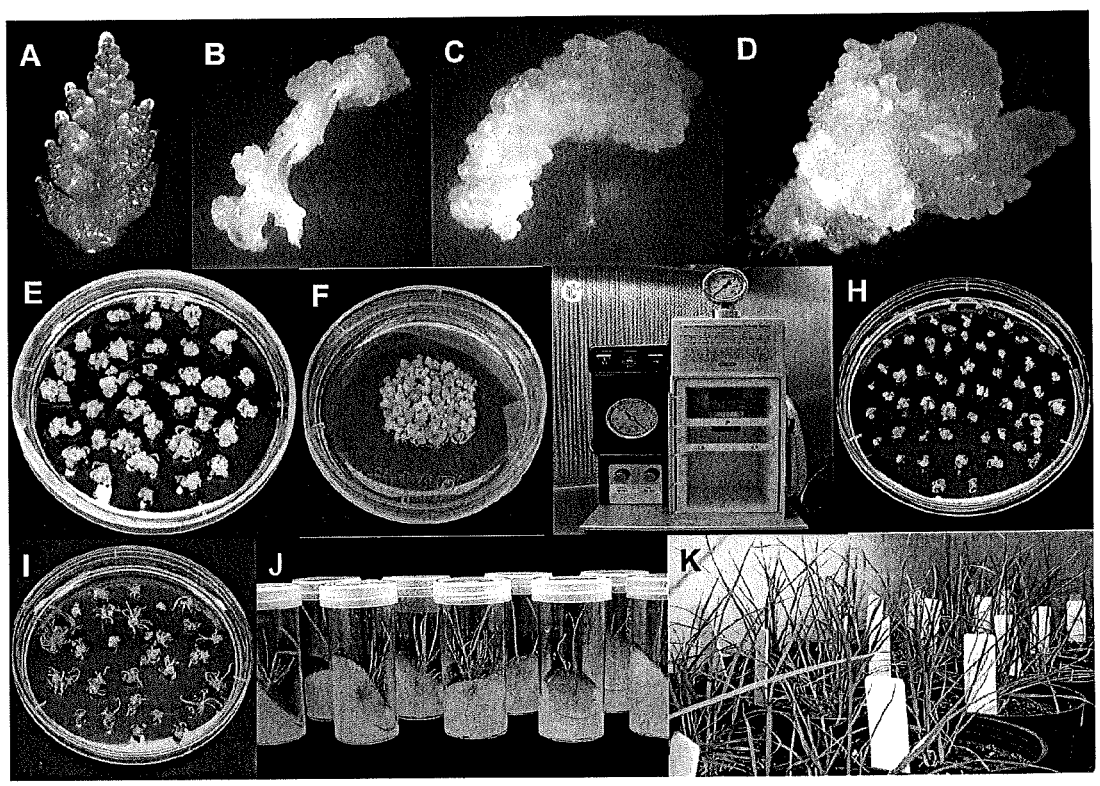

FIG. 50. Production of transgenic perennial ryegrass from microprojectile bombardment of embryogenic calli derived from immature inflorescences. A) Excised immature inflorescence of perennial ryegrass; 2-3 mm; B-E) Induction and proliferation of embryogenic calli; 1-8 weeks after inflorescence excision. F). Distribution of embryogenic calli on high osmotic medium LP3-OS medium prior to biolisitic transformation; G) Biolistic transformation device, PDS-1000/He; H-I) Growth and development of hygromycin-resistant shoots, 30-75 days post bombardment; J) Growth and development of hygromycin-resistant shoots in vitro; K) Hygromycin-resistant plants established in soil and grown under containment glasshouse conditions.

Figure 51:
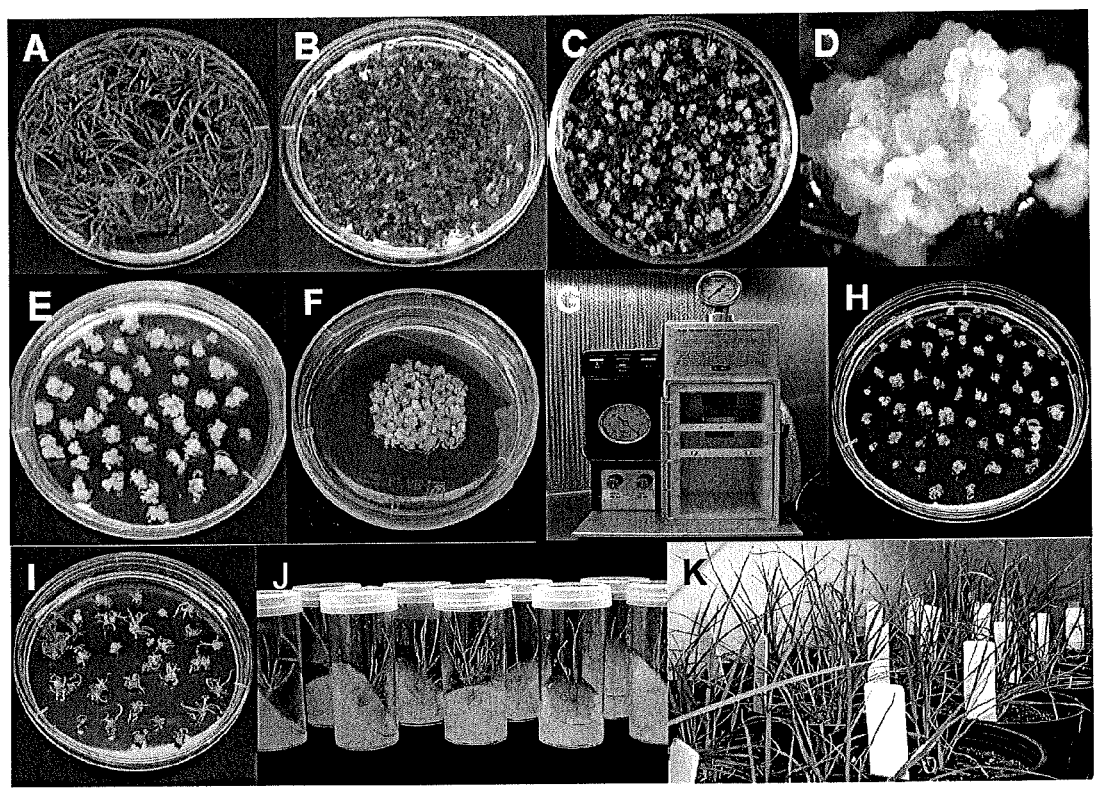

FIG. 51. Production of transgenic perennial ryegrass from microprojectile bombardment of embryogenic calli derived from seedling meristems. A) In vitro shoot culture for basal meristem isolation; regenerated from seedling meristem-derived calli; B) Distribution of basal meristematic material on callus initiation medium; C-E) Induction and proliferation of embryogenic calli from shoot meristems of Lolium perenne; F) Distribution of embryogenic calli on high osmotic medium prior to biolistic transformation; G) Biolistic transformation device, PDS-1000/He; H-I) Growth and development of hygromycin-resistant shoots, 30-84 days post bombardment; J) Growth and development of hygromycin-resistant shoots in vitro; K) Hygromycin-resistant plants established in soil and grown under containment glasshouse conditions.

Figure 52:
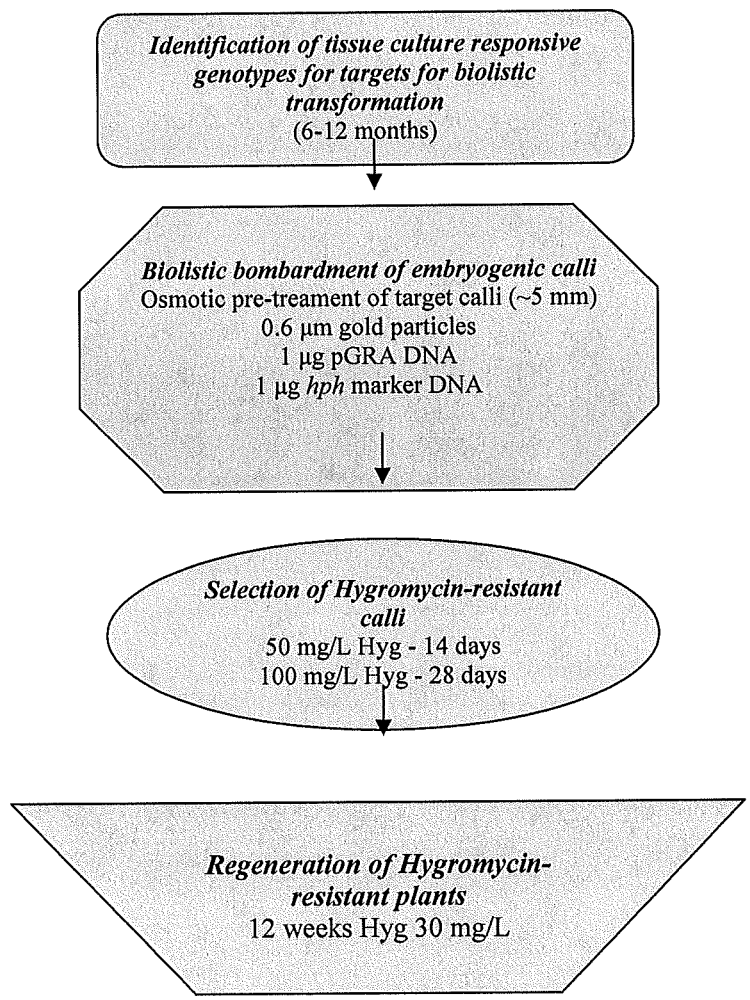

FIG. 52. Flowchart describing the transformation method used to generate transgenic perennial ryegrass containing the expression construct of interest and the selectable marker gene (hph).

Figure 53:
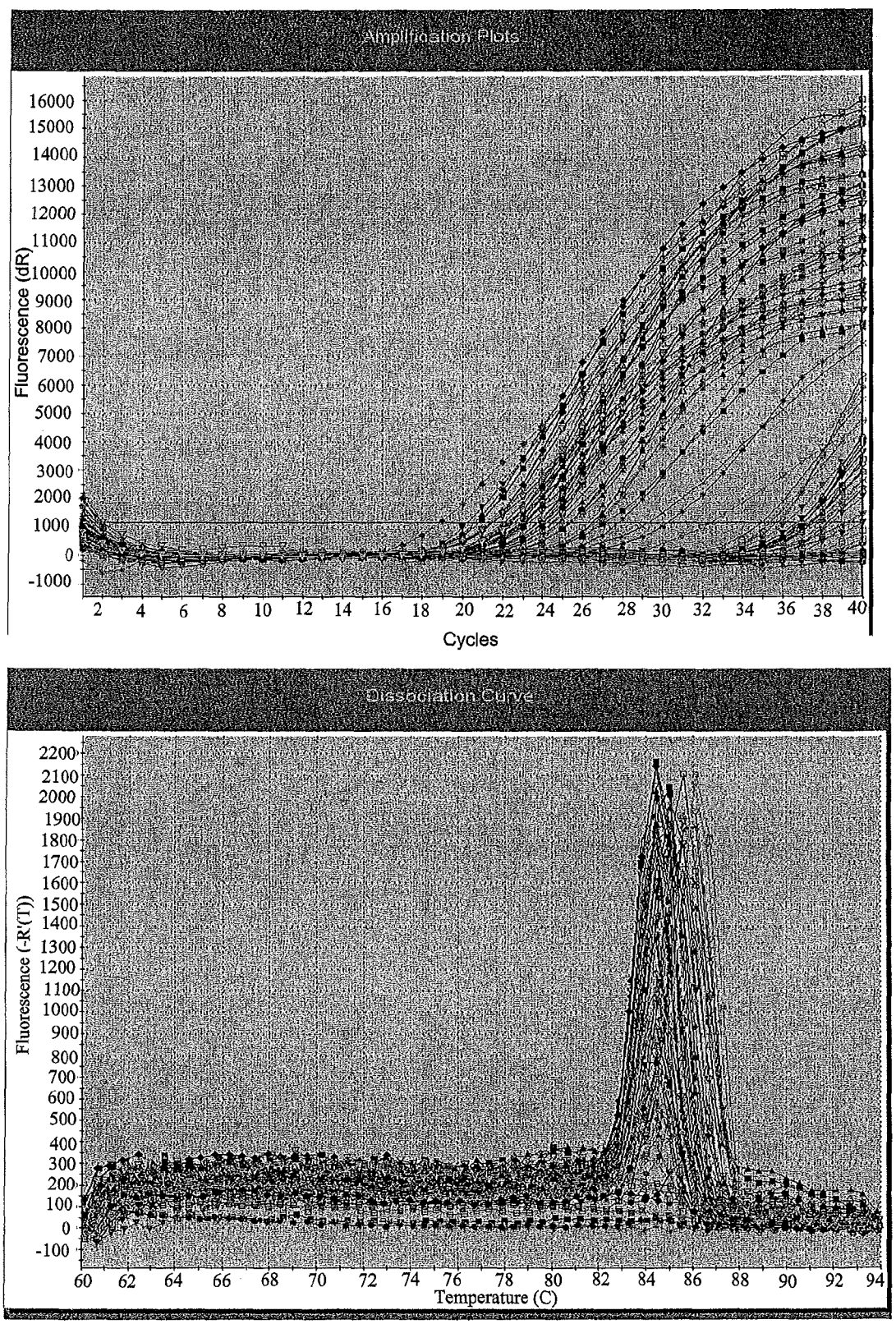

FIG. 53. Amplification of the hygromycin phosphotransferase (hph) gene by Q-PCR in samples of genomic DNA extracted from putative transgenic perennial ryegrass regenerated after co-bombardment with plasmids pAcH1 and pAUX3132-LpCAD2::LpCAD3::LpCAD2.

Figure 54:
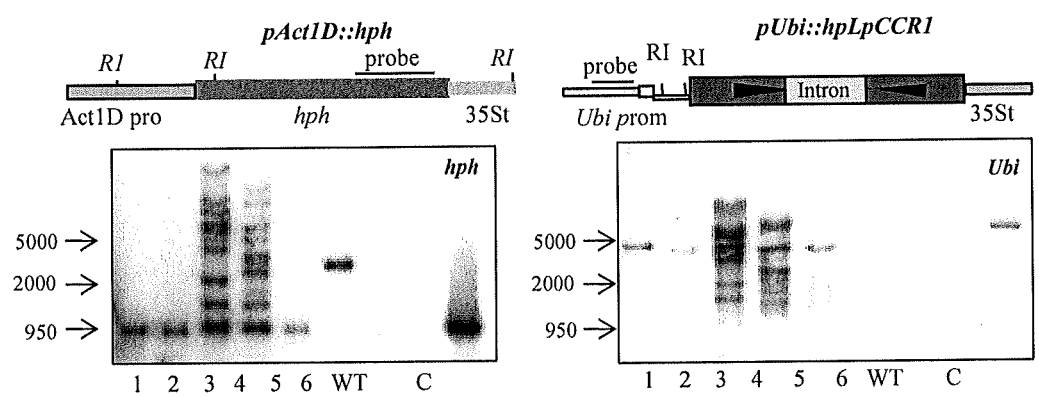

FIG. 54. Southern analysis of genomic DNA digested with Eco R1 (R1) and separated by agarose gel electrophoresis and the transgene detected with either hph or Ubi promoter probes. All six putative transgenic plants were confirmed to contain both hph and the gene-of-interest, hpLpCCR1.

Figure 55:
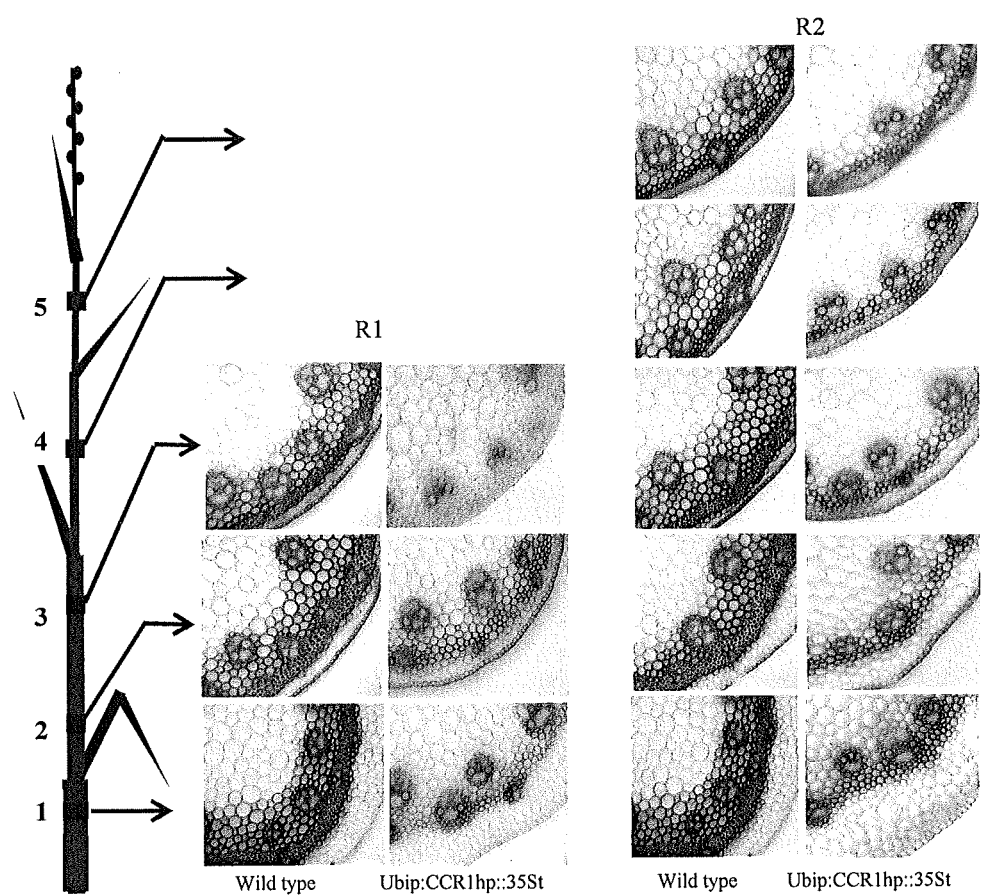

FIG. 55. Mäule staining of cross-sectioned internodes from wild type and transgenic pUbi::hpCCR1::35 S ryegrass at R1 and R2 stage shows a strong decrease of reddish colour in transgenic plants which may suggest a decrease in S lignin content compared to wild type plants.

Figure 56:
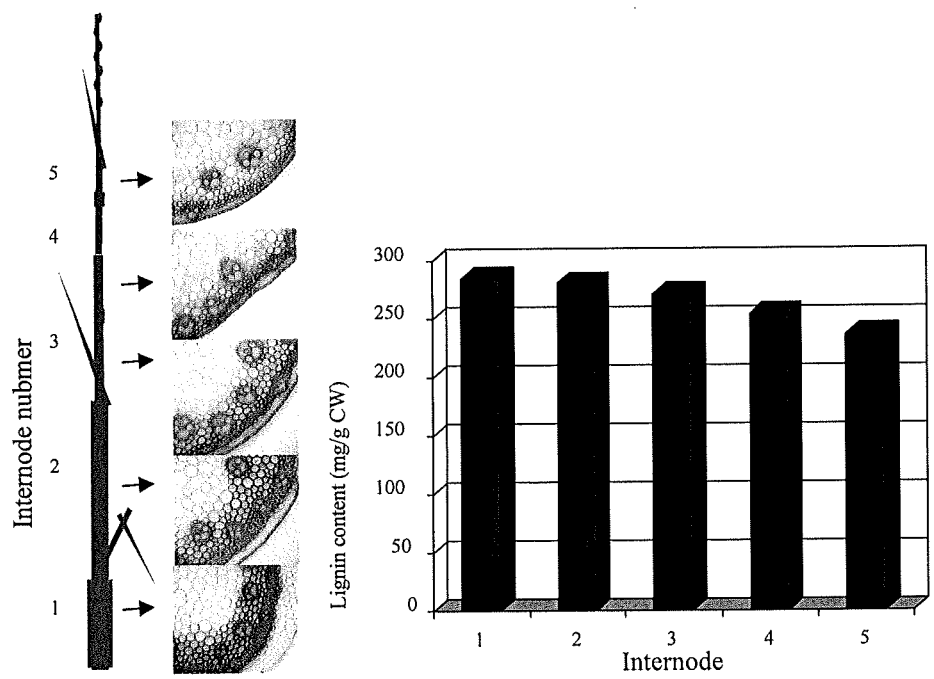

FIG. 56. Total lignin content of perennial ryegrass internodes at the R1 developmental stage shows a progressive reduction in lignin content from internode 1 (base) to internode 5 (top).

Figure 57:
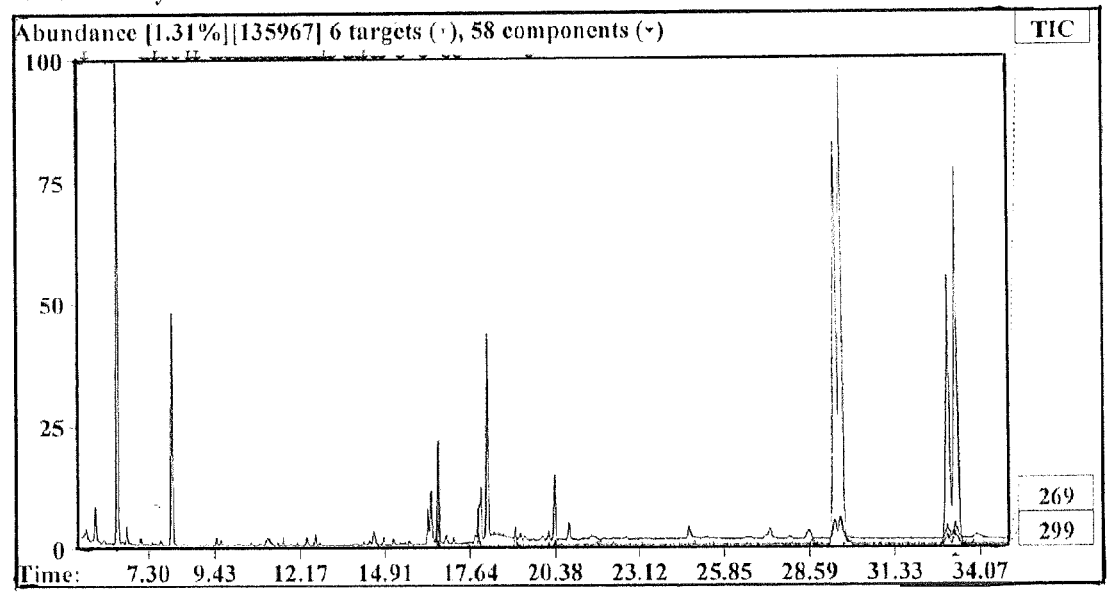

FIG. 57. Example of a gas chromatogram (GC-MS) showing separation and identification of G-lignin and S-lignin monomers after thioacidolysis derivatisation of lignin extracted from wild type perennial ryegrass.

EXAMPLE 1

Isolation and Characterisation of Three 4-Coumarate CoA-Ligase (4CL) cDNAs from *Lolium perenne*

Materials and Methods
Plant Material

Plants and embryogenic cell suspensions of perennial ryegrass (*Lolium perenne* L.) cv Ellet and tall fescue (*Festuca arundinacea* Schreb.) cv Triumph were established and maintained as previously described (Heath et al., 1998). Wounding experiments were performed with 10-day-old seedlings of perennial ryegrass (cv Ellet) as previously described (Heath et al., 1998).

Screening of a cDNA Library

A cDNA library prepared with RNA isolated from perennial ryegrass seedlings (Heath et al., 1998) was screened with a [$^{32}$P]dCTP-labelled rice partial 4CL probe. The rice 4CL probe and consisted of a 844 bp 4CL specific sequence inserted into PUC119. This insert has 93% sequence identity with a rice 4CL cDNA sequence (Genbank, L43362, bases 453-1300). cDNA inserts were excised and recirculized using the ExAssist helper phage with SOLR strain (Stratagene) as described by the manufacturer.

DNA Sequencing cDNA clones were digested with 8 restriction enzymes (BamHI, EcoRI, KpnI, NotI, PstI, SalI, XbaI, XhoI) and selected clones were sequenced on both strands by the dideoxy chain termination method using M13 forward and reverse primers. For sequencing the internal regions of Lp4CL1, Lp4CL2 and Lp4CL3 synthetic oligonucleotide primers were designed from the DNA sequences previously determined. Sequencing was performed using the ABI dye terminator kit and automatic sequencer. Nucleotide sequences were aligned using the SeqEd program (ABI) and further analysis was performed using the HIBIO DNASIS vs2 program (Hitachi Software Engineering).

Genomic DNA Blot Analysis

Genomic DNA was isolated from single genotype-derived cell suspensions of perennial ryegrass and tall fescue according to Lichtenstein and Draper (1985). Ten μg of perennial ryegrass DNA and 20 μg of tall fescue DNA was digested with each of the restriction enzymes HindIII and XbaI, separated on 1% agarose gels, and transferred to Hybond N+ membranes according to the manufacturer's instructions (Amersham). Probes consisted of BamHI/KpnI fragments of Lp4CL1 (1771 bp), Lp4CL2 (2034 bp) or Lp4CL3 (2080 bp) labelled using the Megaprime labelling kit (Amersham) and [$^{32}$P]dCTP. Hybridization was performed at 65° C. in 5×SSPE, 5×Denhardt's solution, 0.5% (w/v) SDS, and 200 μg/mL denatured herring sperm DNA. Membranes were washed three times in 2×SSPE, 0.1% SDS for 10 min at 25° C. and then twice in 0.1×SSPE, 0.1% SDS for 20 min at 65° C.

RNA Blot Analysis

Total RNA (10 μg) was separated on 1.2% formaldehyde gels and transferred to Hybond N (Amersham) membranes according to the manufacturers instructions. Membranes were stained with 0.2% methylene blue to confirm correct loading and transfer of RNA. Hybridisation was performed at 42° C. in 5×SSPE, 5×Denhart's solution, 0.5% SDS, 50% deionized formamide, 200 μg/mL denatured herring sperm DNA. Preparation of probes and washing of membranes was as for DNA blot analysis except for the tall fescue Northern blot when the final two washes were performed with 0.1× SSPE, 0.1% SDS for 10 min at 42° C.

Results

Isolation and Sequence Analysis of Perennial Ryegrass 4CL cDNAs

Figure 1:
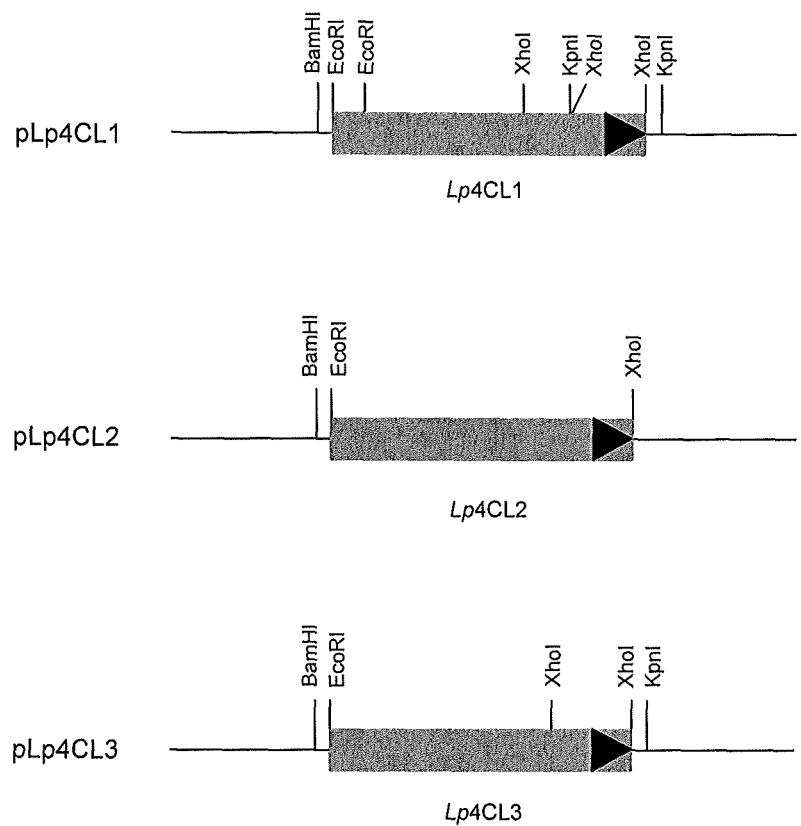
FIG. 1 shows plasmid maps of the three cDNAs encoding perennial ryegrass 4CL homologues.

A cDNA library prepared from RNA extracted from perennial ryegrass seedlings was screened with a rice 4CL hybridization probe and ten cDNAs were isolated from 2×10$^5$ pfu. The cDNAs were characterised by restriction analysis with 8 restriction enzymes. All clones were full length (approximately 2.0-2.2 kb) with poly(A) tails and could be separated into three groups: Lp4CL1 (four clones) Lp4CL2 (five clones) and Lp4CL3 (one clone). Plasmid maps for Lp4CL1, Lp4CL2 and Lp4CL3 are shown (FIG. 1). Lp4CL1, Lp4CL2 and Lp4CL3 were fully sequenced (FIGS. 2, 3 and 4, respectively).

Lp4CL1 is 2284 bp long with an open reading frame (ORF) of 1710 bp, a 5' noncoding region of 322 bp and a 3' noncoding region of 252 bp including a poly(A) tail. Lp4CL2 is 1992 bp long with an ORF of 1668 bp, a 5' noncoding region of 61 bp and a 3' noncoding region of 263 bp including a poly(A) tail. Lp4CL3 is 2038 bp long with an ORF of 1671 bp, a 5' noncoding region of 112 bp and a 3' noncoding region of 255 bp including a poly(A) tail.

Within the coding region, Lp4CL1 has 70% nucleic acid sequence identity with both Lp4CL2 and Lp4CL3, while Lp4CL2 has 79% sequence identity with Lp4CL3. There is little sequence homology in the 3' noncoding regions between clones (52-55%).

Amino Acid Sequence Comparisons

The putative proteins encoded by the three cDNAs consist of 570 amino acids [60290 u (Da)] for Lp4CL1, 556 amino acids (59238 u) for Lp4CL2 and 557 amino acids (59735 u) for Lp4CL3. The deduced amino acid sequences of Lp4CL1, Lp4CL2 and Lp4CL3 are shown (FIG. 5). Lp4CL2 and Lp4CL3 share 79% amino acid sequence identity, Lp4CL1 and Lp4CL2 have 61% amino acid sequence identity, while Lp4CL1 and Lp4CL3 have only 58% amino acid sequence identity. Regions of high sequence homology are more prevalent in the central and c-terminal regions of the enzyme. For example the sequence identity between amino acids 208 to 568 of each enzyme is 85% for Lp4CL2 and Lp4CL3, 72% for Lp4CL1 and Lp4CL2 and 67% for Lp4CL1 and Lp4CL3.

Lp4CL1, Lp4CL2 and Lp4CL3 share several common regions with other plant 4CLs. In particular, they contain the putative AMP-binding domain and the conserved GEICIRG motif, except for Lp4CL3 where the second isoleucine has been replaced with valine (FIG. 5). It has been proposed that domain II is associated with the catalytic activity of 4CL. Also, four Cys residues conserved in plant 4CLs are conserved in Lp4CL1, Lp4CL2 and Lp4CL3 (FIG. 5). These results suggest that the L. perenne cDNAs encode three divergent 4CL enzymes that are likely to have originated from three different 4CL genes.

Expression of Perennial Ryegrass 4CL Genes

Lp4CL1, Lp4CL2 and Lp4CL3 were used as hybridization probes in Northern blots with RNA prepared from different organs of perennial ryegrass at two developmental stages. All three probes hybridized to a single mRNA species of approximately 2.2-2.3 kb. Lp4CL1, Lp4CL2 and Lp4CL3 were expressed at both seedling and mature stages of development and in all organs tested. For Lp4CL2 and Lp4CL3 the strongest signal was found in RNA samples from seedling roots and mature stems (FIG. 6).

Lp4CL1, Lp4CL2 and Lp4CL3 were also used as hybridization probes in Northern blots with RNA prepared from tall fescue. All three probes hybridized to a similar mRNA species (2.3 kb) as that in perennial ryegrass (FIG. 6). The strongest signal was found in RNA samples from mature stems with weaker signals in RNA from roots and seedling shoots. No expression of Lp4CL1, Lp4CL2 or Lp4CL3 was observed in leaves. The three probes varied in their ability to hybridize to the corresponding homologues in tall fescue, with Lp4CL3 resulting in the highest signal and Lp4CL1 hybridizing only weakly.

To determine whether 4CL could be induced under stress conditions, leaves of perennial ryegrass seedlings were wounded. No increase in the transcript level upon wounding was observed with Lp4CL1, Lp4CL2 or Lp4CL3 (FIG. 7).

Genomic Organization of Perennial Ryegrass 4CL Genes

Perennial ryegrass DNA was digested with two restriction enzymes, HindIII or XbaI. Restriction sites for these enzymes are not present in the cDNA sequence of Lp4CL1, Lp4CL2 or Lp4CL3. When Lp4CL1, Lp4CL2 or Lp4CL3 was used as a probe, several DNA hybridizing fragments of varying intensity were revealed (FIG. 8). Each probe hybridized to a unique set of fragments, suggesting that Lp4CL1, Lp4CL2 and Lp4CL3 represent three different genes. Furthermore, Lp4CL1 and Lp4CL2 hybridized to 2 to 3 major fragments per digest which may represent either alleles of the same gene or indicate the presence of more than one gene in each class. The Lp4CL1, Lp4CL2 and Lp4CL3 probes also revealed several different size hybridizing DNA fragments in genomic Southern blots from tall fescue under high stringency conditions (FIG. 8), suggesting that three similar 4CL genes are present in *F. arundinacea*.

EXAMPLE 2

Isolation and Characterisation of a Cinnamoyl CoA Reductase (CCR) cDNA from *Lolium perenne*

A total of 500,000 phage were screened from a cDNA library constructed from ten-day-old etiolated *L. perenne* seedlings using a maize CCR probe. Ninety-three positive plaques were observed in the primary screen and five were subsequently analysed by restriction enzyme digestion. Four out of the five were identical. One of the four identical cDNAs, LpCCR1, was selected for further analysis (FIG. 9).
Nucleic Acid Sequence Analysis of Perennial Ryegrass CCR cDNA The full nucleotide sequence of LpCCR1 was obtained and the amino acid sequence predicted (FIG. 10). LpCCR1 is a 1395 bp cDNA with 149 bp of 5' non-coding region and 160 bp of 3' non-coding region. An open reading frame of 1086 bp encodes a protein of 362 amino acids. The composition of the coding region was found to be 68% G+C rich. Codon usage was also examined and found to be biased towards XXC/G codons (94%), with XCG and XUA codons accounting for only 9% and 0.55% respectively. G+C richness and bias towards G and C in the third position of a codon triplet are previously reported characteristics of monocot genes.
Genomic Organization of Perennial Ryegrass CCR Gene The number of CCR genes present in the ryegrass genome was determined by Southern blot analysis of genomic DNA from double haploid plants, using as probe a fragment of the LpCCR1 cDNA (LpCCR531, FIG. 9). Double haploid DNA reduces the complexity associated with allelic variation. Genomic DNA was cut with enzymes that do not cut the cDNA internally; DraI, BamHI, EcoRI, EcoRV, HindIII and XbaI, and the membrane was hybridised and washed under medium-stringency conditions. A single strongly hybridising band was evident in each lane (FIG. 11) indicating that there is a single copy of the LpCCR1 gene in the perennial ryegrass genome.
Expression of Perennial Ryegrass CCR Gene To investigate the expression profile of the CCR gene in ryegrass, northern hybridisation analysis was carried out with total RNA extracted from roots and shoots at seedling growth stages (0.5-1 cm and 4-6 cm shoots) and roots, stem and leaves at mature growth stages (6 and 10 weeks). Seedlings were grown on filter paper in the dark at 25° C. and then transferred to soil and glasshouse conditions (25° C.) until the 6 and 10-week stages. Whole seedling total RNA from Festuca and Phalaris was included in the northern analysis. Hybridisation with LpCCR531 (FIG. 9) was performed at medium-stringency and the membrane was then washed at high-stringency. A transcript of approximately 1.5 kb was detected in all tissues, the level of expression varying with maturity and from one tissue type to another (FIG. 12). The LpCCR1 transcript appears to be more abundant in roots and stem than shoots and leaves. In the stem, transcript abundance increases from 6-weeks to 10-weeks; indicating that transcription in stem tissue is up-regulated as the plant matures. Expression was found predominantly in tissues such as stems and roots that are forming secondary cell walls indicating that LpCCR1 is constitutively involved in lignification.

EXAMPLE 3

Isolation and Characterisation of Cinnamyl Alcohol Dehydrogenase (CAD) cDNAs from *Lolium perenne*

A 558 bp cinnamyl alcohol dehydrogenase (CAD) fragment was amplified from cDNA synthesised from total RNA prepared from perennial ryegrass seedlings. The conserved amino acid domains between *Pinus radiata*, *Medicago sativa*, *Aralia cordata*, *Eucalyptus botryoides* and *Arabidopsis thaliana* CADs were used to design oligonucleotides for the amplification of the perennial ryegrass CAD. The forward oligonucleotide was designed to the conserved amino acid domain CAGVTVYS and the reverse oligonucleotide to the conserved domain DVRYRFV. The 551 bp PCR fragment was cloned and sequenced to confirm that it corresponded to a perennial ryegrass CAD PCR fragment. A cDNA library prepared from RNA extracted from perennial ryegrass seedlings was screened with the 551 bp PCR fragment specific for perennial ryegrass CAD. Eight cDNAs were isolated and separated into six groups by restriction digest analysis. One representative clone each from two groups (LpCAD1, LpCAD2) were selected for further characterisation.
Nucleic Acid Sequence Analysis of Perennial Ryegrass CAD cDNAs The complete sequence of the perennial ryegrass CAD homologue LpCAD1 was determined (FIG. 13). The 1325 bp clone had a poly (A) tail, typical start and stop codons and the open reading frame (ORF) of this clone coded for a putative protein of 408 amino acids.

The complete nucleotide sequence of the perennial ryegrass CAD homologue LpCAD2 was also determined (FIG. 14).
Expression of Perennial Ryegrass CAD Genes A northern hybridisation analysis with RNA samples isolated from perennial ryegrass at different developmental stages hybridised with the full length LpCAD1 1325 bp cDNA (FIG. 15) was performed to determine patterns of organ and developmental expression. The probe hybridised to a single mRNA species of approximately 1.6 kb. The LpCAD1 transcript was expressed in all tissue tested: roots, shoots, stem and leaves (FIG. 16A). The LpCAD1 transcript was most abundant in root tissue and the mature stem, this expression pattern is typical of a gene involved in the lignification of plant cell walls. Intergeneric homologies were revealed in Festuca and Phalaris.

A similar northern hybridisation analysis was performed with LpCAD2 (FIG. 16B), however the transcript was found to be most abundant in mature stem tissue and the shoots.
Genomic Organization of Perennial Ryegrass CAD Genes A Southern hybridisation analysis using DNA samples isolated from a perennial ryegrass double haploid plant digested with DraI, BamHI, EcoRI, EcoRV, HindII and XbaI and hybridised with a 500 bp LpCAD1 probe was performed. The hybridisation pattern at high stringency revealed the presence of two prominent bands for most digests indicating that LpCAD1 belongs to a small gene family and exists a muliticopy gene in perennial ryegrass (FIG. 17A).

A similar Southern hybridization analysis was performed with LpCAD2 (FIG. 17B) the hybridisation pattern at high stringency revealed the presence of one or two prominent bands for most digests indicating that LpCAD2 exists as a single copy gene or a member of a small gene family in perennial ryegrass (FIG. 17B).

EXAMPLE 4

Isolation and Characterisation of Genomic Clones and Promoters for O-methyltransferase (OMT), Cinnamoyl-CoA Reductase (CCR), 4 Coumarate CoA-ligase (4CL) and Cinnamyl Alcohol Dehydrogenase (CAD) from *Lolium perenne*

Genomic clones and promoters of O-methyltransferase (OMT), cinnamoyl-CoA reductase (CCR), 4 coumarate CoA-ligase (4CL) and cinnamyl alcohol dehydrogenase (CAD) were isolated from a perennial ryegrass genomic library using the corresponding cDNAs as hybridisation probes.

Isolation and Characterisation of Genomic Clones and Promoters for Perennial Ryegrass O-methyltransferase (OMT)

A perennial ryegrass genomic library was screened with the cDNA clone, LpOmt1, (Heath et al. 1998) encoding O-methyltransferase (OMT). The sequence of the 5' untranslated region and the coding region was found to be identical to that of the LpOmt1 cDNA previously isolated. The entire 4.8 kb genomic clone was fully sequenced (FIG. 18).

To further characterise the promoters, transcriptional fusions of the promoter sequence to the β-glucuronidase (GUS) coding sequence (gusA) have been generated (FIG. 19). Direct gene transfer experiments to tobacco protoplasts were performed with the corresponding chimeric genes to transgenically express them in a heterologous system for in planta expression pattern analysis by histochemical GUS assays. A set of transgenic tobacco plants carrying a chimeric gusA gene under the control of the 5' regulatory region of the LpOmt1 promoter was generated to assess the potential use of the LpOmt1 promoter for xylem-specificity and targeted downregulation of genes encoding key lignin biosynthetic enzymes.

The transgenic tobacco plants generated using the LpOmt1 promoter driven chimeric gusA transformation vector were screened by PCR and histochemical GUS assays.

A PCR screening was undertaken using gusA specific primers for the initial identification of transgenic tobacco plants (FIG. 20). PCR positive tobacco plants were screened by histochemical GUS assays for in planta expression pattern analysis (FIG. 20).

Isolation and Characterisation of Genomic Clones and Promoters for Perennial Ryegrass Cinnamoyl-CoA Reductase (CCR)

A CCR genomic clone from perennial ryegrass was isolated containing 6.5 kb of promoter and the entire gene organisation (intron/exon boundaries). The CCR promoter can be used for targeted expression of foreign genes in transgenic plants.

A perennial ryegrass genomic library was screened with the cDNA clone LpCCR1 which codes for the lignin biosynthetic enzyme, cinnamoyl-CoA reductase (CCR). Four different genomic clones were identified based on restriction digest analysis. Clone 6.1.1 a was selected for further analysis. A 6.42 kb XhoI fragment from clone 6.1.1a, which hybridized strongly to the LpCCR1 cDNA probe, was subcloned into pBluescriptSK (FIG. 21A). Sequence analysis revealed that the 6.42 kb XhoI fragment contained the entire LpCCR1 gene and 200 bp of promoter region. The intron/exon boundaries are illustrated in FIG. 21B, the location and the size of the exons appear to be conserved in other CCRs from different species (FIG. 21C).

To isolate the promoter region of LpCCR1, the Southern blot containing digested phage genomic DNA isolated from clone λLp6.1.1a was reprobed with the 200 bp promoter region. The probe hybridized strongly to a 6.5 kb SalI fragment. This genomic fragment LpCCR1 clone 2, was subcloned into pBluescriptSK and sequenced (FIG. 22A). Sequence results revealed that the 6.5 kb SalI fragment contained 6.5 kb of promoter (FIG. 22B). The full sequence of LpCCR1 genomic clone containing the promoter and entire gene sequence (exons and introns) was obtained and is shown on FIG. 39.

Isolation and Characterisation of Genomic Clones and Promoters for Perennial Ryegrass 4 Coumarate CoA-ligase (4CL)

A 4CL2 genomic clone from perennial ryegrass was isolated containing 2.5 kb of promoter and partial gene organisation (intron/exon boundaries). The 4CL2 promoter can be used for targeted expression of foreign genes in transgenic plants. The 2.5 kb promoter has been fused to the reporter gene gusA for expression analysis.

A perennial ryegrass genomic library was screened with an Lp4CL cDNA probe. After tertiary screening positive 4CL genomic clones were obtained and characterised by restriction digest and Southern hybridisation analysis (FIG. 23A).

Sequence analysis revealed that the isolated 4CL genomic clone (4CL2) from perennial ryegrass had 100% nucleotide identity to the Lp4CL2 cDNA clone. To further characterise this 5 kb λLp4CL2 genomic clone and to confirm that it corresponds to the cDNA of Lp4CL2, a number of PCR reactions using primers designed to the cDNA were used. PCR results confirmed that the 5 kb genomic fragment was a partial genomic clone corresponding to the Lp4CL2 cDNA (FIG. 23B). Using primer combinations F1 and R1 the entire 4.8 kb genomic fragment was amplified. To determine the location of introns additional PCR reactions using the primer combinations F1/R2 and F2/R1 were performed, a 1 kb and 3.5 kb bands were amplified respectively. The location and size of the introns could be determined from these results, and further confirmed by sequence analysis. This large 5 kb genomic fragment contains 4 small exons representing the coding sequence of Lp4CL2 between 508 bp and 1490 bp (FIG. 23C).

The genomic clone 1, Lp4CL2 contained no promoter region. To isolate the promoter region of Lp4CL2, the Southern blot containing digested phage genomic DNA isolated from clone λLp4CL2 was reprobed with a 300 bp EcoRI/BglI isolated from the 5' end of the cDNA clone Lp4CL2. The 300 bp probe hybridised strongly to a 2.5 kb BamHI fragment. This genomic fragment Lp4CL2 clone 2, was subcloned into pBluescriptSK and sequenced (FIG. 24A). Sequence results revealed that the 2.5 kb BamHI fragment contained the 508 bp of the 5' ORF of Lp4CL2 missing from genomic clone 1 and 2.0 kb of promoter region (FIG. 24B). The full sequence of the Lp4CL2 genomic clone containing the promoter and partial gene sequence (exons and introns) was obtained and is shown on FIG. 39.

The promoter from Lp4CL2 was thus isolated and used for the production of a chimeric gusA reporter gene (FIG. 25). Isolation and Characterisation of Genomic Clones and Promoters for Perennial Ryegrass Cinnamyl Alcohol Dehydrogenase (CAD)

A CAD genomic clone from perennial ryegrass was isolated containing the gene organisation (intron/exon boundaries) minus intron 1 containing the first 111 bp of the CAD coding region. The genomic clone has allowed the identification of a G at position 851 bp in the coding region of the CAD2 genomic clone isolated from perennial ryegrass cv. Barlano which is absent in the CAD2 cDNA clone isolated from perennial ryegrass cv. Ellett. The SNP (single nucleotide polymorphism) found to exist between the 2 cultivars has the potential utility as a molecular marker for herbage quality, dry matter digestibility, mechanical stress tolerance, disease resistance, insect pest resistance, plant stature and leaf and stem colour.

Results below show the isolation of the genomic clone and sequence analysis of deduced coding sequence from the genomic clone CAD2 from perennial ryegrass cv. Barlano compared to the truncated cDNA CAD2 from the cv Ellett. The missing G in the perennial ryegrass cv. Ellett has been highlighted (FIGS. 26 and 27).

A perennial ryegrass genomic library was screened with a probe corresponding to the 5' end of the LpCAD2 cDNA clone, which codes for the lignin biosynthetic enzyme cinnamyl alcohol dehydrogenase. Ten positive plaques were identified and isolated in the primary library screening. After a secondary and tertiary screening, two positive plaques were obtained and corresponding positive genomic clones were further characterised by restriction digest and Southern hybridization analyses. Both genomic clones were found to be identical based on restriction digest analyses. One clone, named λLpCAD2 was chosen for further Southern hybridization analyses. A 4.5 kb BamHI fragment which hybridized strongly to the LpCAD2 cDNA probe was subcloned into pBluescriptSK and sequenced (FIG. 28A). Sequence analysis revealed that the 4.5 kb BamHI fragment was a partial genomic clone of LpCAD2. This large 4.5 kb genomic fragment contains 4 small exons representing the coding sequence of LpCAD2 between 213 bp and the stop codon at 1213 bp, and the location of the intron/exon boundaries are illustrated in FIG. 28B.

EXAMPLE 5

Development of Transformation Vectors Containing Chimeric Genes with 4CL, CCR and CAD cDNA Sequences from Perennial Ryegrass To alter the expression of the key enzymes involved in lignin biosynthesis 4CL, CCR and CAD, through antisense and/or sense suppression technology and for over-expression of these key enzymes in transgenic plants, a set of sense and antisense transformation vectors was produced. Transformation vectors containing chimeric genes using perennial ryegrass 4CL, CCR and CAD cDNAs in sense and antisense orientations under the control of either the CaMV 35S or the maize ubiquitin promoter were generated (FIGS. 29, 30 and 31).

EXAMPLE 6

Production and Characterisation of Transgenic Tobacco Plants Expressing Chimeric 4CL, CCR and CAD Genes from Perennial Ryegrass A set of transgenic tobacco plants carrying chimeric 4CL, CCR and CAD genes from perennial ryegrass were produced and analysed.

Transformation vectors with Lp4CL1, Lp4CL2 and Lp4CL3 full length cDNA sequences in sense and antisense orientations under the control of either the CaMV 35S or the maize ubiquitin promoters were generated. Transformation vectors with LpCCR1 cDNA in both sense and antisense orientation under the control of either the CaMV 35S and maize ubiquitin promoters were generated. Transformation vectors with 1325 bp full length LpCAD1 cDNA in sense and 1051 bp partial LpCAD1 cDNA in antisense orientation under the control of either the CaMV 35S and maize ubiquitin promoters were generated.

Direct gene transfer experiments to tobacco protoplasts were performed using these transformation vectors.

The production and molecular analysis of transgenic tobacco plants carrying the perennial ryegrass Lp4CL1 and LpCCR1 cDNAs under the control of the constitutive CaMV 35S promoter is described here in detail.

A set of transgenic tobacco plants generated using the Lp4CL1 sense transformation vector was screened by PCR and subjected to Southern and northern hybridization analyses.

A PCR screening was undertaken using npt2 and Lp4CL1 specific primers for the initial identification of transgenic tobacco plants. Independent transgenic tobacco plants were identified to be co-transformed with both the selectable marker npt2 and the Lp4CL1 chimeric genes (FIG. 32).

Southern hybridisation analysis was performed with DNA samples from PCR positive transgenic tobacco plants to demonstrate the integration of the chimeric Lp4CL1 transgene in the tobacco plant genome. Independent transgenic tobacco plants carried between 1 and 5 copies of the Lp4CL1 transgene. No cross-hybridization was observed between the endogenous tobacco 4CL gene and the perennial ryegrass hybridization probe used (FIG. 32).

Northern hybridization analysis using total RNA samples prepared from the transgenic tobacco plants carrying the chimeric sense Lp4CL1 transgene and probed with the Lp4CL1-specific hybridization probe revealed the presence of a 1.2 kb Lp4CL1 transcript strongly expressed in one Lp4CL1-transgenic tobacco plant analysed (FIG. 32).

The sense and antisense transformation vectors of LpCCR1 under the control of the CaMV 35S promoter were introduced into tobacco protoplasts via direct gene transfer. A set of transgenic tobacco plants was generated and screened by PCR with specific primers to identify transgenic tobacco plants carrying chimeric LpCCR1 transgene. The molecular analysis of LpCCR1-transgenic tobacco plants is shown (FIG. 33).

EXAMPLE 7

Production and Characterisation of Transgenic Perennial Ryegrass Plants Expressing Chimeric OMT, 4CL, CCR and CAD Genes from Perennial Ryegrass An improved transformation method was developed for the production of transgenic perennial ryegrass plants by biolistic transformation of embryogenic cells. Transgenic perennial ryegrass plants were generated using chimeric OMT, 4CL, CCR and CAD genes from perennial ryegrass and the improved transformation method.
Improved Method for the Production of Transgenic Perennial Ryegrass Plants This improved procedure utilises embryogenic calli produced from mature seed-derived embryos as direct targets for biolistic transformation without requiring the establishment of embryogenic cell suspensions. The protocol relies on a continuous supply of isolated zygotic embryos for callus induction. Transgenic ryegrass plants can be regenerated 24-28 weeks after embryo isolation (FIG. 34). Isolated embryos are plated onto MSM5 medium to produce embryogenic calli suitable as targets for biolistic transformation within 8 weeks. The embryogenic calli, treated on high-osmoticum medium MSM3 Plus prior to microprojectile bombardment, are selected on MSM3 medium containing 100 mg/l paromomycin (Pm) for 2 weeks before being transferred onto MSK with 100 mg/l Pm for further 4 weeks until differentiation of Pm resistant shoot appear. Regenerated shoots are transferred on to fresh selective media MSK with 100 mg/l Pm for a further 4 weeks (FIG. 34).

Production of Transgenic Perennial Ryegrass Plants Expressing Chimeric OMT, 4CL, CCR and CAD Genes from Perennial Ryegrass Transgenic perennial ryegrass (Lolium perenne) plants were generated using chimeric ryegrass OMT, 4CL, CCR and CAD genes by biolistic transformation of embryogenic calli. Examples of the production and detailed molecular analysis of these transgenic ryegrass plants are described.

Transgenic perennial ryegrass plants for OMT down-regulation were produced using biolistic transformation of embryogenic calli and plant transformation vectors pUbiomt1 and pUbitmo1 carrying LpOmt1 cDNA sequence in sense and antisense orientation under control of the constitutive maize ubiquitin promoter. These transgenic perennial ryegrass plants for down-regulated OMT activity were regenerated from paromomycin resistant calli obtained from biolistic transformation using microprojectiles coated with two plasmids; pHP23 (carrying the chimeric npt2 gene as the selectable marker) and either the sense or antisense LpOmt1 transformation vector driven by the maize Ubi promoter.

Transgenic perennial ryegrass plants were subjected to a polymerase chain reaction (PCR) screening using npt2-specific primers. Independent npt2 PCR-positive transgenic perennial ryegrass plants obtained from biolistic transformation of embryogenic calli—generated from approximately 60,000 isolated mature seed-derived embryos—using LpOmt1 sense (pUbiomt1) and LpOmt1 antisense (pUbitmo1) transformation vectors were identified [16 pUbiomt1 transgenic plants and 27 pUbitmo1 transgenic plants] (FIG. 35).

Southern hybridization analysis was performed with undigested and HindIII-digested DNA samples prepared from the PCR positive transgenic perennial ryegrass plants, to demonstrate their transgenic nature and the integration of the chimeric npt2 and LpOmt1 transgenes. Independent transgenic perennial ryegrass plants co-transformed with both, the selectable marker npt2 gene and LpOmt1 chimeric genes, were identified (FIG. 35). In most instances, the transgenic perennial ryegrass plants recovered contained multiple copies of the selectable marker gene including rearranged transgene copies. No npt2-hybridizing bands were detected in the untransformed negative control.

Samples of HindIII-digested genomic DNA were included in the analysis when the LpOmt1 gene-specific hybridization probe (omt1) was used. The omt1 probe hybridized to a number of bands in DNA samples corresponding to both, the transgenic plants and the untransformed negative control. The omt1-hybridizing bands shared in all samples correspond to endogenous LpOmt1 gene sequences represented as a small multigene family in the perennial ryegrass genome (Heath et al. 1998). The different omt1-hybridizing bands evident in the samples from the transgenic plants and absent in the untransformed negative control sample correspond to antisense (tmo1) and sense (omt1) LpOmt1 transgene integration events (FIG. 35).

Northern hybridization analysis using strand-specific LpOmt1 probes allowed the identification of transgenic perennial ryegrass plants expressing the antisense LpOmt1 transgene (FIG. 35).

The OMT activity of selected antisense and sense LpOmt1 transgenic perennial ryegrass plants was determined. Biochemical assays for OMT activity were initially established in untransformed plants (such as tobacco and perennial ryegrass). The assays utilise radiolabelled S-adenosylmethionine as the methyl donor for the OMT-catalysed conversion of caffeic acid into ferulic acid. The production of radioactive ferulic acid is measured and allows the OMT activity to be determined.

The OMT activity of selected LpOmt1-transgenic perennial ryegrass plants (*L. perenne* cv. Ellett) was determined. Significantly altered OMT activity in individual transformation events was observed (FIG. 36). The manipulation of OMT activity in transgenic perennial ryegrass plants due to the expression of the chimeric ryegrass LpOmt1 gene was thus demonstrated.

Transgenic perennial ryegrass plants were recovered, using biolistic transformation of embryogenic calli, for the manipulation of the expression of genes encoding the key lignin biosynthetic enzyme, 4CL. The plant transformation vectors pUbi4CL2 and pUbi2LC4 carrying chimeric Lp4CL2 cDNA sequences in sense and antisense orientation, respectively, driven by the constitutive maize ubiquitin (Ubi) promoter were used. Perennial ryegrass plants for 4CL manipulation were regenerated from Pm-resistant calli obtained from biolistic transformation of embryogenic calli using microprojectiles coated with the plasmids pHP23, carrying a chimeric npt2 gene as selectable marker gene and the antisense pUbi2LC4.

Transgenic perennial ryegrass plants were subjected to a polymerase chain reaction (PCR) screening using npt2-specific primers. Independent npt2 PCR-positive transgenic perennial ryegrass plants were obtained from biolistic transformation of embryogenic calli (FIG. 37).

Transgenic perennial ryegrass plants were also recovered, using biolistic transformation of embryogenic calli, for the manipulation of the expression of genes encoding the key lignin biosynthetic enzymes, CCR and CAD.

EXAMPLE 8

Genetic Mapping of Perennial Ryegrass OMT, 4CL, CCR and CAD Genes

Lp4CL1, Lp4CL3, LpCAD1, LpCAD2, LpCCR1, LpOMT1 and LpOMT2 clones were PCR amplified and radio-labelled for use as probes to detect restriction fragment length polymorphisms (RFLPs). RFLPs were mapped using 110 progeny individuals of the p150/112 perennial ryegrass reference population restricted with the enzymes described in Table 1 below.

TABLE 1

Mapping of RFLPs

| Clones | Polymorphic in p150/112 | Enzyme mapped with | Locus | Linkage group |
|---|---|---|---|---|
| Lp4CL1 | Y | DraI | Lp4CL1 | 2 |
| Lp4CL3 | Y | EcoRV | Lp4CL3 | 6 |
| LpCAD1 | Y | EcoRV | LpCAD1 | 2 |
| LpCAD1.2.1 | Y | EcoRI | LpCAD2a | 7 |
|  |  |  | LpCAD2b | — |
|  |  |  | LpCAD2c | 2 |
| LpCCR1 | Y | EcoRI | LpCCR1 | 7 |
| LpOMT1 | Y | DraI | LpOMT1 | 7 |
| LpOMT2 | Y | EcoRV | LpOMT2 | 6 |

Lp4CL1, Lp4CL3, LpCAD1, LpCAD2, LpCCR1, LpOMT1 and LpOMT2 loci mapped to the linkage groups as indicated in Table 1 and in FIG. 40. These gene locations can now be used as candidate genes for quantitative trait loci for lignin biosynthesis associated traits such as herbage quality, dry matter digestibility, mechanical stress tolerance, disease resistance, insect pest resistance, plant stature and leaf and stem colour.

EXAMPLE 9

Sense Suppression

DNA Sequence Elements and Construct Production

Three constructs were engineered for development of transgenic perennial ryegrass with modified lignin biosynthesis, using sense suppression technology. The individual components of the sequence elements are listed in Table 2. The promoters and terminators used in construct production originated from perennial ryegrass genomic sequences. The genes were derived from perennial ryegrass cDNA sequences. The origin of the pAUX plasmid vectors has been described previously (Goderis et al., 2002).

TABLE 2

Components used in the generation of constructs for perennial ryegrass transformation.

| Construct No. | Vector backbone | Promoters | Genes | Terminators |
|---|---|---|---|---|
| 1 | pAUX3132 | LpCAD2 | LpCAD3 | LpCAD2 |
| 2 | pAUX3169 | LpCCR1 | LpCCR1 | LpCCR1 |
| 3 | pAUX3169 | LpCCR1 | LpCCR1(fs) | LpCCR1 |

The constructs were produced using Gateway™ technology (Invitrogen). The Gateway™ cloning system consists of one vector backbone and several auxiliary vectors based on pUC18 (Goderis et al., 2002). The multisite recombination cassette was assembled in the auxiliary vectors utilizing the multi-cloning site, flanked by homing endonuclease sites (FIG. 41). Homing endonucleases are rare cutting restriction enzymes minimising the risk of accidental restriction within the expression cassettes if excision of the expression cassette is required.

The respective promoter, cDNA and terminator sequences were amplified by PCR using primers incorporating the appropriate AttB recombination sequences and cloned into separate Gateway™ Entry vectors. For example, three Entry clones were required for the generation of the LpCAD expression vector (Construct 1); the LpCAD3 cDNA (FIG. 42), the LpCAD2 promoter (FIG. 43) and the LpCAD2 terminator (FIG. 44). These were then combined with pAUX3132 for the multi-recombination reaction and generation of the expression cassette pAUX3132-LpCAD2::LpCAD3::LpCAD2 (FIG. 45).

For Construct 2, Entry clones with the individual components; LpCCR1 promoter, LpCCR1 cDNA, and LpCCR1 terminator were generated using the same PCR cloning strategy. The Entry clones were combined in a recombination cloning reaction with base vector pAUX3169 to produce the final construct pAUX3169-LpCCR1::LpCCR1::LpCCR1 (FIG. 46).

For Construct 3, an alternative silencing strategy was employed involving a frame-shift based approach. This method involves the deletion of a single base pair, just downstream of the start site, which is introduced using a forward primer which has the single base deletion (FIG. 47). This construct works via sense suppression, as the transcript produced will not encode the correct protein and no functional protein will be produced.

The Entry clones with individual components LpCCR1 promoter, LpCCR1(fs) cDNA, and LpCCR1 terminator were generated and combined in a recombination cloning reaction with base vector pAUX3169 to produce the final construct pAUX3169-LpCCR1::LpCCR 1 (fs)::LpCCR 1 (FIG. 48).

The plant selectable marker which facilitates selection of putative transgenic ryegrass on the antibiotic Hygromycin B is contained on a separate plasmid, pAcH1. This plasmid utilizes the rice Actin1D promoter to drive in planta expression of the hygromycin phosphotransferase (hph) gene. The pAcH1 plasmid has been used previously in the transformation of forage grasses (Spangenberg et al., 1995).

Transformation Protocols

The protocol developed and established is based on the biolistic transformation of embryogenic calli induced from immature inflorescences isolated from an in planta maintained vernalised collection of perennial ryegrass, or seedling meristems derived from in vitro seedling cultures. Illustrations of the different stages in both processes, from the isolation of explants for the induction and proliferation of embryogenic calli for genetic transformation to the recovery of transgenic plants are shown in FIGS. 50 and 51. Both genetic transformation methods allow for a sustainable, readily-available source of donor plant materials which are highly competent for plant regeneration and genetic transformation and are compatible with biolistic transformation techniques. A general outline of the process involved in transformation is described in FIG. 52.

Molecular Analysis of Putative Transgenic Plants

Molecular analysis of putative transgenic perennial ryegrass plants has been conducted using primers for Q-PCR. The following primers were designed:
1. Primers specific for the hph gene
2. Primers across the CAD2 promoter-CAD3 gene junction
3. Primers specific for the pAUX3169 vector (as primers specific for the CCR1 junctions could also amplify endogenous genomic sequences).

An example of Q-PCR run for detection of hph in extracted genomic DNA is shown in FIG. 53.

The results summarising the number of transgenic perennial ryegrass plants for each Construct is shown in Table 3.

TABLE 3

Summary of transformation progress for perennial ryegrass lines harbouring constructs for the modification of lignin biosynthesis.

| Construct | Vector | No. Putative Transgenics | No. hph positive | No. GOI positive |
|---|---|---|---|---|
| 1 | pAUX3132-LpCAD2::LpCAD3-LpCAD2 | 180 | 65 | 25 |
| 2 | pAUX3169-LpCCR1::LpCCR1::LpCCR1 | 90 | 67 | 38 |
| 3 | pAUX3169-LpCCR1::LpCCR1(fs)::LpCCR1 | 322 | 185 | 141 |
| Total | | 592 | 317 | 204 |

Down-regulation of CAD and CCR Expression by RNA Interference and Sense Suppression In order to modify the expression level of LpCCR1 in perennial ryegrass, an RNA-mediated posttranscriptional gene silencing strategy was employed (RNA interference). The maize Ubiquitin (Ubi) promoter was used to drive expression of a LpCCR1 hairpin (hp) construct containing the variable region of 3' UTR in transgenic perennial ryegrass. Immature inflorescence-derived calli of perennial ryegrass were used as a target for biolistic transformation. hpLpCCR1 transgenic ryegrass plants were confirmed by Southern analysis (FIG. 54).

In the same manner, CAD and CCR expression is modified in perennial ryegrass using constructs 1, 2 and 3 (sense suppression).

Analysis of Lignin in Transgenic Plants

Lignin content and composition is visualised by specialized staining methods, including Mäule histochemical staining which can differentiate between G-lignin and S-lignin monomers (Moore et al., 1991). Mäule staining of flowering stems from different internodes was conducted for wild type and Ubi::hpLpCCR1 transgenic perennial ryegrass. The results demonstrate that there is significantly less lignin accumulating in stems at both the early reproductive (R1) and mid-reproductive (R2) stages (FIG. 55). Furthermore, there is an acropetal (base to apex) decrease in the relative amount of total lignin in the different internodes.

In the same manner, lignin content and composition is analysed in transgenic perennial ryegrass lines harbouring constructs 1, 2 and 3.

Additional lignin analytical methods includes isolation of cell wall material by successive hot water, ethanol and chloroform/methanol extractions (Fukushima and Hatfield, 2001) followed by determination of total lignin content/dry weight, using acetyl bromide method (Liyama and Wallis, 1990) (FIG. 56).

Further lignin monomer analysis to determine the G/S ratio is performed by thioacidoylysis cleavage method (Rolando et al., 1992) and quantification using a gas chromatography (GC-MS) (FIG. 57).

REFERENCES

Fukushima, R. S. and R. D. Hatfield (2001). "Extraction and isolation of lignin for utilization as a standard to determine lignin concentration using acetyl bromide spectrophotometric method." *J. Agri. Food Chem.* 49: 3133-3139.

Goderis, I., M. De Bolle, I. Francois, P. Wouters, W. Broekaert and B. Cammue (2002). "A set of modular plant transformation vectors allowing flexible insertion of up to six expression units." *Plant Mol Biol* 50: 17-27.

Heath et al (1988) cDNA cloning and differential expression of three caffeic acid O-methyltransferase homologues from perennial ryegrass (*Lolium perenne*). Journal of Plant Physiology 153:649-657

Lichtenstein, C, And J. Draper (1985) Genetic engineering of plants. In: D. M. Glover (ed.), DNA Cloning, Vol. 2, pp. 67-119, IRL Press, Washington.

Liyama, K. and A. F. A. Wallis (1990). "Determination of lignin in herbaceous plants by an improved acetyl bromide procedure." *J Sci Food Agric* 51: 145-161.

Moore, K. J., L. E. Moser, K. P. Vogel, S. S. Waller, Johnson B. E. and P. J. F. (1991). "Describing and quantifying growth stages of perennial forage grasses." *Agron. J.* 83: 1073-1077.

Rolando, C., B. Monties and C. Lapierre (1992). Thioacidolysis. *Methods in Lignin Chemistry* S. Y. Lin and C. W. Dence, Springer-Verlag: pp. 334-349.

Spangenberg, G., Z. Y. Wang, X. L. Wu, J. Nagel, V. A. Iglesias and I. Potrykus (1995). "Transgenic tall fescue and red fescue plants from microprojectile bombardment of embryogenic suspension cells." *J Plant Physiol* 145: 693-701.

Finally, it is to be understood that various alterations, modifications and/or additions may be made without departing from the spirit of the present invention as outlined herein.

It will also be understood that the term "comprises" (or its grammatical variants) as used in this specification is equivalent to the term "includes" and should not be taken as excluding the presence of other elements or features.

Documents cited in this specification are for reference purposes only and their inclusion is not an acknowledgement that they form part of the common general knowledge in the relevant art.

The invention claimed is:

1. A vector comprising a substantially purified or isolated nucleic acid or nucleic acid fragment selected from the group consisting of:
   (a) a nucleic acid or nucleic acid fragment encoding a CCR comprising the sequence shown in Sequence ID No: 7;
   (b) an open reading frame encoding a CCR shown in FIG. 10;
   (c) the complements of the sequences recited in (a) and (b);
   (d) sequences antisense to the full length of the sequences recited in (a), (b) and (c); and
   (e) functionally active variants of the sequences recited in (a), (b), (c), and (d), being capable of modifying lignin biosynthesis in a plant and having at least 95% identity to the entirety of the sequence recited in (a), (b), (c) or (d); wherein the nucleic acid or nucleic acid fragment is operably linked to a heterologous regulatory element.

2. The vector according to claim 1 wherein said nucleic acid is from a *Lolium* species selected from the group consisting of *Lolium perenne* or *Lolium arundinaceum*.

3. The vector according to claim 1 comprising:
   a variant of Sequence ID No: 7, wherein said variant is capable of modifying lignin biosynthesis in a plant via sense suppression of a gene encoding a CCR in said plant.

4. The vector according to claim 3, wherein the variant includes a short deletion at or near the 3' or 5' end of the sequence.

5. The vector according to claim 4, wherein the variant includes a frame-shift mutation relative to the sequence.

6. The vector according to claim 5, wherein the variant encodes a polypeptide without enzymatic activity or with substantially reduced enzymatic activity.

7. The vector according to claim 1, further including a promoter and a terminator, said promoter, nucleic acid and terminator being operatively linked.

8. A plant cell, plant, plant seed or other plant part, including the vector according to claim 1.

9. A method of modifying lignin biosynthesis in a plant, said method including introducing into said plant an effective amount of the vector according to claim 1, thereby modifying lignin biosynthesis in the plant.

10. The method according to claim 9 wherein lignin biosynthesis in the plant is reduced as a consequence of sense suppression of lignin biosynthesis.

11. The vector according to claim 1 wherein said nucleic acid or nucleic acid fragment comprises a nucleotide sequence recited in (a), (b) or (c) with substitutions or derivatizations of one or more of the nucleotides in said nucleotide sequence in accordance with (e), wherein the variant comprises a nucleotide sequence having at least 95% identity to the entirety of the sequence recited in (a), (b), (c) or (d).

12. The vector according to claim 1 wherein said nucleic acid is a variant of a nucleotide sequence recited in (a), (b) or (c) with nucleic acid changes that result in a conservative amino acid substitution of one ore more of the residues in the corresponding amino acid sequence in accordance with (e), wherein the variant comprises a nucleotide sequence having at least 95% identity to the entirety of the sequence recited in (a), (b), (c) or (d).

13. The vector according to claim 1 wherein said variants include a nucleotide sequence recited in (a), (b) or (c) with an addition or deletion of one nucleotide in said nucleotide sequence in accordance with (e), wherein the variant comprises a nucleotide sequence having at least 95% identity to the entirety of the sequence recited in (a), (b), (c) or (d).

14. A method of making a lignin having altered composition, said method comprising introducing into a plant, plant seed or other plant part and effective amount of the vector according to claim 1, and substantially or partially purifiying lignin from the plant, plant seed or other plant part.

15. A vector comprising a substantially purified or isolated nucleic acid selected from the group consisting of:
(a) a nucleic acid fragment encoding a CCR comprising the sequence shown in Sequence ID No: 7;
(b) the complement of Sequence ID No: 7;
(c) the antisense sequence to the full length of Sequence ID No: 7; and
(d) a variant of Sequence ID No: 7 including a frame-shift mutation relative to the sequence and having at least 95% identity to the entirety of Sequence ID No: 7; wherein the nucleic acid is operably linked to a heterologous regulatory element.

16. A vector comprising a substantially purified or isolated nucleic acid or nucleic acid fragment, wherein the nucleic acid or nucleic acid fragment is a variant of Sequence ID No: 7 that is a frame-shift mutation relative to the sequence, and wherein said frame-shift mutation comprises a deletion or insertion of a single nucleotide in Sequence ID No: 7; wherein the nucleic acid or nucleic acid fragment is operably linked to a heterologous regulatory element.

17. A vector comprising a nucleic acid comprising a deletion mutant of Seq ID No. 7, wherein the deletion mutant is different from Seq ID No. 7 as a consequence of a deletion of from 1 to 500 nucleotides from (a) a location within 100 bases of the ATG start codon of Seq ID No: 7, or (b) a location starting within 100 bases of the 3' end and extending towards the 5' end of Seq ID No: 7; wherein the nucleic acid is operably linked to a heterologous regulatory element.

18. The vector of claim 17, wherein the deletion occurs within 50 bases downstream of the ATG start codon of Seq ID No. 7.

19. The vector of claim 18, wherein the deletion is from 1 to 100 bases.

20. The vector of claim 17, wherein the deletion occurs at a location starting within 50 bases of the 3' end of seq ID No. 7.

21. The vector of claim 20, wherein the deletion is from 100 to 300 bases.

22. A vector comprising a substantially purified or isolated nucleic acid, wherein the nucleic acid consists of a fragment of a nucleic acid starting sequence, said nucleic acid starting sequences being selected from the group consisting of:
(a) a nucleic or nucleic acid fragment encoding a CCR comprising the sequence shown in Sequence ID No: 7;
(b) an open reading frame encoding a CCR shown in FIG. 10;
(c) the complements of the sequences recited in (a) and (b); and
(d) sequences antisense to the full length of the sequences recited in (a), (b) and (c); wherein the fragment is capable of modifying lignin biosynthesis and has a size of at least 20 nucleotides; wherein the nucleic acid is operably linked to a heterologous regulatory element.

23. The vector according to claim 22 wherein said fragment has a size of at least 50 nucleotides.

24. The vector according to claim 22, said vector consisting of:
a fragment of Sequence ID No: 7, wherein said fragment is capable of modifying lignin biosynthesis in a plant via sense suppression of a gene encoding the CCR in said plant.

25. A vector comprising a substantially purified or isolated nucleic acid, wherein the nucleic acid consists of a fragment of a nucleic acid starting sequence, said nucleic acid starting sequence being selected from the group consisting of:
(a) a nucleic acid or nucleic acid fragment encoding a CCR comprising the sequence shown in Sequence ID No: 7;
(b) an open reading frame encoding a CCR shown in FIG. 10;
(c) the complements of the sequences recited in (a) and (b); and
(d) sequences antisense to the full length of the sequences recited in (a), (b), and (c); wherein the fragment is capable of modifying lignin biosynthesis in a plant via sense suppression and has a size of at least 20 nucleotides, and wherein the fragment includes a short deletion at or near the 3' or 5' end of the sequence; wherein the nucleic acid or nucleic acid fragment is operably linked to a heterologous regulatory element.

26. The vector according to claim 25, wherein the fragment includes a frame-shift mutation relative to Seq ID No. 7.

27. The vector according to claim 26, wherein the fragment encodes a polypeptide without enzymatic activity or with substantially reduced enzymatic activity.

28. The vector according to claim 22, further including a promoter and a terminator, said promoter, nucleic acid and terminator being operatively linked.

29. A method of modifying lignin biosynthesis in a plant, said method including introducing into said plant an effective amount of the vector according to claim 22, thereby modifying lignin biosynthesis in the plant.

30. The method according to claim 29, wherein lignin biosynthesis is reduced as a consequence of sense suppression of lignin biosynthesis.

31. A plant cell, plant, plant seed or other plant part, including the vector according to claim 22.

* * * * *